US012275979B2

(12) United States Patent
Isobe et al.

(10) Patent No.: US 12,275,979 B2
(45) Date of Patent: Apr. 15, 2025

(54) GENE-MODIFIED MICROORGANISM FOR PRODUCING 3-HYDROXYADIPIC ACID, ALPHA-HYDROMUCONIC ACID, AND/OR ADIPIC ACID, AND PRODUCTION METHOD FOR SAID CHEMICAL PRODUCTS

(71) Applicant: TORAY INDUSTRIES, INC., Tokyo (JP)

(72) Inventors: Kyohei Isobe, Kamakura (JP); Kenji Kawamura, Kamakura (JP); Katsushige Yamada, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 16/766,979

(22) PCT Filed: Nov. 29, 2018

(86) PCT No.: PCT/JP2018/044080
§ 371 (c)(1),
(2) Date: May 26, 2020

(87) PCT Pub. No.: WO2019/107516
PCT Pub. Date: Jun. 6, 2019

(65) Prior Publication Data
US 2020/0291435 A1 Sep. 17, 2020

(30) Foreign Application Priority Data
Nov. 30, 2017 (JP) .................. 2017-230407

(51) Int. Cl.
*C12N 1/21* (2006.01)
*C12P 7/42* (2006.01)
*C12P 7/44* (2006.01)

(52) U.S. Cl.
CPC .. *C12P 7/42* (2013.01); *C12P 7/44* (2013.01)

(58) Field of Classification Search
None
See application file for complete search history.

(56) References Cited

U.S. PATENT DOCUMENTS

| 11,078,503 B2 * | 8/2021 | Isobe ........................ C12P 7/44 |
| 2011/0124911 A1 | 5/2011 | Burk et al. | |
| 2012/0021478 A1 * | 1/2012 | Osterhout ................ C12P 7/62 435/167 |
| 2015/0361463 A1 * | 12/2015 | Botes ....................... C12N 9/18 560/181 |
| 2017/0101631 A1 * | 4/2017 | Koepke ................. C12N 9/0008 |

FOREIGN PATENT DOCUMENTS

| EP | 3 467 113 A1 | 4/2019 |
| WO | WO 2009/151728 A2 | 12/2009 |
| WO | WO 2012/018624 A2 | 2/2012 |
| WO | WO 2016/106367 A1 | 6/2016 |
| WO | WO 2017-066498 A1 | 4/2017 |

OTHER PUBLICATIONS

GenBank Database Accession No. WP_033633399, Jun. 2015, 1 page (Year: 2015).*
Singh et al., Curr. Protein Pept. Sci. 18:1-11, 2017 (Year: 2017).*
Zhang et al., Structure 26:1474-1485, 2018 (Year: 2018).*
Zhou et al., Cell Mol Life Sci 63:2260-2290, 2006 (Year: 2006).*
Kozak, M., Gene 234:187-208, 1999 (Year: 1999).*
Birktoft et al., "Structure of L-3-hydroxyacyl-coenzyme A dehydrogenase: Preliminary chain tracing at 2.8-A resolution", Proc. Natl. Acad. Sci. USA, 84:8262-8266, 1987 (Year: 1987).*
Barycki et al., "Biochemical Characterization and Crystal Structure Determination of Human Heart Short Chain L-3-Hydroxyacyl-CoA Dehydrogenase Provide Insights into Catalytic Mechanism", Biochemistry 38:5786-5798, 1999 (Year: 1999).*
Babu et al., "Engineering *Escherichia coli* for the production of adipic acid through the reversed B-oxidation pathway", Process Biochem. 50:2066-2071, 2015 (Year: 2015).*
Database GenBank, "3-hydroxybutyryl-CoA dehydrogenase [Serratia liquefaciens]", Accession No. AMG98270, Feb. 11, 2016, https://www.ncbi.nlm.nih.gov/protein/991935067?sat=4Rsatkey=158110186, pp. 1-2.
Database GenBank, "3-hydroxybutyryl-CoA dehydrogenase [Serratia marcescens]", Accession No. ALL37524, Feb. 28, 2017, https//www.ncbi.nim.nih.gov/protein/943365850, pp. 1-2.
Database GenBank, "3-hydroxybutyryl-CoA dehydrogenase [Serratia marcescens]", Accession No. ASM11478, Jul. 18, 2017, https://www.ncbi.nlm.nih.gov/protein/ASM11476.1, pp. 1-2.

(Continued)

*Primary Examiner* — David Steadman
(74) *Attorney, Agent, or Firm* — Birch, Stewart, Kolasch & Birch, LLP

(57) ABSTRACT

Disclosed is a genetically modified microorganism into which a nucleic acid encoding an enzyme that catalyzes a reaction to reduce 3-oxoadipyl-CoA to 3-hydroxyadipyl-CoA is introduced. In the genetically modified microorganism, a nucleic acid encoding any one of the polypeptides described in (a) to (c) below is introduced or expression of the polypeptide is enhanced: (a) a polypeptide composed of an amino acid sequence represented by any one of SEQ ID NOs: 1 to 6 and 213, (b) a polypeptide composed of the same amino acid sequence as any one of the amino acid sequences, except that one or several amino acids are substituted, deleted, inserted, and/or added, and having enzymatic activity that catalyzes a reaction to reduce 3-oxoadipyl-CoA to 3-hydroxyadipyl-CoA, and (c) a polypeptide composed of an amino acid sequence with a sequence identity of not less than 70% to any one of the amino acid sequences and having activity to reduce 3-oxoadipyl-CoA to 3-hydroxyadipyl-CoA.

8 Claims, 1 Drawing Sheet
Specification includes a Sequence Listing.

(56) References Cited

OTHER PUBLICATIONS

Database GenBank, "3-hydroxybutyryl-CoA dehydrogenase [Serratia nematodiphila DZ0503SBS1]", Accession No. KFF90258, Aug. 7, 2014, https://www.ncbi.nim.nih.gov/protein/KFF90258.1, pp. 1-2.
Database GenBank, "3-hydroxybutyryl-CoA dehydrogenase [Serratia plymuthica S13]", Accession No. AGP43956, Jan. 30, 2014, https://www.ncbi.nim.nih.gov/protein/APG43956.1, pp. 1-2.
Database GenBank, "3-hydroxybutyryl-CpA dehydrogenase [Serratia proteamaculans 568]", Accession No. ABV40935, Jan. 28, 2014, https://www.ncbi.nim.nih.gov/protein/ABV40935.1, pp. 1-2.
Database GenBank, "3-hydroxybutyryl-CoA dehydrogenase [Serratia proteamaculans]", Accession No. SMB31239, Apr. 14, 2017, https://www.ncbi.nim.nih.gov/protein/SMB31239.1, pp. 1-2.
International Search Report dated Feb. 19, 2019 for Application No. PCT/JP2018/044080.
Extended European Search Report issued Nov. 11, 2021, in European Patent Application No. 18883299.2.
Yu et al., "Direct Biosynthesis of Adipic Acid from a Synthetic Pathway in Recombinant *Escherichia coli*," Biotechnol. Bioeng. (2014), vol. 111, pp. 2580-2586.

\* cited by examiner

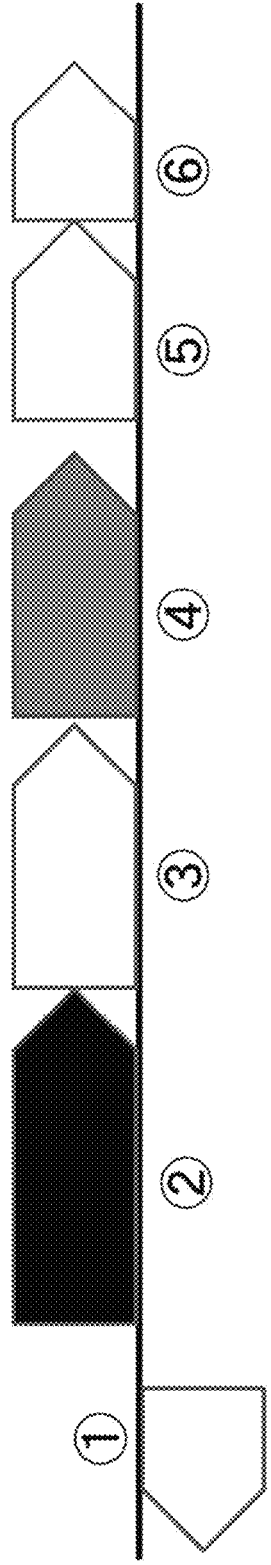

| | Definition(BLAST search result) | Protein ID (Serratia proteamaculans 568) | Gene Position (Gene ID:CP000826.1) |
|---|---|---|---|
| ① | LuxR family transcriptional regulator or quorum-sensing transcriptional activator | ABV40936.1 | 2017190..2017906 |
| ② | 3-hydroxybutyryl-CoA dehydrogenase | ABV40935.1 | 2015313..2016842 (Complement) |
| ③ | acetyl-CoA C-acyltransferase or beta-ketoadipyl CoA thiolase | ABV40934.1 | 2014092..2015303 (Complement) |
| ④ | 5-aminolevulinate synthase | ABV40933.1 | 2012865..2014076 (Complement) |
| ⑤ | MFS transporter or Purine efflux pump PbuE | ABV40932.1 | 2011696..2012868 (Complement) |
| ⑥ | enoyl-CoA hydratase or Carnitinyl-CoA dehydratase | ABV40931.1 | 2010981..2011703 (Complement) |

GENE-MODIFIED MICROORGANISM FOR PRODUCING 3-HYDROXYADIPIC ACID, ALPHA-HYDROMUCONIC ACID, AND/OR ADIPIC ACID, AND PRODUCTION METHOD FOR SAID CHEMICAL PRODUCTS

REFERENCE TO SEQUENCE LISTING SUBMITTED VIA EFS-WEB

This application includes an electronically submitted sequence listing in .txt format. The txt file contains a sequence listing entitled "0760_0515PUS1_Substitute_Sequence_Listing.txt" created on May 10, 2021 and is 604,209 bytes in size. The sequence listing contained in this .txt file is part of the specification and is hereby incorporated by reference herein in its entirety.

TECHNICAL FIELD

The present invention relates to a genetically modified microorganism in which a nucleic acid encoding a polypeptide involved in the production of a substance of interest is introduced or expression of the polypeptide is enhanced, and to a method of producing the substance by using the microorganism.

BACKGROUND ART

3-Hydroxyadipic acid (IUPAC name: 3-hydroxyhexanedioic acid), α-hydromuconic acid (IUPAC name: (E)-hex-2-enedioic acid), and adipic acid (IUPAC name: hexanedioic acid) are dicarboxylic acids containing six carbon atoms. These dicarboxylic acids can be used as raw materials for the production of polyesters by polymerization with polyhydric alcohols or as raw materials for the production of polyamides by polymerization with polyfunctional amines. Additionally, these dicarboxylic acids can be used as raw materials for polyamides by themselves by adding ammonia to the end of these dicarboxylic acids and converting the resultants to lactams.

Examples of the literature relating to the biosynthesis of 3-hydroxyadipic acid using a non-naturally occurring microorganism include Patent Document 1 in which 3-hydroxyadipic acid (3-hydroxyadipate) is described as a metabolic intermediate produced by the microorganism in the pathway of biosynthesis of 1,3-butadiene from succinyl-CoA.

Examples of the literature relating to the biosynthesis of α-hydromuconic acid using a non-naturally occurring microorganism include Patent Document 2 in which α-hydromuconic acid (2,3-dehydroadipate) is described as a metabolic intermediate produced by the microorganism in the pathway of biosynthesis of trans,trans-muconic acid from succinyl-CoA.

Examples of the literature relating to the biosynthesis of adipic acid using a microorganism include Patent Document 3 in which the reverse adipate-degradation pathway is described as a pathway to produce adipic acid from succinyl-CoA.

It is described that all the biosynthesis pathways described in Patent Documents 1 to 3 proceed through an enzymatic reaction that reduces 3-oxoadipyl-CoA to 3-hydroxyadipyl-CoA.

PRIOR ART DOCUMENTS

Patent Documents

Patent Document 1: JP 2013-535203 A
Patent Document 2: US 2011/0124911 A1
Patent Document 3: JP 2011-515111 A

SUMMARY OF THE INVENTION

Problems to be Solved by the Invention

Patent Documents 1 and 2 describe the metabolic pathways that can produce 3-hydroxyadipic acid and α-hydromuconic acid in the microorganisms, but not anything about interruption of the metabolic pathways to secrete 3-hydroxyadipic acid and α-hydromuconic acid into culture medium. Moreover, the prior studies described in Patent Documents 1 to 3 have not examined whether or not 3-hydroxyadipic acid, α-hydromuconic acid, or adipic acid can be actually produced by using the non-naturally occurring microorganisms in which a nucleic acid encoding an enzyme that catalyzes a reaction to reduce 3-oxoadipyl-CoA to 3-hydroxyadipyl-CoA is introduced. Accordingly, it is not known whether the enzyme that catalyzes a reaction to reduce 3-oxoadipyl-CoA to 3-hydroxyadipyl-CoA, as described in Patent Documents 1 to 3, also exhibits excellent activity in the production of 3-hydroxyadipic acid, α-hydromuconic acid, and/or adipic acid.

Accordingly, an object of the present invention is to provide a genetically modified microorganism in which a nucleic acid encoding an enzyme that exhibits excellent activity in a 3-oxoadipyl-CoA reduction reaction is introduced or expression of the enzyme is enhanced, and a method of producing a substance by using the modified microorganism.

Means for Solving the Problem

The inventors intensively studied to achieve the above-described object and consequently found that a group of polypeptides with high similarities in amino acid sequences exhibit an excellent catalytic activity for a reaction to reduce 3-oxoadipyl-CoA to 3-hydroxyadipyl-CoA, to complete the present invention.

That is, the present invention provides the following:

(1) A genetically modified microorganism in which a nucleic acid encoding any one of polypeptides described in (a) to (c) below is introduced or expression of the polypeptide is enhanced:

(a) a polypeptide composed of an amino acid sequence represented by any one of SEQ ID NOs: 1 to 6 and 213;

(b) a polypeptide composed of the same amino acid sequence as that represented by any one of SEQ ID NOs: 1 to 6 and 213, except that one or several amino acids are substituted, deleted, inserted, and/or added, and having an enzymatic activity that catalyzes a reaction to reduce 3-oxoadipyl-CoA to 3-hydroxyadipyl-CoA;

(c) a polypeptide composed of an amino acid sequence with a sequence identity of not less than 70% to the sequence represented by any one of SEQ ID NOs: 1 to 6 and 213 and having an enzymatic activity that catalyzes a reaction to reduce 3-oxoadipyl-CoA to 3-hydroxyadipyl-CoA.

(2) The genetically modified microorganism according to (1), wherein the polypeptide described in either (b) or (c) comprises a region with an amino acid sequence represented by SEQ ID NO: 212.

(3) The genetically modified microorganism according to (2), wherein the amino acid sequence represented by SEQ ID NO: 212 comprises a phenylalanine or leucine residue as the 13th amino acid residue from the N terminus, a leucine or glutamine residue as the 15th amino acid residue from the N terminus, a lysine or asparagine residue as the 16th amino acid residue from the N terminus, a glycine or serine residue as the 17th amino acid residue from the N terminus, a proline or arginine residue as the 19th amino acid residue from the N terminus, and preferably a leucine, methionine, or valine residue as the 21st amino acid residue from the N terminus.

(4) The genetically modified microorganism according to any one of (1) to (3), which is a genetically modified microorganism selected from the group consisting of the genera *Escherichia, Serratia, Hafnia*, and *Pseudomonas*.

(5) The genetically modified microorganism according to any one of (1) to (4), which has an ability to generate 3-oxoadipyl-CoA and coenzyme A from acetyl-CoA and succinyl-CoA; and an ability to generate 3-hydroxyadipic acid from 3-hydroxyadipyl-CoA.

(6) The genetically modified microorganism according to any one of (1) to (4), which has an ability to generate 3-oxoadipyl-CoA and coenzyme A from acetyl-CoA and succinyl-CoA: an ability to generate 2,3-dehydroadipyl-CoA from 3-hydroxyadipyl-CoA: and an ability to generate α-hydromuconic acid from 2,3-dehydroadipyl-CoA.

(7) The genetically modified microorganism according to any one of (1) to (4), which has an ability to generate 3-oxoadipyl-CoA and coenzyme A from acetyl-CoA and succinyl-CoA; an ability to generate 2,3-dehydroadipyl-CoA from 3-hydroxyadipyl-CoA; an ability to generate adipyl-CoA from 2,3-dehydroadipyl-CoA; and an ability to generate adipic acid from adipyl-CoA.

(8) A method of producing 3-hydroxyadipic acid, comprising culturing the genetically modified microorganism according to any one of (1) to (5) in a culture medium containing a carbon source as a material for fermentation.

(9) A method of producing α-hydromuconic acid, comprising culturing the genetically modified microorganism according to any one of (1) to (4) and (6) in a culture medium containing a carbon source as a material for fermentation.

(10) A method of producing adipic acid, comprising culturing the genetically modified microorganism according to any one of (1) to (4) and (7) in a culture medium containing a carbon source as a material for fermentation.

(11) A method of producing one or more substances selected from the group consisting of 3-hydroxyadipic acid. α-hydromuconic acid, and adipic acid, comprising culturing a genetically modified microorganism in a culture medium containing a carbon source as a material for fermentation, wherein a nucleic acid encoding a polypeptide encoded by the 3-hydroxybutyryl-CoA dehydrogenase gene of a microorganism of the genus *Serratia*, which forms a gene cluster with 5-aminolevulinic acid synthase gene in the microorganism, is introduced or expression of the polypeptide is enhanced in the genetically modified microorganism.

Effects of the Invention

The genetically modified microorganism according to the present invention expresses an enzyme that exhibits excellent activity in a reaction to reduce 3-oxoadipyl-CoA to 3-hydroxyadipyl-CoA and thus is excellent in the production of 3-hydroxyadipic acid. α-hydromuconic acid, and/or adipic acid through production of 3-hydroxyadipyl-CoA.

The method of producing a substance according to the present invention uses the genetically modified microorganism which is excellent in the production of 3-hydroxyadipic acid, α-hydromuconic acid, and/or adipic acid through production of 3-hydroxyadipyl-CoA and thus can greatly increase the production of those substances.

BRIEF DESCRIPTION OF THE DRAWING

The FIGURE shows a gene cluster constituted by a 3-hydroxybutyryl-CoA dehydrogenase gene and a 5-aminolevulinic acid synthase gene.

MODE FOR CARRYING OUT THE INVENTION

The microorganism according to the present invention is a genetically modified microorganism in which a nucleic acid encoding any one of the polypeptides described in (a) to (c) below is introduced or expression of the polypeptide is enhanced:

(a) a polypeptide composed of an amino acid sequence represented by any one of SEQ ID) NOs: 1 to 6 and 213;

(b) a polypeptide composed of the same amino acid sequence as that represented by any one of SEQ ID NOs: 1 to 6 and 213, except that one or several amino acids are substituted, deleted, inserted, and/or added, and having an enzymatic activity that catalyzes the reaction to reduce 3-oxoadipyl-CoA to 3-hydroxyadipyl-CoA;

(c) a polypeptide composed of an amino acid sequence with a sequence identity of not less than 70% to the sequence represented by any one of SEQ ID NOs: 1 to 6 and 213 and having an activity to reduce 3-oxoadipyl-CoA to 3-hydroxyadipyl-CoA.

An enzyme that catalyzes the reaction to reduce 3-oxoadipyl-CoA to 3-hydroxyadipyl-CoA is hereinafter referred to as "3-oxoadipyl-CoA reductase" in the specification. Additionally, 3-hydroxyadipic acid may be abbreviated as 3HA, α-hydromuconic acid may be abbreviated as HMA, and adipic acid may be abbreviated as ADA, respectively, in the specification.

In the present invention, introduction of a nucleic acid refers to introducing a nucleic acid from outside into a microorganism to give the microorganism an ability to produce a polypeptide encoded by the nucleic acid. The introduction method is not limited to a particular method, and examples of the method that can be used include a method in which the nucleic acid incorporated in an expression vector capable of autonomous replication in a microorganism is introduced into a host microorganism, and a method in which the nucleic acid is integrated into the genome of a microorganism.

In the present invention, enhancement of polypeptide expression refers to enhancing the expression of a polypeptide which the microorganism originally has. The method for expression enhancement is not limited to a particular method, and examples of the method include a method in which a nucleic acid encoding the polypeptide is increased in copy number, and a method in which a promoter region or a ribosome-binding sequence upstream of the region coding for the polypeptide is modified. These methods may be carried out individually or in combination.

Additionally, one or more nucleic acids may be introduced. Moreover, introduction of a nucleic acid and enhancement of polypeptide expression may be combined.

For the polypeptide used in the present invention and composed of the same amino acid sequence as that represented by any one of SEQ ID NOs: 1 to 6 and 213, except that one or several amino acids are substituted, deleted, inserted, and/or added, and having 3-oxoadipyl-CoA reductase activity, the range represented by the phrase "one or several" is preferably 10 or less, more preferably 5 or less, particularly preferably 4 or less, and most preferably one or two. In the case of amino acid substitution, the activity of the original polypeptide is more likely to be maintained when an amino acid(s) is/are replaced by an amino acid(s) with similar properties (so-called conservative substitution). That is, the physiological activity of the original polypeptide is often maintained when the amino acid(s) is/are replaced by an amino acid(s) with similar properties. Thus, the amino acid(s) is/are preferably replaced by an amino acid(s) with similar properties. That is, the 20 amino acids constituting naturally occurring proteins can be divided into groups with similar properties, such as neutral amino acids with a less polar side chain (Gly, Ile, Val, Leu, Ala, Met, Pro), neutral amino acids with a hydrophilic side chain (Asn, Gln, Thr, Ser, Tyr, Cys), acidic amino acids (Asp, Glu), and basic amino acids (Arg, Lys, His), and aromatic amino acids (Phe, Tyr, Trp); it is often the case that substitution between amino acids in the same group does not change the properties of the original polypeptide.

For the polypeptide used in the present invention and having an amino acid sequence with a sequence identity of not less than 70% to the sequence represented by any one of SEQ ID NOs: 1 to 6 and 213 and having 3-oxoadipyl-CoA reductase activity, the sequence identity is preferably not less than 80%, more preferably not less than 85%, further preferably not less than 90%, still further preferably not less than 95%, yet further preferably not less than 97%, and even further preferably not less than 99%.

In the present invention, the term "sequence identity" means a ratio (percentage) of the number of identical amino acid or nucleotide residues relative to the total number of amino acid or nucleotide residues over the overlapping portion of an amino acid sequence alignment (including an amino acid corresponding to the translation start site) or a nucleotide sequence alignment (including the start codon), which is obtained by aligning two amino acid or nucleotide sequences with or without introduction of gaps for an optimal match, and is calculated by the following formula (1). In the formula (1), the length of a shorter sequence being compared is not less than 400 amino acids; in cases where the length of the shorter sequence is less than 400 amino acids, the sequence identity is not defined. The sequence identity can be easily determined using BLAST (Basic Local Alignment Search Tool), an algorithm widely used in this field. For example, BLAST is publicly available on a website, such as that of NCBI (National Center for Biotechnology Information) or KEGG (Kyoto Encyclopedia of Genes and Genomes), on which the sequence identity can be easily determined using default parameters. Additionally, the sequence identity can also be determined using a similar function implemented in a software program such as Genetyx.

Sequence identity (%)=the number of matches (without counting the number of gaps)/the length of a shorter sequence (excluding the terminal gaps)×100     (1)

Sequence identities among the amino acid sequences represented by SEQ ID NOs: 1 to 6 and 213 are calculated using a function of Genetyx (% Identity Matrix) based on the formula (1); the least sequence identity is 71.51% between SEQ ID NOs: 2 and 4, and a sequence identity of not less than 70% is shared at least among the amino acid sequences represented by SEQ ID NOs: 1 to 6 and 213. The results of calculation of sequence identity using Genetyx are presented in Table 1. In Tables 1 to 5 below, the numbers in the leftmost column represent SEQ ID NOs.

TABLE 1

| [GENETYX: % Identity Matrix] | | | | | | | |
|---|---|---|---|---|---|---|---|
| [%] | 1 Serratia | 2 Serratia | 3 Serratia | 4 Serratia | 5 Serratia | 6 Serratia | 213 Serratia |
| 1 Serratia marcescens ATCC13880 | * | | | | | | |
| 2 Serratia nematodiphila DSM21420 | 98.23 | * | | | | | |
| 3 Serratia plymuthica NBRC102599 | 72.10 | 71.56 | * | | | | |
| 4 Serratia proteamaculans 568 | 72.29 | 71.51 | 86.24 | * | | | |
| 5 Serratia ureilytica Lr5/4 | 90.76 | 90.76 | 72.82 | 73.28 | * | | |
| 6 Serratia sp. BW106 | 72.29 | 71.90 | 87.03 | 92.33 | 73.67 | * | |
| 213 Serratia liquefaciens FK01 | 72.29 | 71.70 | 84.67 | 86.83 | 73.47 | 87.81 | * |
| [Match Count/Length] | 1 Serratia | 2 Serratia | 3 Serratia | 4 Serratia | 5 Serratia | 6 Serratia | 213 Serratia |
| 1 Serratia marcescens ATCC13880 | * | | | | | | |
| 2 Serratia nematodiphila DSM21420 | 500/509 | * | | | | | |
| 3 Serratia plymuthica NBRC102599 | 367/509 | 365/510 | * | | | | |
| 4 Serratia proteamaculans 568 | 368/509 | 364/509 | 439/509 | * | | | |
| 5 Serratia ureilytica Lr5/4 | 462/509 | 462/509 | 371/509 | 373/509 | * | | |
| 6 Serratia sp. BW106 | 368/509 | 366/509 | 443/509 | 470/509 | 375/509 | * | |
| 213 Serratia liquefaciens FK01 | 368/509 | 365/509 | 431/509 | 442/509 | 374/509 | 447/509 | * |

*Gaps are not taken into consideration [%]

When each of the amino acid sequences represented by SEQ ID NOs: 1 to 6 and 213 as queries was compared using BLASTP to all the amino acid sequences registered in the NCBI amino acid database (non-redundant protein sequences) to determine sequence identities, the sequences with a sequence identity of not less than 70% were all derived from bacteria of the genus Serratia.

All the polypeptides represented by SEQ ID NOs: 1 to 6 and 213 as described above in (a) contain a common sequence 1, composed of 24 amino acid residues and represented by SEQ ID NO: 212, within a region from the 15th to the 38th amino acid residues from the N terminus (hereinafter, an amino acid residue at the n-th position from the N terminus may conveniently be represented by n "a.a."; for example, the region from the 15th to the 38th amino acid residues from the N terminus may be thus simply represented by "15 to 38 a.a."). In the common sequence 1, Xaa represents an arbitrary amino acid residue; the 13 a.a. is preferably a phenylalanine or leucine residue; the 15 a.a. is preferably a leucine or glutamine residue; the 16 a.a. is preferably a lysine or asparagine residue; the 17 a.a. is a glycine or serine residue, more preferably glycine residue; the 19 a.a. is preferably a proline or arginine residue, and the 21 a.a. is preferably a leucine, methionine, or valine residue. The common sequence 1 corresponds to the region including the $NAD^+$-binding residue and the surrounding amino acid residues. In the $NAD^+$-binding residues, the 24th amino acid residue in the common sequence 1 is aspartic acid, as described in Biochimie. 2012 February; 94 (2): 471-8., but in the common sequence 1, the residue is asparagine which is characteristic. It is thought that the polypeptides represented by SEQ ID NOs: 1 to 6 and 213 exhibit excellent enzymatic activity as 3-oxoadipyl-CoA reductases due to the presence of the common sequence 1.

The polypeptides as described above in (b) and (c) also preferably contain the common sequence 1, composed of 24 amino acid residues and represented by SEQ ID NO: 212, within a region from 1 to 200 a.a. The common sequence is more preferably contained within a region from 1 to 150 a.a., further preferably from 1 to 100 a.a. Specific examples of the polypeptides include those with the amino acid sequences represented by SEQ ID NOs: 7 to 16 and 70 to 138. In the amino acid sequences represented by SEQ ID NOs: 7 to 16 and 70 to 138, the common sequence 1, composed of 24 amino acid residues and represented by SEQ ID NO: 212, is contained within a region from 15 to 38 a.a. The amino acid sequences represented by SEQ ID NOs: 7 to 16 and 70 to 138 have a sequence identity of not less than 90% to the amino acid sequence represented by any one of SEQ ID NOs: 1 to 6 and 213. The results of calculation of sequence identity using Genetyx are presented in Tables 2-1 to 2-3 and Tables 3-1 to 3-3.

TABLE 2-1

[GENETYX: % Identity Matrix]

| [%] | 1 Serratia | 2 Serratia | 3 Serratia | 4 Serratia | 5 Serratia | 6 Serratia | 213 Serratia |
|---|---|---|---|---|---|---|---|
| 1 Serratia marcescens ATCC13880 | * | | | | | | |
| 2 Serratia nematodiphila DSM21420 | 98.23 | * | | | | | |
| 3 Serratia plymuthica NBRC102599 | 72.1 | 71.51 | * | | | | |
| 4 Serratia proteamaculans 568 | 72.29 | 71.51 | 86.24 | * | | | |
| 5 Serratia ureilytica Lr5/4 | 90.76 | 90.76 | 72.88 | 73.28 | * | | |
| 6 Serratia sp. BW106 | 72.29 | 71.9 | 87.03 | 92.33 | 73.67 | * | |
| 213 Serratia liquefaciens FK01 | 72.29 | 71.7 | 84.67 | 86.83 | 73.47 | 87.81 | * |
| 7 Serratia sp. S119 | 94.89 | 94.3 | 72.88 | 72.49 | 91.55 | 73.08 | 72.88 |
| 8 Serratia sp. YD25 | 92.33 | 92.33 | 72.49 | 72.49 | 93.51 | 72.69 | 72.88 |
| 9 Serratia sp. FS14 | 98.62 | 99.6 | 71.7 | 71.7 | 91.15 | 72.1 | 72.1 |
| 10 Serratia sp. HMSC15F11 | 94.89 | 94.3 | 73.28 | 73.28 | 91.35 | 73.47 | 73.47 |
| 11 Serratia sp. JKS000199 | 90.76 | 90.76 | 72.69 | 73.08 | 99.41 | 73.47 | 73.28 |
| 12 Serratia sp. TEL | 90.56 | 90.56 | 72.88 | 73.28 | 99.8 | 73.67 | 73.47 |
| 13 Serratia sp. ISTD04 | 90.56 | 90.56 | 72.49 | 73.08 | 99.41 | 73.47 | 73.28 |
| 14 Serratia sp. SCBI | 90.76 | 90.76 | 72.88 | 73.28 | 99.6 | 73.47 | 73.47 |
| 15 Serratia sp. S4 | 72.1 | 71.31 | 86.44 | 98.62 | 73.08 | 91.94 | 86.64 |
| 16 Serratia sp. C-1 | 72.49 | 71.9 | 98.03 | 86.05 | 73.28 | 86.64 | 84.08 |
| 70 Serratia marcescens 532 | 99.8 | 98.03 | 72.29 | 72.1 | 90.56 | 72.1 | 72.1 |
| 71 Serratia marcescens 2880STDY5683033 | 99.6 | 97.83 | 72.1 | 72.29 | 90.37 | 72.1 | 72.29 |
| 72 Serratia marcescens WW4 | 98.42 | 99.41 | 71.9 | 71.9 | 90.96 | 72.29 | 71.9 |
| 73 Serratia marcescens K27 | 98.23 | 99.21 | 71.31 | 71.31 | 90.96 | 71.7 | 71.7 |
| 74 Serratia marcescens 280 | 98.42 | 99.41 | 71.7 | 71.7 | 90.96 | 72.1 | 72.1 |
| 75 Serratia marcescens 19F | 98.42 | 99.41 | 71.51 | 71.7 | 90.96 | 72.1 | 72.1 |
| 76 Serratia marcescens 1185 | 98.23 | 99.6 | 71.31 | 71.31 | 90.37 | 71.7 | 71.51 |

* Gaps are not taken into consideration

TABLE 2-2

| | | | | | | | |
|---|---|---|---|---|---|---|---|
| 77 Serratia marcescens S217 | 98.23 | 99.21 | 71.31 | 71.51 | 90.96 | 71.9 | 71.9 |
| 78 Serratia marcescens KHCo-24B | 98.03 | 99.8 | 71.31 | 71.31 | 90.56 | 71.7 | 71.9 |
| 79 Serratia marcescens Z6 | 98.03 | 99.01 | 71.7 | 71.9 | 90.56 | 72.29 | 71.9 |
| 80 Serratia marcescens 546 | 97.83 | 99.21 | 71.51 | 71.7 | 90.37 | 72.1 | 71.7 |
| 81 Serratia nematodiphila MB307 | 98.03 | 99.8 | 71.31 | 71.51 | 90.56 | 71.9 | 71.7 |
| 82 Serratia marcescens VGH107 | 98.03 | 99.01 | 71.31 | 71.51 | 90.56 | 71.9 | 71.9 |
| 83 Serratia marcescens MCB | 95.28 | 95.28 | 72.29 | 72.69 | 91.15 | 72.88 | 72.69 |
| 84 Serratia marcescens AH0650 | 95.67 | 95.48 | 72.29 | 72.69 | 90.76 | 73.28 | 72.69 |
| 85 Serratia marcescens UMH12 | 95.48 | 95.28 | 72.1 | 72.49 | 90.56 | 73.08 | 72.49 |
| 86 Serratia sp. OMLW3 | 95.48 | 95.28 | 72.29 | 72.49 | 90.76 | 73.28 | 72.69 |
| 87 Serratia marcescens UMH11 | 95.28 | 95.08 | 72.1 | 72.69 | 90.56 | 73.47 | 72.49 |
| 88 Serratia marcescens UMH1 | 95.08 | 94.89 | 72.29 | 72.49 | 90.17 | 73.08 | 72.29 |
| 89 Serratia marcescens 2880STDY5683020 | 95.48 | 94.89 | 73.08 | 72.69 | 92.14 | 73.28 | 73.08 |
| 90 Serratia marcescens 99 | 95.48 | 94.69 | 73.28 | 72.88 | 91.55 | 73.67 | 73.28 |
| 91 Serratia marcescens 374 | 94.89 | 94.69 | 72.29 | 72.29 | 90.17 | 73.08 | 72.29 |
| 92 Serratia marcescens 2880STDY5683036 | 95.28 | 94.49 | 73.08 | 72.69 | 91.35 | 73.47 | 73.08 |
| 93 Serratia marcescens 2880STDY5683034 | 95.28 | 94.69 | 73.08 | 72.69 | 91.94 | 73.28 | 73.08 |

TABLE 2-2-continued

| | | | | | | | |
|---|---|---|---|---|---|---|---|
| 94 Serratia marcescens 2880STDY5682892 | 95.28 | 94.69 | 73.28 | 72.88 | 91.94 | 73.47 | 73.28 |
| 95 Serratia marcescens SM39 | 95.08 | 94.49 | 73.28 | 72.69 | 92.14 | 73.28 | 73.28 |
| 96 Serratia marcescens 189 | 95.08 | 94.49 | 73.28 | 72.88 | 92.14 | 73.47 | 73.28 |
| 97 Serratia marcescens SMB2099 | 95.08 | 94.49 | 73.47 | 72.69 | 91.74 | 73.67 | 73.47 |
| 98 Serratia marcescens 2880STDY5682862 | 94.89 | 94.3 | 73.47 | 72.88 | 91.55 | 73.47 | 73.47 |
| 99 Serratia marcescens SE4145 | 94.89 | 94.3 | 73.08 | 72.49 | 91.94 | 73.08 | 73.08 |
| 100 Serratia marcescens 2880STDY5682876 | 95.08 | 94.49 | 73.28 | 72.88 | 91.74 | 73.47 | 73.28 |
| 101 Serratia marcescens 709 | 95.08 | 94.49 | 73.08 | 72.69 | 91.74 | 73.28 | 73.08 |
| 102 Serratia marcescens MGH136 | 94.89 | 94.3 | 72.88 | 72.49 | 91.94 | 73.08 | 72.88 |
| 103 Serratia marcescens 2880STDY5682884 | 94.69 | 94.1 | 72.88 | 72.49 | 91.74 | 73.08 | 73.08 |
| 104 Serratia marcescens D-3 | 95.08 | 94.49 | 73.08 | 72.69 | 91.74 | 73.28 | 73.08 |
| 105 Serratia marcescens 2880STDY5682957 | 94.89 | 94.3 | 72.88 | 72.69 | 91.55 | 73.28 | 72.88 |
| 106 Serratia marcescens YDC563 | 94.69 | 94.1 | 72.88 | 72.69 | 91.35 | 73.28 | 72.88 |
| 107 Serratia marcescens 2880STDY5683035 | 94.89 | 94.3 | 73.08 | 72.69 | 91.55 | 73.28 | 73.08 |

TABLE 2-3

| | | | | | | | |
|---|---|---|---|---|---|---|---|
| 108 Serratia marcescens 2880STDY5682930 | 94.69 | 94.1 | 72.88 | 72.49 | 91.35 | 73.08 | 72.88 |
| 109 Serratia marcescens 790 | 94.49 | 94.3 | 73.28 | 72.88 | 91.35 | 73.47 | 73.28 |
| 110 Serratia marcescens UMH5 | 93.51 | 92.92 | 72.69 | 72.88 | 90.37 | 72.69 | 72.49 |
| 111 Serratia marcescens 2880STDY5682988 | 93.32 | 92.73 | 72.69 | 72.88 | 90.17 | 72.69 | 72.49 |
| 112 Serratia marcescens 945154301 | 94.89 | 94.3 | 73.28 | 73.28 | 91.35 | 73.67 | 73.47 |
| 113 Serratia marcescens at10508 | 94.69 | 94.1 | 73.47 | 73.47 | 91.15 | 73.67 | 73.67 |
| 114 Serratia marcescens ML2637 | 94.49 | 93.9 | 73.28 | 73.47 | 90.96 | 73.67 | 73.67 |
| 115 Serratia marcescens SM1978 | 94.3 | 93.71 | 73.28 | 73.28 | 90.76 | 73.67 | 73.67 |
| 116 Serratia marcescens PWN146 | dehydroge | 93.51 | 72.88 | 72.88 | 90.96 | 72.88 | 73.28 |
| 117 Serratia marcescens H1q | 92.53 | 92.53 | 72.49 | 72.49 | 93.51 | 72.69 | 73.08 |
| 118 Serratia marcescens UMH6 | 91.15 | 91.15 | 72.69 | 73.08 | 99.6 | 73.47 | 73.28 |
| 119 Serratia nematodiphila WCU338 | 91.15 | 91.15 | 72.69 | 73.08 | 99.41 | 73.47 | 73.28 |
| 120 Serratia sp. OLEL1 | 90.96 | 90.96 | 72.88 | 73.28 | 99.8 | 73.67 | 73.47 |
| 121 Serratia marcescens 7209 | 90.96 | 90.96 | 72.49 | 72.88 | 99.41 | 73.28 | 73.08 |
| 122 Serratia marcescens sicaria (Ss1) | 90.96 | 90.96 | 72.69 | 73.08 | 99.41 | 73.28 | 73.28 |
| 123 Serratia sp. OLFL2 | 90.76 | 90.76 | 72.69 | 73.08 | 99.6 | 73.47 | 73.28 |
| 124 Serratia marcescens BIDMC 81 | 90.76 | 90.76 | 72.88 | 73.28 | 99.6 | 73.67 | 73.47 |
| 125 Serratia marcescens BIDMC 50 | 90.76 | 90.76 | 72.69 | 73.08 | 99.21 | 73.47 | 73.28 |
| 126 Serratia marcescens UMH7 | 90.56 | 90.56 | 72.88 | 73.28 | 99.8 | 73.67 | 73.47 |
| 127 Serratia marcescens RSC-14 | 90.56 | 90.56 | 72.88 | 73.47 | 99.21 | 73.87 | 73.67 |
| 128 Serratia marcescens SM03 | 92.33 | 92.33 | 72.29 | 72.29 | 93.51 | 72.49 | 72.88 |
| 129 Serratia marcescens 90-166 | 90.17 | 89.78 | 72.49 | 73.47 | 96.66 | 73.67 | 73.08 |
| 130 Serratia marcescens UMH2 | 90.76 | 90.76 | 72.88 | 73.28 | 99.21 | 73.67 | 73.47 |
| 131 Serratia plymuthica AS9 | 72.49 | 71.9 | 96.66 | 85.06 | 73.47 | 86.05 | 83.69 |
| 132 Serratia plymuthica tumat 205 | 72.69 | 72.1 | 98.03 | 86.24 | 73.47 | 86.64 | 84.28 |
| 133 Serratia plymuthica A30 | 72.29 | 71.7 | 98.82 | 85.65 | 72.88 | 86.44 | 84.08 |
| 134 Serratia plymuthica 4Rx13 | 72.29 | 71.7 | 97.83 | 85.85 | 73.08 | 86.44 | 84.28 |
| 135 Serratia plymuthica V4 | 72.29 | 71.7 | 98.42 | 85.85 | 73.08 | 86.44 | 84.28 |
| 136 Serratia plymuthica 3Rp8 | 72.29 | 71.7 | 98.62 | 86.05 | 73.08 | 86.64 | 84.08 |
| 137 Serratia proteamaculans MFPA44A14 | 72.29 | 71.9 | 87.03 | 92.53 | 73.28 | 98.82 | 87.22 |
| 138 Serratia plymuthica A153 | 72.1 | 71.51 | 99.21 | 86.05 | 72.88 | 86.64 | 84.47 |

TABLE 3-1

| [Match Count/Length] | 1 Serratia | 2 Serratia | 3 Serratia | 4 Serratia | 5 Serratia | 6 Serratia | 213 Serratia |
|---|---|---|---|---|---|---|---|
| 1 Serratia marcescens ATCC13880 | * | | | | | | |
| 2 Serratia nematodiphila DSM21420 | 500/509 | * | | | | | |
| 3 Serratia plymuthica NBRC102599 | 367/509 | 364/509 | * | | | | |
| 4 Serratia proteamaculans 568 | 368/509 | 364/509 | 439/509 | * | | | |
| 5 Serratia ureilytica Lr5/4 | 462/509 | 462/509 | 371/509 | 373/509 | * | | |
| 6 Serratia sp. BW106 | 368/509 | 366/509 | 443/509 | 470/509 | 375/509 | * | |
| 213 Serratia liquefaciens FK01 | 368/509 | 365/509 | 431/509 | 442/509 | 374/509 | 447/509 | * |
| 7 Serratia sp. S119 | 483/509 | 480/509 | 371/509 | 369/509 | 466/509 | 372/509 | 371/509 |
| 8 Serratia sp. YD25 | 470/509 | 470/509 | 369/509 | 369/509 | 476/509 | 370/509 | 371/509 |
| 9 Serratia sp. FS14 | 502/509 | 507/509 | 365/509 | 365/509 | 464/509 | 367/509 | 367/509 |
| 10 Serratia sp. HMSC15F11 | 483/509 | 480/509 | 373/509 | 373/509 | 465/509 | 374/509 | 374/509 |
| 11 Serratia sp. JKS000199 | 462/509 | 462/509 | 370/509 | 372/509 | 506/509 | 374/509 | 373/509 |
| 12 Serratia sp. TEL | 461/509 | 461/509 | 371/509 | 373/509 | 508/509 | 375/509 | 374/509 |
| 13 Serratia sp. ISTD04 | 461/509 | 461/509 | 369/509 | 372/509 | 506/509 | 374/509 | 373/509 |
| 14 Serratia sp. SCBI | 462/509 | 462/509 | 371/509 | 373/509 | 507/509 | 374/509 | 374/509 |
| 15 Serratia sp. S4 | 367/509 | 363/509 | 440/509 | 502/509 | 372/509 | 468/509 | 441/509 |
| 16 Serratia sp. C-1 | 369/509 | 366/509 | 499/509 | 438/509 | 373/509 | 441/509 | 428/509 |

TABLE 3-1-continued

| [Match Count/Length] | 1 *Serratia* | 2 *Serratia* | 3 *Serratia* | 4 *Serratia* | 5 *Serratia* | 6 *Serratia* | 213 *Serratia* |
|---|---|---|---|---|---|---|---|
| 70 *Serratia marcescens* 532 | 508/509 | 499/509 | 368/509 | 367/509 | 461/509 | 367/509 | 367/509 |
| 71 *Serratia marcescens* 2880STDY5683033 | 507/509 | 498/509 | 367/509 | 368/509 | 460/509 | 367/509 | 368/509 |
| 72 *Serratia marcescens* WW4 | 501/509 | 506/509 | 366/509 | 366/509 | 463/509 | 368/509 | 366/509 |
| 73 *Serratia marcescens* K27 | 500/509 | 505/509 | 363/509 | 363/509 | 463/509 | 365/509 | 365/509 |
| 74 *Serratia marcescens* 280 | 501/509 | 506/509 | 365/509 | 365/509 | 463/509 | 367/509 | 367/509 |
| 75 *Serratia marcescens* 19F | 501/509 | 506/509 | 364/509 | 365/509 | 463/509 | 367/509 | 367/509 |
| 76 *Serratia marcescens* 1185 | 500/509 | 507/509 | 363/509 | 363/509 | 460/509 | 365/509 | 364/509 |

TABLE 3-2

| | | | | | | | |
|---|---|---|---|---|---|---|---|
| 77 *Serratia marcescens* S217 | 500/509 | 505/509 | 363/509 | 364/509 | 463/509 | 366/509 | 366/509 |
| 78 *Serratia marcescens* KHCo-24B | 499/509 | 508/509 | 363/509 | 363/509 | 461/509 | 365/509 | 366/509 |
| 79 *Serratia marcescens* Z6 | 499/509 | 504/509 | 365/509 | 366/509 | 461/509 | 368/509 | 366/509 |
| 80 *Serratia marcescens* 546 | 498/509 | 505/509 | 364/509 | 365/509 | 460/509 | 367/509 | 365/509 |
| 81 *Serratia nematodiphila* MB307 | 499/509 | 508/509 | 363/509 | 364/509 | 461/509 | 366/509 | 365/509 |
| 82 *Serratia marcescens* VGH107 | 499/509 | 504/509 | 363/509 | 364/509 | 461/509 | 366/509 | 366/509 |
| 83 *Serratia marcescens* MCB | 486/509 | 485/509 | 368/509 | 370/509 | 464/509 | 371/509 | 370/509 |
| 84 *Serratia marcescens* AH0650 | 487/509 | 486/509 | 368/509 | 370/509 | 462/509 | 373/509 | 370/509 |
| 85 *Serratia marcescens* UMH12 | 486/509 | 485/509 | 367/509 | 369/509 | 461/509 | 372/509 | 369/509 |
| 86 *Serratia* sp. OMLW3 | 486/509 | 485/509 | 368/509 | 369/509 | 462/509 | 373/509 | 370/509 |
| 87 *Serratia marcescens* UMH1 1 | 485/509 | 484/509 | 367/509 | 370/509 | 461/509 | 374/509 | 369/509 |
| 88 *Serratia marcescens* UMH1 | 484/509 | 483/509 | 368/509 | 369/509 | 459/509 | 372/509 | 368/509 |
| 89 *Serratia marcescens* 2880STDY5683020 | 486/509 | 483/509 | 372/509 | 370/509 | 469/509 | 373/509 | 372/509 |
| 90 *Serratia marcescens* 99 | 486/509 | 482/509 | 373/509 | 371/509 | 466/509 | 375/509 | 373/509 |
| 91 *Serratia marcescens* 374 | 483/509 | 482/509 | 368/509 | 368/509 | 459/509 | 372/509 | 368/509 |
| 92 *Serratia marcescens* 2880STDY5683036 | 485/509 | 481/509 | 372/509 | 370/509 | 465/509 | 374/509 | 372/509 |
| 93 *Serratia marcescens* 2880STDY5683034 | 485/509 | 482/509 | 372/509 | 370/509 | 468/509 | 373/509 | 372/509 |
| 94 *Serratia marcescens* 2880STDY5682892 | 485/509 | 482/509 | 373/509 | 371/509 | 468/509 | 374/509 | 373/509 |
| 95 *Serratia marcescens* SM39 | 484/509 | 481/509 | 373/509 | 370/509 | 469/509 | 373/509 | 373/509 |
| 96 *Serratia marcescens* 189 | 484/500 | 481/509 | 373/509 | 371/509 | 469/509 | 374/509 | 373/509 |
| 97 *Serratia marcescens* SMB2099 | 484/509 | 481/509 | 374/509 | 370/509 | 467/509 | 375/509 | 374/509 |
| 98 *Serratia marcescens* 2880STDY5682862 | 483/509 | 480/509 | 374/509 | 371/509 | 466/509 | 374/509 | 374/509 |
| 99 *Serratia marcescens* SE4145 | 483/509 | 480/509 | 372/509 | 369/509 | 468/509 | 372/509 | 372/509 |
| 100 *Serratia marcescens* 2880STDY5682876 | 484/509 | 481/509 | 373/509 | 371/509 | 467/509 | 374/509 | 373/509 |
| 101 *Serratia marcescens* 709 | 484/509 | 481/509 | 372/509 | 370/509 | 467/509 | 373/509 | 372/509 |
| 102 *Serratia marcescens* MGH136 | 483/509 | 480/509 | 371/509 | 369/509 | 468/509 | 372/509 | 371/509 |
| 103 *Serratia marcescens* 2880STDY5682884 | 482/509 | 479/509 | 371/509 | 369/509 | 467/509 | 372/509 | 372/509 |
| 104 *Serratia marcescens* D-3 | 484/509 | 481/509 | 372/509 | 370/509 | 467/509 | 373/509 | 372/509 |
| 105 *Serratia marcescens* 2880STDY5682957 | 483/509 | 480/509 | 371/509 | 370/509 | 466/509 | 373/509 | 371/509 |
| 106 *Serratia marcescens* YDC563 | 482/509 | 479/509 | 371/509 | 370/509 | 465/509 | 373/509 | 371/509 |
| 107 *Serratia marcescens* 2880STDY5683035 | 483/509 | 480/509 | 372/509 | 370/509 | 466/509 | 373/509 | 372/509 |

TABLE 3-3

| | | | | | | | |
|---|---|---|---|---|---|---|---|
| 108 *Serratia marcescens* 2880STDY5682930 | 482/509 | 479/509 | 371/509 | 369/509 | 465/509 | 372/509 | 371/509 |
| 109 *Serratia marcescens* 790 | 481/509 | 480/509 | 373/509 | 371/509 | 465/509 | 374/509 | 373/509 |
| 110 *Serratia marcescens* UMH5 | 476/509 | 473/509 | 370/509 | 371/509 | 460/509 | 370/509 | 369/509 |
| 111 *Serratia marcescens* 2880STDY5682988 | 475/509 | 472/509 | 370/509 | 371/509 | 459/509 | 370/509 | 369/509 |
| 112 *Serratia marcescens* 945154301 | 483/509 | 480/509 | 373/509 | 373/509 | 465/509 | 375/509 | 374/509 |
| 113 *Serratia marcescens* at10508 | 482/509 | 479/509 | 374/509 | 374/509 | 464/509 | 375/509 | 375/509 |
| 114 *Serratia marcescens* ML2637 | 481/509 | 478/509 | 373/509 | 374/509 | 463/509 | 375/509 | 375/509 |
| 115 *Serratia marcescens* SM1978 | 480/509 | 477/509 | 373/509 | 373/509 | 462/509 | 375/509 | 375/509 |
| 116 *Serratia marcescens* PWN146 | dehydroge | 476/509 | 371/509 | 371/509 | 463/509 | 371/509 | 373/509 |
| 117 *Serratia marcescens* H1q | 471/509 | 471/509 | 369/509 | 369/509 | 476/509 | 370/509 | 372/509 |
| 118 *Serratia marcescens* UMH6 | 464/509 | 464/509 | 370/509 | 372/509 | 507/509 | 374/509 | 373/509 |
| 119 *Serratia nematodiphila* WCU338 | 464/509 | 464/509 | 370/509 | 372/509 | 506/509 | 374/509 | 373/509 |
| 120 *Serratia* sp. OLEL1 | 463/509 | 462/509 | 371/509 | 373/509 | 58/509 | 375/509 | 374/509 |
| 121 *Serratia marcescens* 7209 | 463/509 | 463/509 | 369/509 | 371/509 | 506/509 | 373/509 | 372/509 |
| 122 *Serratia marcescens* sicaria (Ss1) | 463/509 | 463/509 | 370/509 | 372/509 | 506/509 | 373/509 | 373/509 |
| 123 *Serratia* sp. OLFL2 | 462/509 | 462/509 | 370/509 | 372/509 | 507/509 | 374/509 | 373/509 |
| 124 *Serratia marcescens* BIDMC 81 | 462/509 | 462/509 | 371/509 | 373/509 | 507/509 | 375/509 | 374/509 |
| 125 *Serratia marcescens* BIDMC 50 | 462/509 | 462/509 | 370/509 | 372/509 | 505/509 | 374/509 | 373/509 |
| 126 *Serratia marcescens* UMH7 | 461/509 | 461/509 | 371/509 | 373/509 | 508/509 | 375/509 | 374/509 |
| 127 *Serratia marcescens* RSC-14 | 461/509 | 461/509 | 371/509 | 374/509 | 505/509 | 376/509 | 375/509 |
| 128 *Serratia marcescens* SM03 | 470/509 | 470/509 | 368/509 | 368/509 | 476/509 | 369/509 | 371/509 |
| 129 *Serratia marcescens* 90-166 | 459/509 | 457/509 | 369/509 | 374/509 | 492/509 | 375/509 | 372/509 |
| 130 *Serratia marcescens* UMH2 | 462/509 | 462/509 | 371/509 | 373/509 | 505/509 | 375/509 | 374/509 |
| 131 *Serratia plymuthica* AS9 | 369/509 | 366/509 | 492/509 | 433/509 | 374/509 | 438/509 | 426/509 |

TABLE 3-3-continued

| | | | | | | | |
|---|---|---|---|---|---|---|---|
| 132 Serratia plymuthica tumat 205 | 370/509 | 367/509 | 499/509 | 439/509 | 374/509 | 441/509 | 429/509 |
| 133 Serratia plymuthica A30 | 368/509 | 365/509 | 503/509 | 436/509 | 371/509 | 440/509 | 428/509 |
| 134 Serratia plymuthica 4Rx13 | 368/509 | 365/509 | 498/509 | 437/509 | 372/509 | 440/509 | 429/509 |
| 135 Serratia plymuthica V4 | 368/509 | 365/509 | 501/509 | 437/509 | 372/509 | 440/509 | 429/509 |
| 136 Serratia plymuthica 3Rp8 | 368/509 | 365/509 | 502/509 | 438/509 | 372/509 | 441/509 | 428/509 |
| 137 Serratia proteamaculans MFPA44A14 | 368/509 | 366/509 | 443/509 | 471/509 | 373/509 | 503/509 | 444/509 |
| 138 Serratia plymuthica A153 | 367/509 | 364/509 | 505/509 | 438/509 | 371/509 | 441/509 | 430/509 |

The nucleic acids encoding the polypeptides described in (a) to (c) according to the present invention may contain an additional sequence that encodes a peptide or protein added to the original polypeptides at the N terminus and/or the C terminus. Examples of such a peptide or protein can include secretory signal sequences, translocation proteins, binding proteins, tag peptides applicable for purification, and fluorescent proteins. Among those peptides or proteins, a peptide or protein with a desired function can be selected depending on the purpose and added to the polypeptides of the present invention by those skilled in the art. It should be noted that the amino acid sequence of such a peptide or protein is not included in the calculation of sequence identity.

The nucleic acids encoding the polypeptides represented by SEQ ID NOs: 1 to 16, 70 to 138, and 213 are not particularly limited, provided that those nucleic acids are composed of nucleotide sequences which can be translated into the amino acid sequences represented by SEQ ID NOs: 1 to 16 and 70 to 138, and the nucleotide sequences can be determined by considering a set of codons (standard genetic code) corresponding to each amino acid. In this respect, the nucleotide sequences may be redesigned using codons that are frequently used by a host microorganism used in the present invention.

Specific examples of the nucleotide sequences of the nucleic acids that encode the polypeptides with the amino acid sequences represented by SEQ ID NOs: 1 to 16, 70 to 138, and 213 include the nucleotide sequences represented by SEQ ID NOs: 54 to 69, 139 to 207, and 214, respectively.

In the present invention, whether or not a polypeptide encoded by a certain nucleic acid has 3-oxoadipyl-CoA reductase activity is determined as follows: transformant strains A and B described below are produced and grown in a culture test, and if the presence of 3-hydroxyadipic acid or α-hydromuconic acid in the resulting culture fluid is confirmed, it is judged that the nucleic acid encodes a polypeptide having 3-oxoadipyl-CoA reductase activity. The determination method will be described using the scheme 1 below which shows a biosynthesis pathway.

[Chem 1]

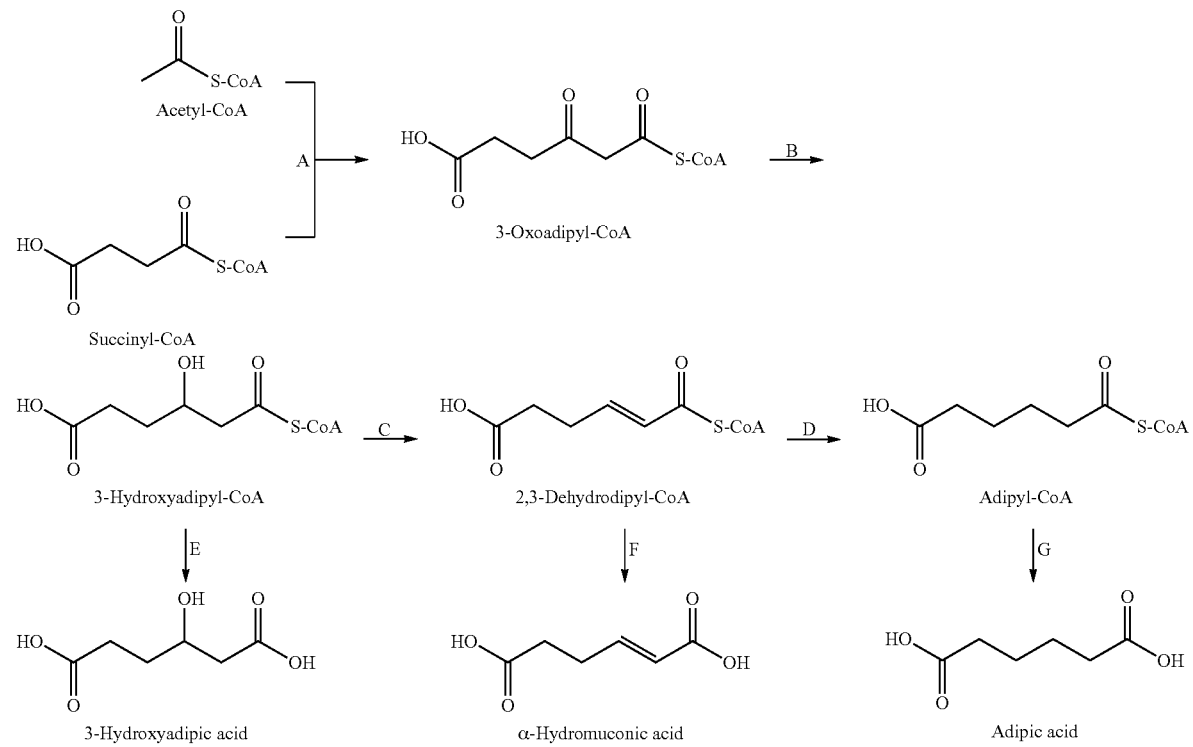

The above scheme 1 shows an exemplary reaction pathway required for the production of 3-hydroxyadipic acid, α-hydromuconic acid, and/or adipic acid. In this scheme, the reaction A represents a reaction that generates 3-oxoadipyl-CoA and coenzyme A from acetyl-CoA and succinyl-CoA. The reaction B represents a reaction that generates 3-hydroxyadipyl-CoA from 3-oxoadipyl-CoA. The reaction C represents a reaction that generates 2,3-dehydroadipyl-CoA from 3-hydroxyadipyl-CoA. The reaction D represents a reaction that generates adipyl-CoA from 2,3-dehydroadipyl-CoA. The reaction E generates 3-hydroxyadipic acid from 3-hydroxyadipyl-CoA. The reaction F represents a reaction that generates α-hydromuconic acid from 2,3-dehydroadipyl-CoA. The reaction G represents a reaction that generates adipic acid from adipyl-CoA.

The transformant strain A has enzymes that catalyze the reactions A, E, and F. The transformant strain B has enzymes that catalyze the reactions A, C, E, and F.

The transformant strain A is first produced. Plasmids for the expression of enzymes that catalyze the reactions A, E, and F, respectively, are produced. The reactions E and F can be catalyzed by an identical enzyme. The plasmids are introduced into *Escherichia coli* (*E. coli*) strain BL21 (DE3), which is a microorganism strain lacking abilities to produce all of 3-hydroxyadipic acid, α-hydromuconic acid, and adipic acid. An expression plasmid in which a nucleic acid encoding a polypeptide, which is a subject of analysis for the presence of the enzymatic activity of interest, is incorporated downstream of a suitable promoter is introduced to the obtained transformant strain, to obtain the transformant strain A. The transformant strain A is cultured, and the post-culture fluid is examined for the presence of 3-hydroxyadipic acid. Once the presence of 3-hydroxyadipic acid in the culture fluid is successfully confirmed, the transformant strain B is then produced. The transformant strain B is obtained by introducing a plasmid for the expression of an enzyme that catalyzes the reaction C into the transformant strain A. The transformant strain B is cultured, and the post-culture fluid is examined for the presence of α-hydromuconic acid. When the presence of α-hydromuconic acid in the post-culture fluid is confirmed, it indicates that 3-hydroxyadipic acid produced in the transformant strain A and α-hydromuconic acid produced in the transformant strain B are generated through production of 3-hydroxyadipyl-CoA and that the subject polypeptide has 3-oxoadipyl-CoA reductase activity.

As the gene encoding the enzyme that catalyzes the reaction A, pcaF from *Pseudomonas putida* strain KT2440 (NCBI Gene ID: 1041755; SEQ ID NO: 20) is used.

As the genes encoding the enzyme that catalyzes the reactions E and F, a continuous sequence including the full lengths of pcaI and pcaJ from *Pseudomonas putida* strain KT2440 (NCBI Gene IDs: 1046613 and 1046612; SEQ ID NOs: 23 and 24) is used. The polypeptides encoded by pcaI and pcaJ forms a complex and then catalyze the reactions E and F.

As the nucleic acid encoding the enzyme that catalyzes the reaction C, the paaF gene from *Pseudomonas putida* strain KT2440 (NCBI Gene ID: 1046932, SEQ ID NO: 47) is used.

The method of culturing the transformant strain A and the transformant strain B is as follows. Antibiotics for stable maintenance of the plasmids and/or a substance that induces the expression of the polypeptides encoded by the incorporated nucleic acids may be added as appropriate. A loopful of either the transformant strain A or B is inoculated into 5 mL of the culture medium I (10 g/L Bacto Tryptone (manufactured by Difco Laboratories), 5 g/L Bacto Yeast Extract (manufactured by Difco Laboratories), 5 g/L sodium chloride) adjusted at pH 7, and incubated at 30° C. with shaking at 120 min$^{-1}$ for 18 hours to prepare a preculture fluid. Subsequently, 0.25 mL of the preculture fluid is added to 5 mL of the culture medium 11 (10 g/L succinic acid, 10 g/L glucose, 1 g/L ammonium sulfate, 50 mM potassium phosphate, 0.025 g/L magnesium sulfate, 0.0625 mg/L iron sulfate, 2.7 mg/L manganese sulfate, 0.33 mg/L calcium chloride, 1.25 g/L sodium chloride, 2.5 g/L Bacto Tryptone, 1.25 g/L Bacto Yeast Extract) adjusted to pH 6.5, and incubated at 30° C. with shaking at 120 min$^{-1}$ for 24 hours. The obtained culture fluid is examined for the presence of 3-hydroxyadipic acid or α-hydromuconic acid.

The presence of 3-hydroxyadipic acid or α-hydromuconic acid in the culture fluid can be confirmed by centrifuging the culture fluid and analyzing the supernatant with LC-MS/MS. The analysis conditions are as described below:

HPLC: 1290 Infinity (manufactured by Agilent Technologies, Inc.)
Column: Synergi hydro-RP (manufactured by Phenomenex Inc.), length: 100 mm, internal diameter: 3 mm, particle size: 2.5 μm
Mobile phase: 0.1% aqueous formic acid solution/methanol=70/30
Flow rate: 0.3 mL/min
Column temperature: 40° C.
LC detector: DA) (210 nm)
MS/MS: Triple-Quad LC/MS (manufactured by Agilent Technologies, Inc.)
Ionization method: ESI in negative mode.

The 3-oxoadipyl-CoA reductase activity value can be calculated by quantifying 3-hydroxyadipyl-CoA generated from 3-oxoadipyl-CoA used as a substrate by purified 3-oxoadipyl-CoA reductase, wherein the 3-oxoadipyl-CoA is prepared from 3-oxoadipic acid by an enzymatic reaction. The specific method is as follows.

3-Oxoadipic acid can be prepared by a known method (for example, a method described in Reference Example 1 of WO 2017/099209).

Preparation of 3-oxoadipyl-CoA solution: A PCR using the genomic DNA of *Pseudomonas putida* strain KT2440 as a template is performed in accordance with routine procedures, to amplify a nucleic acid encoding a CoA transferase (pcaI and pcaJ; NCBI-GeneIDs: 1046613 and 1046612) in the full-length form. The nucleotide sequences of primers used in this PCR are, for example, those represented by SEQ ID NOs: 25 and 26. The amplified fragment is inserted into the KpnI site of pRSF-1b (manufactured by Novagen), an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a CoA transferase solution. The solution is used to prepare an enzymatic reaction solution for 3-oxoadipyl-CoA preparation with the following composition, which is allowed to react at 25° C. for 3 minutes and then filtered through a UF membrane (Amicon Ultra-0.5 mL 10K; manufactured by Merck Millipore) to remove the enzyme, and the obtained filtrate is designated as 3-oxoadipyl-CoA solution:

Enzymatic Reaction Solution for 3-Oxoadipyl-CoA Preparation:
100 mM Tris-HCl (pH 8.2)
10 mM MgCl$_2$
0.5 mM succinyl-CoA
5 mM 3-oxoadipic acid sodium salt
2 μM CoA transferase.

Identification of 3-oxoadipyl-CoA reductase activity: A PCR using the genomic DNA of a subject microorganism strain as a template is performed in accordance with routine procedures, to amplify a nucleic acid encoding 3-oxoadipyl-CoA reductase in the full-length form. The nucleotide sequences of primers used in this PCR are, for example, those represented by SEQ ID NOs: 31 and 32. The amplified fragment is inserted into the BamHI site of pACYCDuet-1 (manufactured by Novagen), an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a 3-oxoadipyl-CoA reductase solution. The 3-oxoadipyl-CoA reductase activity can be determined by using the enzyme solution to prepare an enzymatic reaction solution with the following composition and quantifying 3-hydroxyadipyl-CoA generated at 25° C.

100 mM Tris-HCl (pH 8.2)
10 mM $MgCl_2$
150 μL/mL 3-oxoadipyl-CoA solution
0.5 mM NADH
1 mM dithiothreitol
10 μM 3-oxoadipyl-CoA reductase.

In the present invention, the genetically modified microorganism in which expression of any one of the polypeptides described in (a) to (c) is enhanced is a microorganism as a host which originally has the nucleic acids encoding any one of the polypeptides described in (a) to (c) and is genetically modified to increasingly express any one of the polypeptides described in (a) to (c) which are owned by the host microorganism.

Specific examples of the microorganisms which originally have a nucleic acid encoding any one of the polypeptides described in (a) to (c) include the following microorganisms of the genus *Serratia*: *Serratia marcescens* (a microorganism having the sequences represented by SEQ ID NOs: 1, 70 to 80, 82 to 85, and 87 to 118). *Serratia nematodiphila* (a microorganism having the sequences represented by SEQ ID NOs: 2, 81, and 119), *Serratia plymuthica* (a microorganism having the sequences represented by SEQ ID NOs: 3, 131 to 136, and 138). *Serratia proteamaculans* (a microorganism having the sequences represented by SEQ ID NOs: 4 and 137). *Serratia ureilytica* (a microorganism having the sequence represented by SEQ ID NO: 5), *Serratia* sp. BW106 (a microorganism having the sequence represented by SEQ ID NO: 6), *Serratia* sp. S19 (a microorganism having the sequence represented by SEQ ID NO: 7), *Serratia* sp. YD25 (a microorganism having the sequence represented by SEQ ID NO: 8), *Serratia* sp. FS14 (a microorganism having the sequence represented by SEQ ID NO: 9), *Serratia* sp. HMSC15F11 (a microorganism having the sequence represented by SEQ ID NO: 10). *Serratia* sp. JKS000199 (a microorganism having the sequence represented by SEQ ID NO: 11), *Serratia* sp. TEL (a microorganism having the sequence represented by SEQ ID NO: 12), *Serratia* sp. ISTD04 (a microorganism having the sequence represented by SEQ ID NO: 13), *Serratia* sp. SCB1 (a microorganism having the sequence represented by SEQ ID NO: 14), *Serratia* sp. S4 (a microorganism having the sequence represented by SEQ ID NO: 15), *Serratia* sp. C-1 (a microorganism having the sequence represented by SEQ ID NO: 16), *Serratia* sp. OMLW3 (a microorganism having the sequence represented by SEQ ID NO: 86), *Serratia* sp. OLEL1 (a microorganism having the sequence represented by SEQ ID NO: 120). *Serratia* sp. OLEL2 (a microorganism having the sequence represented by SEQ ID NO: 123), *Serratia liquefaciens* (a microorganism having the sequence represented by SEQ ID NO: 213), and the like.

Each of the polypeptides as described above in (a), (b), and (c) also has 3-hydroxybutyryl-CoA dehydrogenase activity, and the 3-hydroxybutyryl-CoA dehydrogenase is encoded by the 3-hydroxybutyryl-CoA dehydrogenase gene, which forms a gene cluster with the 5-aminolevulinic acid synthase gene in the microorganisms of the genus *Serratia*.

As used herein, the term "gene cluster" in the phrase "the 3-hydroxybutyryl-CoA dehydrogenase gene, which forms a gene cluster with 5-aminolevulinic acid synthase gene in the microorganisms of the genus *Serratia*" refers to a region in which a set of nucleic acids encoding related functions are located in close proximity to each other. Specific components in a gene cluster include, for example, nucleic acids which are transcribed under control of a single transcription regulator, and those in an operon which are transcribed under control of a single transcription promoter. Whether or not a certain nucleic acid is a nucleic acid component of a gene cluster can also be investigated using an online gene cluster search program, such as antiSMASH. Additionally, whether or not a certain polypeptide is classified as a 3-hydroxybutyryl-CoA dehydrogenase or a 5-aminolevulinic acid synthase can be determined by performing a BLAST (Basic Local Alignment Search Tool) search on a website, such as that of NCBI (National Center for Biotechnology Information) or KEGG (Kyoto Encyclopedia of Genes and Genomes), to find any enzyme with high homology of the amino acid sequence to the polypeptide. For example, the amino acid sequence represented by SEQ ID NO: 4 is registered in an NCBI database under Protein ID: ABV40935.1, which is annotated as a putative protein with 3-hydroxybutyryl-CoA dehydrogenase activity, as judged from the amino acid sequence. A gene encoding the amino acid sequence represented by SEQ ID NO: 4 is registered in an NCBI database under Gene ID: CP000826.1, and can be identified through a database search as conserved on the genome of *Serratia proteamaculans* strain 568 or as conserved from 2015313 to 2016842 bp on the sequence of Gene ID: CP000826.1. Furthermore, the positional information of the gene can lead to identification of the sequences of flanking genes, from which the gene can be found to form a gene cluster with the 5-aminolevulinic acid synthase gene (Protein ID: ABV40933.1), as shown in the FIGURE. Similarly, for the amino acid sequences represented by SEQ ID NOs: 1 to 3, 6 to 16, 70 to 72, 74 to 82, 84 to 87, 89, 90, 92, 94 to 100, 103 to 108, 111 to 115, 117, 118, 120 to 125, 127 to 133, 135 to 137, and 213, the information can be checked on the NCBI site with Protein IDs and Gene IDs presented in Table 13.

TABLE 13

| SEQ ID NO. | Gene ID: Position (from . . . to) | Protein ID |
|---|---|---|
| 1 | JMPQ01000047.1: 133194 . . . 134723 | KFD11732.1 |
| 2 | JPUX00000000.1: 4202615 . . . 4204144 | WP_033633399.1 |
| 3 | BCTU01000013.1: 85647 . . . 87176 | WP_063199278.1 |
| 4 | CP000826.1: 2015313 . . . 2016842 | ABV40935.1 |
| 6 | MCGS01000002.1: 43811 . . . 45340 | WP_099061672.1 |
| 7 | MSFH01000022.1: 147976 . . . 149505 | ONK16968.1 |
| 8 | CP016948.1: 1213474 . . . 1215003 | AOE98783.1 |
| 9 | CP005927.1: 4244665 . . . 4246194 | WP_044031504.1 |
| 10 | LWNG01000196.1: 83086 . . . 84615 | OFS85208.1 |
| 11 | LT907843.1: 1172733 . . . 1174262 | SNY82966.1 |
| 12 | LDEG01000005.1: 19627 . . . 21156 | KLE40298.1 |
| 13 | MBDW01000089.1: 53478 . . . 55007 | ODJ15373.1 |
| 14 | CP003424.1: 1869825 . . . 1871300 | AIM21329.1 |
| 15 | APLA01000003.1: 1964823 . . . 1966352 | WP_017892361.1 |
| 16 | CAQ001000118.1: 101692 . . . 103221 | WP_062792820.1 |
| 70 | JVDI01000070.1: 19399 . . . 20928 | WP_049300487.1 |
| 71 | FCGF01000001.1: 938090 . . . 939619 | WP_060444298.1 |
| 72 | NC_020211.1: 1963542 . . . 1965071 | WP_015377392.1 |

TABLE 13-continued

| SEQ ID NO. | Gene ID: Position (from . . . to) | Protein ID |
| --- | --- | --- |
| 74 | JVNC01000043.1: 47711 . . . 49240 | WP_049187553.1 |
| 75 | MCNK01000010.1: 591271 . . . 592800 | WP_076740355.1 |
| 76 | JVZV01000138.1: 53080 . . . 54609 | WP_049277247.1 |
| 77 | CP021984.1: 1963542 . . . 1965071 | WP_088381461.1 |
| 78 | NERL01000025.1: 86571 . . . 88100 | WP_060559176.1 |
| 79 | MTEH01000001.1: 215863 . . . 217392 | WP_085336366.1 |
| 80 | JVCS01000001.1: 19397 . . . 20926 | WP_049239700.1 |
| 81 | MTBJ01000002.1: 216232 . . . 217761 | WP_082996863.1 |
| 82 | AORJ01000010.1: 70272 . . . 71801 | WP_033645451.1 |
| 84 | LFJS01000012.1: 944087 . . . 945616 | WP_025302345.1 |
| 85 | CP018930.1: 1161338 . . . 1162867 | WP_060447438.1 |
| 86 | MSTK01000013.1: 54046 . . . 55575 | WP_099817374.1 |
| 87 | CP018929.1: 1167577 . . . 1170106 | WP_089180755.1 |
| 89 | FCGS01000006.1: 98915 . . . 100444 | WP_060438851.1 |
| 90 | MQRI01000002.1: 585500 . . . 587029 | WP_060387554.1 |
| 92 | FCFE01000001.1: 962839 . . . 964368 | WP_060435888.1 |
| 94 | FCIO01000002.1: 145369146898 . . . | WP_033637938.1 |
| 95 | AP013063.1: 1329259 . . . 1330788 | WP_041034581.1 |
| 96 | MQRJ01000004.1: 178926 . . . 180455 | WP_074026553.1 |
| 97 | HG738868.1: 1928329 . . . 1929858 | WP_060437960.1 |
| 98 | FCHQ01000006.1: 51377 . . . 52906 | WP_060420535.1 |
| 99 | NPGG01000001.1: 301231 . . . 302760 | WP_047568134.1 |
| 100 | FCME01000002.1: 205632 . . . 207161 | WP_060443161.1 |
| 103 | FCIH01000014.1: 52403 . . . 53932 | WP_060429049.1 |
| 104 | NBWV01000007.1: 110621 . . . 112150 | WP_039566649.1 |
| 105 | FCKI01000001.1: 594106 . . . 595635 | WP_060429902.1 |
| 106 | JPOB01000010.1: 81351 . . . 82880 | WP_033654196.1 |
| 107 | FCFI01000001.1: 582222 . . . 583751 | WP_060443342.1 |
| 108 | FCML01000001.1: 1005802 . . . 1007331 | WP_060456892.1 |
| 111 | FCMR01000001.1: 1873566 . . . 1875095 | WP_060440240.1 |
| 112 | LJEV02000002.1: 115432 . . . 116961 | WP_047727865.1 |
| 113 | NPIX01000027.1: 38249 . . . 39778 | WP_094461128.1 |
| 114 | NDXU01000091.1: 70343 . . . 71872 | WP_048233299.1 |
| 115 | FNXW01000055.1: 13619 . . . 15148 | WP_080490898.1 |
| 117 | AYMO01000023.1: 23978 . . . 25507 | WP_025160335.1 |
| 118 | CP018926.1: 1215941 . . . 1217470 | WP_089191486.1 |
| 120 | MORG01000026.1: 13723 . . . 15252 | WP_099782744.1 |
| 121 | PEHC01000008.1: 57274 . . . 58803 | PHY81681.1 |
| 122 | MEDA01000063.1: 13491 . . . 15020 | WP_072627918.1 |
| 123 | MORH01000030.1: 13633 . . . 15162 | WP_099789708.1 |
| 124 | KK214286.1: 392757 . . . 394286 | WP_033650708.1 |
| 125 | KI929259.1: 1574567 . . . 1576096 | WP_033642621.1 |
| 127 | CP012639.1: 230596 . . . 232125 | WP_060659686.1 |
| 128 | LZOB01000011.1: 1613417 . . . 1614946 | WP_074054551.1 |
| 129 | LCW101000024.1: 46336 . . . 47865 | WP_046899223.1 |
| 130 | CP018924.1: 1213305 . . . 1214834 | WP_089194521.1 |
| 131 | NC_015567.1: 1930552 . . . 1932081 | WP_013812379.1 |
| 132 | MQML01000205.1: 9362 . . . 10891 | WP_073439751.1 |
| 133 | AMSV01000032.1: 251478 . . . 253007 | WP_006324610.1 |
| 135 | CP007439.1: 1991332 . . . 1992861 | AHY06789.1 |
| 136 | CP012096.1: 319897 . . . 321426 | WP_037432641.1 |
| 137 | FWWG01000018.1: 38528 . . . 40057 | WP_085116175.1 |
| 213 | CP006252.1: 1825868 . . . 1827397 | AGQ30498.1 |

A nucleic acid encoding a polypeptide encoded by the 3-hydroxybutyryl-CoA dehydrogenase gene of a microorganism of the genus Serratia, which forms a gene cluster with the 5-aminolevulinic acid synthase gene, is hereinafter referred to as "the 3-hydroxybutyryl-CoA dehydrogenase gene used in the present invention," and the polypeptide encoded by the 3-hydroxybutyryl-CoA dehydrogenase gene is referred as "the 3-hydroxybutyryl-CoA dehydrogenase used in the present invention."

A gene cluster including the 3-hydroxybutyryl-CoA dehydrogenase gene used in the present invention may include other nucleic acids, provided that at least the 3-hydroxybutyryl-CoA dehydrogenase gene and the 5-aminolevulinic acid synthase gene are included in the gene cluster. FIG. 1 shows a specific example of the gene cluster including the 3-hydroxybutyryl-CoA dehydrogenase gene used in the present invention.

Specific examples of the microorganisms of the genus Serratia that contain the above gene cluster include S. marcescens, S. nematodiphila, S. plymuthica, S. proteamaculans, S. ureilytica, S. liquefaciens, Serratia sp. BW106, Serratia sp. SI 19, Serratia sp. YD25, Serratia sp. FS14, Serratia sp. HMSC15F11, Serratia sp. JKS000199, Serratia sp. TEL, Serratia sp. ISTD04, Serratia sp. SCBHI, Serratia sp. S4, Serratia sp. C-1, Serratia sp. OMLW3, Serratia sp. OLEL1, Serratia sp. OLEL2, and S. liquefaciens.

The 3-hydroxybutyryl-CoA dehydrogenase used in the present invention has an excellent 3-oxoadipyl-CoA reductase activity. Whether or not a 3-hydroxybutyryl-CoA dehydrogenase-encoding nucleic acid has a 3-oxoadipyl-CoA reductase activity can be determined by the same method as described above.

The polypeptide encoded by the 3-hydroxybutyryl-CoA dehydrogenase gene used in the present invention is characterized by containing the common sequence 1. Specific examples of amino acid sequences of such polypeptides include the amino acid sequences represented by SEQ ID NOs: 1 to 16, 70 to 138, and 213.

In the present invention, a nucleic acid encoding a polypeptide composed of the same amino acid sequence as that represented by any one of SEQ ID NOs: 7 to 16 or 70 to 138, except that one or several amino acids are substituted, deleted, inserted, and/or added, and having an enzymatic activity that catalyzes a reaction to reduce 3-oxoadipyl-CoA to 3-hydroxyadipyl-CoA, can be suitably used, provided that the common sequence 1 is contained in the polypeptide. In this respect, the range represented by the phrase "one or several" is preferably 10 or less, further preferably 5 or less, particularly preferably 4 or less, and most preferably one or two. In the case of amino acid substitution, the activity of the original polypeptide is more likely to be maintained when the amino acids are replaced by amino acids with similar properties (i.e., conservative substitution as described above). A nucleic acid encoding a polypeptide composed of an amino acid sequence with a sequence identity of not less than 70%, preferably not less than 80%, more preferably not less than 85%, further preferably not less than 90%, still further preferably not less than 95%, yet further preferably not less than 97%, even further preferably not less than 99%, to the sequence represented by any one of SEQ ID NOs: 7 to 16 or 70 to 138 and having an enzymatic activity that catalyzes a reaction to reduce 3-oxoadipyl-CoA to 3-hydroxyadipyl-CoA can also be suitably used.

On the other hand, examples of a polypeptide that is not the 3-hydroxybutyryl-CoA dehydrogenase used in the present invention but has 3-oxoadipyl-CoA reductase activity include PaaH from *Pseudomonas putida* strain KT2440 (SEQ ID NO: 208), PaaH from *Escherichia coli* str. K-12 substr. MG1655 (SEQ ID NO: 209). DcaH from *Acinetobacter baylyi* strain ADP1 (SEQ ID NO: 210), and PaaH from *Serratia plymuthica* strain NBRC102599 (SEQ ID NO: 211); these polypeptides are found not to contain the common sequence 1, as shown in Tables 4 and 5. It should be noted that those polypeptides are neither (b) polypeptides composed of the same amino acid sequence as that represented by any one of SEQ ID NOs: 1 to 6 and 213, except that one or several amino acids are substituted, deleted, inserted, and/or added, and having an enzymatic activity that catalyzes a reaction to reduce 3-oxoadipyl-CoA to 3-hydroxyadipyl-CoA, nor (c) polypeptides having an amino acid sequence with a sequence identity of not less than 70% to the sequence represented by any one of SEQ ID NOs: 1 to 6 and 213 and having an enzymatic activity that catalyzes a reaction to reduce 3-oxoadipyl-CoA to 3-hydroxyadipyl-CoA, polypeptide.

TABLE 4-1

Consensus sequence1
GAGTMGRGIAYLXAXXXIXTXLYN

| | |
|---|---|
| 1 Serratia marcescens ATCC13880 | 1 MAESNAAIQSAAIGAGTMGRGIAYLFAQKGIRTVLYNRN 40 |
| 2 Serratia nematodiphila DSM21420 | 1 MAESNAAIQSAAIGAGTMGRGIAYLFAQKGIETMLYNRN 40 |
| 3 Serratia plymuthica NBRC102599 | 1 MAENNSAIRSAAVIGAGTMGRGIAYLIALNGIRTVLYNRN 40 |
| 4 Serratia proteamaculans 568 | 1 MAENNSAIESVAVIGAGTMGRGIAYLIAQNGIRTILYNRS 40 |
| 5 Serratia ureilytica Lr5/4 | 1 MAESNAAIQSAAIGAGTMGRGIAYLIAQKSIRTVLYNRN 40 |
| 6 Serratia sp. BW106 | 1 MAENNSAIESVAVIGAGTMGRGIAYLIAQNGIRTILYNRS 40 |
| 213 Serratia liquefaciens FK01 | 1 MAENNSAIESVAVIGAGTMGRGIAYLIALNGIRTILYNRN 40 |
| 7 Serratia sp. S119 | 1 MAESNAAIQSAAIGAGTMGRGIAYLFAQKGIRTVLYNRN 40 |
| 8 Serratia sp. YD25 | 1 MAERNAAIQSAAIGAGTMGRGIAYLFAQKGIRTVLYNRN 40 |
| 9 Serratia sp. FS14 | 1 MAESNAAIQSAAIGAGTMGRGIAYLFAQKGIETMLYNRN 40 |
| 10 Serratia sp. HMSC15F11 | 1 MAESNAAIQSAAIGAGTMGRGIAYLFAQKGIRTVLYNRN 40 |
| 11 Serratia sp. JKS000199 | 1 MAESNAAIQSAAIGAGTMGRGIAYLIAQKSIPTMLYNRN 40 |
| 12 Serratia sp. TEL | 1 MAESNAAIQSAAIGAGTMGRGIAYLIAQKSIPTMLYNRN 40 |
| 12 Serratia sp. ISTD04 | 1 MAESNAAIQSAAIGAGTMGRGIAYLIAQKSIPTMLYNRN 40 |
| 13 Serratia sp. SCBI | 1 MAESNAAIQSAAIGAGTMGRGIAYLIAQKSIPTMLYNRN 40 |
| 14 Serratia sp. S4 | 1 MAENNSAIESVAVIGAGTMGRGIAYLIAQNGIRTILYNRS 40 |
| 15 Serratia sp. C-1 | 1 MAENNSAIRSAAVIGAGTMGRGIAYLIALNGIRTILYNRN 40 |
| 70 Serratia marcescens 532 | 1 MAESNAAIQSAAIGAGTMGRGIAYLFAQKGIRTVLYNRN 40 |
| 71 Serratia marcescens 2880STDY5683033 | 1 MAESNAAIQSAAIGAGTMGRGIAYLFAQKGIRTVLYNRN 40 |

40

TABLE 4-2

| | |
|---|---|
| 72 Serratia marcescens WW4 | 1 MAESNAAIQSAAIGAGTMGRGIAYLFAQKGIETMLYNRN 40 |
| 73 Serratia marcescens K27 | 1 MAESNAAIQSAAIGAGTMGRGIAYLFAQKGIETMLYNRN 40 |
| 74 Serratia marcescens 280 | 1 MAESNAAIQSAAIGAGTMGRGIAYLFAQKGIETMLYNRN 40 |
| 75 Serratia marcescens 19F | 1 MAESNAAIQSAAIGAGTMGRGIAYLFAQKGIETMLYNRN 40 |
| 76 Serratia marcescens 1185 | 1 MAESNAAIQSAAIGAGTMGRGIAYLFAQKGIETMLYNRN 40 |
| 77 Serratia marcescens S217 | 1 MAESNAAIQSAAIGAGTMGRGIAYLFAQKGIETMLYNRN 40 |
| 78 Serratia marcescens KHCo-24B | 1 MAESNAAIQSAAIGAGTMGRGIAYLFAQKGIETMLYNRN 40 |
| 79 Serratia marcescens Z6 | 1 MAESNAAIQSAAIGAGTMGRGIAYLFAQKGIETMLYNRN 40 |
| 80 Serratia marcescens 546 | 1 MAESNAAIQSAAIGAGTMGRGIAYLFAQKGIETMLYNRN 40 |
| 81 Serratia nematodiphila MB307 | 1 MAESNAAIQSAAIGAGTMGRGIAYLFAQKGIETMLYNRN 40 |
| 82 Serratia marcescens VGH107 | 1 MAESNAAIQSAAIGAGTMGRGIAYLFAQKGIETMLYNRN 40 |
| 83 Serratia marcescens MCB | 1 MAESNAAIQSAAIGAGTMGRGIAYLFAQKGIRTVLYNRN 40 |
| 84 Serratia marcescens AH0650 | 1 MAESNAAIQSAAIGAGTMGRGIAYLFAQKGIRTVLYNRN 40 |
| 85 Serratia marcescens UMH12 | 1 MAESNAEIQSAAIGAGTMGRGIAYLFAQKGIRTVLYNRN 40 |
| 86 Serratia sp. OMLW3 | 1 MAESNAAIQSAAIGAGTMGRGIAYLFAQKGIRTVLYNRN 40 |
| 87 Serratia marcescens UMH11 | 1 MAESNAAIQSAAIGAGTMGRGIAYLFAQKGIRTVLYNRN 40 |
| 88 Serratia marcescens UMH11 | 1 MAESNAAIQSAAIGAGTMGRGIAYLFAQKGIRTVLYNRN 40 |
| 89 Serratia marcescens 2880STDY5683020 | 1 MAESNAAIQSAAIGAGTMGRGIAYLFAQKGIRTVLYNRN 40 |
| 90 Serratia marcescens 99 | 1 MAESNAAIQSAAIGAGTMGRGIAYLFAQKGIRTVLYNRN 40 |
| 91 Serratia marcescens 374 | 1 MAESNAAIQSAAIGAGTMGRGIAYLFAQKGIRTVLYNRN 40 |
| 92 Serratia marcescens 2880STDY5683036 | 1 MAESNAAIQSAAIGAGTMGRGIAYLFAQKGIRTVLYNRN 40 |

TABLE 5-1

| | | |
|---|---|---|
| 93 Serratia marcescens 2880STDY5683034 | 1 MAESNAAIQSAAI | GAGTMGRGIAYLFAQKGIRTVLYNRN 40 |
| 94 Serratia marcescens 2880STDY5682892 | 1 MAESNAAIQSAAI | GAGTMGRGIAYLFAQKGIRTVLYNRN 40 |
| 95 Serratia marcescens SM39 | 1 MAESNAAIQSAAI | GAGTMGRGIAYLFAQKGIRTVLYNRN 40 |
| 96 Serratia marcescens 189 | 1 MAESNAAIQSAAI | GAGTMGRGIAYLFAQKGIRTVLYNRN 40 |
| 97 Serratia marcescens SMB2099 | 1 MAESNAAIQSAAI | GAGTMGRGIAYLFAQKGIRTVLYNRN 40 |
| 98 Serratia marcescens 2880STDY5682862 | 1 MAESNAAIQSAAI | GAGTMGRGIAYLFAQKGIRTVLYNRN 40 |
| 99 Serratia marcescens SE4145 | 1 MAESNAEIQSAAI | GAGTMGRGIAYLFAQKGIRTVLYNRN 40 |
| 100 Serratia marcescens 2880STDY5682876 | 1 MAESNAAIQSAAI | GAGTMGRGIAYLFAQKGIRTVLYNRN 40 |
| 101 Serratia marcescens 709 | 1 MAESNAAIQSAAI | GAGTMGRGIAYLFAQKGIRTVLYNRN 40 |
| 102 Serratia marcescens MGH136 | 1 MAESNAAIQSAAI | GAGTMGRGIAYLFAQKGIRTVLYNRN 40 |
| 103 Serratia marcescens 2880STDY5682884 | 1 MAESNAAIQSAAI | GAGTMGRGIAYLFAQKGIRTVLYNRN 40 |
| 104 Serratia marcescens D-3 | 1 MAESNAAIQSAAI | GAGTMGRGIAYLFAQKGIRTVLYNRN 40 |
| 105 Serratia marcescens 2880STDY5682957 | 1 MAESNAAIQSAAI | GAGTMGRGIAYLFAQKGIRTVLYNRN 40 |
| 106 Serratia marcescens YDC563 | 1 MAESNAAIQSAAI | GAGTMGRGIAYLFAQKGIRTVLYNRN 40 |
| 107 Serratia marcescens 2880STDY5683035 | 1 MAESNAAIQSAAI | GAGTMGRGIAYLFAQKGIRTVLYNRN 40 |
| 108 Serratia marcescens 2880STDY5682930 | 1 MAESNAAIQSAAI | GAGTMGRGIAYLFAQKGIRTVLYNRN 40 |
| 109 Serratia marcescens 790 | 1 MAESNAAIQSAAI | GAGTMGRGIAYLFAQKGIRTVLYNRN 40 |
| 110 Serratia marcescens UMH5 | 1 MAESNAAIQSAAI | GAGTMGRGIAYLFAQKGIRTVLYNRN 40 |
| 111 Serratia marcescens 2880STDY5682988 | 1 MAESNAAIQSAAI | GAGTMGRGIAYLFAQKGIRTVLYNRN 40 |
| 112 Serratia marcescens 945154301 | 1 MAESNAAIQSAAI | GAGTMGRGIAYLFAQKGIRTVLYNRN 40 |
| 113 Serratia marcescens at10508 | 1 MAESNAAIQSAAI | GAGTMGRGIAYLFAQKGIRTVLYNRN 40 |
| 114 Serratia marcescens ML2637 | 1 MAESNAAIQSAAI | GAGTMGRGIAYLFAQKGIRTVLYNRN 40 |
| 115 Serratia marcescens SM1978 | 1 MAESNAAIQSAAI | GAGTMGRGIAYLFAQKGIRTVLYNRN 40 |
| 116 Serratia marcescens PWN146 | 1 MAESNAAIQSAAI | GAGTMGRGIAYLFAQKGIRTVLYNRN 40 |
| 117 Serratia marcescens H1q | 1 MARSNAAIQSAAI | GAGTMGRGIAYLFAQKGIRTVLYNRN 40 |

TABLE 5-2

| | | |
|---|---|---|
| 118 Serratia marcescens UMH6 | 1 MAESNAAIQSAAI | GAGTMGRGIAYLFAQKSIRTVLYNRN 40 |
| 119 Serratia nematodiphila WCU338 | 1 MAESNAAIQSAAI | GAGTMGRGIAYLFAQKSIRTVLYNRN 40 |
| 120 Serratia sp. 0LEL1 | 1 MAESNAAIQSAAI | GAGTMGRGIAYILAQKSIRTVLYNRN 40 |
| 121 Serratia marcesens 7209 | 1 MAESNAAIQSAAI | GAGTMGRGIAYLFAQKSIRTVLYNRN 40 |
| 122 Serratia marcescens sicaria (Ss1) | 1 MAESNAAIQSAAI | GAGTMGRGIAYLFAQKSIRTVLYNRN 40 |
| 123 Serratia sp. 0LFL2 | 1 MAESNAAIQSAAI | GAGTMGRGIAYILAQKSIRTVLYNRN 40 |
| 124 Serratia marcescens BIDMC 81 | 1 MAESNAAIQSAAI | GAGTMGRGIAYILAQKSIRTVLYNRN 40 |
| 125 Serratia marcescens BIDMC 50 | 1 MAESNAAIQSAAI | GAGTMGRGIAYLFAQKSIRTVLYNRN 40 |
| 126 Serratia marcescens UMH7 | 1 MAESNAAIQSAAI | GAGTMGRGIAYILAQKSIRTVLYNRN 40 |
| 127 Serratia marcescens RSC-14 | 1 MAESNAAIQSAAI | GAGTMGRGIAYILAQKSIRTVLYNRN 40 |
| 128 Serratia marcescens SM03 | 1 MAERNAAIQSAAI | GAGTMGRGIAYLFAQKGIRTVLYNRN 40 |
| 129 Serratia marcescens 90-166 | 1 MAESNAAIQSAAI | GAGTMGRGIAYLFAQKGIRTVLYNRN 40 |
| 130 Serratia marcescens UMH2 | 1 MAESNAAIQSAAI | GAGTMGRGIAYILAQKSIRTVLYNRN 40 |
| 131 Serratia plymuthica AS9 | 1 MAENNSAIRSAAVI | GAGTMGRGIAYLIALNGIRTVLYNRN 40 |
| 132 Serratia plymuthica tumat 205 | 1 MAENNSAIRSAAVI | GAGTMGRGIAYLIALNGIRTVLYNRN 40 |
| 133 Serratia plymuthica A30 | 1 MAENNSAIRSAAVI | GAGTMGRGIAYLIALNGIRTVLYNRN 40 |
| 134 Serratia plymuthica 4Rx13 | 1 MAENNSAIRSAAVI | GAGTMGRGIAYLIALNGIRTVLYNRN 40 |
| 135 Serratia plymuthica V4 | 1 MAENNSAIRSAAVI | GAGTMGRGIAYLIALNGIRTVLYNRN 40 |
| 136 Serratia plymuthica 3Rp8 | 1 MAENNSAIRSAAVI | GAGTMGRGIAYLIALNGIRTVLYNRN 40 |
| 137 Serratia proteamaculans MFPA44A14 | 1 MAENNSAIHSVAVI | GAGTMGRGIAYLIAQNGIRTILYNRS 40 |
| 138 Serratia plymuthica A153 | 1 MAENNSAIRSAAVI | GAGTMGRGIAYLIALNGIRTVLYNRN 40 |

In the present invention, examples of the microorganisms that can be used as hosts to obtain the genetically modified microorganisms include microorganisms belonging to the genera *Escherichia, Serratia, Hafnia, Pseudomonas, Corynebacterium, Bacillus, Streptomyces, Cupriavidus, Acinetobacter, Alcaligenes, Brevibacterium, Delftia, Shimwellia, Aerobacter, Rhizobium, Thermobifida, Clostridium, Schizosaccharomyces, Kluyveromyces, Pichia,* and *Candida.* Among them, microorganisms belonging to the genera *Escherichia, Serratia, Hafnia,* and *Pseudomonas* are preferable.

The method of producing 3-hydroxyadipic acid, α-hydromuconic acid, and/or adipic acid by using a genetically modified microorganisms according to the present invention will be described.

Any genetically modified microorganism according to the present invention can produce 3-hydroxyadipic acid, provided that the microorganism has an ability to generate 3-oxoadipyl-CoA and coenzyme A from acetyl-CoA and succinyl-CoA (the reaction A) and an ability to generate 3-hydroxyadipic acid from 3-hydroxyadipyl-CoA (the reaction E). By using a microorganism with these production abilities as the host microorganism, a genetically modified microorganism that can abundantly produce 3-hydroxyadipic acid can be obtained. Microorganisms that are speculated to originally have the above production abilities include the following microorganisms: microorganisms of the genus *Escherichia*, such as *Escherichia fergusonii* and *Escherichia coli*; the genus *Pseudomonas*, such as *Pseudomonas chlororaphis, Pseudomonas putida, Pseudomonas azotoformans*, and *Pseudomonas chlororaphis* subsp. *aureofaciens*; the genus *Hafnia*, such as *Hafnia alvei*; the genus *Corynebacterium*, such as *Corynebacterium acetoacidophilum, Corynebacterium acetoglutamicum, Corynebacterium ammoniagenes*, and *Corynebacterium glutamicum*; the genus *Bacillus*, such as *Bacillus badius, Bacillus magalerium*, and *Bacillus roseus*; the genus *Streptomyces*, such as *Streptomyces vinaceus, Streptomyces karnatakensis*, and *Streptomyces olivaceus*; the genus *Cupriavidus*, such as *Cupriavidus metallidurans, Cupriavidus necator*, and *Cupriavidus oxalaticus*; the genus *Acinetobacter*, such as *Acinetobacter baylyi* and *Acinetobacter radioresistens*; the genus *Alcaligenes*, such as *Alcaligenes faecalis*; the genus *Nocardioides*, such as *Nocardioides albus*; the genus *Brevibacterium*, such as *Brevibacterium iodinum*; the genus *Delftia*, such as *Delftia acidovorans*; the genus *Shimwellia*, such as *Shimwellia blattae*; the genus *Aerobacter*, such as *Aerobacter cloacae*; the genus *Rhizobium*, such as *Rhizobium radiobacter*; the genus *Serratia*, such as *Serratia grimesii, Serratia ficaria, Serratia fonticola, Serratia odorifera, Serratia plymuthica, Serratia entomophila*, and *Serratia nematodiphila*. Any of these microorganisms can be used as a host microorganism to obtain a genetically modified microorganism according to the present invention, which results in generation of a genetically modified microorganism that abundantly produces 3-hydroxyadipic acid.

Into a genetically modified microorganism according to the present invention which originally has no abilities to generate 3-oxoadipyl-CoA and coenzyme A from acetyl-CoA and succinyl-CoA (the reaction A) and/or to generate 3-hydroxyadipic acid from 3-hydroxyadipyl-CoA (the reaction E), an appropriate combination of nucleic acids encoding enzymes that catalyze the reactions A and E can be introduced to give the microorganisms these production abilities.

Any genetically modified microorganism according to the present invention can produce α-hydromuconic acid, provided that the microorganism has an ability to generate 3-oxoadipyl-CoA and coenzyme A from acetyl-CoA and succinyl-CoA (the reaction A), an ability to generate 2,3-dehydroadipyl-CoA by dehydrating 3-hydroxyadipyl-CoA (the reaction C), and an ability to generate α-hydromuconic acid from 2,3-dehydroadipyl-CoA (the reaction F). By using a microorganism with these production abilities as a host microorganism, a genetically modified microorganism that can abundantly produce α-hydromuconic acid can be obtained. Microorganisms that are speculated to originally have the above production abilities include the following microorganisms: microorganisms of the genus *Escherichia*, such as *Escherichia fergusonii* and *Escherichia coli*; the genus *Pseudomonas*, such as *Pseudomonas fluorescens, Pseudomonas putida, Pseudomonas azotoformans*, and *Pseudomonas chlororaphis* subsp. *aureofaciens*; the genus *Hafnia*, such as *Hafnia alvei*; the genus *Bacillus*, such as *Bacillus badius*; the genus *Cupriavidus*, such as *Cupriavidus metallidurans, Cupriavidus numazuensis*, and *Cupriavidus oxalaticus*; the genus *Acinetobacter*, such as *Acinetobacter baylyi* and *Acinetobacter radioresistens*; the genus *Alcaligenes*, such as *Alcaligenes faecalis*; the genus *Delftia*, such as *Delftia acidovorans*; the genus *Shimwellia*, such as *Shimwellia blantae*; the genus *Serratia*, such as *Serratia grimesii, Serratia ficaria, Serratia fonticola, Serratia odorifera, Serratia plymuthica, Serratia entomophila*, and *Serratia nematodiphila*.

Into a genetically modified microorganism according to the present invention which originally has no abilities to generate 3-oxoadipyl-CoA and coenzyme A from acetyl-CoA and succinyl-CoA (the reaction A), to generate 2,3-dehydroadipyl-CoA by dehydrating 3-hydroxyadipyl-CoA (the reaction C), and to generate α-hydromuconic acid from 2,3-dehydroadipyl-CoA (the reaction F), an appropriate combination of nucleic acids encoding enzymes that catalyze the reactions A, C, and F can be introduced to give the microorganism these production abilities.

Any genetically modified microorganism according to the present invention can produce adipic acid, provided that the microorganism has an ability to generate 3-oxoadipyl-CoA and coenzyme A from succinyl-CoA (the reaction A), an ability to generate 2,3-dehydroadipyl-CoA by dehydrating 3-hydroxyadipyl-CoA (the reaction C), an ability to generate adipyl-CoA by reducing 2,3-dehydroadipyl-CoA (the reaction D), and an ability to generate adipic acid from adipyl-CoA (the reaction G). By using a microorganism with these production abilities as a host microorganism, a genetically modified microorganism that can abundantly produce adipic acid can be obtained. Microorganisms that are speculated to originally have the above production abilities include microorganisms of the genus *Thermobifida*, such as *Thermobifida fusca*.

In cases where a genetically modified microorganism according to the present invention originally has no abilities to generate 3-oxoadipyl-CoA and coenzyme A from succinyl-CoA (the reaction A), to generate 2,3-dehydroadipyl-CoA by dehydrating 3-hydroxyadipyl-CoA (the reaction C), to generate adipyl-CoA by reducing 2,3-dehydroadipyl-CoA (the reaction D), and to generate adipic acid from adipyl-CoA (the reaction G), an appropriate combination of nucleic acids encoding enzymes that catalyze the reactions A, C, D, and G can be introduced into the microorganism to give the microorganism these production abilities.

Specific examples of the enzymes that catalyze the reactions A and C to G are presented below.

As an enzyme that catalyzes the reaction A to generate 3-oxoadipyl-CoA, for example, an acyl transferase (β-ketothiolase) can be used. The acyl transferase is not limited by a particular number in the EC classification, and is preferably an acyl transferase classified into EC 2.3.1.-, specifically including an enzyme classified as 3-oxoadipyl-CoA thiolase and classified into EC 2.3.1.174, an enzyme classified as acetyl-CoA C-acetyltransferase and classified into EC 2.3.1.9, and an enzyme classified as acetyl-CoA C-acyl transferase and classified into EC 2.3.1.16. Among them, PaaJ from *Escherichia coli* strain MG1655 (NCBI-ProteinID: NP_415915). PcaF from *Pseudomonas putida* strain KT2440 (NCBI-ProteinID: NP_743536), and the like can be suitably used.

Whether or not the above acyl transferases can generate 3-oxoadipyl-CoA from succinyl-CoA and acetyl-CoA used as substrates can be determined by measuring a decrease in NADH coupled with reduction of 3-oxoadipyl-CoA in a combination of the reaction to generate 3-oxoadipyl-CoA by purified acyl transferase and the reaction to reduce 3-oxoadipyl-CoA used as a substrate by purified 3-oxoadipyl-CoA reductase. The specific measurement method is, for example, as follows.

Identification of acyl transferase activity: A PCR using the genomic DNA of a subject microorganism strain as a template is performed in accordance with routine procedures, to amplify a nucleic acid encoding an acyl transferase in the full-length form. The amplified fragment is inserted into the SacI site of pACYCDuet-1 (manufactured by Novagen), an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain an acyl transferase solution. The acyl transferase activity can be determined by using the enzyme solution to prepare an enzymatic reaction solution with the following composition and measuring a decrease in absorbance at 340 nm coupled with oxidation of NADH at 30° C.

100 mM Tris-HCl (pH 8.0)
10 mM $MgCl_2$
0.1 mM succinyl-CoA
0.2 mM acetyl-CoA
0.2 mM NADH
1 mM dithiothreitol
10 μg/mL 3-oxoadipyl-CoA reductase
5 μg/mL acyltransferase.

Whether or not an enzyme originally expressed in a host microorganism used in the present invention has acyl transferase activity can be determined by performing the above-described measurement using cell homogenate (cell free extract: CFE) instead of purified acyl transferase. The specific measurement method targeted to *E. coli* is, for example, as follows.

Preparation of CFE: A loopful of *E. coli* strain MG1655 to be subjected to the measurement of the activity is inoculated into 5 mL of a culture medium (culture medium composition: 10 g/L tryptone, 5 g/L yeast extract, 5 g/L sodium chloride) adjusted to pH 7, and incubated at 30° C. with shaking for 18 hours. The obtained culture fluid is added to 5 mL of a culture medium (culture medium composition: 10 g/L tryptone, 5 g/L yeast extract, 5 g/L sodium chloride, 2.5 mM ferulic acid, 2.5 mM p-coumaric acid, 2.5 mM benzoic acid, 2.5 mM cis,cis-muconic acid, 2.5 mM protocatechuic acid, 2.5 mM catechol, 2.5 mM 3OA, 2.5 mM 3-hydroxyadipic acid, 2.5 mM α-hydromuconic acid, 2.5 mM adipic acid, 2.5 mM phenylethylamine) adjusted to pH 7, and incubated at 30° C. with shaking for 3 hours.

The obtained culture fluid is supplemented with 10 mL of 0.9% sodium chloride and then centrifuged to remove the supernatant from bacterial cells, and this operation is repeated three times in total to wash the bacterial cells. The washed bacterial cells are suspended in 1 mL of a Tris-HCl buffer composed of 100 mM Tris-HCl (pH 8.0) and 1 mM dithiothreitol, and glass beads (with a diameter of 0.1 mm) are added to the resulting suspension to disrupt the bacterial cells at 4° C. with an ultrasonic disruptor. The resulting bacterial homogenate is centrifuged to obtain the supernatant, and 0.5 mL of the supernatant is filtered through a UF membrane (Amicon Ultra-0.5 mL 10K; manufactured by Merck Millipore) to remove the resulting filtrate, followed by application of 0.4 mL of the Tris-HCl buffer to the UF membrane, and this operation is repeated three times in total to remove low-molecular-weight impurities, and the resulting supernatant is then resuspended in the Tris-HCl buffer to a final volume of 0.1 mL, which is designated as CFE. Instead of purified enzyme, 0.05 mL of the CFE is added to a total of 0.1 mL of the enzymatic reaction solution to determine the enzymatic activity.

As an enzyme that catalyzes the reaction C to generate 2,3-dehydroadipyl-CoA, for example, an enoyl-CoA hydratase can be used. The enoyl-CoA hydratase is not limited by a particular number in the EC classification, and is preferably an enoyl-CoA hydratase classified into EC 4.2.1.-, specifically including an enzyme classified as enoyl-CoA hydratase or 2,3-dehydroadipyl-CoA hydratase and classified into EC 4.2.1.17. Among them. PaaF from *Escherichia coli* strain MG1655 (NCBI-ProteinID: NP_415911), PaaF from *Pseudomonas putida* strain KT2440 (NCBI-ProteinID: NP_745427), and the like can be suitably used.

Since the reaction catalyzed by enoyl-CoA hydratase is generally reversible, whether or not an enoyl-CoA hydratase has an activity to catalyze a reaction that generates 2,3-dehydroadipyl-CoA from 3-hydroxyadipyl-CoA used as a substrate can be determined by detecting 3-hydroxyadipyl-CoA generated using purified enoyl-CoA hydratase with 2,3-dehydroadipyl-CoA used as a substrate thereof, which is prepared from α-hydromuconic acid through an enzymatic reaction. The specific measurement method is, for example, as follows.

The α-hydromuconic acid used in the above reaction can be prepared by a known method (for example, a method described in Reference Example 1 of WO 2016/199858 A1).

Preparation of 2,3-dehydroadipyl-CoA solution: A PCR using the genomic DNA of *Pseudomonas putida* strain KT2440 as a template is performed in accordance with routine procedures, to amplify a nucleic acid encoding a CoA transferase (including pcaI and pcaJ; NCBI-GeneIDs: 1046613 and 1046612) in the full-length form. The amplified fragment is inserted into the KpnI site of pRSF-1b (manufactured by Novagen), an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a CoA transferase solution. The solution is used to prepare an enzymatic reaction solution for 2,3-dehydroadipyl-CoA preparation with the following composition, which is allowed to react at 30° C. for 10 minutes and then filtered through a UF membrane (Amicon Ultra-0.5 mL 10K; manufactured by Merck Millipore) to remove the enzyme, and the obtained filtrate is designated as 2,3-dehydroadipyl-CoA solution.

Enzymatic reaction solution for 2,3-dehydroadipyl-CoA preparation
100 mM Tris-HCl (pH 8.0)
10 mM $MgCl_2$
0.4 mM succinyl-CoA
2 mM α-hydromuconic acid sodium salt
20 μg/mL CoA transferase.

Identification of enoyl-CoA hydratase activity: A PCR using the genomic DNA of a subject microorganism strain as a template is performed in accordance with routine procedures, to amplify a nucleic acid encoding an enoyl-CoA hydratase in the full-length form. The amplified fragment is inserted into the NdeI site of pET-16b (manufactured by Novagen), an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain an enoyl-CoA hydratase solution. The solution is used to prepare an enzymatic reaction solution with the following composition, which is allowed to react at 30° C. for 10 minutes and then filtered through a UF membrane (Amicon Ultra-0.5 mL 10K; manufactured by Merck Millipore) to remove the enzyme. The enoyl-CoA hydratase activity can be confirmed by detecting 3-hydroxyadipyl-CoA in the resulting filtrate on high-performance liquid chromatograph-tandem mass spectrometer (LC-MS/MS) (Agilent Technologies, Inc.).

100 mM Tris-HCl (pH 8.0)
10 mM $MgCl_2$
300 μL/mL 2,3-dehydroadipyl-CoA solution
1 mM dithiothreitol
20 μg/mL enoyl-CoA hydratase.

Whether or not an enzyme originally expressed in a host microorganism used in the present invention has enoyl-CoA hydratase activity can be determined by adding 0.05 mL of the CFE, instead of purified enoyl-CoA hydratase, to a total of 0.1 mL of the enzymatic reaction solution and performing the above-described measurement. The specific CFE preparation method targeted to *E. coli* is as described for that used in determination of acyl transferase activity.

As an enzyme that catalyzes the reaction D to generate adipyl-CoA, for example, an enoyl-CoA reductase can be used. The enoyl-CoA reductase is not limited by a particular number in the EC classification, and is preferably an enoyl-CoA reductase classified into EC 1.3.-.-, specifically including an enzyme classified as trans-2-enoyl-CoA reductase and classified into EC 1.3.1.44, and an enzyme classified as acyl-CoA dehydrogenase and classified into EC 1.3.8.7. These specific examples are disclosed in, for example JP 2011-515111 A, J Appl Microbiol. 2015 October; 119 (4): 1057-63, and the like; among them, TER from *Euglena gracilis* strain Z (UniProtKB: Q5EU90), Tfu_1647 from *Thermobifida fusca* strain YX (NCBI-ProteinID: AAZ55682), DcaA from *Acinetobacter baylyi* strain ADP1 (NCBI-ProteinID: AAL09094.1), and the like can be suitably used.

Whether or not an enoyl-CoA reductase has an activity to generate adipyl-CoA from 2,3-dehydroadipyl-CoA used as a substrate can be determined by measuring a decrease in NADH coupled with reduction of 2,3-dehydroadipyl-CoA in a reaction using purified enoyl-CoA reductase with 2,3-dehydroadipyl-CoA used as a substrate thereof, which is prepared from α-hydromuconic acid through another enzymatic reaction.

Preparation of α-hydromuconic acid and a 2,3-dehydroadipyl-CoA solution can be performed in the same manner as described above.

Identification of enoyl-CoA reductase activity: A PCR using the genomic DNA of a subject microorganism strain as a template is performed in accordance with routine procedures, to amplify a nucleic acid encoding an enoyl-CoA reductase in the full-length form. The amplified fragment is inserted into the NdeI site of pET-16b (manufactured by Novagen), an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain an enoyl-CoA reductase solution. The enoyl-CoA reductase activity can be determined by using the enzyme solution to prepare an enzymatic reaction solution with the following composition and measuring a decrease in absorbance at 340 nm coupled with oxidation of NADH at 30° C.

100 mM Tris-HCl (pH 8.0)
10 mM $MgCl_2$
300 μL/mL 2,3-dehydroadipyl-CoA solution
0.2 mM NADH
1 mM dithiothreitol
20 μg/mL enoyl-CoA reductase.

Whether or not an enzyme originally expressed in a host microorganism used in the present invention has enoyl-CoA reductase activity can be determined by adding 0.05 mL of the CFE, instead of purified enoyl-CoA reductase, to a total of 0.1 mL of the enzymatic reaction solution and performing the above-described measurement. The specific CFE preparation method targeted to *E. coli* is as described for that used in determination of acyl transferase activity.

As an enzyme that catalyzes the reaction E to generate 3-hydroxyadipic acid, the reaction F to generate α-hydromuconic acid, and the reaction G to generate adipic acid, for example, a CoA transferase or an acyl-CoA hydrolase, preferably a CoA transferase, can be used.

The CoA transferase is not limited by a particular number in the EC classification, and is preferably a CoA transferase classified into EC 2.8.3.-, specifically including an enzyme classified as CoA transferase or acyl-CoA transferase and classified into EC 2.8.3.6, and the like.

In the present invention, the term "CoA transferase" refers to an enzyme with activity (CoA transferase activity) to catalyze a reaction that generates carboxylic acid and succinyl-CoA from acyl-CoA and succinic acid used as substrates.

As an enzyme that catalyzes the reaction E to generate 3-hydroxyadipic acid and the reaction F to generate α-hydromuconic acid, PcaI and PcaJ from *Pseudomonas putida* strain KT2440 (NCBI-ProteinIDs: NP_746081 and NP_746082), and the like can be suitably used, among others.

As an enzyme that catalyzes the reaction G to generate adipic acid, DcaI and DcaJ from *Acinetobacter baylyi* strain ADP1 (NCBI-ProteinIDs: CAG68538 and CAG68539), and the like can be suitably used.

Since the above enzymatic reactions are reversible, the CoA transferase activity against 3-hydroxyadipyl-CoA, 2,3-dehydroadipyl-CoA, or adipyl-CoA used as a substrate can be determined by detecting 3-hydroxyadipyl-CoA, 2,3-dehydroadipyl-CoA, or adipyl-CoA generated respectively using purified CoA transferase with 3-hydroxyadipic acid and succinyl-CoA, α-hydromuconic acid and succinyl-CoA, or adipic acid and succinyl-CoA used as substrates thereof. The specific measurement method is, for example, as follows.

Preparation of 3-hydroxyadipic acid: Preparation of 3-hydroxyadipic acid is performed according to the method described in Reference Example 1 of WO 2016/199856 A1.

Identification of CoA transferase activity using 3-hydroxyadipic acid as a substrate: A PCR using the genomic DNA of a subject microorganism strain as a template is performed in accordance with routine procedures, to amplify a nucleic acid encoding a CoA transferase in the full-length form. The amplified fragment is inserted into the KpnI site of pRSF-1b (manufactured by Novagen), an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a CoA transferase solution. The solution is used to prepare an enzymatic reaction solution with the following composition, which is allowed to react at 30° C. for 10 minutes and then filtered through a UF membrane (Amicon Ultra-0.5 mL 10K; manufactured by Merck Millipore) to remove the enzyme. The CoA transferase activity can be confirmed by detecting 3-hydroxyadipyl-CoA in the resulting filtrate on high-performance liquid chromatograph-tandem mass spectrometer (LC-MS/MS) (Agilent Technologies, Inc.).
  100 mM Tris-HCl (pH 8.0)
  10 mM MgCl$_2$
  0.4 mM succinyl-CoA
  2 mM 3-hydroxyadipic acid sodium salt
  20 µg/ml, CoA transferase.

Preparation of α-hydromuconic acid: Preparation of α-hydromuconic acid can be performed according to a method described in Reference Example 1 of WO 2016/199858 A1.

Identification of CoA transferase activity using α-hydromuconic acid as a substrate: A PCR using the genomic DNA of a subject microorganism strain as a template is performed in accordance with routine procedures, to amplify a nucleic acid encoding a CoA transferase in the full-length form. The amplified fragment is inserted into the KpnI site of pRSF-1b (manufactured by Novagen), an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a CoA transferase solution. The solution is used to prepare an enzymatic reaction solution with the following composition, which is allowed to react at 30° C. for 10 minutes and then filtered through a UF membrane (Amicon Ultra-0.5 mL 10K; manufactured by Merck Millipore) to remove the enzyme. The CoA transferase activity can be confirmed by detecting 2,3-dehydroadipyl-CoA in the resulting filtrate on high-performance liquid chromatograph-tandem mass spectrometer (LC-MS/MS) (Agilent Technologies, Inc.).
  100 mM Tris-HCl (pH 8.0)
  10 mM MgCl$_2$
  0.4 mM succinyl-CoA
  2 mM α-hydromuconic acid sodium salt
  20 µg/mL CoA transferase.

Identification of CoA transferase activity using adipic acid as a substrate: A PCR using the genomic DNA of a subject microorganism strain as a template is performed in accordance with routine procedures, to amplify a nucleic acid encoding a CoA transferase in the full-length form. The amplified fragment is inserted into the KpnI site of pRSF-1b (manufactured by Novagen), an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a CoA transferase solution. The solution is used to prepare an enzymatic reaction solution with the following composition, which is allowed to react at 30° C. for 10 minutes and then filtered through a UF membrane (Amicon Ultra-0.5 mL 10K; manufactured by Merck Millipore) to remove the enzyme. The CoA transferase activity can be confirmed by detecting adipyl-CoA in the resulting filtrate on high-performance liquid chromatograph-tandem mass spectrometer (LC-MS/MS) (Agilent Technologies, Inc.).
  100 mM Tris-HCl (pH 8.0)
  10 mM MgCl$_2$
  0.4 mM succinyl-CoA
  2 mM adipic acid sodium salt
  20 µg/mL CoA-transferase.

Whether or not an enzyme originally expressed in a host microorganism used in the present invention has CoA transferase activity can be determined by adding 0.05 mL of the CFE, instead of purified CoA transferase, to a total of 0.1 mL of the enzymatic reaction solution and performing the above-described measurement. The specific CFE preparation method targeted to *E. coli* is as described for that used in determination of acyl transferase activity.

Either the polypeptides described in (a) to (c) or the 3-hydroxybutyryl-CoA dehydrogenase in the present invention is characterized by having higher activity than 3-oxoadipyl-CoA reductases used in conventional techniques. In this respect, the phrase "higher activity" refers to production of 3-hydroxyadipic acid, α-hydromuconic acid, or adipic acid with a higher yield in a genetically modified microorganism expressing any one of the polypeptides than in a genetically modified microorganism expressing a conventional 3-oxoadipyl-CoA reductase when those microorganisms are derived from the same host microorganism species and are cultured under the same expression conditions in a culture medium containing a carbon source as a material for fermentation. In this respect, the yield of 3-hydroxyadipic acid is calculated according to the formula (3). The yield of α-hydromuconic acid or adipic acid is calculated according to the formula (3), where 3-hydroxyadipic acid is replaced by α-hydromuconic acid or adipic acid, respectively.

Yield (%)=amount of formed 3-hydroxyadipic acid (mol)/amount of consumed carbon source (mol)×100    (3)

The specific method to confirm the higher activity of either the polypeptides described in (a) to (c) or the 3-hydroxybutyryl-CoA dehydrogenase in the present invention compared to the activity of 3-oxoadipyl-CoA reductases used in conventional techniques is as follows. The pBBR1MCS-2 vector, which is able to self-replicate in *E. coli* (ME Kovach, (1995), Gene 166: 175-176), is cleaved with XhoI to obtain pBBR1MCS-2/XhoI. To integrate a constitutive expression promoter into the vector, an upstream 200-b region of gapA (NCBI Gene ID: NC_000913.3) is amplified by PCR using the genomic DNA of *Escherichia coli* K-12 MG1655 as a template in accordance with routine procedures (for example, primers represented by SEQ ID NOs: 18 and 19 are used), and the resulting fragment and the pBBR1MCS-2/XhoI are ligated together using the In-Fusion HD Cloning Kit (manufactured by Clontech) to obtain the plasmid pBBR1MCS-2::Pgap. The pBBR1MCS-2::Pgap is cleaved with ScaI to obtain pBBR1MCS-2::Pgap/ScaI. A nucleic acid encoding an acyl transferase in the full length form is amplified by PCR in accordance with routine procedures (for example, primers represented by SEQ ID NOs: 21 and 22 are used), and the resulting fragment and the pBBR1MCS-2::Pgap/ScaI are ligated together using the In-Fusion HD Cloning Kit to obtain the plasmid pBBR1MCS-2::AT. The pBBR1MCS-2::AT is cleaved with HpaI to obtain pBBR1MCS-2::AT/HpaI. A nucleic acid encoding a CoA transferase in the full length form is amplified by PCR in accordance with routine procedures (for example, primers represented by SEQ ID NOs: 25 and 26 are used), and the resulting fragment and the pBBR1MCS-2::AT/HpaI are ligated together using the In-Fusion HD Cloning Kit to obtain the plasmid pBBR1MCS-2::ATCT.

On the other hand, the pACYCDuet-1 expression vector (manufactured by Novagen), which is able to self-replicate in *E. coli*, is cleaved with BamHI to obtain pACYCDuet- 1/BamHI. A nucleic acid encoding a polypeptide represented by any one of SEQ ID NOs: 1 to 16 or 70 to 138, or encoding a conventionally used 3-oxoadipyl-CoA reductase, is amplified by PCR in accordance with routine procedures (for example, primers represented by SEQ ID NOs: 31 and 32 are used), and the resulting fragment and the pACYCDuct-1/BamHI are ligated together using the In-Fusion HD Cloning Kit (manufactured by Clontech) to obtain a plasmid for expression of the polypeptide represented by any one of SEQ ID NOs: 1 to 16 or 70 to 138, or expression of the conventionally used 3-oxoadipyl-CoA reductase.

The obtained plasmid and the pBBR1MCS-2::ATCT are introduced into *E. coli* strain BL21 (DE3) by electroporation (N M Calvin, P C Hanawalt. J. Bacteriol, 170 (1988), pp. 2796-2801). A loopful of the strain after the introduction is inoculated into 5 mL of the culture medium I (10 g/L Bacto Tryptone (manufactured by Difco Laboratories), 5 g/L Bacto Yeast Extract (manufactured by Difco Laboratories), 5 g/L sodium chloride, 25 µg/mL, kanamycin, and 15 µg/mL chloramphenicol) adjusted to pH 7, and incubated at 30° C. with shaking at 120 min$^{-1}$ for 18 hours. Subsequently, 0.25 mL of the culture fluid is added to 5 mL of the culture medium II (10 g/L succinic acid, 10 g/L glucose, 1 g/L ammonium sulfate, 50 mM potassium phosphate, 0.025 g/L magnesium sulfate, 0.0625 mg/L iron sulfate, 2.7 mg/L manganese sulfate, 0.33 mg/L calcium chloride, 1.25 g/L sodium chloride, 2.5 g/L Bacto Tryptone, 1.25 g/L Bacto Yeast Extract, 25 µg/mL kanamycin, 15 µg/mL chloramphenicol, and 0.01 mM IPTG) adjusted to pH 6.5, and incubated at 30° C. with shaking at 120 min$^{-1}$ for 24 hours. The supernatant separated from bacterial cells by centrifugation of the culture fluid is processed by membrane treatment using Millex-GV (0.22 µm; PVDF; manufactured by Merck KGaA), and the resulting filtrate is analyzed to measure the 3-hydroxyadipic acid and carbon source concentrations in the culture supernatant. Quantitative analysis of 3-hydroxyadipic acid on LC-MS/MS is performed under the following conditions.

HPLC: 1290 Infinity (manufactured by Agilent Technologies, Inc.)
Column: Synergi hydro-RP (manufactured by Phenomenex Inc.), length: 100 mm, internal diameter: 3 mm, particle size: 2.5 µm
Mobile phase: 0.1% aqueous formic acid solution/methanol=70/30
Flow rate: 0.3 mL/min
Column temperature: 40° C.
LC detector: DAD (210 nm)
MS/MS: Triple-Quad LC/MS (manufactured by Agilent Technologies, Inc.) Ionization method: ESI in negative mode.

Quantitative analysis of carbon sources, such as sugars and succinic acid, on HPLC is performed under the following conditions.

HPLC: Shimadzu Prominence (manufactured by Shimadzu Corporation)
Column: Shodex Sugar SH1011 (manufactured by Showa Denko K.K.), length: 300 mm, internal diameter: 8 mm, particle size: 6 µm
Mobile phase: 0.05M aqueous sulfuric acid solution
Flow rate: 0.6 mL/min
Column temperature: 65° C.
Detector: RI.

When a nucleic acid encoding any one selected from the group of the acyl transferase, the CoA transferase, the enoyl-CoA hydratase, and the enoyl-CoA reductase is introduced into a host microorganism in the present invention, the nucleic acid may be artificially synthesized based on the amino acid sequence information of the enzyme in a database, or isolated from the natural environment. In cases where the nucleic acid is artificially synthesized, the usage frequency of codons corresponding to each amino acid in the nucleic acid sequence may be changed depending on the host microorganism into which the nucleic acid is introduced.

In the present invention, the method of introducing a nucleic acid encoding any one selected from the group of the acyl transferase, the CoA transferase, the enoyl-CoA hydratase, and the enoyl-CoA reductase into the host microorganism method is not limited to a particular method; for example, a method in which the nucleic acid is integrated into an expression vector capable of autonomous replication in the host microorganism and then introduced into the host microorganism, a method in which the nucleic acid is integrated into the genome of the host microorganism, and the like can be used.

In cases where nucleic acids encoding the enzymes are isolated from the natural environment, the organisms as sources of the genes are not limited to particular organisms, and examples of the organisms include those of the genus *Acinetobacter*, such as *Acinetobacter baylyi* and *Acinetobacter radioresistens*; the genus *Aerobacter*, such as *Aerobacter cloacae*; the genus *Alcaligenes*, such as *Alcaligenes faecalis*; the genus *Bacillus*, such as *Bacillus badius*, *Bacillus magaterium*, and *Bacillus roseus*; the genus *Brevibacterium*, such as *Brevibacterium iodinum*; the genus *Corynebacterium*, such as *Corynebacterium acetoacidophilum*, *Corynebacterium acetoglutamicum*, *Corynebacterium ammoniagenes*, and *Corynebacterium glutamicum*; the genus *Cupriavidus*, such as *Cupriavidus metallidurans*, *Cupriavidus necator*, *Cupriavidus numazuensis*, and *Cupriavidus oxalaticus*; the genus *Delftia*, such as *Delftia acidovorans*; the genus *Escherichia*, such as *Escherichia coli* and *Escherichia fergusonii*; the genus *Hafnia*, such as *Hafnia alvei*; the genes *Microbacterium*, such as *Microbacterium ammoniaphilum*; the genus *Nocardioides*, such as *Nocardioides albus*; the genus *Planomicrobium*, such as *Planomicrobium okeanokoites*; the genus *Pseudomonas*, such as *Pseudomonas azotoformans*, *Pseudomonas chlororaphis*, *Pseudomonas fluorescens*, *Pseudomonas fragi*, *Pseudomonas putida*, and *Pseudomonas reptilivora*; the genus *Rhizobium*, such as *Rhizobium radiobacter*; the genus *Rhodosporidium*, such as *Rhodosporidium toruloides*; the genus *Saccharomyces*, such as *Saccharomyces cerevisiae*; the genus *Serratia*, such as *Serratia entomophila*, *Serratia ficaria*, *Serratia fonticola*, *Serratia grimesii*, *Serratia nematodiphila*, *Serratia odorifera*, and *Serratia plymuthica*; the genus *Shimwellia*, such as *Shimwellia blattae*; the genus *Streptomyces*, such as *Streptomyces vinaceus*, *Streptomyces karnatakensis*, *Streptomyces olivaceus*, and *Streptomyces vinaceus*; the genus *Yarrowia*, such as *Yarrowia lipolytica*; the genus *Yersinia*, such as *Yersinia ruckeri*; the genus *Euglena*, such as *Euglena gracilis*; and the genus *Thermobifida*, such as *Thermobifida fusca*; preferably those of the genera *Acinetobacter*, *Corynebacterium*, *Escherichia*, *Pseudomonas*, *Serratia*, *Euglena*, and *Thermobifida*.

When a nucleic acid encoding a polypeptide expressed in the present invention is integrated into an expression vector or the genome of a host microorganism, the nucleic acid being integrated into the expression vector or the genome is preferably composed of a promoter, a ribosome-binding sequence, a nucleic acid encoding the polypeptide to be expressed, and a transcription termination sequence, and may additionally contain a gene that controls the activity of the promoter.

The promoter used in the present invention is not limited to a particular promoter, provided that the promoter drives expression of the enzyme in the host microorganism; examples of the promoter include gap promoter, trp promoter, lac promoter, tac promoter, and T7 promoter.

In cases where an expression vector is used in the present invention to introduce the nucleic acid or to enhance the expression of the polypeptide, the expression vector is not limited to a particular vector, provided that the vector is capable of autonomous replication in the microorganism; examples of the vector include pBBR1MCS vector, pBR322 vector, pMW vector, pET vector, pRSF vector, pCDF vector, pACYC vector, and derivatives of the above vectors.

In cases where a nucleic acid for genome integration is used in the present invention to introduce the nucleic acid or to enhance the expression of the polypeptide, the nucleic acid for genome integration is introduced by site-specific homologous recombination. The method for site-specific homologous recombination is not limited to a particular method, and examples of the method include a method in which λ Red recombinase and FLP recombinase are used (Proc Natl Acad Sci U.S.A. 2000 Jun. 6; 97 (12): 6640-6645.), and a method in which. Red recombinase and the sacB gene are used (Biosci Biotechnol Biochem. 2007 December; 71 (12):2905-11.).

The method of introducing the expression vector or the nucleic acid for genome integration is not limited to a particular method, provided that the method is for introduction of a nucleic acid into a microorganism; examples of the method include the calcium ion method (Journal of Molecular Biology, 53, 159 (1970)), and electroporation (N M Calvin, P C Hanawalt. J. Bacteriol, 170 (1988), pp. 2796-2801).

In the present invention, a genetically modified microorganism in which a nucleic acid encoding a 3-oxoadipyl-CoA reductase is introduced or expression of the corresponding polypeptide is enhanced is cultured in a culture medium, preferably a liquid culture medium, containing a carbon source as a material for fermentation which can be used by ordinary microorganisms. The culture medium used contains, in addition to the carbon source that can be used by the genetically modified microorganism, appropriate amounts of a nitrogen source, inorganic salts, and, if necessary, organic trace nutrients such as amino acids and vitamins. Any of natural and synthetic culture media can be used as long as the medium contains the above-described nutrients.

The material for fermentation is a material that can be metabolized by the genetically modified microorganism. The term "metabolize" refers to conversion of a chemical substance, which a microorganism has taken up from the extracellular environment or intracellularly generated from a different chemical substance, to another chemical substance through an enzymatic reaction. Sugars can be suitably used as the carbon source. Specific examples of the sugars include monosaccharides, such as glucose, sucrose, fructose, galactose, mannose, xylose, and arabinose; disaccharides and polysaccharides formed by linking these monosaccharides; and saccharified starch solution, molasses, and saccharified solution from cellulose-containing biomass, each containing any of those saccharides.

Other than the above sugars, succinic acid, a substrate of the CoA transferase, can also be added to the culture medium for efficient production of 3-hydroxyadipic acid, α-hydromuconic acid, and/or adipic acid.

The above-listed carbon sources may be used individually or in combination. When a carbon source is added, the concentration of the carbon source in the culture medium is not particularly limited, and can be appropriately selected depending on the type of the carbon source: in the case of sugars, the concentration is preferably from 5 g/L to 300 g/L; in the case of succinic acid, the concentration is preferably from 0.1 g/L to 100 g/L.

As the nitrogen source used for culturing the genetically modified microorganism, for example, ammonia gas, aqueous ammonia, ammonium salts, urea, nitric acid salts, other supportively used organic nitrogen sources, such as oil cakes, soybean hydrolysate, casein degradation products, other amino acids; vitamins, corn steep liquor, yeast or yeast extract, meat extract, peptides such as peptone, and bacterial cells and hydrolysate of various fermentative bacteria can be used. The concentration of the nitrogen source in the culture medium is not particularly limited, and is preferably from 0.1 g/L to 50 g/L.

As the inorganic salts used for culturing the genetically modified microorganism, for example, phosphoric acid salts, magnesium salts, calcium salts, iron salts, and manganese salts can be appropriately added to the culture medium and used.

The culture conditions for the genetically modified microorganism to produce 3-hydroxyadipic acid, α-hydromuconic acid, and/or adipic acid are set by appropriately adjusting or selecting, for example, the culture medium with the above composition, culture temperature, stirring speed, pH, aeration rate, and inoculation amount, depending on, for example, the species of the genetically modified microorganism and external conditions. In cases where foam is formed in a liquid culture, an antifoaming agent such as a mineral oil, silicone oil, or surfactant may be appropriately added to the culture medium.

After a recoverable amount of 3-hydroxyadipic acid, α-hydromuconic acid, and/or adipic acid is produced during culturing of the microorganism, the produced products can be recovered. The produced products can be recovered, for example isolated, according to a commonly used method, in which the culturing is stopped once a product of interest is accumulated to an appropriate level, and the fermentation product is collected from the culture. Specifically, the products can be isolated from the culture by separation of bacterial cells through, for example, centrifugation or filtration prior to, for example, column chromatography, ion exchange chromatography, activated charcoal treatment, crystallization, membrane separation, or distillation. More specifically, examples include, but are not limited to, a method in which an acidic component is added to salts of the products, and the resulting precipitate is collected; a method in which water is removed from the culture by concentration using, for example, a reverse osmosis membrane or an evaporator to increase the concentrations of the products and the products and/or salts of the products are then crystallized and precipitated by cooling or adiabatic crystallization to recover the crystals of the products and/or salts of the products by, for example, centrifugation or filtration; and a method in which an alcohol is added to the culture to produce esters of the products and the resulting esters of the products are subsequently collected by distillation and then hydrolyzed to recover the products. These recovery methods can be appropriately selected and optimized depending on, for example, physical properties of the products.

EXAMPLES

The present invention will now be specifically described by way of Examples.

Reference Example 1

Production of a Plasmid for Expression of an Enzyme Catalyzing a Reaction to Generate 3-Oxoadipyl-CoA and Coenzyme a from Acetyl-CoA and Succinyl-CoA (the Reaction A) and an Enzyme Catalyzing a Reaction to Generate 3-Hydroxyadipic Acid from 3-Hydroxyadipyl-CoA (the Reaction E) and a Reaction to Generate α-Hydromuconic Acid from 2,3-Dehydroadipyl-CoA (the Reaction F)

The pBBR1MCS-2 vector, which is capable of autonomous replication in *E. coli* (ME Kovach, (1995), Gene 166: 175-176), was cleaved with XhoI to obtain pBBR1MCS-2/XhoI. To integrate a constitutive expression promoter into the vector, primers (SEQ ID NOs: 18 and 19) were designed for use in amplification of an upstream 200-b region (SEQ ID NO: 17) of gapA (NCBI Gene ID: NC_000913.3) by PCR using the genomic DNA of *Escherichia coli* K-12 MG1655 as a template, and a PCR reaction was performed in accordance with routine procedures. The resulting fragment and the pBBR1MCS-2/XhoI were ligated together using the In-Fusion HI) Cloning Kit (manufactured by Clontech), and the resulting plasmid was introduced into *E. coli* strain DH5a. The nucleotide sequence on the plasmid extracted from the obtained recombinant *E. coli* strain was confirmed in accordance with routine procedures, and the plasmid was designated as pBBR1MCS-2::Pgap. Then, the pBBR1MCS-2::Pgap was cleaved with ScaI to obtain pBBR1MCS-2::Pgap/ScaI. To amplify a gene encoding an enzyme catalyzing the reaction A, primers (SEQ ID NOs: 21 and 22) were designed for use in amplification of the full length of the acyl transferase gene pcaF (NCBI Gene ID: 1041755; SEQ ID NO: 20) by PCR using the genomic DNA of *Pseudomonas putida* strain KT2440 as a template, and a PCR reaction was performed in accordance with routine procedures. The resulting fragment and the pBBR1MCS-2::Pgap/ScaI were ligated together using the In-Fusion HD Cloning Kit, and the resulting plasmid was introduced into *E. coli* strain DH5a. The nucleotide sequence on the plasmid isolated from the obtained recombinant strain was confirmed in accordance with routine procedures, and the plasmid was designated as pBBR1MCS-2::AT. Then, the pBBR1MCS-2::AT was cleaved with HpaI to obtain pBBR1MCS-2::AT/HpaI. To amplify a gene encoding an enzyme catalyzing the reactions E and F, primers (SEQ ID NOs: 25 and 26) were designed for use in amplification of a continuous sequence including the full lengths of genes together encoding a CoA transferase, pcaI and pcaJ (NCBI Gene IDs: 1046613 and 1046612, SEQ ID NOs: 23, 24), by PCR using the genomic DNA of *Pseudomonas putida* strain KT2440 as a template, and a PCR reaction was performed in accordance with routine procedures. The resulting fragment and the pBBR1MCS-2::AT/HpaI were ligated together using the In-Fusion HD Cloning Kit. and the resulting plasmid was introduced into *E. coli* strain DH5α. The nucleotide sequence on the plasmid isolated from the obtained recombinant strain was confirmed in accordance with routine procedures, and the plasmid was designated as pBBR1MCS-2::ATCT.

Reference Example 2

Production of Plasmids for Expression of Polypeptides Represented by SEQ ID NOs: 1, 2, 3, 4, 5, 6, and 213

The pACYCDuet-1 expression vector (manufactured by Novagen), which is capable of autonomous replication in *E. coli*, was cleaved with BamHI to obtain pACYCDuet-1/BamHI. To amplify a nucleic acid encoding a polypeptide represented by SEQ ID NO: 1, primers (SEQ ID NOs: 31 and 32) were designed for use in amplification of a nucleic acid represented by SEQ ID NO: 54 using the genomic DNA of *Serratia marcescens* strain ATCC 13880 as a template, and a PCR reaction was performed in accordance with routine procedures. To amplify a nucleic acid encoding a polypeptide represented by SEQ ID NO: 2, primers (SEQ ID NOs: 33 and 34) were designed for use in amplification of a nucleic acid represented by SEQ ID NO: 55 using the genomic DNA of *Serratia nematodiphila* strain DSM21420 as a template, and a PCR reaction was performed in accordance with routine procedures. To amplify a nucleic acid encoding a polypeptide represented by SEQ ID NO: 3, primers (SEQ ID NOs: 35 and 36) were designed for use in amplification of a nucleic acid represented by SEQ ID NO: 56 using the genomic DNA of *Serratia plymuthica* strain NBRC102599 as a template, and a PCR reaction was performed in accordance with routine procedures. To amplify a nucleic acid encoding a polypeptide represented by SEQ ID NO: 4, primers (SEQ ID NOs: 37 and 38) were designed for use in amplification of a nucleic acid represented by SEQ ID NO: 57 using the genomic DNA of *Serratia proteamaculans* strain 568 as a template, and a PCR reaction was performed in accordance with routine procedures. To amplify a nucleic acid encoding a polypeptide represented by SEQ ID NO: 5, primers (SEQ ID NOs: 215 and 216) were designed for use in amplification of a nucleic acid represented by SEQ ID NO: 58 using the genomic DNA of *Serratia ureilytica* strain Lr5/4 as a template, and a PCR reaction was performed in accordance with routine procedures. To amplify a nucleic acid encoding a polypeptide represented by SEQ ID NO: 6, primers (SEQ ID NOs: 217 and 218) were designed for use in amplification of a nucleic acid represented by SEQ ID NO: 59 using the genomic DNA of *Serratia* sp. strain BW106 as a template, and a PCR reaction was performed in accordance with routine procedures. To amplify a nucleic acid encoding a polypeptide represented by SEQ ID NO: 213, primers (SEQ ID NOs: 219 and 220) were designed for use in amplification of a nucleic acid represented by SEQ ID NO: 214 using the genomic DNA of *Serratia liquefaciens* strain FK01 as a template, and a PCR reaction was performed in accordance with routine procedures. Each of the obtained fragments and the pACYCDuet-1/BamHI were ligated together using the In-Fusion HD Cloning Kit (manufactured by Clontech), and each of the resulting plasmids was introduced into *E. coli* strain DH5α. The nucleotide sequences on the plasmids isolated from the obtained recombinant strains were confirmed in accordance with routine procedures. The expression of the 3-oxoadipyl-CoA reductase gene integrated into each of the plasmids is induced by IPTG, which resulted in addition of 14 extra amino acids including a histidine tag to the N terminus of the expressed polypeptide.

The plasmid for expression of the polypeptide represented by SEQ ID NO: 1 is designated as "pACYCDuet-1::Smr1"; the plasmid for expression of the polypeptide represented by SEQ ID NO: 2 is designated as "pACYCDuet-1::Snm1"; the plasmid for expression of the polypeptide represented by SEQ ID NO: 3 is designated as "pACYCDuet-1::Spl1"; the plasmid for expression of the polypeptide represented by SEQ ID NO: 4 is designated as "pACYCDuet-1::Spe1"; the plasmid for expression of the polypeptide represented by SEQ ID NO: 5 is designated as "pACYCDuet-1:Sur1": the plasmid for expression of the polypeptide represented by SEQ ID NO: 6 is designated as "pACYCDuet-1::Ssp1"; and the plasmid for expression of the polypeptide represented by SEQ ID NO: 213 is designated as "pACYCDuet-1::Slq1". The information about these plasmids is presented in Table 6.

Reference Example 3

Production of Plasmids for Expression of 3-Oxoadipyl-CoA Reductase

Other than plasmids for expression of the polypeptides described in (a) to (c) according to the present invention, plasmids for expression of four different enzymes, each of which catalyzes a reduction reaction to generate 3-hydroxyacyl-CoA from 3-oxoacyl-CoA used as a substrate, were produced. Four genes, namely paaH from *Pseudomonas putida* strain KT2440 (SEQ ID NO: 27), paaH from *Escherichia coli* str. K-12 substr. MG1655 (SEQ ID NO: 28), dcaH from *Acinetobacter baylyi* strain ADP1 (SEQ ID NO: 29), and paaH from *Serratia plymuthica* strain NBRC102599 (SEQ ID NO: 30), were used. The plasmids were produced in the same manner as in Reference Example 2, except that primers (SEQ ID NOs: 39 and 40) for amplification of a nucleic acid represented by SEQ ID NO: 27, primers (SEQ ID NOs: 41 and 42) for amplification of a nucleic acid represented by SEQ ID NO: 28, primers (SEQ ID NOs: 43 and 44) for amplification of a nucleic acid represented by SEQ ID NO: 29, and primers (SEQ ID NOs: 45 and 46) for amplification of a nucleic acid represented by SEQ ID NO: 30 were used.

The plasmid for expression of the polypeptide encoded by the nucleic acid represented by SEQ ID NO: 27 is designated as "pACYCDuet-1::Ppu1"; the plasmid for expression of the polypeptide encoded by the nucleic acid represented by SEQ ID NO: 28 is designated as "pACYCDuet-1::Eco1"; the plasmid for expression of the polypeptide encoded by the nucleic acid represented by SEQ ID NO: 29 is designated as "pACYCDuct-1::Aci1"; and the plasmid for expression of the polypeptide encoded by the nucleic acid represented by SEQ ID NO: 30 is designated as "pACYCDuet-1::Spl2". The information about these plasmids is presented in Table 6.

TABLE 6

| Plasmid | Source organism | Gene ID | SEQ ID NO |
|---|---|---|---|
| pACYCDuct-1::Smr1 | *Serratia marcescens* ATCC 13880 | JMPQ01000047.1 | 54 |
| pACYCDuet-1::Snm1 | *Serratia nematodiphila* DSM21420 | JPUX00000000.1 | 55 |
| pACYCDuet-1::Spl1 | *Serratia plymuthica* NBRC102599 | BCTU01000013.1 | 56 |
| pACYCDuet-1::Spe1 | *Serratia proteamaculans* 568 | CP000826.1 | 57 |
| pACYCDuct-1::Ppu1 | *Pseudomonas putida* KT2440 | NC_002947.4 | 27 |
| pACYCDuet-1::Eco1 | *Escherichia coli* str. K-12 substr. MG1655 | NC_000913.3 | 28 |
| pACYCDuet-1::Aci1 | *Acinetobacter baylyi* ADP1 | CR543861.1 | 29 |
| pACYCDuet-1::Spl2 | *Serratia plymuthica* NBRC102599 | NZ_BCTU01000001.1 | 30 |

TABLE 6-continued

| Plasmid | Source organism | Gene ID | SEQ ID NO |
|---|---|---|---|
| pACYCDuet-1::Sur1 | *Serratia ureilytica* Lr5/4 | JSFB01000001 | 58 |
| pACYCDuet-1::Ssp1 | *Serratia* sp. BW106 | MCGS01000002.1 | 59 |
| pACYCDuet-1::Slq1 | *Serratia liquefaciens* FK01 | CP006252.1 | 214 |

Example 1

Generation of *E. coli* Strains Having an Ability to Produce 3-Hydroxyadipic Acid by Introduction of Each of the Nucleic Acids Encoding the Polypeptides Represented by SEQ ID NOs: 1, 2, 3, 4, 5, 6, and 213

The plasmid pBBR1MCS-2::ATCT produced in Reference Example 1 was introduced into *E. coli* strain BL21 (DE3) by electroporation (N M Calvin, P C Hanawalt. J. Bacteriol, 170 (1988), pp. 2796-2801). The strain after the introduction was cultured on LB agar medium containing 25 μg/mL of kanamycin at 37° C. The obtained recombinant strain was designated as BL21 (DE3)/pBBR1MCS-2::ATCT.

Next, each of the seven plasmids produced in Reference Example 2 was individually introduced into the BL21 (DE3)/pBBR1MCS-2::ATCT by electroporation. Each of the strains after the introduction was cultured on LB agar medium containing 25 μg/mL kanamycin and 15 μg/mL chloramphenicol at 37° C. The recombinant strain in which "pACYCDuet-1::Smr1" is introduced is designated as "Ec/Smr1_3HA"; the recombinant strain in which "pACYCDuet-1::Snm1" is introduced is designated as "Ec/Snm1_3HA"; the recombinant strain in which "pACYCDuet-1::Spl1" is introduced is designated as "Ec/Spl1_3HA"; the recombinant strain in which "pACYCDuet-1::Spe1" is introduced is designated as "Ec/Spe1_3HA"; the recombinant strain in which "pACYCDuct-1::Sur1" is introduced is designated as "Ec/Sur1_3HA"; the recombinant strain in which "pACYCDuet-1::Ssp1" is introduced is designated as "Ec/Ssp1_3HA"; and the recombinant strain in which "pACYCDuet-1::Slq1" is introduced is designated as "Ec/Slq1_3HA". The information about the recombinant strains obtained in this example is presented in Table 7.

Comparative Example 1

Generation of *E. coli* Strains Having an Ability to Produce 3-Hydroxyadipic Acid by Introduction of Each of the Nucleic Acids Encoding 3-Oxoadipyl-CoA Reductases The plasmid pBBR1MCS-2::ATCT produced in Reference Example 1 was introduced into *E. coli* strain BL21 (DE3) by electroporation (N M Calvin, P C Hanawalt. J. Bacteriol, 170 (1988), pp. 2796-2801). The strain after the introduction was cultured on LB agar medium containing 25 μg/mL kanamycin at 37° C. The obtained recombinant strain was designated as BL21 (DE3)/pBBR1MCS-2::ATCT.

Next, each of the four plasmids produced in Reference Example 3 was individually introduced into the BL21 (DE3)/pBBR1MCS-2::ATCT by electroporation. Each of the strains after the introduction was cultured on LB agar medium containing 25 μg/mL kanamycin and 15 μg/mL chloramphenicol at 37° C.

The recombinant strain in which "pACYCDuet-1::Ppu1" is introduced is designated as "Ec/Ppu1_3HA"; the recombinant strain in which "pACYCDuct-1::Eco1" is introduced is designated as "Ec/Eco1_3HA"; the recombinant strain in which "pACYCDuet-1::Aci1" is introduced is designated as "Ec/Aci1_3HA"; and the recombinant strain in which "pACYCDuet-1::Spl2" is introduced is designated as "Ec/Spl2_3HA". The information about the recombinant strains obtained in this comparative example is presented in Table 7.

Example 2

Test for 3-Hydroxyadipic Acid Production Using the *E. coli* Strains Having an Ability to Produce 3-Hydroxyadipic Acid by Introduction of Each of the Nucleic Acids Encoding the Polypeptides Represented by SEQ ID NOs: 1, 2, 3, 4, 5, 6, and 213

The recombinant *E. coli* strains produced in Example 1 were used to perform a test for 3-hydroxyadipic acid production.

A loopful of each recombinant strain produced in Example 1 was inoculated into 5 mL of the culture medium 1 (10 g/L Bacto Tryptone (manufactured by Difco Laboratories), 5 g/l, Bacto Yeast Extract (manufactured by Difco Laboratories), 5 g/L sodium chloride, 25 µg/mL kanamycin, and 15 µg/mL chloramphenicol) adjusted to pH 7, and incubated at 30° C. with shaking at 120 min$^{-1}$ for 18 hours. Subsequently, 0.25 mL of the culture fluid was added to 5 mL of the culture medium II (10 g/L succinic acid, 10 g/L glucose, 1 g/L ammonium sulfate, 50 mM potassium phosphate, 0.025 g/L magnesium sulfate, 0.0625 mg/L iron sulfate, 2.7 mg/L manganese sulfate, 0.33 mg/L calcium chloride, 1.25 g/L sodium chloride, 2.5 g/L Bacto Tryptone, 1.25 g/L Bacto Yeast Extract, 25 µg/mL kanamycin, 15 µg/mL chloramphenicol, and 0.01 mM IPTG) adjusted to pH 6.5, and incubated at 30° C. with shaking at 120 min$^{-1}$ for 24 hours.

Quantitative Analyses of 3-Hydroxyadipic Acid and Carbon Sources

The supernatant separated from bacterial cells by centrifugation of the culture fluid was processed by membrane treatment using Millex-GV (0.22 µm; PVDF; manufactured by Merck KGaA), and the resulting filtrate was analyzed according to the following method to measure the accumulated 3-hydroxyadipic acid and carbon source concentrations in the culture supernatant. The results are presented in Table 7. Additionally, the yield of 3-hydroxyadipic acid calculated according to the formula (3) is presented in Table 7.

Quantitative analysis of 3-hydroxyadipic acid by LC-MS/MS
  HPLC: 1290 Infinity (manufactured by Agilent Technologies, Inc.)
  Column: Synergi hydro-RP (manufactured by Phenomenex Inc.), length: 100 mm, internal diameter: 3 mm, particle size: 2.5 µm
  Mobile phase: 0.1% aqueous formic acid solution/methanol=70/30
  Flow rate: 0.3 mL/min
  Column temperature: 40° C.
  LC detector: DAD (210 nm)
  MS/MS: Triple-Quad LC/MS (manufactured by Agilent Technologies, Inc.) Ionization method: ESI in negative mode.
Quantitative Analysis of Sugars and Succinic Acid by HPLC
  HPLC: Shimadzu Prominence (manufactured by Shimadzu Corporation)
  Column: Shodex Sugar SH1011 (manufactured by Showa Denko K.K.), length: 300 mm, internal diameter: 8 mm, particle size: 6 µm
  Mobile phase: 0.05M aqueous sulfuric acid solution
  Flow rate: 0.6 mL/min
  Column temperature: 65° C.
  Detector: RI
  HPLC: 1290 Infinity (manufactured by Agilent Technologies, Inc.)
  Column: Synergi hydro-RP (manufactured by Phenomenex Inc.), length: 100 mm, internal diameter: 3 mm, particle size: 2.5 µm
  Mobile phase: 0.1% aqueous formic acid solution/methanol=70/30
  Flow rate: 0.3 mL/min
  Column temperature: 40° C.
  LC detector: DAD (210 nm)
  MS/MS: Triple-Quad LC/MS (manufactured by Agilent Technologies, Inc.) Ionization method: ESI in negative mode.

Comparative Example 2

Test for 3-Hydroxyadipic Acid Production Using the *E. coli* Strains Having an Ability to Produce 3-Hydroxyadipic Acid by Introduction of Each of the Nucleic Acids Encoding 3-Oxoadipyl-CoA Reductases The results of a test for 3-hydroxyadipic acid production performed in the same manner as in Example 2 by using the *E. coli* strains produced in Comparative Example 1 are presented in Table 7.

The results presented in Table 7 indicate that the yield of 3-hydroxyadipic acid was increased in the recombinant strains used in Example 2 compared to that in the recombinant strains used in Comparative Example 2. That is, it was demonstrated that the production of 3-hydroxyadipic acid was much increased by introduction of any of the nucleic acids encoding the polypeptides represented by SEQ ID NOs: 1, 2, 3, 4, 5, 6, and 213 into microorganisms.

TABLE 7

|  | Strain | 3HA Concentration (g/L) | 3HA Yield (%) |
| --- | --- | --- | --- |
| Example 2 | Ec/Smr1_3HA | 1.65 | 12.6 |
|  | Ec/Snm1_3HA | 2.69 | 18.9 |
|  | Ec/Spl1_3HA | 2.18 | 17.0 |
|  | Ec/Spe1_3HA | 2.72 | 19.3 |
|  | Ec/Sur1_3HA | 3.42 | 25.8 |
|  | Ec/Ssp1_3HA | 1.94 | 18.0 |
|  | Ec/Slq1_3HA | 2.67 | 21.8 |
| Comparative Example 2 | Ec/Ppu1_3HA | 0.67 | 5.7 |
|  | Ec/Eco1_3HA | 0.88 | 7.2 |
|  | Ec/Aci1_3HA | 0.82 | 6.8 |
|  | Ec/Spl2_3HA | 0.91 | 7.4 |

Reference Example 4

Production of a Plasmid for Expression of an Enzyme Catalyzing a Reaction to Generate 2,3-Dehydroadipyl-CoA from 3-Hydroxyadipyl-CoA (the Reaction C)

The pCDF-1b expression vector (manufactured by Novagen), which is capable of autonomous replication in *E. coli*, was cleaved with KpnI to obtain pCDF-1b/KpnI. To amplify a gene encoding an enzyme catalyzing the reaction C, primers (SEQ ID NOs: 48 and 49) were designed for use in amplification of the full length of the enoyl-CoA hydratase gene paaF (NCBI Gene ID: 1046932, SEQ ID NO: 47) by PCR using the genomic DNA of *Pseudomonas putida* strain KT2440 as a template, and a PCR reaction was performed in accordance with routine procedures. The resulting fragment and the pCDF-1b/KpnI were ligated together using the In-Fusion HD Cloning Kit (manufactured by Clontech), and the resulting plasmid was introduced into *E. coli* strain DH5α. The nucleotide sequence on the plasmid extracted from the obtained recombinant strain was confirmed in accordance with routine procedures. The expression of the enoyl-CoA hydratase gene integrated into the plasmid is induced by IPTG, which resulted in addition of 11 extra amino acids including a histidine tag to the N terminus of the expressed polypeptide. The obtained plasmid was designated as "pCDF-1b::EHa."

Example 3

Generation of *E. coli* Strains Having an Ability to Produce α-Hydromuconic Acid by Introduction of the Nucleic Acids Encoding the Polypeptides Represented by SEQ ID NOs: 1, 2, 3, 4, 5, 6, and 213

The plasmid pCDF-1b::EHa produced in Reference Example 4 was introduced by electroporation into the *E. coli* strain BL21 (DE3)/pBBR1MCS-2::ATCT produced in Example 1. The strain after the introduction was cultured on LB agar medium containing 25 μg/mL kanamycin and 50 μg/mL streptomycin at 37° C. The resulting recombinant strain was designated as BL21 (DE3)/pBBR1MCS-2::ATCT/pCDF-1b::EHa.

Next, each of the plasmids produced in Reference Example 2, namely "pACYCDuet-1::Smr1," "pACYCDuet-1::Snm1", "pACYCDuet-1::Spl1", "pACYCDuet-1::Spe1", "pACYCDuet-1::Sur1", and "pACYCDuet-1::Ssp1," "pACYCDuet-1::Slq1," was individually introduced into the BL21 (DE3)/pBBR1MCS-2::ATCT/pCDF-1b::EHa by electroporation. Each of the strains after the introduction was cultured on LB agar medium containing 25 μg/mL kanamycin, 50 μg/mL streptomycin, and 15 μg/mL chloramphenicol at 37° C. The recombinant strain in which "pACYCDuet-1::Smr1" is introduced is designated as "Ec/Smr1_HMA": the recombinant strain in which "pACYCDuet-1::Snm1" is introduced is designated as "Ec/Snm1_HMA"; the recombinant strain in which "pACYCDuct-1::Spl1" is introduced is designated as "Ec/Spl1_HMA": the recombinant strain in which "pACYCDuet-1::Spe1" is introduced is designated as "Ec/Spe1_HMA"; the recombinant strain in which "pACYCDuet-::Sur1" is introduced is designated as "Ec/Sur1_HMA"; the recombinant strain in which "pACYDuet-1::Ssp1" is introduced is designated as "Ec/Ssp1_HMA"; and the recombinant strain in which "pACYCDuet-1::Slq1" is introduced is designated as "Ec/Slq1_HMA". The information about the recombinant strains obtained in this example is presented in Table 8.

Comparative Example 3

Generation of *E. coli* Strains Having an Ability to Produce α-Hydromuconic Acid by Introduction of Each of the Nucleic Acids Encoding 3-Oxoadipyl-CoA Reductases The plasmid pCDF-1b::EHa produced in Reference Example 4 was introduced by electroporation into the *E. coli* strain BL21 (DE3)/pBBR1MCS-2::ATCT produced in Reference Example 2. The strain after the introduction was cultured on LB agar medium containing 25 μg/mL kanamycin and 50 μg/mL streptomycin at 37° C. The obtained recombinant strain was designated as BL21 (DE3)/pBBR1MCS-2::ATCT/pCDF-1b::EHa.

Next, each of the plasmids produced in Reference Example 3, namely "pACYCDuet-1::Ppu1," "pACYCDuet-1::Eco1," "pACYCDuet-1::Aci1," and "pACYDuet-1::Spl2," was individually introduced into the BL21 (DE3)/pBBR1MCS-2::ATCT/pCDF-1b::EHa by electroporation. Each of the strains after the introduction was cultured on LB agar medium containing 25 μg/mL kanamycin, 50 μg/mL streptomycin, and 15 μg/mL chloramphenicol at 37° C.

The recombinant strain in which "pACYCDuet-1::Ppu1" is introduced is designated as "Ec/Ppu1_HMA"; the recombinant strain in which "pACYCDuet-1::Eco1" is introduced is designated as "Ec/Eco1_HMA": the recombinant strain in which "pACYCDuet-1::Aci1" is introduced is designated as "Ec/Aci1_HMA"; and the recombinant strain in which "pACYCDuet-1::Spl2" is introduced is designated as "Ec/Spl2_HMA". The information about the recombinant strains obtained in this comparative example is presented in Table 8.

Example 4

Test for α-Hydromuconic Acid Production Using the *E. coli* Strains Having an Ability to Produce α-Hydromuconic Acid by Introduction of the Nucleic Acids Encoding the Polypeptides Represented by SEQ ID NOs: 1, 2, 3, 4, 5, 6, and 213

The *E. coli* strains produced in Example 3 were used to perform a test for α-hydromuconic acid production. A loopful of each recombinant *E. coli* strain produced in Example 3 was inoculated into 5 mL of the culture medium I (10 g/L Bacto Tryptone (manufactured by Difco Laboratories), 5 g/L Bacto Yeast Extract (manufactured by Difco Laboratories), 5 g/L sodium chloride, 25 μg/mL kanamycin, 50 μg/mL streptomycin, and 15 μg/mL chloramphenicol) adjusted to pH 7, and incubated at 30° C. with shaking at 120 $min^{-1}$ for 18 hours. Subsequently, 0.25 mL of the culture fluid was added to 5 mL of the culture medium II (10 g/L succinic acid, 10 g/L glucose, 1 g/L ammonium sulfate, 50 mM potassium phosphate, 0.025 g/L magnesium sulfate, 0.0625 mg/L iron sulfate, 2.7 mg/L manganese sulfate, 0.33 mg/L calcium chloride, 1.25 g/L sodium chloride, 2.5 g/L Bacto Tryptone, 1.25 g/L Bacto Yeast Extract, 25 μg/mL kanamycin, 50 μg/mL streptomycin, 15 g/mL chloramphenicol and 0.01 mM IPTG) adjusted to pH 6.5, and incubated at 30° C. with shaking at 120 $min^{-1}$ for 24 hours.

Quantitative Analyses of α-Hydromuconic Acid and Carbon Sources

The supernatant separated from bacterial cells by centrifugation of the culture fluid was processed by membrane treatment using Millex-GV (0.22 μm; PVDF; manufactured by Merck KGaA), and the resulting filtrate was analyzed by LC-MS/MS in the same manner as in Example 2. The results of the quantitative analysis of α-hydromuconic acid accumulated in the culture supernatant, and the yield of α-hydromuconic acid calculated according to the formula (3) are presented in Table 8.

Comparative Example 4

Test for α-Hydromuconic Acid Production Using the *E. coli* Strains Having an Ability to Produce α-Hydromuconic Acid by Introduction of Each of the Nucleic Acids Encoding 3-Oxoadipyl-CoA Reductases The results of a test for α-hydromuconic acid production performed in the same manner as in Example 4 using the *E. coli* strains produced in Comparative Example 3 are presented in Table 8.

The results presented in Table 8 indicate that the yield of α-hydromuconic acid was increased in the recombinant strains used in Example 4 compared to that in the recombinant strains used in Comparative Example 4. That is, it was demonstrated that the production of α-hydromuconic acid was much increased by introduction of any of the nucleic acids encoding the polypeptides represented by SEQ ID NOs: 1, 2, 3, 4, 5, 6, and 213 into microorganisms.

TABLE 8

|  | Strain | HMA Concentration (mg/L) | HMA Yield (%) |
|---|---|---|---|
| Example 4 | Ec/Smr1_HMA | 42.9 | 0.660 |
|  | Ec/Snm1_HMA | 50.6 | 0.755 |
|  | Ec/Spl1_HMA | 39.1 | 0.629 |
|  | Ec/Spe1_HMA | 47.7 | 0.731 |
|  | Ec/Sur1_HMA | 62.4 | 0.801 |
|  | Ec/Ssp1_HMA | 35.6 | 0.626 |
|  | Ec/Slq1_HMA | 48.5 | 0.719 |
| Comparative | Ec/Ppu1_HMA | 0.7 | 0.012 |
| Example 4 | Ec/Eco1_HMA | 1.4 | 0.023 |
|  | Ec/Aci1_HMA | 2.1 | 0.035 |
|  | Ec/Spl2_HMA | 2.1 | 0.034 |

Reference Example 5

Production of Plasmids to Enhance Expression of the Polypeptides Represented by SEQ ID NOs: 2 and 3

Different plasmids were produced for constitutive expression of the polypeptides represented by SEQ ID NOs: 2 and 3.

To amplify a nucleic acid encoding the polypeptide represented by SEQ ID NO: 2, primers (SEQ ID NOs: 50 and 51) were designed for use in amplification of the nucleic acid represented by SEQ ID NO: 55 using the genomic DNA of *Serratia nematodiphila* strain DSM21420 as a template, and a PCR reaction was performed in accordance with routine procedures. To amplify a nucleic acid encoding the polypeptide represented by SEQ ID NO: 3, primers (SEQ ID NOs: 52 and 53) were also designed for use in amplification of the nucleic acid represented by SEQ ID NO: 56 using the genomic DNA of *Serratia plymuthica* strain NBRC102599 as a template, and a PCR reaction was performed in accordance with routine procedures. Each of the resulting fragments and the pBBR1MCS-2::Pgap/ScaI produced in Reference Example 1 were ligated together using the In-Fusion HD Cloning Kit, and the resulting plasmids were individually introduced into *E. coli* strain DH5α. The nucleotide sequences on the plasmids isolated from the obtained recombinant strains were confirmed in accordance with routine procedures, and the plasmids were designated as "pBBR1MCS-2::Snm1" and "pBBR1MCS-2::Spl1", respectively.

Example 5

Generation of Microorganisms of the Genus *Serratia* Modified to Enhance Expression of the Polypeptides Represented by SEQ ID NOs: 2 and 3

*Serratia nematodiphila* strain DSM21420, which is a microorganism originally having the nucleic acid encoding the polypeptide represented by SEQ ID NO: 2, and *Serratia plymuthica* strain NBRC102599, which is a microorganism originally having the nucleic acid encoding the polypeptide represented by SEQ ID NO: 3, were used as host microorganisms to produce recombinant strains with enhanced expression of the polypeptides. The pBBR1MCS-2::Snm1 or pBBR1MCS-2::Spl1 produced in Reference Example 5 was introduced into each of the above described microorganism strains of the genes *Serratia* by electroporation (NM Calvin. PC Hanawalt. J. Bacteriol. 170 (1988), pp. 2796-2801). The strains after the introduction were cultured on LB agar medium containing 25 g/mL kanamycin at 30° C. The recombinant strains obtained in this example were designated as Sn/Snm1 and Sp/Spl1.

Example 6

Test for 3-Hydroxyadipic Acid and α-Hydromuconic Acid Production Using the Microorganisms of the Genus *Serratia* Modified to Enhance Expression of the Polypeptides Represented by SEQ ID NOs: 2 and 3

To evaluate the effects of enhanced expression of the polypeptides represented by SEQ ID NOs: 2 and 3, the recombinant microorganism strains of the genus *Serratia* produced in Example 5 were used to perform a test for 3-hydroxyadipic acid and α-hydromuconic acid production.

A loopful of each recombinant strain produced in Example 5 was inoculated into 5 mL of the culture medium I (10 g/L Bacto Tryptone (manufactured by Difco Laboratories), 5 g/L Bacto Yeast Extract (manufactured by Difco Laboratories), 5 g/L, sodium chloride, 25 μg/mL kanamycin) adjusted to pH 7, and incubated at 30° C. with shaking at 120 min$^{-1}$ for 18 hours. Subsequently, 0.25 mL of the culture fluid was added to 5 mL of the culture medium 11 (10 g/L succinic acid, 10 g/L glucose, 1 g/L ammonium sulfate, 50 mM potassium phosphate, 0.025 g/L magnesium sulfate, 0.0625 mg/L iron sulfate, 2.7 mg/L manganese sulfate, 0.33 mg/L calcium chloride, 1.25 g/L sodium chloride, 2.5 g/L Bacto Tryptone, 1.25 g/L Bacto Yeast Extract, 25 μg/mL kanamycin) adjusted to pH 6.5, and incubated at 30° C. with shaking at 120 min$^{-1}$ for 24 hours.

Quantitative Analyses of 3-Hydroxyadipic Acid, α-Hydromuconic Acid, and Carbon Sources The supernatant separated from bacterial cells by centrifugation of the culture fluid was processed by membrane treatment using Millex-GV (0.22 μm; PVDF; manufactured by Merck KGaA), and the resulting filtrate was analyzed by LC-MS/MS in the same manner as in Example 2. The results of the quantitative analyses of 3-hydroxyadipic acid and α-hydromuconic acid accumulated in the culture supernatant, and the yields of those products are presented in Table 9.

Comparative Example 5

Generation of Microorganisms of the Genus *Serratia* not Modified to Enhance Expression of the Polypeptides Represented by SEQ ID NOs: 2 and 3

The pBBR1MCS-2::gap was introduced into each of *Serratia nematodiphila* strain DSM21420 and *Serratia plymuthica* strain NBRC102599 in the same manner as in Example 5. The resulting recombinant strains were designated as Sn/NC and Sp/NC.

Comparative Example 6

Test for 3-Hydroxyadipic Acid and α-Hydromuconic Acid Production Using the Microorganisms of the Genus *Serratia* not Modified to Enhance Expression of the Polypeptides Represented by SEQ ID NOs: 2 and 3

The microorganisms of the genus *Serratia* produced in Comparative Example 5 were used to perform a test for 3-hydroxyadipic acid and α-hydromuconic acid production in the same manner as in Example 6. The results are presented in Table 9.

The results presented in Table 9 indicate that the yields of 3-hydroxyadipic acid and α-hydromuconic acid were increased in the recombinant strains used in Example 6 with enhanced expression of the polypeptides represented by SEQ ID NOs: 2 and 3 compared to those in the recombinant strains used in Comparative Example 6 without enhanced expression of the polypeptides represented by SEQ ID NOs: 2 and 3. That is, it was demonstrated that the production of 3-hydroxyadipic acid and α-hydromuconic acid was much increased by enhancing the expression of the polypeptides represented by SEQ ID NOs: 2 and 3.

TABLE 9

|  | Strain | 3HA Concentraiton (mg/L) | 3HA Yield (%) | HMA Concentration (mg/L) | HMA Yield (%) |
|---|---|---|---|---|---|
| Example 6 | Sn/Snm1 | 37.4 | 0.193 | 13.7 | 0.077 |
|  | Sp/Spl1 | 64.1 | 0.331 | 14.2 | 0.080 |
| Comparative Example 6 | Sn/NC | 2.5 | 0.013 | 1.7 | 0.010 |
|  | Sp/NC | 4.6 | 0.024 | 4.1 | 0.023 |

Comparative Example 7

Control Test for Confirming the Activity of Each of the Polypeptides Represented by SEQ ID NOs: 1, 2, 3, 4, 5, 6, and 213 to Reduce 3-Oxoadipyl-CoA to 3-Hydroxyadipyl-CoA An *E. coli* recombinant expressing the enzymes catalyzing the reactions A, E, and F was produced. The pACYC-Duet-1 was introduced into the BL21 DE3)/pBBR1MCS-2::ATCT in the same manner as in Example 1. The resulting recombinant strain was designated as Ec/NC_3HA.

An *E. coli* recombinant expressing the enzymes catalyzing the reactions A, E, F, and C was produced. The pACYC-Duet-1 was introduced into the BL21 (DE3)/pBBR1MCS-2::ATCT/pCDF-1b::EHa in the same manner as in Example 3. The resulting recombinant strain was designated as Ec/NC_HMA.

Ec/NC_3HA, Ec/NC_HMA, the seven recombinant *E. coli* strains produced in Example 1 (Ec/Smr1_3HA, Ec/Snm1_3HA, Ec/Spl1_3HA, Ec/Spe1_3HA, Ec/Sur1_3HA, Ec/Ssp1_3HA, Ec/Slq1_3HA), and the seven recombinant *E. coli* strains produced in Example 3 (Ec/Smr1_HMA, Ec/Snm1_HMA, Ec/Spl1_HMA, Ec/Spe1_HMA, Ec/Sur1_HMA, Ec/Ssp1_HMA, Ec/Slq1_HMA) were used and cultured under the same conditions as in either Example 2 or Example 4 to quantify 3-hydroxyadipic acid or α-hydromuconic acid in culture fluid. The results are presented in Table 10.

The results presented in Table 10 indicate that neither 3-hydroxyadipic acid nor α-hydromuconic acid was detected in Ec/NC_3HA and Ec/NC_HMA, and confirmed that the successful production of 3-hydroxyadipic acid and α-hydromuconic acid in Example 2 and 4 was caused by expression of each of the polypeptides represented by SEQ ID NOs: 1, 2, 3, 4, 5, 6, and 213. Additionally, the results indicate that α-hydromuconic acid was not detected in Ec/Smr1_3HA, Ec/Snm1_3HA, Ec/Spl1_3HA, Ec/Spe1_3HA, Ec/Sur1_3HA, Ec/Ssp1_3HA, and Ec/Slq1_3HA, and confirmed that expression of the enzyme catalyzing the reaction C in Ec/Smr1_HMA, Ec/Snm1_HMA, Ec/Spl1 HMA, Ec/Spe1_HMA, Ec/Sur1_HMA, Ec/Ssp1_HMA, and Ec/Slq1_HMA resulted in production of α-hydromuconic acid. This indicates that 3-hydroxyadipic acid produced in Ec/Smr1_3HA, Ec/Snm1_3HA, Ec/Spl1_3HA, Ec/Spe1_3HA, Ec/Sur1_3HA, Ec/Ssp1_3HA, and Ec/Slq1_3HA, and α-hydromuconic acid produced in Ec/Smr1_HMA, Ec/Snm1_HMA, Ec/Spl1_HMA, Ec/Spe1_HMA, Ec/Sur1_HMA, Ec/Ssp1_HMA, and Ec/Slq1_HMA were both produced through production of 3-hydroxyadipyl-CoA. Thus, it was found that the polypeptides represented by SEQ ID NOs: 1, 2, 3, 4, 5, 6, and 213 have an activity to reduce 3-oxoadipyl-CoA to 3-hydroxyadipyl-CoA.

TABLE 10

|  | Strain | 3HA Concentration (g/L) | HMA Concentration (mg/L) |
|---|---|---|---|
| Example 2 | Ec/Smr1_3HA | 1.65 | N.D. |
|  | Ec/Snm1_3HA | 2.69 | N.D. |
|  | Ec/Spl1_3HA | 2.18 | N.D. |
|  | Ec/Spe1_3HA | 2.72 | N.D. |
|  | Ec/Sur1_3HA | 3.42 | N.D. |
|  | Ec/Ssp1_3HA | 1.94 | N.D. |
|  | Ec/Slq1_3HA | 2.67 | N.D. |
| Example 4 | Ec/Smr1_HMA | 0.85 | 42.9 |
|  | Ec/Snm1_HMA | 0.98 | 50.6 |
|  | Ec/Spl1_HMA | 0.67 | 39.1 |
|  | Ec/Spe1_HMA | 0.96 | 47.7 |
|  | Ec/Sur1_HMA | 1.37 | 62.4 |
|  | Ec/Ssp1_HMA | 0.84 | 35.6 |
|  | Ec/Slq1_HMA | 0.93 | 48.5 |
| Comparative Example 7 | Ec/NC_3HA | N.D. | N.D. |
|  | Ec/NC_HMA | N.D. | N.D. |

Reference Example 6

Production of a Plasmid for Expression of the Enzyme Catalyzing a Reaction to Generate 3-Oxoadipyl-CoA and Coenzyme a from Acetyl-CoA and Succinyl-CoA (the Reaction A) and an Enzyme Catalyzing a Reaction to Generate Adipic Acid from Adipyl-CoA (the Reaction G)

A 6.6-kb fragment obtained by cleaving the pBBR1MCS-2::AT produced in Reference Example 1 with HpaI was designated as pBBR1MCS-2::AT/HpaI. To amplify a gene encoding an enzyme catalyzing the reaction G, primers (SEQ ID NOs: 223 and 224) were designed for use in amplification of a continuous sequence including the full-length CoA transferase genes dcaI and dcaJ (NCBI Gene ID: CR543861.1, SEQ ID NOs: 221 and 222) by PCR using the genomic DNA of *Acinetobacter baylyi* strain ADP1 as a template, and a PCR reaction was performed in accordance with routine procedures. The resulting fragment and the pBBR1MCS-2::AT/HpaI were ligated together using the In-Fusion HD Cloning Kit, and the resulting plasmid was introduced into *E. coli* strain DH5α. The nucleotide sequence on the plasmid isolated from the obtained recombinant strain was confirmed in accordance with routine procedures, and the plasmid was designated as pBBR1MCS-2::ATCT2.

Reference Example 7

Production of a Plasmid for Expression of an Enzyme Catalyzing a Reaction to Generate Adipyl-CoA from 2,3-Dehydroadipyl-CoA (the Reaction D)

The pMW19 expression vector (manufactured by Nippon Gene Co., Ltd.), which is capable of autonomous replication in *E. coli*, was cleaved with SacI to obtain pMW119/SacI. To integrate a constitutive expression promoter into the vector, primers (SEQ ID NOs: 225 and 226) were designed for use in amplification of an upstream 200-b region (SEQ ID NO: 17) of gapA (NCBI Gene ID: NC_000913.3) by PCR using the genomic DNA of Escherichia coli K-12 MG1655 as a template, and a PCR reaction was performed in accordance with routine procedures. The resulting fragment and the pMW119/SacI were ligated together using the In-Fusion HD Cloning Kit (manufactured by Clontech), and the resulting plasmid was introduced into E. coli strain DH5α. The nucleotide sequence on the plasmid isolated from the obtained recombinant E. coli strain was confirmed in accordance with routine procedures, and the plasmid was designated as pMW119::Pgap. Then, the pMW119::Pgap was cleaved with SphI to obtain pMW119::Pgap/SphI. To amplify a gene encoding an enzyme catalyzing the reaction D, primers (SEQ ID NOs: 228 and 229) were designed for use in amplification of the full length of dcaA from Acinetobacter baylyi strain ADP1 (NCBI-ProteinID: AAL09094.1, SEQ ID NO: 227) by PCR, and a PCR reaction was performed in accordance with routine procedures. The resulting fragment and the pMW119::Pgap/SphI were ligated together using the In-Fusion HD Cloning Kit (manufactured by Clontech), and the resulting plasmid was introduced into E. coli strain DH5α. The nucleotide sequence on the plasmid isolated from the obtained recombinant strain was confirmed in accordance with routine procedures, and the plasmid was designated as pMW119::ER.

Example 7

Generation of E. coli Strains Having an Ability to Produce Adipic Acid by Introduction of the Nucleic Acids Encoding the Polypeptides Represented by SEQ ID NOs: 1, 2, 3, 4, 5, 6, and 213

The plasmid pBBR1MCS-2::ATCT2 produced in Reference Example 6 was introduced into E. coli strain BL21 (DE3) by electroporation (N M Calvin, P C Hanawalt. J. Bacteriol, 170 (1988), pp. 2796-2801). The strain after the introduction was cultured on LB agar medium containing 25 µg/mL kanamycin at 37° C. The resulting recombinant strain was designated as BL21 (DE3)/pBBR1MCS-2::ATCT2.

The plasmid pCDF-1b::EHa produced in Reference Example 4 was introduced into the BL21 (DE3)/pBBR1MCS-2::ATCT2 by electroporation. The strain after the introduction was cultured on LB agar medium containing 25 µg/mL kanamycin and 50 g/mL streptomycin at 37° C. The resulting recombinant strain was designated as BL21 (DE3)/pBBR1MCS-2::ATCT2/pCDF-1b::EHa.

The plasmid pMW119::ER produced in Reference Example 7 was introduced into the BL21 (DE3)/pBHR1MCS-2::ATCT2/pCDF-1b::EHa by electroporation. The strain after the introduction was cultured on LB agar medium containing 25 µg/mL kanamycin, 50 µg/mL streptomycin, and 100 µg/mL ampicillin at 37° C. The resulting recombinant strain was designated as BL21 (DE3)/pBBR1MCS-2::ATCT2/pCDF-1b::EHa/pMW119::ER.

Each of the seven plasmids produced in Reference Example 2 was individually introduced into the BL21 (DE3)/pBBR1MCS-2::ATCT2/pCDF-1b::EHa/pMW119::ER by electroporation. The strains after the introduction were cultured on LB agar medium containing 25 µg/mL kanamycin, 50 µg/mL streptomycin, 100 µg/mL ampicillin, and 15 µg/ml chloramphenicol at 37° C. The recombinant strain in which "pACYCDuet-1::Smr1" is introduced is designated as "Ec/Smr1_ADA"; the recombinant strain in which "pACYCDuet-1::Snm1" is introduced is designated as "Ec/Snm1_ADA"; the recombinant strain in which "pACYCDuet-1::Spl1" is introduced is designated as "Ec/Spl1_ADA"; the recombinant strain in which "pACYCDuet-1::Spe1" is introduced is designated as "Ec/Spe1_ADA"; the recombinant strain in which "pACYCDuet-1::Sur1" is introduced is designated as "Ec/Sur1_ADA"; the recombinant strain in which "pACYCDuet-1::Ssp1" is introduced is designated as "Ec/Ssp1_ADA"; and the recombinant strain in which "pACYCDuet-1::Slq1" is introduced is designated as "Ec/Slq1_ADA". The information about the recombinant strains obtained in this example is presented in Table 11.

Comparative Example 8

Generation of E. coli Strains Having an Ability to Produce Adipic Acid by Introduction of Each of the Nucleic Acids Encoding 3-Oxoadipyl-CoA Reductases Each of the plasmids produced in Reference Example 3, namely "pACYCDuet-1::Ppu1", "pACYCDuet-1::Eco1", "pACYCDuet-1::Aci1" and "pACYCDuet-1::Spl2" was individually introduced into the BL21 (DE3)/pBBR1MCS-2::ATCT2/pCDF-1b::EHa/pMW119::ER by electroporation. The strains after the introduction were cultured on LB agar medium containing 25 µg/mL kanamycin, 50 µg/mL streptomycin, 100 µg/mL ampicillin, and 15 µg/mL chloramphenicol at 37° C.

The recombinant strain in which "pACYCDuet-1::Ppu1" is introduced is designated as "Ec/Ppu1_ADA"; the recombinant strain in which "pACYCDuet-1::Eco1" is introduced is designated as "Ec/Eco1_ADA"; the recombinant strain in which "pACYCDuet-1::Aci1" is introduced is designated as "Ec/Aci1_ADA"; and the recombinant strain in which "pACYCDuet-1::Spl2" is introduced is designated as "Ec/Spl2_ADA". The information about the recombinant strains obtained in this comparative example is presented in Table 1.

Example 8

Test for Adipic Acid Production Using the E. coli Strains Having an Ability to Produce Adipic Acid by Introduction of the Nucleic Acids Encoding the Polypeptides Represented by SEQ ID NOs: 1, 2, 3, 4, 5, 6, and 213

The E. coli strains produced in Example 7 were used to perform a test for adipic acid production. A loopful of each recombinant E. coli strain produced in Example 3 was inoculated into 5 mL of the culture medium 1 (10 g/L Bacto Tryptone (manufactured by Difco Laboratories), 5 g/L Bacto Yeast Extract (manufactured by Difco Laboratories), 5 g/L sodium chloride, 25 µg/mL kanamycin, 50 µg/mL streptomycin, 100 µg/mL ampicillin, and 15 µg/mL chloramphenicol) adjusted to pH 7, and incubated at 30° C. with shaking at 120 $min^{-1}$ for 18 hours. Subsequently, 0.25 mL of the culture fluid was added to 5 mL of the culture medium II (10 g/L succinic acid, 10 g/L glucose, 1 g/L ammonium sulfate, 50 mM potassium phosphate, 0.025 g/L, magnesium sulfate, 0.0625 mg/L iron sulfate, 2.7 mg/L manganese sulfate, 0.33 mg/L calcium chloride, 1.25 g/L sodium chloride, 2.5 g/L Bacto Tryptone, 1.25 g/L Bacto Yeast Extract, 25 µg/mL kanamycin, 50 µg/mL streptomycin, 100 g/ml, ampicillin, and 15 µg/mL chloramphenicol, and 0.01 mM IPTG) adjusted to pH 6.5, and incubated at 30° C. with shaking at 120 $min^{-1}$ for 24 hours.

Quantitative Analyses of Adipic Acid and Carbon Sources

The supernatant separated from bacterial cells by centrifugation of the culture fluid was processed by membrane treatment using Millex-GV (0.22 μm; PVDF: manufactured by Merck KGaA), and the resulting filtrate was analyzed by LC-MS/MS in the same manner as in Example 2. The results of the quantitative analysis of adipic acid accumulated in the culture supernatant, and the yield of adipic acid calculated according to the formula (3) are presented in Table 11.

Comparative Example 9

Test for Adipic Acid Production Using the *E. coli* Strains Having an Ability to Produce Adipic Acid by Introduction of Each of the Nucleic Acids Encoding 3-Oxoadipyl-CoA Reductases The results of a test for adipic acid production performed in the same manner as in Example 8 by using the *E. coli* strains produced Comparative Example 8 are presented in Table 11.

The results presented in Table 11 indicate that the yield of adipic acid was increased in the recombinant strains used in Example 8 compared to that in the recombinant strains used in Comparative Example 9. That is, it was demonstrated that the production of adipic acid was significantly increased by introduction of any of the nucleic acids encoding the polypeptides represented by SEQ ID NOs: 1, 2, 3, 4. 5, 6, and 213 into microorganisms.

TABLE 11

| | Strain | ADA Concentration (mg/L) | ADA Yield (%) |
|---|---|---|---|
| Example 8 | Ec/Smr1_ADA | 5.18 | 0.076 |
| | Ec/Snm1_ADA | 6.94 | 0.084 |
| | Ec/Spl1_ADA | 5.38 | 0.075 |
| | Ec/Spe1_ADA | 6.01 | 0.093 |
| | Ec/Sur1_ADA | 7.93 | 0.101 |
| | Ec/Ssp1_ADA | 4.76 | 0.072 |
| | Ec/Slq1_ADA | 6.82 | 0.082 |
| Comparative Example 9 | Ec/Ppu1_ADA | N.D. | N.D. |
| | Ec/Eco1_ADA | N.D. | N.D. |
| | Ec/Aci1_ADA | N.D. | N.D. |
| | Ec/Spl2_ADA | N.D. | N.D. |

Example 9

Confirmation of 3-Oxoadipyl-CoA Reductase Activity of the Polypeptides Represented by SEQ ID NOs: 2 and 4

Each of the plasmids produced in Reference Example 2, namely pACYCDuet-1::Snm1 and pACYCDuet-1::Spe1, was introduced into *E. coli* strain BL21 (DE3) by electroporation. The strains after the introduction were cultured on LB agar medium containing 15 μg/mL chloramphenicol at 37° C. The resulting recombinant strains were designated as BL21 (DE3)/pACYCDuet-1::Snm1 and BL21 (DE3)/pACYCDuet-1::Spe1.

A loopful of either the BL21 (DE3)/pACYCDuet-1::Snm1 or the BL21 (DE3)/pACYCDuet-1::Spe1 was inoculated into 20 mL of the culture medium I (10 g/l, Bacto Tryptone (manufactured by Difco Laboratories), 5 g/L Bacto Yeast Extract (manufactured by Difco Laboratories), 5 g/L sodium chloride, and 15 μg/mL chloramphenicol) adjusted to pH 7, and incubated at 37° C. with rotation at 120 rpm for 17 hours. Subsequently, 10 mL of the culture fluid was added to 2 L of the culture medium 1, and incubated at 37° C. with shaking at 100 min$^{-1}$ for 2 hours. The culture fluid was supplemented with IPTG to a concentration of 500 μM, and incubated at 16° C. with shaking at 100 min$^{-1}$ for 18 hours. The culture fluid was then centrifuged at 6000 rpm at 4° C. for 15 minutes to remove the supernatant, and the resulting cell pellet was suspended in the Binding Buffer provided in the His-Bind Buffer Kit (manufactured by Merck KGaA). The obtained cell suspension was subjected to sonication with Digital Sonifier (manufactured by Branson Ultrasonics Co.), while being cooled on ice. The sonicated solution was centrifuged at 13,000 rpm at 4° C. for 30 minutes, and the obtained supernatant was designated as cell homogenate.

A suitable volume of the His-Bind Resin solution was added to 30 mL of the cell homogenate, and the resulting solution was incubated at 4° C. for 1 hour. The solution was centrifuged at 4000 rpm at 4° C. for 5 minutes to remove 20 mL of the supernatant, and the remaining His-Bind Resin solution was then loaded onto a column, which was washed with 10 mL of the Binding Buffer twice, and subsequently with 10 mL of the Wash Buffer 1 (with 25 mM imidazole) twice, and then 10 mL of the Wash Buffer 2 (with 60 mM imidazole) twice. Finally, elution was performed with 2 mL of the Elution Buffer (with 1 mM imidazole) four times, and the resulting fractions were collected.

A fraction showing a band corresponding to a polypeptide of around 55 kDa, which is equal to the molecular weight of each of the target enzymes, was centrifuged at 8000 rpm at 4° C. for 15 minutes to remove the supernatant, and 5 mL of the Strage Buffer was then added to the remains for washing. The resulting suspension was further centrifuged at 8000 rpm at 4° C. for 15 minutes to remove the supernatant, and 3 mL of the Strage Buffer was then added to the remains, and this operation was repeated twice in total. The obtained solutions were designated as enzyme solutions Snm1 and Spe1.

Preparation of 3-oxoadipic acid: Preparation of 3-oxoadipic acid was performed according to the method described in Reference Example 1 of WO 2017/099209.

Preparation of 3-oxoadipyl-CoA solution: The pRSF-1b expression vector (manufactured by Novagen), which is capable of autonomous replication in *E. coli*, was cleaved with KpnI to obtain pRSF-1b/KpnI. To amplify a gene encoding an enzyme catalyzing the reaction E, primers (SEQ ID NOs: 230 and 231) were designed for use in amplification of the full-length CoA transferase genes pcaI and pcaJ (NCBI-GeneIDs: 1046613 and 1046612, SEQ ID NOs: 23 and 24) by PCR using the genomic DNA of *Pseudomonas putida* strain KT2440 as a template, and a PCR reaction was performed in accordance with routine procedures. The resulting fragment and the pRSF-1b/KpnI were ligated together using the In-Fusion HD Cloning Kit (manufactured by Clontech), and the resulting plasmid was introduced into *E. coli* strain DH5α. The nucleotide sequence on the plasmid extracted from the obtained recombinant strain was confirmed in accordance with routine procedures. The obtained plasmid was designated as "pRSF-1b::CT".

The pRSF-1b::CT was introduced into *E. coli* BL21 (DE3), and expression of the enzyme was induced with isopropyl-β-thiogalactopyranoside (IPTG) in accordance with routine procedures and the enzyme was purified using the histidine tag from the culture fluid to obtain a CoA transferase solution. The solution was used to prepare an enzymatic reaction solution for 3-oxoadipyl-CoA preparation with the following composition, which was allowed to react at 25° C. for 3 minutes and then filtered through a UF membrane (Amicon Ultra-0.5 mL 10K; manufactured by Merck Millipore) to remove the enzyme, and the obtained filtrate was designated as 3-oxoadipyl-CoA solution.

Enzymatic reaction solution for 3-oxoadipyl-CoA preparation:
- 100 mM Tris-HCl (pH 8.2)
- 10 mM MgCl$_2$
- 0.5 mM succinyl-CoA
- 5 mM 3-oxoadipic acid sodium salt
- 2 µM CoA transferase.

Identification of 3-oxoadipyl-CoA reductase activity: The 3-oxoadipyl-CoA reductase activity was determined by measuring 3-hydroxyadipyl-CoA production. Each of the enzyme solutions Snm1 and Spe1 was used to prepare an enzymatic reaction solution with the following composition, which was allowed to react at 25° C. for 1 hour and then processed by membrane treatment using Millex-GV (0.22 µm; PVDF; manufactured by Merck KGaA), and the resulting filtrate was analyzed by LC-MS/MS in the same manner as in Example 2. In this respect, the concentration of 3-oxoadipyl-CoA was measured according to a method of Kaschabek et al. (J Bacteriol. 2002 January: 184 (1): 207-215), and adjusted to 15 µM in the enzymatic reaction solution. The result is presented in Table 12, along with the result from a similar reaction as a control in which Tris-HCl is added instead of the enzyme solution.

- 100 mM Tris-HCl (pH 8.2)
- 10 mM MgCl$_2$
- 150 µL/mL 3-oxoadipyl-CoA solution
- 0.5 mM NADH
- 1 mM dithiothreitol
- 10 µM 3-oxoadipyl-CoA reductase.

The results presented in Table 12 confirmed production of 3-hydroxyadipyl-CoA in the reactions using the enzyme solutions Snm1 and Spe1. In contrast, 3-hydroxyadipyl-CoA was not detected in the control. Thus, it was demonstrated that the enzyme solutions Snm1 and Spe1 had 3-oxoadipyl-CoA reductase activity.

TABLE 12

|  | Enzyme Solution | 3-hydroxyadipyl-CoA concentration (µM) |
| --- | --- | --- |
| Example 9 | Snm1 | 13.9 |
|  | Spe1 | 13.8 |
|  | control | N.D. |

The invention claimed is:

1. A genetically modified non-naturally occurring microorganism comprising a genetic modification in which a nucleic acid encoding a polypeptide is introduced or expression of the polypeptide is enhanced as compared to an otherwise identical microorganism without the genetic modification, so as to increase an amount of 3-hydroxy adipic acid, α-hydromuconic acid or adipic acid produced by said non-naturally occurring microorganism compared to an otherwise identical microorganism without the genetic modification;
   wherein the polypeptide is composed of an amino acid sequence selected from the group consisting of SEQ ID NOs: 1 to 6 and 213; and
   wherein an amount of 3-hydroxy adipic acid, α-hydromuconic acid or adipic acid produced by said non-naturally occurring microorganism is increased compared to an otherwise identical microorganism without the genetic modification.

2. The genetically modified non-naturally occurring microorganism according to claim 1, which is a genetically modified microorganism selected from the group consisting of the genera *Escherichia*, *Serratia*, *Hafnia*, and *Pseudomonas*.

3. The genetically modified non-naturally occurring microorganism according to claim 1, which has an ability to generate 3-oxoadipyl-CoA and coenzyme A from acetyl-CoA and succinyl-CoA; and an ability to generate 3-hydroxyadipic acid from 3-hydroxyadipyl-CoA.

4. The genetically modified non-naturally occurring microorganism according to claim 1, which has an ability to generate 3-oxoadipyl-CoA and coenzyme A from acetyl-CoA and succinyl-CoA; an ability to generate 2,3-dehydroadipyl-CoA from 3-hydroxyadipyl-CoA; and an ability to generate a-hydromuconic acid from 2,3-dehydroadipyl-CoA.

5. The genetically modified non-naturally occurring microorganism according to claim 1, which has an ability to generate 3-oxoadipyl-CoA and coenzyme A from acetyl-CoA and succinyl-CoA; an ability to generate 2,3-dehydroadipyl-CoA from 3-hydroxyadipyl-CoA; an ability to generate adipyl-CoA from 2,3-dehydroadipyl-CoA; and an ability to generate adipic acid from adipyl-CoA.

6. A method of producing 3-hydroxyadipic acid, comprising culturing the genetically modified non-naturally occurring microorganism according to claim 3 in a culture medium containing a carbon source as a material for fermentation.

7. A method of producing a-hydromuconic acid, comprising culturing the genetically modified non-naturally occurring microorganism according to claim 4 in a culture medium containing a carbon source as a material for fermentation.

8. A method of producing adipic acid, comprising culturing the genetically modified non-naturally occurring microorganism according to claim 5 in a culture medium containing a carbon source as a material for fermentation.

* * * * *

SEQUENCE LISTING

<160> NUMBER OF SEQ ID NOS: 231

<210> SEQ ID NO 1
<211> LENGTH: 509
<212> TYPE: PRT
<213> ORGANISM: Serratia marcescens ATCC13880

<400> SEQUENCE: 1

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Gly Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys His Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Ala Gln Ile Asp Arg Ala Leu Lys
```

```
                210                 215                 220
Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Thr Ala Pro Pro Val Thr Ala Ala Ser Asn Ala Asp Val Glu
        290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ser Ala Val Gln Ile Asn Asp Ala Phe Thr Val
            340                 345                 350

Ser Ile Thr Asp Gly Arg Thr Ala Ser Gln Leu Ala Glu Gln Thr Ala
            355                 360                 365

Ala Asp Ala Phe Val Val Asp Val Ala Leu Asn Tyr Ala Asp Thr Thr
        370                 375                 380

Tyr Leu Ala Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Gly Gly Ile Phe
        450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 2
<211> LENGTH: 509
<212> TYPE: PRT
<213> ORGANISM: Serratia nematodiphila DSM21420

<400> SEQUENCE: 2

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Pro Thr Met Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
        50                  55                  60

Ala Leu Arg Asp Lys Asp Ala Val Leu Ala Asn Leu Met Phe Thr Ser
65                  70                  75                  80
```

```
Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Ala Gln Ile Asp Arg Ala Leu Lys
210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Pro Val Thr Ala Ala Asn Asn Ala Asp Val Glu
290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Gln Ile Asn Asp Ala Phe Thr Val
            340                 345                 350

Ser Ile Thr Asp Gly Arg Thr Ala Ser Gln Leu Ala Glu Gln Thr Ala
        355                 360                 365

Ala Asp Ala Phe Val Val Asp Leu Ala Leu Asn Tyr Ala Asp Thr Thr
370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Gly Gly Ile Phe
450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
```

<210> SEQ ID NO 3
<211> LENGTH: 509
<212> TYPE: PRT
<213> ORGANISM: Serratia plymuthica NBRC102599

<400> SEQUENCE: 3

Met Ala Glu Asn Asn Ser Ala Ile Arg Ser Ala Val Ile Gly Ala
1               5                   10                  15

Gly Thr Met Gly Arg Gly Ile Ala Tyr Leu Leu Ala Leu Asn Gly Ile
            20                  25                  30

Arg Thr Val Leu Tyr Asn Arg Asn Gly Asn Asn Leu Asn Gln Ala Arg
        35                  40                  45

Asp Tyr Ile Val Ser Asp Leu Asp Arg Lys Ile Asp Asn Gly Lys Ile
    50                  55                  60

Thr Leu Gln Lys Lys Gly Gln Ile Leu Ala Asn Ile Ile Phe Ser Asp
65                  70                  75                  80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ala Ile Ala Ala Thr
            100                 105                 110

Val Lys Pro Glu Ala Ile Ile Ala Thr Asn Thr Ser Ser Leu Ser Leu
        115                 120                 125

Asn Lys Leu Ala Ala Gly Val Glu Asn Asn Pro Arg Phe Ile Gly Leu
130                 135                 140

His Phe Phe Asn Pro Ala Pro Leu Met Lys Leu Ile Glu Ile Ile Pro
145                 150                 155                 160

Ser Tyr Phe Thr Ser Arg Ala Thr Ser Leu Arg Cys Gln Gln Leu Val
                165                 170                 175

Thr Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
                245                 250                 255

Gln Phe Asp Pro Arg Tyr Thr Pro Gly His Leu Gln Arg Ser Leu Val
            260                 265                 270

Asp Ala Gly Leu Leu Gly Arg Lys Asn Gly Arg Ser Phe Phe Ala Ser
        275                 280                 285

Gln Pro Ala Thr Pro Pro Asn Pro Thr Thr Glu Gly Asp Thr Pro Thr
    290                 295                 300

Ser Leu His Phe Tyr Gly Glu His Ala Leu Phe Asp His Leu Gln Gln
305                 310                 315                 320

Arg Ala Leu Ala Thr Trp Pro Ala Leu Arg Val Gln Arg Leu Pro Glu
                325                 330                 335

Arg Pro Glu Leu Gly Arg Phe Ile Leu Val Asn Asn Arg Leu Ala Ile
            340                 345                 350

Lys Ile Thr Asp Gly Arg Thr Ala Asn Leu Leu Ala Gly Leu Thr Ala
        355                 360                 365

```
Leu Asp Thr Phe Val Ile Asp Ala Ala Leu Asn Tyr Ala Asp Thr Ala
    370                 375                 380

Tyr Leu Val Ala Ala His Asn Gln His Ala Thr Glu Thr Asn Lys Ala
385                 390                 395                 400

Leu Phe Leu Thr Leu Leu Gln Thr Leu Ile Ala Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Ala Asp
        435                 440                 445

Ile Asp Ile Ala Ala Val Ala Gly Val Asn Tyr Ala Asp Gly Ile Phe
    450                 455                 460

Ala Trp Leu Ala Gln Leu Gly Gln Lys Asn Val Lys Ser Thr Leu Asp
465                 470                 475                 480

Asn Met Ala Gln Leu Leu His Ser Thr Arg Tyr Tyr Pro His Tyr Ser
                485                 490                 495

Leu Leu Asn Ala Ala Arg Pro Glu Leu Ala Val Ala Pro
            500                 505

<210> SEQ ID NO 4
<211> LENGTH: 509
<212> TYPE: PRT
<213> ORGANISM: Serratia proteamaculans 568

<400> SEQUENCE: 4

Met Ala Glu Asn Asn Ser Ala Ile His Ser Val Ala Val Ile Gly Ala
1               5                   10                  15

Gly Thr Met Gly Arg Gly Ile Ala Tyr Leu Leu Ala Gln Asn Gly Ile
                20                  25                  30

Arg Thr Leu Leu Tyr Asn Arg Ser Gly Asn Asn Leu Asn Gln Ala Arg
            35                  40                  45

Asp Tyr Ile Ile Arg Asp Leu Asp Lys Lys Ile Asp Gly Gly Lys Ile
    50                  55                  60

Ser Pro Gln Lys Lys Gly Glu Ile Leu Ala Asn Leu Val Phe Ser Pro
65                  70                  75                  80

Ile Phe Glu Ala Ile Ala Asp Ser Asp Leu Val Ile Glu Thr Ile Ala
                85                  90                  95

Glu His Glu Ala Thr Lys His Glu Ile Leu Ala Ala Ile Ala Ala Thr
                100                 105                 110

Val Lys Lys Glu Ala Ile Ile Ala Thr Asn Thr Ser Ser Leu Ser Leu
            115                 120                 125

Asn Lys Leu Ala Ala Gly Val Glu Asn Asn Ala Arg Phe Ile Gly Leu
    130                 135                 140

His Phe Phe Asn Pro Ala Pro Leu Met Lys Leu Ile Glu Ile Ile Pro
145                 150                 155                 160

Ser Tyr Phe Thr Ser Arg Ala Thr Ser Leu Arg Cys Gln Gln Leu Val
                165                 170                 175

Thr Ala Ile Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
    195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240
```

```
Gly Gln Asp Ile Asn Tyr Gln Val Ser Ser Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Phe Phe Thr Pro
        275                 280                 285

Ser Ser Ala Glu Pro Ser Ser Ala Asp Ala Gly Ser Gly Thr Pro Thr
    290                 295                 300

Ser Leu Asn Phe Tyr Gly Glu His Pro Leu Phe Asp Leu Leu Gln Gln
305                 310                 315                 320

Arg Ala Leu Ala Leu Trp Pro Arg Val Gln Ile Asn Arg Gln Ser Glu
                325                 330                 335

Gln Pro Thr Leu Gly Arg Phe Ile Arg Val Asn Asp Ala Met Ala Ile
            340                 345                 350

Lys Ile Thr Asp Gly Arg Thr Ala Asn Leu Leu Ala Glu Leu Thr Glu
        355                 360                 365

Leu Asp Thr Phe Val Ile Asp Ala Ala Leu Asn Tyr Ala Asp Thr Ala
    370                 375                 380

Tyr Leu Ala Ala Ala His Ser Gln Asp Ala Ser Ala Ala Asn Lys Ala
385                 390                 395                 400

Leu Phe Leu Thr Leu Leu Gln Thr Leu Ile Pro Gln Val Glu Phe Ile
                405                 410                 415

Lys Asp Ser Pro Gly Leu Ile Val Ala Arg Val Leu Ser Ser Leu Ile
            420                 425                 430

Asn Glu Ser Val Ile Met Val Glu Ser Gly Val Cys Ser Arg Ala Asp
        435                 440                 445

Ile Asp Ile Ala Ala Val Ala Gly Val Asn Tyr Ala Asp Gly Ile Phe
    450                 455                 460

Ser Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Thr Pro Arg Pro Glu Leu Ala Val Ala Pro
            500                 505

<210> SEQ ID NO 5
<211> LENGTH: 509
<212> TYPE: PRT
<213> ORGANISM: Serratia ureilytica Lr5/4

<400> SEQUENCE: 5

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
            20                  25                  30

Arg Thr Val Leu Tyr Asn Arg Asn Gly Asn Thr Leu Asn Gln Ala Arg
        35                  40                  45

Asp Ala Ile Val Gln Asp Leu Asn Lys Lys Val Glu Gln Gly Lys Leu
    50                  55                  60

Ala Leu Gln Asp Lys Asp Ala Val Leu Ala Asn Leu Thr Phe Ser Ala
65                  70                  75                  80

Glu Phe Gly Ala Ile Ala Asp Ser Asp Leu Val Ile Glu Thr Ile Ala
                85                  90                  95

Glu His Glu Gln Ala Lys Leu Glu Val Leu Ala Ala Ile Ala Ala Thr
```

```
             100                 105                 110
Val Lys Pro Asp Thr Leu Ile Ala Thr Asn Thr Ser Ser Leu Ser Leu
         115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
        275                 280                 285

Glu Glu Ser Pro Pro Pro Leu Ala Ala Val Asp Ala Glu Val Glu
    290                 295                 300

Thr Leu Arg Ile Tyr Gly Glu His Pro Leu Phe Thr Leu Leu Gln Gln
305                 310                 315                 320

Arg Ala Thr Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
        355                 360                 365

Ala Asp Ala Phe Val Val Asp Val Ala Leu Asn Tyr Gly Asp Thr Ala
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
    450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505
```

<210> SEQ ID NO 6

```
<211> LENGTH: 509
<212> TYPE: PRT
<213> ORGANISM: Serratia sp. BW106

<400> SEQUENCE: 6
```

| | | | | | | | | | | | | | | |
|---|---|---|---|---|---|---|---|---|---|---|---|---|---|---|
| Met | Ala | Glu | Asn | Asn | Ser | Ala | Ile | His | Ser | Val | Ala | Val | Ile | Gly | Ala |
| 1 | | | | 5 | | | | | 10 | | | | | 15 | |

Gly Thr Met Gly Arg Gly Ile Ala Tyr Leu Leu Ala Gln Asn Gly Ile
          20                  25                  30

Arg Thr Leu Leu Tyr Asn Arg Ser Gly Asn Asn Leu Asp Gln Ala Arg
         35                  40                  45

Asp Tyr Ile Ile Arg Asp Leu Asp Lys Lys Ile Asp Asn Gly Lys Ile
 50                  55                  60

Ser Gln Gln Lys Lys Gly Glu Val Leu Ala Asn Leu Val Phe Ser Pro
 65                  70                  75                  80

Ile Phe Asp Ala Ile Ala Asp Ser Asp Leu Val Ile Glu Thr Ile Ala
                 85                  90                  95

Glu His Glu Thr Thr Lys His Glu Ile Leu Ala Ile Ala Ala Thr
                100                 105                 110

Val Lys Gln Glu Ala Ile Ile Ala Thr Asn Thr Ser Ser Leu Ser Leu
         115                 120                 125

Asn Lys Leu Ala Ala Gly Val Glu Asn Asn Ala Arg Phe Ile Gly Leu
 130                 135                 140

His Phe Phe Asn Pro Ala Pro Leu Met Lys Leu Ile Glu Ile Ile Pro
145                 150                 155                 160

Ser Tyr Phe Thr Ser Arg Ala Thr Ser Leu Arg Cys Gln Gln Leu Val
                165                 170                 175

Thr Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Ser Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Phe Phe Ala Ala
        275                 280                 285

Pro Ser Ser Glu Ser Asn Pro Leu Asp Ala Gly Asn Gly Thr Leu Thr
    290                 295                 300

Ser Leu His Phe Tyr Gly Glu His Thr Leu Phe Asp Leu Leu Gln Gln
305                 310                 315                 320

Arg Ala Leu Ala Ile Trp Pro Thr Leu Gln Ile His Gln Pro Glu
                325                 330                 335

Arg Pro Thr Leu Gly Arg Phe Ile Arg Val Asn Asp Ala Leu Ala Val
            340                 345                 350

Lys Ile Thr Asp Gly Arg Thr Ala Asn Leu Leu Ala Glu Leu Thr Asp
        355                 360                 365

Leu Asp Thr Phe Val Ile Asp Ala Ala Leu Asn Tyr Ser Asp Thr Ala
    370                 375                 380

Tyr Leu Val Ala Ala His Asn Gln Asp Ala Ala Glu Ala Asn Lys Ala

```
                385                 390                 395                 400
Leu Phe Leu Ser Leu Leu Gln Thr Leu Ile Pro Gln Val Glu Phe Ile
                405                 410                 415

Lys Asp Ser Pro Gly Leu Ile Val Ala Arg Val Leu Ser Ser Leu Ile
            420                 425                 430

Asn Glu Ser Val Ile Met Val Glu Ser Gly Val Cys Ser Arg Ala Asp
        435                 440                 445

Ile Asp Ile Ala Ala Val Ala Gly Val Asn Tyr Ala Asp Gly Ile Phe
    450                 455                 460

Ala Trp Leu Thr Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Ala Pro Arg Pro Glu Leu Ala Val Ala Pro
                500                 505

<210> SEQ ID NO 7
<211> LENGTH: 509
<212> TYPE: PRT
<213> ORGANISM: Serratia sp. S119

<400> SEQUENCE: 7

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
        50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Asp Leu Val Ile Glu Thr Ile Ala
                85                  90                  95

Glu Gln Glu Gln Thr Lys Leu Glu Val Leu Ala Ala Ile Ala Ala Ala
                100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255
```

Gln Tyr Asp Pro Arg Tyr Thr Pro Gly His Leu Gln Arg Ser Leu Val
              260                 265                 270

Asp Ala Gly Leu Leu Gly Lys Lys Asn Gly Arg Ser Tyr Phe Ala Ala
          275                 280                 285

Glu Glu Asn Ala Leu Pro Val Thr Ala Ala Thr Asp Ala Asp Val Glu
      290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
              325                 330                 335

Leu Pro Gly Leu Gly Pro Ala Val Gln Ile Asn Glu Ala Phe Thr Val
          340                 345                 350

Ser Val Thr Asp Gly Arg Thr Ala Ser Gln Leu Ala Glu Leu Thr Ala
      355                 360                 365

Ala Asp Ala Phe Val Val Asp Val Ala Leu Asn Tyr Ala Asp Thr Ala
370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
              405                 410                 415

Lys Asp Ser Pro Ala Leu Ile Val Ala Arg Val Leu Ser Ser Leu Ile
          420                 425                 430

Asn Glu Ser Val Ile Met Val Glu Ser Gly Val Cys Ser Arg Glu Asp
      435                 440                 445

Ile Asn Val Ala Ala Val Ala Gly Val Asn Tyr Ala Asp Gly Ile Phe
450                 455                 460

Gly Leu Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
              485                 490                 495

Leu Leu His Ala Ala Gln Pro Ala Leu Thr Thr Thr Pro
          500                 505

<210> SEQ ID NO 8
<211> LENGTH: 509
<212> TYPE: PRT
<213> ORGANISM: Serratia sp. YD25

<400> SEQUENCE: 8

Met Ala Glu Arg Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
              20                  25                  30

Arg Thr Val Leu Tyr Asn Arg Asn Gly Asn Thr Leu Ile Gln Ala Arg
          35                  40                  45

Glu Tyr Ile Val Gln Asp Leu Asp Lys Lys Val Glu Gln Gly Arg Leu
      50                  55                  60

Ala Pro Gln Asp Lys Asp Ala Val Leu Ala Asn Leu Gln Phe Ser Ser
65                  70                  75                  80

Val Phe Glu Ala Ile Val Asp Ser Asp Leu Val Leu Thr Ile Ala
              85                  90                  95

Glu Gln Glu Gln Ala Lys Leu Glu Val Leu Ala Ala Ile Ala Ala Ala
          100                 105                 110

Val Lys Pro Asp Thr Leu Ile Ala Thr Asn Thr Ser Ser Leu Ser Leu
      115                 120                 125

-continued

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Thr Gln Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
        275                 280                 285

Glu Glu Thr Ala Pro Pro Val Glu Ala Ala Glu Ala Asp Val Glu
290                 295                 300

Thr Leu Arg Ile Tyr Gly Glu His Pro Leu Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Ser Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
        355                 360                 365

Ala Asp Ala Phe Val Val Asp Val Ala Leu Asn Tyr Ala Asp Thr Ala
370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Leu Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
450                 455                 460

Gly Trp Leu Thr Arg Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 9
<211> LENGTH: 509
<212> TYPE: PRT
<213> ORGANISM: Serratia sp. FS14

<400> SEQUENCE: 9

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Pro Thr Met Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
        50                  55                  60

Ala Leu Gln Asp Lys Asp Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
                100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Ala Gln Ile Asp Arg Ala Leu Lys
    210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Val Thr Ala Ala Asn Asn Ala Asp Val Glu
290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Gln Ile Asn Asp Ala Phe Thr Val
            340                 345                 350

Ser Ile Thr Asp Gly Arg Thr Ala Ser Gln Leu Ala Glu Gln Thr Ala
        355                 360                 365

Ala Asp Ala Phe Val Val Asp Val Ala Leu Asn Tyr Ala Asp Thr Thr
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415
```

```
Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Gly Gly Ile Phe
450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 10
<211> LENGTH: 509
<212> TYPE: PRT
<213> ORGANISM: Serratia sp. HMSC15F11

<400> SEQUENCE: 10

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Asp Tyr Ile Glu Leu Asp Leu Asn Lys Val Glu Gln Gly Lys Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ile Ala Ala Ala
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Ala Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Val
```

```
                275                 280                 285
Glu Glu Asn Ala Pro Pro Val Met Ala Ala Thr Asp Ala Asp Ile Glu
290                 295                 300

Thr Leu His Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Pro Ala Val Arg Ile Asn Asp Ala Phe Thr Val
                340                 345                 350

Ser Ile Thr Asp Gly Arg Thr Ala Asn Gln Leu Ala Glu Gln Thr Ala
                355                 360                 365

Ala Asp Ala Phe Val Val Asp Val Ala Leu Asn Tyr Ala Asp Thr Ala
                370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
                435                 440                 445

Ile Asp Val Ala Ala Val Ala Gly Val Asn Tyr Ala Asp Gly Ile Phe
                450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505

<210> SEQ ID NO 11
<211> LENGTH: 509
<212> TYPE: PRT
<213> ORGANISM: Serratia sp. JKS000199

<400> SEQUENCE: 11

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
                20                  25                  30

Arg Thr Val Leu Tyr Asn Arg Asn Gly Asn Thr Leu Asn Gln Ala Arg
                35                  40                  45

Asp Ala Ile Val Gln Asp Leu Asn Lys Lys Val Glu Gln Gly Lys Leu
                50                  55                  60

Ala Leu Gln Asp Lys Asp Ala Val Leu Ala Asn Leu Thr Phe Ser Thr
65                  70                  75                  80

Glu Phe Gly Ala Ile Ala Asp Ser Asp Leu Val Ile Glu Thr Ile Ala
                85                  90                  95

Glu His Glu Gln Ala Lys Leu Glu Val Leu Ala Ala Ile Ala Ala Thr
                100                 105                 110

Val Lys Pro Asp Thr Leu Ile Ala Thr Asn Thr Ser Ser Leu Ser Leu
                115                 120                 125

Asn Lys Leu Ala Thr Ala Val Thr His Ser Glu Arg Phe Ile Gly Leu
                130                 135                 140
```

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ser Ala
            275                 280                 285

Glu Glu Ser Pro Pro Pro Leu Ala Ala Ala Val Asp Ala Glu Val Glu
    290                 295                 300

Thr Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
                340                 345                 350

Ser Val Thr Asp Gly Arg Thr Ala Asn Gln Leu Ala Glu Gln Thr Ala
            355                 360                 365

Ala Asp Ala Phe Val Val Asp Val Ala Leu Asn Tyr Gly Asp Thr Ala
            370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Leu Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
            450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505

<210> SEQ ID NO 12
<211> LENGTH: 509
<212> TYPE: PRT
<213> ORGANISM: Serratia sp. TEL

<400> SEQUENCE: 12

Met Ala Glu Ser Asn Ala Ala Ile Gln Ser Ala Ala Ile Ile Gly Ala
1               5                   10                  15

-continued

```
Gly Thr Met Gly Arg Gly Ile Ala Tyr Leu Ala Gln Lys Ser Ile
        20                  25                  30
Arg Thr Val Leu Tyr Asn Arg Asn Gly Asn Thr Leu Asn Gln Ala Arg
        35                  40                  45
Asp Ala Ile Val Gln Asp Leu Asn Lys Val Glu Gln Gly Lys Leu
 50                  55                  60
Ala Leu Gln Asp Lys Asp Ala Val Leu Ala Asn Leu Thr Phe Ser Ala
 65                  70                  75                  80
Glu Phe Gly Ala Ile Ala Asp Ser Asp Leu Val Ile Glu Thr Ile Ala
                 85                  90                  95
Glu His Glu Gln Ala Lys Leu Glu Val Leu Ala Ala Ile Ala Ala Thr
                100                 105                 110
Val Lys Pro Asp Thr Leu Ile Ala Thr Asn Thr Ser Ser Leu Ser Leu
         115                 120                 125
Asn Lys Leu Ala Thr Ala Val Thr His Ser Glu Arg Phe Ile Gly Leu
130                 135                 140
His Phe Phe Asn Pro Ala Pro Leu Met Lys Leu Ile Glu Ile Ile Pro
145                 150                 155                 160
Ala Tyr Phe Thr Ala Gln Val Thr Thr Glu Arg Cys Arg Gln Leu Val
                165                 170                 175
Ala Ala Leu Gly Lys Arg Asp Val Val Cys Gln Ala Thr Pro Gly Phe
        180                 185                 190
Ile Val Asn Arg Met Ala Arg Pro Tyr Tyr Leu Glu Gly Phe Arg Leu
        195                 200                 205
Leu Glu Glu His Val Ala Arg Ala Pro Gln Ile Asp Arg Ala Leu Lys
    210                 215                 220
Ala Gly Gly His Phe Arg Met Gly Pro Leu Glu Leu Thr Asp Phe Ile
225                 230                 235                 240
Gly Gln Asp Ile Asn Tyr Gln Val Ser Arg Gln Ile Trp Gln Asp Met
                245                 250                 255
Gln Tyr Asp Pro Arg Tyr Thr Pro Gly His Leu Gln Arg Ser Leu Val
        260                 265                 270
Asp Ala Gly Leu Leu Gly Lys Lys Asn Gly Arg Ser Tyr Phe Ser Ala
        275                 280                 285
Glu Glu Ser Pro Pro Pro Leu Ala Ala Ala Val Asp Ala Glu Val Glu
    290                 295                 300
Thr Leu Arg Ile Tyr Gly Glu His Pro Leu Phe Thr Leu Leu Gln Gln
305                 310                 315                 320
Arg Ala Thr Leu Gln Trp Pro Arg Leu Arg Val Glu Gln Arg Pro Thr
                325                 330                 335
Leu Pro Gly Leu Gly Ala Ala Ile Gln Val Asn Asp Ala Phe Thr Val
        340                 345                 350
Ser Val Thr Asp Gly Arg Thr Ala Asn Gln Leu Ala Glu Gln Thr Ala
        355                 360                 365
Ala Asp Ala Phe Val Val Asp Val Ala Leu Asn Tyr Gly Asp Thr Ala
    370                 375                 380
Tyr Leu Val Ala Ala His Ser Arg His Ala Ser Ala Ala Asn Lys Ala
385                 390                 395                 400
Leu Phe Leu Arg Leu Leu His Thr Ala Ile Pro Gln Val Glu Phe Ile
                405                 410                 415
Lys Asp Ser Pro Ala Leu Ile Val Ala Arg Val Leu Ser Ser Leu Ile
        420                 425                 430
```

```
Asn Glu Ser Val Ile Met Val Glu Ser Gly Val Cys Ser Arg Glu Asp
            435                 440                 445

Ile Asp Val Ala Val Ala Gly Val Asn Tyr Ala Asp Gly Ile Phe
450                 455                 460

Gly Trp Leu Thr Arg Leu Gly Glu Glu Asn Val Arg Ala Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 13
<211> LENGTH: 509
<212> TYPE: PRT
<213> ORGANISM: Serratia sp. ISTD04

<400> SEQUENCE: 13

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
            20                  25                  30

Arg Thr Val Leu Tyr Asn Arg Asn Gly Asn Thr Leu Asn Gln Ala Arg
        35                  40                  45

Asp Ala Ile Val Gln Asp Leu Asn Lys Lys Val Glu Gln Gly Lys Leu
    50                  55                  60

Ala Leu Gln Asp Lys Asp Ala Val Leu Ala Asn Leu Thr Phe Ser Ala
65                  70                  75                  80

Glu Phe Gly Val Ile Ala Asp Ser Asp Leu Val Ile Glu Thr Ile Ala
                85                  90                  95

Glu His Glu Gln Ala Lys Leu Glu Val Leu Ala Ala Ile Ala Ala Thr
            100                 105                 110

Val Lys Ser Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
        275                 280                 285

Glu Glu Ser Pro Pro Leu Ala Ala Ala Val Asp Ala Glu Val Glu
    290                 295                 300
```

```
Thr Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
        355                 360                 365

Ala Asp Ala Phe Val Val Asp Val Ala Leu Asn Tyr Gly Asp Thr Ala
370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 14
<211> LENGTH: 509
<212> TYPE: PRT
<213> ORGANISM: Serratia sp. SCBI

<400> SEQUENCE: 14

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
                20                  25                  30

Arg Thr Val Leu Tyr Asn Arg Asn Gly Asn Thr Leu Asn Gln Ala Arg
            35                  40                  45

Asp Ala Ile Val Gln Asp Leu Asn Lys Lys Val Glu Gln Gly Lys Leu
        50                  55                  60

Ala Leu Gln Asp Lys Asp Ala Val Leu Ala Asn Leu Thr Phe Ser Ala
65                  70                  75                  80

Glu Phe Gly Ala Ile Ala Asp Ser Asp Leu Val Ile Glu Thr Ile Ala
                85                  90                  95

Glu His Glu Gln Ala Lys Leu Glu Val Leu Ala Ala Ile Ala Ala Thr
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
```

```
                165                 170                 175
Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
            210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ser Thr
                275                 280                 285

Glu Glu Ser Pro Pro Pro Leu Ala Ala Ala Val Asp Ala Glu Val Glu
            290                 295                 300

Thr Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
                355                 360                 365

Ala Asp Ala Phe Val Val Asp Val Leu Asn Tyr Gly Asp Thr Ala
            370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
            450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 15
<211> LENGTH: 509
<212> TYPE: PRT
<213> ORGANISM: Serratia sp. S4

<400> SEQUENCE: 15

Met Ala Glu Asn Asn Ser Ala Ile His Ser Val Ala Val Ile Gly Ala
1               5                   10                  15

Gly Thr Met Gly Arg Gly Ile Ala Tyr Leu Leu Ala Gln Asn Gly Ile
            20                  25                  30
```

```
Arg Thr Leu Leu Tyr Asn Arg Ser Gly Asn Asn Leu Asn Gln Ala Arg
             35                  40                  45

Asp Tyr Ile Ile Arg Asp Leu Asp Lys Lys Ile Asp Gly Gly Lys Ile
 50                  55                  60

Ser Leu Gln Lys Lys Gly Glu Ile Leu Ala Asn Leu Val Phe Ser Pro
 65                  70                  75                  80

Ile Phe Glu Ala Ile Ala Asp Ser Asp Leu Val Ile Glu Thr Ile Ala
                 85                  90                  95

Glu His Glu Ser Thr Lys His Glu Ile Leu Ser Ala Ile Ala Ala Thr
                100                 105                 110

Val Lys Lys Glu Ala Ile Ile Ala Thr Asn Thr Ser Ser Leu Ser Leu
            115                 120                 125

Asn Lys Leu Ala Ala Gly Val Glu Asn Asn Ala Arg Phe Ile Gly Leu
130                 135                 140

His Phe Phe Asn Pro Ala Pro Leu Met Lys Leu Ile Glu Ile Ile Pro
145                 150                 155                 160

Ser Tyr Phe Thr Ser Arg Ala Thr Ser Leu Arg Cys Gln Gln Leu Val
                165                 170                 175

Thr Val Ile Gly Lys Gln Phe Val Val Cys Lys Ala Thr Pro Gly Phe
                180                 185                 190

Ile Val Asn Arg Met Ala Arg Pro Phe Tyr Leu Glu Gly Phe Arg Leu
            195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Ser Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Phe Phe Thr Pro
            275                 280                 285

Ser Ser Ala Thr Pro Ser Ser Ala Asp Ala Gly Ser Gly Thr Pro Thr
290                 295                 300

Ser Leu Asn Phe Tyr Gly Glu His Pro Leu Phe Asp Leu Leu Gln Gln
305                 310                 315                 320

Arg Ala Leu Ala Leu Trp Pro Arg Leu Gln Ile Asn Arg Gln Ser Glu
                325                 330                 335

Gln Pro Thr Leu Gly Arg Phe Ile Arg Val Asn Asp Ala Met Ala Ile
            340                 345                 350

Lys Ile Thr Asp Gly Arg Thr Ala Asn Leu Leu Ala Glu Leu Thr Glu
                355                 360                 365

Leu Asp Thr Phe Val Ile Asp Ala Ala Leu Asn Tyr Ala Asp Thr Ala
    370                 375                 380

Tyr Leu Ala Ala Ala His Ser Gln Asp Ala Ser Thr Ala Asn Lys Ala
385                 390                 395                 400

Leu Phe Leu Thr Leu Leu Gln Thr Leu Ile Pro Gln Val Glu Phe Ile
                405                 410                 415

Lys Asp Ser Pro Gly Leu Ile Val Ala Arg Val Leu Ser Ser Leu Ile
            420                 425                 430

Asn Glu Ser Val Ile Met Val Glu Ser Gly Val Cys Ser Arg Ala Asp
                435                 440                 445

Ile Asp Ile Ala Ala Val Ala Gly Val Asn Tyr Ala Asp Gly Ile Phe
```

```
                    450                 455                 460
Ser Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Thr Pro Arg Pro Glu Leu Ala Val Ala Pro
            500                 505
```

<210> SEQ ID NO 16
<211> LENGTH: 509
<212> TYPE: PRT
<213> ORGANISM: Serratia sp. C-1

<400> SEQUENCE: 16

```
Met Ala Glu Asn Asn Ser Ala Ile Arg Ser Ala Val Ile Gly Ala
1               5                   10                  15

Gly Thr Met Gly Arg Gly Ile Ala Tyr Leu Leu Ala Leu Asn Gly Ile
                20                  25                  30

Arg Thr Val Leu Tyr Asn Arg Asn Gly Asn Asn Leu Asn Gln Ala Arg
            35                  40                  45

Asp Tyr Ile Val Ser Asp Leu Asp Arg Lys Ile Asp Asn Gly Lys Ile
50                  55                  60

Thr Leu Gln Lys Lys Gly Gln Ile Leu Ala Asn Ile Ile Phe Ser Ala
65                  70                  75                  80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ala Ile Ala Ala Thr
            100                 105                 110

Val Lys Pro Glu Ala Ile Ile Ala Thr Asn Thr Ser Ser Leu Ser Leu
        115                 120                 125

Asn Lys Leu Ala Ala Gly Val Glu Asn Asn Pro Arg Phe Ile Gly Leu
130                 135                 140

His Phe Phe Asn Pro Ala Pro Leu Met Lys Leu Ile Glu Ile Ile Pro
145                 150                 155                 160

Ser Tyr Phe Thr Ser His Ala Thr Ser Leu Arg Cys Gln Lys Leu Val
                165                 170                 175

Ile Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
                245                 250                 255

Gln Phe Asp Pro Arg Tyr Thr Pro Gly His Leu Gln Arg Ser Leu Val
            260                 265                 270

Asp Ala Gly Leu Leu Gly Arg Lys Asn Gly Arg Ser Phe Phe Ala Ser
        275                 280                 285

Gln Pro Ala Thr Pro Pro Thr Pro Thr Thr Glu Ser Asp Thr Pro Thr
    290                 295                 300

Ser Leu His Phe Tyr Gly Glu His Ala Leu Phe Asp His Leu Gln Gln
305                 310                 315                 320
```

```
Arg Ala Leu Ala Ala Trp Pro Ala Leu Arg Val Gln Arg Leu Pro Glu
            325                 330                 335

Arg Pro Glu Leu Gly Arg Phe Ile Leu Val Asn Asn Ala Leu Ala Ile
        340                 345                 350

Lys Ile Thr Asp Gly Arg Thr Ala Asn Leu Leu Ala Gly Leu Thr Ala
    355                 360                 365

Leu Asp Thr Phe Val Ile Asp Ala Ala Leu Asn Tyr Ala Asp Thr Ala
370                 375                 380

Tyr Leu Val Ala Ala His Asn Gln His Ala Thr Glu Thr Asn Lys Ala
385                 390                 395                 400

Leu Phe Leu Thr Leu Leu Gln Thr Val Ile Ala Gln Val Glu Phe Ile
            405                 410                 415

Lys Asp Ser Pro Ala Leu Ile Val Ala Arg Val Leu Ser Ser Leu Ile
        420                 425                 430

Asn Glu Ser Val Ile Met Val Glu Ser Gly Val Cys Ser Arg Ala Asp
    435                 440                 445

Ile Asp Ile Ala Ala Val Ala Gly Val Asn Tyr Ala Asp Gly Ile Phe
450                 455                 460

Ala Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
            485                 490                 495

Leu Leu Asn Ala Ala Arg Pro Glu Leu Ala Val Ala Pro
        500                 505

<210> SEQ ID NO 17
<211> LENGTH: 200
<212> TYPE: DNA
<213> ORGANISM: Escherichia coli str. K-12 substr. MG1655

<400> SEQUENCE: 17
cgtaattgcc ctttaaaatt cggggcgccg accccatgtg gtctcaagcc caaaggaaga      60
gtgaggcgag tcagtcgcgt aatgcttagg cacaggattg atttgtcgca atgattgaca     120
cgattccgct tgacgctgcg taaggttttt gtaattttac aggcaacctt ttattcacta     180
acaaatagct ggtggaatat                                                 200

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
taccgtcgac ctcgacgtaa ttgcccttta                                       30

<210> SEQ ID NO 19
<211> LENGTH: 41
<212> TYPE: DNA
<213> ORGANISM: Artificial sequence
<220> FEATURE:
<223> OTHER INFORMATION: primer

<400> SEQUENCE: 19
ggccccccct cgagtcatta agtactatat tccaccagct a                          41

<210> SEQ ID NO 20
<211> LENGTH: 774
```

<212> TYPE: DNA
<213> ORGANISM: Pseudomonas putida KT2440

<400> SEQUENCE: 20

```
atgccgcgat atatcgatgt gcaggcgccc gaacatggcg ttcagctcat taccctgcaa      60
cggcccgagg ccttgaatgc cctgtgcacc gagctactgg cagaactggc cgctgcgctg     120
caggctgccg ggaacgacga gcatgtccgt gccacagtga ttaccggcag cgccaaggca     180
ttcgccgcag gcgccgacat ccgcgagatg gccgatcgcg acctggtcgg catcctcaat     240
gacccgcgcg tagcgcattg gcaaagcatc gccgcattcg ccaaaccgct gattgctgca     300
gtcaacggct atgccctggg tggcggttgc gaactggcaa tgtgcgccga catcgtcatc     360
gccagtaccg acgcccgttt cggccagccg gaaatcaacc ttggcatcat ccccggtgct     420
ggcggcaccc agcgcctgtt acgtgccgtc ggtaagccgt tggccatgca gatggtgctg     480
acggggaag ccatcactgc cctccgcgcc cagcaggccg gcctggtcag cgaaatcacc      540
cagcccgaac tcaccgtaga acgcgccatg caggttgccc gcagcatcgc cgccaaagcg     600
ccgctggctg tgcgcctggc caaggaggcg ttactgaagg ccggtgatac cgacctggcc     660
agcggcctgc gcttcgagcg ccatgccttc accctgctgg cgggcaccgc cgaccgcgat     720
gaaggcatcc gcgccttcca ggaaaagcgc caggcccgct ccaagggcg ctga            774
```

<210> SEQ ID NO 21
<211> LENGTH: 32
<212> TYPE: DNA
<213> ORGANISM: Artificial sequence
<220> FEATURE:
<223> OTHER INFORMATION: primer

<400> SEQUENCE: 21

```
ctggtggaat atatgcacga cgtattcatc tg                                    32
```

<210> SEQ ID NO 22
<211> LENGTH: 41
<212> TYPE: DNA
<213> ORGANISM: Artificial sequence
<220> FEATURE:
<223> OTHER INFORMATION: primer

<400> SEQUENCE: 22

```
ctcgagtcat taagtgttaa ctcaaacccg ctcgatggcc a                          41
```

<210> SEQ ID NO 23
<211> LENGTH: 696
<212> TYPE: DNA
<213> ORGANISM: Pseudomonas putida KT2440

<400> SEQUENCE: 23

```
ttgatcaata aaacgtacga gtccatcgcc agcgcggtgg aagggattac cgacggttcg      60
accatcatgg tcggtggctt cggcacggct ggcatgccgt ccgagctgat cgatggcctc     120
attgccaccg gtgcccgcga cctgaccatc atcagcaaca acgccggcaa cggcgagatc     180
ggcctggccg ccctgctcat ggcaggcagc gtgcgcaagg tggtctgctc gttcccgcgc     240
cagtccgact cctacgtgtt cgacgaactg taccgcgccg gcaagatcga gctggaagtg     300
gtcccgcagg gcaacctggc cgagcgtatc cgcgccgcag gctccggcat tggtgcgttc     360
ttctcgccaa ccggctacgg caccctgctg gccgagggca aggaaacccg tgagatcgat     420
ggccgcatgt acgtgctgga aatgccgctg cacgccgact tcgcactgat caaggcgcac     480
```

```
aagggtgacc gttggggcaa cctgacctac cgcaaggccg cccgcaactt cggcccgatc    540
atggccatgg ctgccaagac cgccatcgcc caggtcgacc aggtcgtcga actcggtgaa    600
ctggacccgg aacacatcat cacccccggt atcttcgtcc agcgcgtggt cgccgtcacc    660
ggtgctgccg cttcttcgat tgccaaagct gtctga                              696

<210> SEQ ID NO 24
<211> LENGTH: 642
<212> TYPE: DNA
<213> ORGANISM: Pseudomonas putida KT2440

<400> SEQUENCE: 24
atgaccatca ccaaaaagct ctcccgcacc gagatggccc aacgcgtggc cgcagacatc     60
caggaaggcg cgtacgtaaa cctgggcatc ggcgcaccga ccctggtggc caactacctg    120
ggcgacaagg aagtgttcct gcacagcgag aacggcctgc tgggcatggg cccaagccct    180
gcgccgggcg aggaagacga tgacctgatc aacgccggca agcagcacgt caccctgctg    240
accggtggtg ccttcttcca ccatgccgat tcgttctcga tgatgcgtgg cggccacctg    300
gacatcgctg tactgggcgc cttccaggtg tcggtcaagg gcgacctggc caactggcac    360
acgggtgccg aaggctcgat cccggccgta ggcggtgcaa tggacctggc caccggcgcc    420
cgccaggtgt tcgtgatgat ggaccacctg accaagaccg gcgaaagcaa gctggtgccc    480
gagtgcacct acccgctgac cggtatcgct tgcgtcagcc gcatctacac cgacctggcc    540
gtactggaag tgacacctga agggctgaaa gtggtcgaaa tctgcgcgga catcgacttt    600
gacgagctgc agaaactcag tggcgtgccg ctgatcaagt ga                       642

<210> SEQ ID NO 25
<211> LENGTH: 55
<212> TYPE: DNA
<213> ORGANISM: Artificial sequence
<220> FEATURE:
<223> OTHER INFORMATION: primer

<400> SEQUENCE: 25
gagcgggttt gagttcaatt gtagctggtg gaatatttga tcaataaaac gtacg          55

<210> SEQ ID NO 26
<211> LENGTH: 34
<212> TYPE: DNA
<213> ORGANISM: Artificial sequence
<220> FEATURE:
<223> OTHER INFORMATION: primer

<400> SEQUENCE: 26
gagtcattaa gtgtttcact tgatcagcgg cacg                                 34

<210> SEQ ID NO 27
<211> LENGTH: 1518
<212> TYPE: DNA
<213> ORGANISM: Pseudomonas putida KT2440

<400> SEQUENCE: 27
atggccgcac tcgcaagcaa tgtgcaggtg gcggtgatcg gtgccggcgc catgggcgcc     60
ggtatcgccc aggtcgcggc ccaggccggc caccccgtca agctctacga taaccgcccg    120
ggtgctgccg cccaggcggt gacgggtatc gatcgccaac tggcccggct ggtggacaaa    180
ggaaagttac tggccgctga acgcgaaacg atcaatgccc gcctgtgccc ggtcgataca    240
ctcgaagcct tggcagatgc cggcctggtg attgaagcca tcgtcgaaaa cctgcaggtg    300
```

```
aagcaggcgc tgttcagtca gctcgaaacc ctgtgcgcgg ccgactgtat ccttgccagc    360
aatacttcgt cactgtccat caccagcctc gccgctggcc ttgaacgccc gcagcacgtg    420
gtcggtatgc acttcttcaa cccggcaccg ctgatggcgc ttgtcgaggt ggtgtcgggc    480
ctggcaaccg accctgcagt cgccgcatgc atctacgcca ctgcccaggc ctggggcaag    540
cagccggtcc atgcgcgctc tacaccgggc ttcatcgtca accgggtagc gcggccgttc    600
tatgccgaaa gcctacgcct gctgcaggaa ggtgccgccg attgcgccag cctggatgcg    660
ctgatgcgtg actcgggtgg cttccgcatg ggggcgttcg agctgaccga cctgattggc    720
catgacgtca attacgctgt cacctgttcc gtattcgatg ctttctatgg cgatttccgc    780
ttccagcctt cgctggtgca aaggaactg gtagacgccg gtcacctggg gcgcaagacc    840
ggccaaggct tctatcgcta tgccgaaggc gtcgagcgcc gcagccggc cgaactgcac    900 agctccgcct gcgcagaggc ctgcgttgtc gagggcaacc tgggggtgat gcagccgctg    960
gtcgagcgcc ttcgccaaag cggcattgcc gtgaccagc gcgccggtag tggcctgatc    1020
caggtgggcg acgccaccct ggccctgtcc gacggccgcc tggccagcca acgtgcccgt    1080
gaggacgggt gcgcaacct ggtgctgctc gaccttgcgc tggactacag cagcgccacg    1140
cgcattgcca tcagctggtc agcggatacc agcgacagcg cccgtgacca ggccgtagcc    1200
ctgctgcagc gtgccggcct gaaagtgacc ggtgtcgccg acctgcccgg cctggtggta    1260
ctgcgcaccg tggcaatgct tgccaacgag gccgccgatg cggtgcttca gggcgtcggc    1320
agcgccgccg acatcgacct ggccatgcgc gccggcgtca attaccctg cggcccgctg    1380 gcctgggcgg cgaacatcgg tattgcccat acctgcgcg tgctcgacaa cctgcagtgc    1440
agctatggcg agagccgcta ccgcccttcc ctgttgttac gccgctgtga agccaaagga    1500
ggcaccctac atgactga                                                  1518
```

<210> SEQ ID NO 28
<211> LENGTH: 1428
<212> TYPE: DNA
<213> ORGANISM: Escherichia coli str. K-12 substr. MG1655

<400> SEQUENCE: 28

```
atgatgataa atgtgcaaac tgtggcagtg attgggagcg gcaccatggg ggcaggcatt     60
gctgaagttg ctgccagtca tggacaccag gttttactgt atgacatttc tgctgaagcg    120
ctgacccgcg caatcgacgg gatacacgcg cggctaaatt cacgcgtgac gcggggaaaa    180
ctgactgctg aaacctgtga acgcacattg aaacgcctga tcccggtgac cgatattcac    240
gcgctggcag ctgcggacct ggtcattgaa gcggcgtctg aacgtctgga agtcaaaaaa    300
gcgctctttg cacagctggc ggaagtttgc ccgccacaaa cgctattgac cactaacact    360
tcgtcaatct ctataaccgc gattgctgcg gagataaaaa atcctgaacg tgttgcgggg    420
ctgcattttt ttaacccggc accggtgatg aagttggtgg aggtggtcag tgggctggca    480
acggcggcgg aagttgttga gcagttgtgt gaactaacgt tgagttgggg taagcagcct    540
gtgcgctgtc attcgactcc tggatttatc gttaaccgtg ttgcgcgtcc ttattattcc    600
gaggcctggc gggcactgga agagcaggtt gctgcaccag aagtgattga cgctgcactt    660
cgcgatggcg ctggtttccc gatggggccg ctggaattaa ccgatctgat tggtcaggac    720
gtcaattttg ctgtcacctg ttcggtgttt aacgctttct ggcaggagcg tcgttttta    780 ccttcgctgg tgcaacagga actggtgatt ggtgacggt tgggcaagaa aagtgggctg    840
```

```
ggcgtgtacg actggcgcgc ggaacgtgag gcagttgttg gcctggaagc ggtaagcgac    900
agttttagcc caatgaaagt agaaaagaaa agtgacggtg tcacggaaat tgacgatgtt    960
ttattgattg agacacaagg cgagacggca caggcgctgg caatacgact ggcacgcccg   1020
gtggtagtga tcgataaaat ggcgggcaag gtggtgacca ttgctgctgc agcggtgaac   1080
ccggactcag cgacccgcaa ggccatttat tacctgcaac agcagggcaa aacagtgctg   1140
caaattgcag attacccagg aatgctgatt tggcgaacgg tagcaatgat catcaatgaa   1200
gcccttgatg cgcttcaaaa aggcgtggcc tctgaacagg atatcgatac cgccatgcgt   1260
cttggggtga attatccata tggcccactt gcctggggag cgcaacttgg ctggcagcga   1320
atattaaggc tccttgaaaa tctacagcat cactatggcg aagaacgcta tcgcccatgt   1380
tcattgctgc gccaacgggc gcttctggag agcggttatg agtcataa               1428
```

<210> SEQ ID NO 29
<211> LENGTH: 1518
<212> TYPE: DNA
<213> ORGANISM: Acinetobacter baylyi ADP1

<400> SEQUENCE: 29

```
atgcacacatc caattaagaa aattgccatt attggcgttg gtgtaatggg tagtggtatc     60
gcccaaattg ccgcacaatc aggacatata acttatttat atgacgctaa agcaggtgca    120
gcacaacagg ccaaacaaca attagcaatt acgtttcaaa aactgcttga taaaaacaaa    180
ataacgactg aatacgcaga tgcagccaat gccaatcttc tgattgccaa cgaactgcat    240
gatttaaaag actgtgactt aatcgttgaa gcaattgttg aacgtctgga cattaaacag    300
tcattgatga gtcagcttga ggcaattgta cccgaaacca caattttggc ttcaaacact    360
tcctcacttt caattacagc gattgcctcc aactgcaagc atcctgagcg tgtcgctggc    420
tatcatttct ttaatcctgt accactcatg aaggtggtag aagtgattca gggtttaaag    480
actgatccca aacacattga aaccttgaat caattatcgc gggtattggg tcatcgccca    540
gttgtcgcaa aagataccccc aggatttatt attaaccatg cgggtcgtgc ttatggcaca    600
gaagccttaa aaatcctgaa tgaaaatgtc acagatatta gtgaaattga ccgtattttta    660 cgtgatggcg tcggctttag aatgggacca ttcgagctta tggatctcac tggacttgat    720
gtttcacatc cagtgatgga atcaatttat catcaatatt atgaagaagc acgttatcgt    780
ccaaattcat tgaccaaaca aatgctcgaa gcgaaacaat taggtcgtaa agtgggtcaa    840 ggttttttatg attatcgtac agggagcaaa actggtgaga cttctgccaa agtggctgaa    900
cgcttaacac tgtacccaaa agtatggatt gctgctgatt ttgaagatga taaacaatta    960
cttataaatt atctcaccac acacaatatt caacttgatg taggtgccaa gccgcaggcg   1020
gacagtttat gtttgttggc ttgttatggg gaagatacaa cgcatgcagc gctacgtctc   1080
aatgttaatc cagcacatag tgttgcaatt gatatgctct acggcattga aaaacaccgt   1140
actttaatgc catcactcat aaccgaagtg acgtatagtc atgcagctca ttcgatcttc   1200
aatttagatg gtgcaatggt tagcactatt ggtgaaagta tcggctttgt ggcacagcgc   1260
atattggcta tggtcatcaa cttaggctgt gatatagctc aacaagcaat tgcctctgtg   1320
gatgatatta atgcagccgt aaggttgggc ttgggctatc catttgggcc aattgaatgg   1380
ggtgatgaaa ttggttcgaa taagatctta cttattctaa accgcattac tgcattgacc   1440
tctgacccac gttaccgccc tagtccatgg ttacaacgcc gtgttgcgct taatcttcca   1500
cttacattta ctacttaa                                                 1518
```

<210> SEQ ID NO 30
<211> LENGTH: 1521
<212> TYPE: DNA
<213> ORGANISM: Serratia plymuthica NBRC102599

<400> SEQUENCE: 30

```
atgagcctgc cgaacttcaa cggaaccgtg gcggtgattg gcgcgggcac catgggcatc      60
ggcattgccc aggtggcggc ccatgccggg catcaggtga aactgtttga tatcgccgca     120
accgctgccc aaaacgcgct gggcgcctta agcctgcgat tgcgccagcg tgtggcggcc     180
ggcaaagccg atgcggacgc caccgaggca ttgctggcgc gcatccagcc ggtggatacg     240
cttgaacaac tggccgacag cacactgatc atagaggcgg tagccgaaaa actggcgatc     300
aaacaaagcc tgtttcggga gctggaagcc ctgtgctcac ccgccacgct gtttgccagc     360
aacacctcgt cgctgtcgat taccgccatc ggcggcgcgc tgcagcatcc gcaacgcctg     420
gccgggctgc acttctttaa cccggcgccg ctgatgacgc tggtggagat cgtcagcggg     480
ctggacaccg cgccgatac cgtcgccact ctgcaaacgc tggcccggca atggggcaaa     540
cagagcgtgc tgtgccgttc cacaccgggg tttatcgtca accgcgtggc gcggccttttt    600
tacgccgaaa ccctgcgcgc gctggaagaa cgggtggccg atgtcgccac gcttgatgcg     660
gtgatgcgcg atgccggctg tttcgccatg gggccgctgc aactgaccga tctgattggc     720
caggatatta actatgccgt caccgagtcg gtgtttcagg ccttttttcca ggacccgcga     780
tttacgccgt cgctggtaca gcaagagctg gtggccgccg ggcgtctggg ccgcaaaagc     840
ggctgcggct tttatcgtta tgatggcgaa caaacgtcgt cgaccgccgt ctgcctgccc     900
ctctcgcagg cggagccgcc acgcagcatc caactgcacg gcgacgaagc gggcgtggcg     960
tttttggccg gattgctgac gggaaatgcg gaggcgatca tacaacctgg ccagaccagc    1020
gcctttgccc ggatcgacga agttacattt atgttaacca atggtaaaac agccagccag    1080
attgccgagg aaaccggaac ccccgtggtg ctgtttgatc tgtctgccaa ctattcgcaa    1140
gcccctgcg tcgccatcag ctgcgcaatg caaaacgacg cacggcacaa cgacaaggta    1200
gtgcgcctgc tgcaatcgtt cggtaagcag gtgattttgc tgccggatta ccctggcctg    1260
ttggtgatgc gaaccctcgc catgctgagc aacgaggcgc tggatgcggt aaataaaggc    1320
gtcgccagcg ccgaagatat cgatagcgcc ctgcgttgcg gcgtcaatta cccgcgcggc    1380
ccgctggaat ggggggctgc gctcggctgg cggcaaatcc tcgctacgct ggaaaacctg    1440
catcgctact acggcgagcc gcgttatcgg ccaatgccgt tgctgcgcca ctacgctttc    1500
ctctcttcag gagccgaatg a                                              1521
```

<210> SEQ ID NO 31
<211> LENGTH: 34
<212> TYPE: DNA
<213> ORGANISM: Artificial sequence
<220> FEATURE:
<223> OTHER INFORMATION: primer

<400> SEQUENCE: 31

```
accacagcca ggatcctatg gcagaaagta atgc                                  34
```

<210> SEQ ID NO 32
<211> LENGTH: 34
<212> TYPE: DNA
<213> ORGANISM: Artificial sequence
<220> FEATURE:

```
<223> OTHER INFORMATION: primer

<400> SEQUENCE: 32
gctcgaattc ggatccttaa ggcgtggtcg tcag                              34

<210> SEQ ID NO 33
<211> LENGTH: 34
<212> TYPE: DNA
<213> ORGANISM: Artificial sequence
<220> FEATURE:
<223> OTHER INFORMATION: primer

<400> SEQUENCE: 33
accacagcca ggatcctatg gcagaaagta atgc                              34

<210> SEQ ID NO 34
<211> LENGTH: 34
<212> TYPE: DNA
<213> ORGANISM: Artificial sequence
<220> FEATURE:
<223> OTHER INFORMATION: primer

<400> SEQUENCE: 34
gctcgaattc ggatccttaa ggcgtggtcg tcag                              34

<210> SEQ ID NO 35
<211> LENGTH: 34
<212> TYPE: DNA
<213> ORGANISM: Artificial sequence
<220> FEATURE:
<223> OTHER INFORMATION: primer

<400> SEQUENCE: 35
accacagcca ggatcctatg gcagagaata attc                              34

<210> SEQ ID NO 36
<211> LENGTH: 34
<212> TYPE: DNA
<213> ORGANISM: Artificial sequence
<220> FEATURE:
<223> OTHER INFORMATION: primer

<400> SEQUENCE: 36
gctcgaattc ggatccttag ggcgctacag ccag                              34

<210> SEQ ID NO 37
<211> LENGTH: 34
<212> TYPE: DNA
<213> ORGANISM: Artificial sequence
<220> FEATURE:
<223> OTHER INFORMATION: primer

<400> SEQUENCE: 37
accacagcca ggatcctatg gcagagaata attc                              34

<210> SEQ ID NO 38
<211> LENGTH: 33
<212> TYPE: DNA
<213> ORGANISM: Artificial sequence
<220> FEATURE:
<223> OTHER INFORMATION: primer

<400> SEQUENCE: 38
gctcgaattc ggatccttag ggcgcgacgg cca                               33
```

-continued

```
<210> SEQ ID NO 39
<211> LENGTH: 34
<212> TYPE: DNA
<213> ORGANISM: Artificial sequence
<220> FEATURE:
<223> OTHER INFORMATION: primer

<400> SEQUENCE: 39
accacagcca ggatcctatg gccgcactcg caag                              34

<210> SEQ ID NO 40
<211> LENGTH: 34
<212> TYPE: DNA
<213> ORGANISM: Artificial sequence
<220> FEATURE:
<223> OTHER INFORMATION: primer

<400> SEQUENCE: 40
gctcgaattc ggatcctcag tcatgtaggg tgcc                              34

<210> SEQ ID NO 41
<211> LENGTH: 34
<212> TYPE: DNA
<213> ORGANISM: Artificial sequence
<220> FEATURE:
<223> OTHER INFORMATION: primer

<400> SEQUENCE: 41
accacagcca ggatcctatg atgataaatg tgca                              34

<210> SEQ ID NO 42
<211> LENGTH: 34
<212> TYPE: DNA
<213> ORGANISM: Artificial sequence
<220> FEATURE:
<223> OTHER INFORMATION: primer

<400> SEQUENCE: 42
gctcgaattc ggatccttat gactcataac cgct                              34

<210> SEQ ID NO 43
<211> LENGTH: 34
<212> TYPE: DNA
<213> ORGANISM: Artificial sequence
<220> FEATURE:
<223> OTHER INFORMATION: primer

<400> SEQUENCE: 43
accacagcca ggatcctatg acacatccaa ttaa                              34

<210> SEQ ID NO 44
<211> LENGTH: 34
<212> TYPE: DNA
<213> ORGANISM: Artificial sequence
<220> FEATURE:
<223> OTHER INFORMATION: primer

<400> SEQUENCE: 44
gctcgaattc ggatccttaa gtagtaaatg taag                              34

<210> SEQ ID NO 45
<211> LENGTH: 34
<212> TYPE: DNA
<213> ORGANISM: Artificial sequence
<220> FEATURE:
<223> OTHER INFORMATION: primer
```

<400> SEQUENCE: 45
accacagcca ggatcctatg agcctgccga actt                              34

<210> SEQ ID NO 46
<211> LENGTH: 34
<212> TYPE: DNA
<213> ORGANISM: Artificial sequence
<220> FEATURE:
<223> OTHER INFORMATION: primer

<400> SEQUENCE: 46
gctcgaattc ggatcctcat tcggctcctg aaga                              34

<210> SEQ ID NO 47
<211> LENGTH: 774
<212> TYPE: DNA
<213> ORGANISM: Pseudomonas putida KT2440

<400> SEQUENCE: 47
atgccgcgat atatcgatgt gcaggcgccc gaacatggcg ttcagctcat taccctgcaa    60
cggcccgagg ccttgaatgc cctgtgcacc gagctactgg cagaactggc cgctgcgctg   120
caggctgccg ggaacgacga gcatgtccgt gccacagtga ttaccggcag cgccaaggca   180
ttcgccgcag gcgccgacat ccgcgagatg gccgatcgcg acctggtcgg catcctcaat   240
gacccgcgcg tagcgcattg gcaaagcatc gccgcattcg ccaaaccgct gattgctgca   300
gtcaacggct atgccctggg tggcggttgc gaactggcaa tgtgcgccga catcgtcatc   360
gccagtaccg acgcccgttt cggccagccg gaaatcaacc ttggcatcat ccccggtgct   420
ggcggcaccc agcgcctgtt acgtgccgtc ggtaagccgt tggccatgca gatggtgctg   480
acgggggaag ccatcactgc cctccgcgcc agcaggccg gcctggtcag cgaaatcacc    540
cagcccgaac tcaccgtaga acgcgccatg caggttgccc gcagcatcgc cgccaaagcg   600
ccgctggctg tgcgcctggc caaggaggcg ttactgaagg ccggtgatac cgacctggcc   660
agcggcctgc gcttcgagcg ccatgccttc accctgctgg cgggcaccgc cgaccgcgat   720
gaaggcatcc gcgccttcca ggaaaagcgc caggcccgct ccaagggcg ctga          774

<210> SEQ ID NO 48
<211> LENGTH: 34
<212> TYPE: DNA
<213> ORGANISM: Artificial sequence
<220> FEATURE:
<223> OTHER INFORMATION: primer

<400> SEQUENCE: 48
accaccatca cgtgggtacc atgccgcgat atat                              34

<210> SEQ ID NO 49
<211> LENGTH: 34
<212> TYPE: DNA
<213> ORGANISM: Artificial sequence
<220> FEATURE:
<223> OTHER INFORMATION: primer

<400> SEQUENCE: 49
tcatcattcg aaccgtcagc gcccttggaa gcgg                              34

<210> SEQ ID NO 50
<211> LENGTH: 35
<212> TYPE: DNA
<213> ORGANISM: Artificial sequence -continued

```
<220> FEATURE:
<223> OTHER INFORMATION: primer

<400> SEQUENCE: 50
ctggtggaat atagtatggc agaaagtaat gcggc                              35

<210> SEQ ID NO 51
<211> LENGTH: 35
<212> TYPE: DNA
<213> ORGANISM: Artificial sequence
<220> FEATURE:
<223> OTHER INFORMATION: primer

<400> SEQUENCE: 51
ctcgagtcat taagtttaag gcgtggtcgt cagcg                              35

<210> SEQ ID NO 52
<211> LENGTH: 35
<212> TYPE: DNA
<213> ORGANISM: Artificial sequence
<220> FEATURE:
<223> OTHER INFORMATION: primer

<400> SEQUENCE: 52
ctggtggaat atagtatggc agagaataat tcggc                              35

<210> SEQ ID NO 53
<211> LENGTH: 35
<212> TYPE: DNA
<213> ORGANISM: Artificial sequence
<220> FEATURE:
<223> OTHER INFORMATION: primer

<400> SEQUENCE: 53
ctcgagtcat taagtttagg gcgctacagc cagct                              35

<210> SEQ ID NO 54
<211> LENGTH: 1530
<212> TYPE: DNA
<213> ORGANISM: Serratia marcescens ATCC13880

<400> SEQUENCE: 54
atggcagaaa gtaatgcggc aattcaatcg gctgcgatta tcggcgcggg aacgatgggc      60
agaggcatcg cttatctttt cgcgcaaaaa ggcattcgca cggtgcttta taatcgcaac     120 ggcaatacccc tcaatcaggc tcgcgaatat atcgcgcaag acctgaacaa gaaagtcgaa     180
cagggcaaga tcgcgctgca ggataaaggc gcggtgctgg ccaatctaat gttcacttca     240
gtgtttgagg ccatcgccga cagcgagctg gtgatagaaa ccatcgccga gcaagaacaa     300
accaaacttg aggtgctggc ggccatcgcc gcggtggtca agcccgacac gctgatcgcc     360 accaataccct cctcactgtc gcttaacaag ctggctactg cggtgacgca cagcgaacgc     420
tttatcggtt tgcatttttt caaccccgcg ccgctgatga agctgattga aatcattccg     480
gcctacttta ccgcgcacgc caccaccgaa cgctgccgcc aactggtggc ggcgttgggg     540
aaacacgatg tcgtctgcca ggccacgccg gggttcatcg tcaatcgcat ggcccgcccc     600
tactacctgg aagggttccg cctgttggaa gaacacgtgg cgcgcgcggc tcagatcgac     660
cgcgccctca aggccggcgg gcgcttccgc atggggccgc tcgagctgac cgattttatc     720
ggccaagaca tcaactatca ggtcagtcgg caaatctggc aggatatgca atacgacccg     780
cgctataccc ccggtcatct gcagcgttca ctggtcgatg ccggtctgtt ggggaaaaag     840
```

| | |
|---|---|
| aacggccgct cctattttgc cgccgaagaa accgccccgc cggtgacggc cgccagcaat | 900 |
| gcagacgtcg agacgctgcg cgtttacggc gagcacccct tttttaccct gttacagcag | 960 |
| cgagccgcgc ttcagtggcc acagctgcgc gtggaacaac ggccggcatt accggggctg | 1020 |
| gggtcggccg tccagatcaa tgacgctttc accgtcagca tcaccgatgg ccgcacggcg | 1080 |
| agccaactgg ccgagcagac ggcagcggat gcctttgtgg tcgatgtcgc cctgaactac | 1140 |
| gccgacacga cgtatctggc ggcggcgcac agccgccacg cctctgcggc caataaggcg | 1200 |
| ctgtttttac gcctgctgca cacggcaatc ccgcaggttg aatttatcaa ggactctccg | 1260 |
| gcgcttatcg tcgcccgcgt cctcagcagc ctgatcaatg agtcggtgat catggtggaa | 1320 |
| agcggcgtct gcagccggga agacatcgat gtcgccgccg tcgcgggcgt taactacgcc | 1380 |
| ggcggcattt tcgactggct cggcaaactg ggggagaaaa acgtcaggac aacgctgagc | 1440 |
| aatctggctc agctgctgca cgcggcgcgc tatgcgccgc attacaccct tctgcacgcc | 1500 |
| gcgcaaccgg cgctgacgac cacgccttaa | 1530 |

<210> SEQ ID NO 55
<211> LENGTH: 1530
<212> TYPE: DNA
<213> ORGANISM: Serratia nematodiphila DSM21420

<400> SEQUENCE: 55

| | |
|---|---|
| atggcagaaa gtaatgcggc aattcaatcg gctgcgatta tcggcgcggg aacgatgggc | 60 |
| agaggcatcg cttatctttt cgcgcaaaaa ggcattccca cgatgcttta taatcgcaac | 120 |
| ggcaataccc tcaatcaagc tcgcgaatat atcgcgcaag acctgaataa gaaagtcgaa | 180 |
| cagggcaaga tcgcgctgcg ggataaagac gcggtgctgg ccaatctgat gttcacttcc | 240 |
| gtgtttgagg ccatcgccga cagcgagctg gtgatagaaa ccatcgccga gcaagaacaa | 300 |
| accaaacttg aggtgctggc ggccatcgcc gcagtggtca agcccgacac gctgatcgcc | 360 |
| accaataccT cctcactgtc gctcaacaag ctggcaacgg cggtaacgca cagcgaacgc | 420 |
| tttatcggtt tgcatttttt caaccccgcg ccgctgatga agctgattga aatcattccg | 480 |
| gcctacttta ccgcgcacgc caccacggaa cgctgccgcc aactggtggc ggcgttgggg | 540 |
| aaacgcgatg tcgtctgcca ggccacgccg gggttcatcg tcaatcgcat ggcccgcccc | 600 |
| tactacctgg aagggttccg cctgttggaa gaacatgtgg cgcgcgcggc gcagatcgac | 660 |
| cgcgccctca aagccggcgg gcgcttccgc atggggccgc tcgagctgac cgattttatc | 720 |
| ggccaagaca tcaactatca ggtcagccgg caaatctggc aggacatgca atacgacccg | 780 |
| cgctatacCC ctggtcatct gcagcgttca ctggtcgatg ccggtctgtt ggggaaaaag | 840 |
| aacggccgct cctattttgc cgccgaagaa accgccccgc cggtgacggc cgccaacaat | 900 |
| gcagacgtcg agacgctgcg cgtttacggc gagcatcctt tttttaccct gttgcagcag | 960 |
| cgagccgcgc ttcagtggcc acagctgcgc gtggaacaac ggccggcatt accggggctg | 1020 |
| ggagcggccg tccagatcaa tgacgctttc accgtcagca tcaccgatgg ccgcacggcg | 1080 |
| agccaactgg ccgagcagac ggcagcggat gcctttgtgg tcgatctcgc cctgaactac | 1140 |
| gccgacacca cgtatctggt ggcggcgcac agccgccacg cctctgcggc caataaggcg | 1200 |
| ctgtttttac gcctgctgca cacggcaatc cctcaggttg aatttatcaa ggactctccg | 1260 |
| gcgcttatcg tcgcccgcgt cctcagcagc ctgatcaatg agtcggtgat catggtggaa | 1320 |
| agcggcgtct gcagccggga agacatcgat gtcgccgccg tcgcgggcgt taactacgcc | 1380 |
| ggcggcattt tcgactggct cggcaaactg ggggagaaaa acgtcaggac aacgctgagc | 1440 | aatctggcgc agctgctgca cgcggcgcgc tatgcgccgc attacaccct tctgcacgcc    1500 gcgcaaccgg cgctgacgac cacgccttaa                                     1530

<210> SEQ ID NO 56
<211> LENGTH: 1530
<212> TYPE: DNA
<213> ORGANISM: Serratia plymuthica NBRC102599

<400> SEQUENCE: 56
atggcagaga ataattcggc aatccgttca gccgccgtta ttggtgcggg gaccatgggc      60
agaggcatcg cctatctcct ggcgctgaac ggcatacgaa ccgtacttta taatcgcaat    120
ggtaataatc tcaatcaggc ccgtgactat attgtcagcg acctggacag aaaaatagat    180
aacgaaaaaa taaccctgca gaaaaaaggc cagatattag ccaatattat tttctcggac    240
gtctttgacg ccataaccga cagcgatctg gtgattgaaa ccattgcgga agatgagcaa    300
accaagcatg aaatcctggc agccattgcg gcgacggtaa aaccggaggc gatcattgcg    360
accaatactt cctctctgtc gctgaacaaa ctggcggcgg gggtggaaaa caacccgcgc    420
tttatcggcc tgcattttttt caatccggcg ccgctgatga agttgatcga aattattccc    480
tcttatttca cctctcgcgc caccagtcta cgctgccagc agttggtaac agcgttgggt    540
aaacagtttg tggtctgcaa agccacgccg ggctttattg ttaaccgcat ggcgcggcct    600
ttctatctgg aagggttccg gctgctggag gaaaacgtgg cgctggcgcc acagatcgac    660
cgcgccctca aggccggcgg gcattttcgc atggggcctt tagaactgac tgattttatc    720
ggccaggata tcaactatca ggtcagcaag cagatttggc aggatatgca gttcgatccc    780
cgctataccc ccggccattt gcaacgctcg ctggtggatg ccgggctgct ggggaggaaa    840
aacgggcgct cttttttttgc ttcccaacct gctacaccac ccaacccaac cacagagggc    900
gacacgccaa cttcactgca tttttatggt gaacacgctt tattcgatca cctgcaacag    960
cgcgctttgg ccacctggcc tgcgctgcgc gttcagcggt gccggaacg gccggaactg   1020 gggcgtttta tcctggtgaa taacaggctg gcgatcaaaa tcactgatgg cagaacggcg   1080
aacctgctcg ccggcttaac cgctctcgac accttcgtga ttgacgccgc gctgaactac   1140
gccgacaccg cctatctggt ggccgcccac aatcaacatg ccacagagac gaataaagcg   1200
ctgtttctga cgctgctgca aaccctcatc gctcaggtgg agtttattaa agattcccct   1260
gccctgatcg ttgcccgcgt actgagcagc ctgatcaatg aatcggtgat catggtggag   1320
agcggcgttt gcagccgggc agatatcgat atcgccgccg tggccggcgt gaactatgcc   1380
gacggcattt ttgcctggtt ggcgcagctc gggcagaaaa acgtgaaatc gacgctggat   1440
aacatggcgc aattgctgca ctccacgcgc tattacccgc attactcatt gctgaacgcg   1500
gcccggcctg agctggctgt agcgccctaa                                    1530

<210> SEQ ID NO 57
<211> LENGTH: 1530
<212> TYPE: DNA
<213> ORGANISM: Serratia proteamaculans 568

<400> SEQUENCE: 57
atggcagaga ataattcggc aatccattcg gtcgctgtta ttggtgccgg gaccatgggc      60
agaggtattg cctatcttct ggcgcaaaac ggcatacgaa ccctgcttta taatcgtagc    120
ggtaataatc tgaatcaggc cagggactat attattcgtg acctggataa gaaaatagat    180

| | |
|---|---|
| ggcggaaaaa taagcccgca gaaaaaggc gagatattgg ccaatctggt tttctctccc | 240 |
| attttcgagg ctattgccga cagcgatctg gtgattgaaa ccatcgcgga acatgaggca | 300 |
| accaagcatg agatcctcgc ggcgattgcg gccacggtga aaaagaggc gattatcgcc | 360 |
| accaataccct cctcgctgtc attgaataag ctggccgcag cgtcgaaaa taacgcccgg | 420 |
| tttatcggcc tgcacttctt caatccggcc ccgctgatga aactgatcga aattattccg | 480 |
| tcttacttta ccagccgggc caccagcctg cgttgccagc agttggtgac ggcgataggc | 540 |
| aaacagtttg tggtctgcaa agccacgccg ggctttatcg tcaaccggat ggcgcgaccct | 600 |
| tttatctgg aagggttccg gctgttggaa gagaacgtgg cgctggcgcc gcagatcgac | 660 |
| cgcgcactca aggccggtgg ccactttcgc atgggacctt tagagctgac cgattttatc | 720 |
| ggccaggata ttaactatca ggtcagcagc cagatttggc aggacatgca gtacgatccc | 780 |
| cgctataccc ccggccattt gcaacgttcg ctggtggatg ccgggctgct ggggaagaaa | 840 |
| aacggccgat ccttttttac cccctcttcc gccgaaccca gctccgccga tgcaggtagc | 900 |
| ggcacgccga cctcactgaa ttttatggt gaacatcccc tgttcgacct gttgcaacag | 960 |
| cgcgctttgg cgctctggcc aagggtgcag attaatcgcc aatcggaaca gccaacgctg | 1020 |
| ggccgcttta tccgggtgaa tgacgcaatg gccatcaaaa tcaccgatgg ccgcaccgcc | 1080 |
| aatctgctgg ctgaattgac cgaactcgat accttcgtga tcgacgccgc gctcaactac | 1140 |
| gccgataccg cctatctggc ggctgcccac agccaggatg ccagcgcggc caataaagcg | 1200 |
| ctgtttctga cgctgctgca aacgttgatc ccgcaggtgg agtttattaa agactccccg | 1260 |
| ggcctgattg tcgcccgcgt cctgagcagc ctgatcaatg agtcggtgat tatggtggag | 1320 |
| agcggggttt gcagccgggc ggacatcgat atcgccgcgg tggccggcgt taactatgcc | 1380 |
| gatggcatct ttagctggct ggcgcagctt ggcaaaaaaa acgtgaagtc gacgctggac | 1440 |
| aatatggcgc aactgctgca ttccgcccgc tattaccccgc attactcttt gctcaatacc | 1500 |
| ccccggccag agctggccgt cgcgcccctaa | 1530 |

<210> SEQ ID NO 58
<211> LENGTH: 1530
<212> TYPE: DNA
<213> ORGANISM: Serratia ureilytica Lr5/4

<400> SEQUENCE: 58

| | |
|---|---|
| atggcagaaa gtaatgcggc aattcaatcg gctgcgatta tcggcgcggg aacgatgggc | 60 |
| agaggcatcg cttatctttt ggcgcaaaaa agcattcgta cggtgcttta taatcgcaac | 120 |
| ggcaataccc tcaatcaagc tcgcgacgct atcgtgcaag acctgaacaa aaaggtggaa | 180 |
| cagggcaagc tcgcgctgca ggacaaagac gcggtgctgg ctaatctgac gttctccgcg | 240 |
| gaatttgggg ccatcgccga cagcgatctg gtgatcgaaa ccatcgcaga gcatgagcaa | 300 |
| gccaaactcg aggtgctggc ggccatcgcc gcgacggtca gcccgacac gctgatcgcc | 360 |
| accaataccct cctcactgtc gcttaataag ctggcgacgg cggtgacgca cagcgaacgc | 420 |
| tttatcggtt tgcacttttt caaccccgcg ccgctgatga agctgattga aatcattccg | 480 |
| gcctatttta ccgcacaggt caccaccgaa cgttgccgtc aactggtggc ggcgttgggg | 540 |
| aaacgcgatg tcgtctgtca ggccacgccg ggatttatcg tcaaccgtat ggcccgcccc | 600 |
| tactatctgg aagggttccg cctgttggaa gaacacgtgg cgcgtgcgcc gcagatcgac | 660 |
| cgcgccctca aagccggcgg acactttcgc atggggccgc tcgaactgac cgattttatc | 720 |
| ggtcaggaca tcaactatca ggtcagccgg caaatttggc aggacatgca gtacgatccg | 780 |

```
cgctataccc cgggccatct gcagcgctcg ctggtcgatg ccggtctgtt gggcaaaaag    840
aacggccgct cctattttc cgccgaagaa tctcctccgc cgcttgcggc cgccgtcgat    900
gcggaggtcg agacgctacg catttacggt gaacatcctc tctttactct gctacagcag    960
cgggccaccc tgcaatggcc gcggctgcgc gtggaacaac ggccgacatt accgggcctg   1020
ggcgccgcca ttcaggttaa tgacgctttc accgtcagcg ttaccgatgg ccgcacggca   1080
aaccagcttg ccgaacagac cgcggcggac gcctttgtcg tcgatgtcgc cctgaactac   1140
ggcgatacgg cgtacctggt ggcggcgcat agccgccacg cctctgcagc caataaggcg   1200 ctgttttac gcctgctgca caccgcgatc ccgcaggtgg aatttatcaa ggattccccg   1260
gccttgatcg tcgcccgcgt gctcagcagc ctgatcaacg agtcggtgat catggtggaa   1320
agcggcgtct gcagccggga agacattgat gtcgccgccg tcgccggcgt gaactacgcc   1380
gacggtattt tcggctggct cactcgcctc ggggaggaaa atgtcaggac gacgctgagc   1440
aacctggcgc aattgctgca cgcggcgcgc tatgcgccgc attcaccct tctgcacgcc   1500 gcccaaccgg cgctgaccac cacgccttaa                                    1530

<210> SEQ ID NO 59
<211> LENGTH: 1530
<212> TYPE: DNA
<213> ORGANISM: Serratia sp. BW106

<400> SEQUENCE: 59
atggcagaga ataattcggc aatccattcg gtcgctgtta ttggtgccgg aaccatgggc     60
agaggtattg cctatcttct ggcgcagaac ggcatacgaa ccctgcttta taatcgtagc    120
ggtaataatc tggatcaggc ccgcgactat attatccgtg acctggataa gaaaatagac    180
aacgggaaaa taagccaaca gaaaaaaggc gaagtattgg ccaacctggt tttctctccc    240
attttcgacg ctatcgccga cagcgacctg gtgattgaaa ccatcgcgga gcatgagacc    300
accaagcatg aaatcctcgc ggcgattgcg gccacggtga acaagaggc cattatcgcc    360 accaacacct catcgctgtc gttgaataag ctggcggcag cgtcgaaaa caacgcccgt    420 tttatcggcc tgcacttctt caatccggcc ccgctgatga aactgatcga gattattccg    480 tcctattta ccagccgggc caccagcctg cgctgccagc agttggtgac ggcgctaggc    540
aaacagtttg tggtctgcaa agccacgccg ggttttatcg tcaaccggat ggcacggcct    600
ttttatctgg aaggattccg gctgttggaa gaaaacgtag cattggcacc gcagatcgac    660
cgcgccctca aggccggtgg ccactttcgc atgggccctt tagagctgac cgactttatc    720
ggccaggata ttaactatca ggtcagcagc cagatttggc aggacatgca gtacgaccct    780
cgctataccc ccggccattt gcaacgttcg ctggtggatg ccgggttgtt ggggaagaaa    840
aacggccgat ccttttttgc tgccccttct tccgaatcga cccctcga cgcaggcaac     900 ggcacgctga cttccctgca tttttatggc gaacataccc tgtttgacct gctgcaacag    960
cgcgccttgg ctatctggcc aacgctgcag attattcacc agccggaacg gccgacgctg   1020
ggacgcttta tccgggtgaa tgacgcattg gccgtcaaaa tcaccgatgg tcgcaccgcc   1080
aatctgctcg ctgaattgac cgatctcgac acctttgtga tcgacgccgc actgaattac   1140
agcgatacgg cctatctggt ggccgcccac aatcaggacg ccgccgaggc caataaagcg   1200
ctgttcctgt cgctgctgca aacgttgatc ccgcaggtgg agtttattaa agactctcca   1260
ggcctgatcg tcgcccgggt tctgagcagt ctgatcaatg agtcggtgat catggtggag   1320
```

| | |
|---|---|
| agcggggttt gcagccgggc agatatcgat attgccgccg tggcgggcgt taactatgcc | 1380 |
| gatggcatct ttgcctggct gacgcagctc gggcaaaaaa acgtgaaatc aacgctggat | 1440 |
| aatatggcgc aactgctgca ttccgcccgc tattacccgc attactcatt gctgaatgcc | 1500 |
| ccccggcccg aactggccgt cgcgccgtaa | 1530 |

<210> SEQ ID NO 60
<211> LENGTH: 1530
<212> TYPE: DNA
<213> ORGANISM: Serratia sp. S119

<400> SEQUENCE: 60

| | |
|---|---|
| atggcagaaa gtaatgcggc aattcaatcg gctgcgatta tcggcgcggg aacgatgggc | 60 |
| agaggcatcg cttatctttt cgcgcaaaaa ggcattcgca cggtgcttta taatcgcaac | 120 |
| ggcaatacccc tcaatcaggc tcgcgaatat atcgcgcaag acctgaacaa gaaagtcgaa | 180 |
| cagggcaaga tcgcgctgca ggataaaggc gcagtgctgg ctaatctggt gttcacctcg | 240 |
| gtgtttgaga ctatcgccga cagcgatcta gtgatagaaa ccatcgccga gcaagagcaa | 300 |
| accaaacttg aggtgctggc ggccatcgcc gcggcggtca gcccgacac gctgatcgcc | 360 |
| accaatacat cctcactgtc gcttaacaag ctggcaaccg cggtgacaca cagcgagcgg | 420 |
| tttatcggtt tgcacttttt caatcccgcg ccgctgatga aactgattga atcatcccg | 480 |
| gcctacttta ccgcacgcgc caccaccgaa cgttgccgtc agctggtggc cgcgttgggg | 540 |
| aaacgcgatg tcgtctgcca ggccacgccg gggtttatcg tcaaccgcat ggcccgcccc | 600 |
| tactacctgg aagggttccg cctgttggaa gaacacgtgg cgcgcgcgcc gcagatcgac | 660 |
| cgcgccctca aggccggcgg gcactttcgc atggggccgc tcgagctgac cgattttatc | 720 |
| ggccaggaca tcaactatca ggtcagccgg caaatctggc aggacatgca atacgatccg | 780 |
| cgctataccc ccggccatct gcagcgttcg ctggtcgatg ccggtctgtt ggggaaaaag | 840 |
| aacgccgct cctattttgc cgccgaagaa aacgccttac cggtaacggc cgccaccgat | 900 |
| gcagacgtcg agacgctgcg cgtttacggc gaacacccct tttttaccct gttgcaacag | 960 |
| cgggccgcgc ttcagtggcc acggctgcgc gtggagcaac ggccggcctt accgggcctg | 1020 |
| gggccggccg tccagatcaa tgaggctttc accgtcagcg tcaccgatgg ccgcacggcg | 1080 |
| agccagttgg cggagctgac ggcggcggat gcctttgtgg tcgatgtcgc cctgaactac | 1140 |
| gccgacacgg cgtatctggt ggcagcgcac aaccgccacg cctctgcggc caataaggcg | 1200 |
| ctgttttac gcctgctgca cacggcaatc ccgcaggttg aatttatcaa ggactccccg | 1260 |
| gcgctgatcg tcgcccgcgt cctcagcagc ctgatcaacg agtcggtgat catggtggaa | 1320 |
| agcggcgtct gcagccggga agacatcaat gtcgccgccg tcgccggcgt taactacgcc | 1380 |
| gacggcattt tcggcttgct cgatagcctg ggggagaaaa acgtcaggac gacgctgagc | 1440 |
| aacctggcgc agctgctgca cgcggcacgc tatgcgccgc attacaccct tctacacgcc | 1500 |
| gcgcaaccgg cgctgacgac cacgccttaa | 1530 |

<210> SEQ ID NO 61
<211> LENGTH: 1530
<212> TYPE: DNA
<213> ORGANISM: Serratia sp. YD25

<400> SEQUENCE: 61

| | |
|---|---|
| atggcagaac gtaatgcggc aattcaatcg gctgcgatta tcggcgcggg aacgatgggc | 60 |
| agaggcatcg cttatctttt cgcgcaaaaa ggcattcgta cggtgcttta taatcgcaac | 120 |

```
ggcaataccc tcattcaggc tcgtgaatat atcgtgcaag acctggacaa aaaggtcgaa       180
cagggcaggc tcgcgccgca ggataaagac gcggtgctgg ccaatctgca gttctcatcg       240
gtgtttgaag ctatcgtcga cagcgatttg gtgctcgaaa ctatcgccga gcaagagcaa       300
gccaaactcg aggtgctggc cgccatcgct gcggcggtca aacccgacac gctgatcgcc       360
accaatactt cctcattgtc gctcaataag ctggcaacgg cggtgaccca cagcgaacgc       420
tttatcggtt tgcactttt caatcccgca ccgctaatga agctgattga aatcattccg        480
gcctacttta ccacccaagc caccactgaa cgttgccgcc aactggtggc ggcattgggg       540
aaacgcgatg tcgtctgcca ggctacgccg gggttcatcg tcaaccgtat ggcccgcccc       600
tactacctgg aaggctttcg cctgttggaa gagcacgtgg cgcgcgcgcc gcagatcgac       660
cgcgccctca aggccggcgg acactttcgc atggggccgc tcgagctgac cgatttatc       720 ggccaggaca tcaactatca ggtcagccgg caaatttggc aggacatgca gtacgacccg       780
cgctataccc ccggccatct gcagcgttcg ctggtcgatg ccgggctgct ggggaaaaag       840
aacggtcgct cctattttc cgccgaagaa accgccccgc cggttgaggc cgccgccgag       900
gcggatgtcg agacgctgcg catttacggc gaacacccct tgtttaccct gctgcaacag       960
cgagccgcac tgcaatggcc gcagttgcgc gtggaacagc ggccggcctt gtcgggcctg      1020
ggagcggcca ttcaggtcaa tgacgctttc accgtcagcg tcaccgatgg ccgcacggca      1080
aatcagttgg ccgagcagac ggcggcggac gcctttgtgg tcgatgtcgc cctgaactac      1140
gccgacacgg cgtatctggt ggcggcgcac agccgccacg cctctgcggc taataaggcg      1200 ttgttttgc gcctgctgca caccgcgctt ccgcaggttg aatttatcaa ggactccccg       1260
gcgctgatcg tcgcccgcgt cctcagcagc ctgatcaacg agtcggtgat catggtggaa      1320
agcggcgtct gcagccggga agacatcgat gtcgccgccg tcgccggcgt gaactacgcc      1380
gacggcattt tcggctggct cactcgcctg ggggagaaaa acgtcaggac gacgctgagc      1440
aacctggcgc agctgctgca cgcggcccgc tatgcgccgc attacaccct tctgcacgcc      1500
gcccaaccgg cgctgaccac cacgccttaa                                       1530
```

<210> SEQ ID NO 62
<211> LENGTH: 1530
<212> TYPE: DNA
<213> ORGANISM: Serratia sp. FS14

<400> SEQUENCE: 62

```
atggcagaaa gtaatgcggc aattcaatcg gctgcgatta tcggcgcggg aacgatgggc       60
agaggcatcg cttatctttt cgcgcaaaaa ggcattccca cgatgcttta taatcgcaac      120
ggcaataccc tcaatcaagc tcgcgaatat atcgcgcaag acctgaacaa gaaagtcgaa      180
cagggcaaga tcgcgttgca ggataaagac gcggtgctgg ccaatctgat gttcacttcc      240
gtgtttgagg ccatcgccga cagcgagctg gtgatagaaa ccatcgccga gcaagaacaa      300
accaaacttg aggtgctggc ggccatcgcc gcggtggtca agcccgacac gctgatcgcc      360
accaatacct cctcactgtc gcttaacaag ctggcaactg cggtgacgca cagcgagcgc      420
tttatcggtt tacatttttt caaccccgct ccgctgatga agctgattga aatcattccg      480
gcctacttta ccgcgcacgc caccacggaa cgctgccgcc aactggtggc ggcgttgggg      540
aaacgcgatg tcgtctgcca ggccacgccg gggttcatcg tcaatcgcat ggcccgcccc      600
tactacctgg aagggttccg cctgttggaa gaacatgtgg cgcgcgcggc gcagatcgac       660
```

| | |
|---|---|
| cgcgccctca aggccggcgg gcgcttccgc atggggccgc tcgagctgac cgattttatc | 720 |
| ggccaagaca ttaactatca ggtcagccgg caaatctggc aggacatgca atacgacccg | 780 |
| cgctataccc ctggtcatct gcagcgttca ctggtcgatg ccggtctgtt ggggaaaaag | 840 |
| aacggccgct cctattttgc cgccgaagaa accgccccgc cggtgacggc cgccaacaat | 900 |
| gcagacgtcg agacgctgcg cgtttacggc gagcatcctt tttttaccct gttgcagcag | 960 |
| cgagccgcgc ttcagtggcc acagctgcgc gtggaacaac ggccggcatt accggggctg | 1020 |
| ggagcggccg tccagatcaa tgacgctttc accgtcagca tcaccgatgg ccgcacggcg | 1080 |
| agccaactgg ccgagcagac ggcagcggat gcctttgtgg tcgatgtcgc cctgaactac | 1140 |
| gccgacacca cgtacctggt ggcggcgcac agtcgccacg cttctgcggc caataaggcg | 1200 |
| ctgttttac gcctgctgca cacggcaatc ccacaggttg aatttatcaa ggactctccg | 1260 |
| gcgcttatcg tcgcccgcgt cctcagcagc ctgatcaatg agtcggtgat catggtggaa | 1320 |
| agcggcgtct gcagccggga agacatcgat gtcgccgccg tcgcgggcgt taactacgcc | 1380 |
| ggcggcattt tcgactggct cggcaaactg ggggagaaaa acgtcaggac gacgctgagc | 1440 |
| aatctggcac agctgctgca cgcggcgcgc tatgcgccgc attacacccct tctgcacgcc | 1500 |
| gcgcaaccgg cgctgacgac cacgccttaa | 1530 |

<210> SEQ ID NO 63
<211> LENGTH: 1530
<212> TYPE: DNA
<213> ORGANISM: Serratia sp. HMSC15F11

<400> SEQUENCE: 63

| | |
|---|---|
| atggcagaaa gtaatgcggc aattcagtcg gctgcgatta tcggcgcggg aacgatgggc | 60 |
| agaggcatcg cttatctttt cgcgcaaaaa ggcattcgca cggtgcttta taatcgcaac | 120 |
| ggcaataccc tcaatcaggc tcgcgactat atcgagctag acctgaacaa gaaagtcgaa | 180 |
| cagggtaaga tcgcgctgca ggataaaggc gcggtgttgg ccaatctggt gttcacctcg | 240 |
| gtatttgaga ccattgccga cagcgagctg gtgatagaaa ccatcgccga gcaagagcaa | 300 |
| accaaacttg aggtgctggc ggccatcgcc gcggcagtca agcccgacac gctgatcgcc | 360 |
| accaataccct cctcactgtc gctgaataag ctggcaaccg cggtgacgca cagcgagcgg | 420 |
| tttatcggtt tgcactttt taaccccgcg ccgctgatga actgattga aatcatcccg | 480 |
| gcctacttta ccgcacacgc caccacggag cgttgccgtc aactggtggc cgcgttgggg | 540 |
| aaacgcgatg ttgtctgcca ggccacgccg gggtttatcg tcaaccgcat ggcccgcccc | 600 |
| tactacctgg aagggttccg cctattggaa gaacacgtgg cgcgcgcgcc gcagatcgac | 660 |
| cgtgccctca aggccggcgg gcactttcgt atggggccgc tcgagctgac cgattttatc | 720 |
| ggccaggaca tcaactatca ggtcagtcgg caaatctggc aggacatgca atacgacgcg | 780 |
| cgctataccc ccggccacct gcagcgttcg ctggtcgatg ccggtctatt ggggaaaaag | 840 |
| aacggccgct cctattttgc cgtcgaagaa acgccccgc cggtgatggc cgccaccgat | 900 |
| gcagacattg agacgctgca cgtttacggc gaacacccctt tttttaccct gttacaacaa | 960 |
| cgtgccgcgc ttcagtggcc acagctgcgc gtggaacaac ggccggcatt accgggcctg | 1020 |
| gggccggccg tccggatcaa tgacgctttc accgtcagca tcaccgatgg ccgcacggca | 1080 |
| aaccagctgg ccgagcagac ggcggcggat gcctttgtgg tcgatgtcgc cctgaattac | 1140 |
| gccgacacgg cgtatctggt ggcagcgcac agccgccacg cctctgcagc caataaagcg | 1200 |
| ctgttcttac gcctgctgca cacggcaatc ccgcaggttg aatttatcaa ggattccccg | 1260 |

```
gcgctgatcg tcgcccgcgt cctcagcagc ctaatcaacg agtcggtgat catggtggaa    1320
agcggcgtct gcagccggga agacatcgat gtcgccgccg tcgccggcgt taactacgcc    1380
gacggcattt tcggctggct agatagcctg ggggagaaaa acgtcaggac gacgctgagc    1440
aacctggcgc agctgctgca cgcagcacgc tatgcgccgc attacaccct tctgcacgcc    1500
gcgcaaccgg cgctgacgac cacgccttaa                                     1530
```

```
<210> SEQ ID NO 64
<211> LENGTH: 1530
<212> TYPE: DNA
<213> ORGANISM: Serratia sp. JKS000199

<400> SEQUENCE: 64
atggcagaaa gtaatgcggc aattcaatcg gctgcgatta tcggcgcggg aacgatgggc     60
agaggcatcg cttatctttt ggcgcaaaaa agcattcgta cggtgcttta taatcgcaac    120
ggcaataccc tcaatcaagc tcgcgacgct atcgtgcaag acctgaacaa aaaggtggaa    180
cagggcaagc tcgcgctgca ggacaaagac gcggtgctgg ctaatctgac gttctccacg    240
gaatttgggg ccatcgccga cagcgatctg gtgatcgaaa ccatcgcaga gcatgagcaa    300
gccaaactcg aagtgctggc ggccatcgcc gcgacggtca gcccgacac gctgatcgcc    360 accaatacct cctcactgtc gcttaataag ctggcgacgg cggtgacgca cagcgaacgc    420
tttatcggtt tgcactttt caaccccgcg ccgctgatga agctgattga aatcattccg    480
gcctatttta ccgcacaggt caccaccgaa cgttgccgtc aactggtggc ggcgttaggg    540
aaacgcgatg tcgtctgtca ggccacgccg ggatttatcg tcaaccgtat ggcccgcccc    600
tactatctgg aagggttccg cctgttggaa gaacacgtgg cgcgtgcgcc gcagatcgac    660
cgcgccctca aagccggcgg acactttcgc atggggccgc tcgagctgac cgattttatc    720
ggtcaggaca tcaactatca ggtcagccgg caaatttggc aggacatgca gtacgatccg    780
cgctataccc cgggccatct gcagcgctcg ctggtcgatg ccggtctgtt gggcaaaaag    840
aacggccgct cctattttc cgccgaagaa tctccccgc gcttgcggc gccgtcgat      900 gcggaagtcg agacgctacg catttacggt gaacatcctc tctttaccct gctacagcag    960
cgggccgccc tgcaatggcc gcggctgcgc gtgaacaac ggccgacatt accgggcctg    1020
ggcgccgcca ttcaggtcaa tgacgctttc accgtcagcg ttaccgatgg ccgcacggca    1080
aaccagcttg ccgaacagac cgcggcggac gcctttgtcg tcgatgtcgc cctgaactac    1140
ggcgatacgc cgtacctggt ggcggcgcat agccgccacg cctctgcggc caataaggcg    1200
ctgtttttgc gcctgctgca caccgcgatc ccgctggtgg aatttatcaa ggattccccg    1260
gccttgatcg tcgcccgcgt gctcagcagc ctgatcaacg agtcggtgat catggtggaa    1320
agcggcgtct gcagccggga agacattgat gtcgccgccg tcgccggcgt gaactacgcc    1380
gacggtattt tcggctggct cactcgcctc ggggaggaaa atgtcaggac gacgctgagc    1440
aacctggcgc aattgctgca cgcggcgcgc tatgcgccgc attacaccct tctgcacgcc    1500
gcccaaccgg cgctgaccac cacgccttaa                                     1530
```

```
<210> SEQ ID NO 65
<211> LENGTH: 1530
<212> TYPE: DNA
<213> ORGANISM: Serratia sp. TEL

<400> SEQUENCE: 65
```

| | |
|---|---:|
| atggcagaaa gtaatgcggc aattcaatcg gctgcgatta tcggcgcggg aacgatgggc | 60 |
| agaggcatcg cttatctttt ggcgcaaaaa agcattcgta cggtgcttta taatcgcaac | 120 |
| ggcaataccc tcaatcaagc tcgcgacgct atcgtgcaag acctgaacaa aaaggtggaa | 180 |
| cagggcaagc tcgcgctgca ggacaaagac gcggtgctgg ctaatctgac gttctccgcg | 240 |
| gaatttgggg ccatcgccga cagcgatctg gtgatcgaaa ccatcgcaga gcatgagcaa | 300 |
| gccaaactcg aggtgctggc ggccatcgcc gcgacggtca gcccgacac gctgatcgcc | 360 |
| accaataccct cctcactgtc gcttaataag ctggcgacgg cggtgacgca cagcgaacgc | 420 |
| tttatcggtt tgcacttttt caaccccgcg ccgctgatga agctgattga aatcattccg | 480 |
| gcctatttta ccgcacaggt caccaccgaa cgttgccgtc aactggtggc ggcgttgggg | 540 |
| aaacgcgatg tcgtctgtca ggccacgccg ggatttatcg tcaaccgtat ggcccgcccc | 600 |
| tactatctgg aagggttccg cctgttggaa gaacacgtgg cgcgtgcgcc gcagatcgac | 660 |
| cgcgccctca agccggcgg acactttcgc atggggccgc tcgaactgac cgatttatc | 720 |
| ggtcaggaca tcaactatca ggtcagccgg caaatttggc aggacatgca gtacgatccg | 780 |
| cgctataccc cgggccatct gcagcgctcg ctggtcgatg ccggtctgtt gggcaaaaag | 840 |
| aacgccgct cctattttc cgccgaagaa tctcctccgc cgcttgcggc cgccgtcgat | 900 |
| gcggaggtcg agacgctacg catttacggt gaacatcctc tctttactct gctacagcag | 960 |
| cgggccaccc tgcaatggcc gcggctgcgc gtggaacaac ggccgacatt accgggcctg | 1020 |
| ggcgccgcca ttcaggttaa tgacgctttc accgtcagcg ttaccgatgg ccgcacggca | 1080 |
| aaccagcttg ccgaacagac cgcggcggac gcctttgtcg tcgatgtcgc cctgaactac | 1140 |
| ggcgatacgg cgtacctggt ggcggcgcat agccgccacg cctctgcagc caataaggcg | 1200 |
| ctgtttttac gcctgctgca caccgcgatc ccgcaggtgg aatttatcaa ggattccccg | 1260 |
| gccttgatcg tcgcccgcgt gctcagcagc ctgatcaacg agtcggtgat catggtggaa | 1320 |
| agcggcgtct gcagccggga agacattgat gtcgccgccg tcgccggcgt gaactacgcc | 1380 |
| gacggtattt tcggctggct cactcgcctc ggggaggaaa atgtcagggc gacgctgagc | 1440 |
| aacctggcgc aattgctgca cgcggcgcgc tatgcgccgc attacaccct tctgcacgcc | 1500 |
| gcccaaccgg cgctgaccac cacgccttaa | 1530 |

<210> SEQ ID NO 66
<211> LENGTH: 1530
<212> TYPE: DNA
<213> ORGANISM: Serratia sp. ISTD04

<400> SEQUENCE: 66

| | |
|---|---:|
| atggcagaaa gtaatgcggc aattcaatcg gctgcgatta tcggcgcggg aacgatgggc | 60 |
| agaggcatcg cttatctttt ggcgcaaaaa agcattcgta cggtgcttta taatcgcaac | 120 |
| ggcaataccc tcaatcaagc tcgcgacgct atcgtgcaag acctgaacaa aaaggtggaa | 180 |
| cagggcaagc tcgcgctgca ggacaaagac gcggtgctgg ctaatctgac gttctccgca | 240 |
| gaatttgggg tcatcgccga cagcgatctg gtgatcgaaa ccatcgcaga acatgagcaa | 300 |
| gccaaactcg aggtgctggc ggccatcgcc gcgacggtca gtccgacac gctgatcgcc | 360 |
| accaataccct cctcactgtc gcttaataag ctggcgacgg cggtgacgca cagcgaacgc | 420 |
| tttatcggtt tgcacttttt caaccccgcg ccgctgatga agctgattga aatcattccg | 480 |
| gcctatttta ccgcacaggt caccaccgaa cgttgccgtc aactggtggc ggcgttaggg | 540 |
| aaacgcgatg tcgtctgtca ggccacgccg ggatttatcg tcaaccgtat ggcccgcccc | 600 |

```
tactatctgg aagggttccg cctgttggaa gaacacgtgg cgcgtgcgcc gcagatcgac    660
cgcgccctca agccggcgg acactttcgc atggggccgc tcgagctgac cgattttatc    720
ggtcaggaca tcaactatca ggtcagccgg caaatttggc aggacatgca gtacgatccg    780
cgctataccc cgggccatct gcagcgctcg ctggtcgatg ccggtctgtt gggcaaaaag    840
aacggccgct cctatttttc cgccgaagaa tctcccccgc cgcttgcggc cgccgtcgat    900
gcggaagtcg agacgctacg catttacggt gaacatcctc tctttactct gctacagcag    960
cgggccgccc tgcaatggcc gcggctgcgc gtggaacaac ggccgacatt accgggcctg   1020
ggcgccgcca ttcaggtcaa tgacgctttc accgtcagcg ttaccgatgg ccgcacggca   1080
aaccagcttg ccgaacagac cgcggcggac gcctttgtcg tcgatgtcgc cctgaactac   1140
ggcgatacgg cgtacctggt ggcggcacat agccgccatg cctctgcggc caataaggcg   1200 ctgttttttac gcctgctgca caccgcgatc ccgcaggtgg aatttatcaa ggattccccg   1260
gccttgatcg tcgcccgcgt gctcagcagc ctgatcaacg agtcggtgat catggtggaa   1320
agcggcgtct gcagccggga agacattgat gtcgccgccg tcgccggcgt gaactacgcc   1380 gacggtatt tcggctggct cactcgcctc ggggaggaaa atgtcaggac gacgctgagc   1440
aacctggcgc aattgctgca cgcggcgcgc tatgcgccgc attacaccct tctgcacgcc   1500
gcccaaccgg cgctgaccac cacgcccttaa                                  1530

<210> SEQ ID NO 67
<211> LENGTH: 1530
<212> TYPE: DNA
<213> ORGANISM: Serratia sp. SCBI

<400> SEQUENCE: 67
atggcagaaa gtaatgcggc aattcaatcg gctgcgatta tcggcgcggg aacgatgggc     60
agaggcatcg cttatctttt ggcgcaaaaa agcattcgta cggtgctttta taatcgcaac    120 ggcaatacccc tcaatcaagc tcgcgacgct atcgtgcaag acctgaacaa aaaggtggaa    180
cagggcaagc tcgcgctgca ggacaaagac gcggtgctgg ctaatctgac gttctccgcg    240
gaatttgggg ccatcgccga cagcgatctg gtgatcgaaa ccatcgcaga gcatgagcaa    300
gccaaactcg aggtgctggc ggccatcgcc gcgacggtca gcccgacac gctgatcgcc    360 accaatacct cctcactgtc gcttaataag ctggcgacgg cggtgacgca cagcgaacgc    420
tttatcggtt tgcacttttt caaccccgcg ccgctgatga agctgattga aatcattccg    480
gcctatttta ccgcacaggt taccaccgaa cgttgccgtc aactggtggc ggcgttgggg   540
aaacgcgatg tcgtctgtca ggccacgccg ggatttatcg tcaaccgtat ggcccgcccc    600
tactatctgg aagggttccg cctgttggaa gaacacgtgg cgcgtgcgcc gcagatcgac    660
cgcgccctca agccggcgg acactttcgc atggggccgc tcgagctgac cgattttatc    720
ggtcaggaca tcaactatca ggtcagccgg caaatttggc aggacatgca gtacgatccg    780
cgctataccc cgggccatct gcagcgctcg ctggtcgatg ccggtctgtt gggcaaaaag    840
aacggccgct cctatttttc caccgaagaa tctcccccgc cgcttgcggc cgccgtcgat    900
gcggaggtcg agacgctacg catttacggt gaacatcctc tctttaccct gctacagcag    960
cgggccgccc tgcaatggcc gcggctgcgc gtggaacaac ggccgacatt accgggcctg   1020
ggcgccgcca ttcaggtcaa tgacgctttc accgtcagcg ttaccgatgg ccgcacggca   1080
aaccagcttg ccgaacagac cgcggcggac gcctttgtcg tcgatgtcgc cctgaactac   1140
```

| | |
|---|---|
| ggcgatacgg cgtacctggt ggcggcgcat agccgccacg cctctgcggc caataaggcg | 1200 |
| ctgttttttac gcctgctgca caccgcgatc ccgcaggtgg aatttatcaa ggattccccg | 1260 |
| gccttgatcg tcgcccgcgt gctcagcagc ctgatcaacg agtcggtgat catggtggaa | 1320 |
| agcggcgtct gcagccggga agacattgat gtcgccgccg tcgccggcgt gaactacgcc | 1380 |
| gacggcattt tcggctggct cactcgcctc ggggaggaaa atgtcaggac gacgctgagc | 1440 |
| aacctggcgc aattgctgca cgcggcgcgc tatgcgccgc attacaccct tctgcacgcc | 1500 |
| gcccaaccgg cgctgaccac cacgccttaa | 1530 |

<210> SEQ ID NO 68
<211> LENGTH: 1530
<212> TYPE: DNA
<213> ORGANISM: Serratia sp. S4

<400> SEQUENCE: 68

| | |
|---|---|
| atggcagaga ataattcggc aatccattcg gtcgctgtta ttggtgccgg gaccatgggc | 60 |
| agaggtattg cctatcttct ggcgcaaaac ggcatacgaa ccctgcttta taatcgtagc | 120 |
| ggtaataatc tgaatcaggc cagggactat attatccgtg acctggataa gaaaatagat | 180 |
| ggcggtaaaa taagcctgca gaagaaaggc gagatattgg ccaatctggt tttctctcct | 240 |
| attttcgagg ctattgccga cagcgacctg gtgattgaaa ccatcgcgga acatgagtca | 300 |
| accaagcatg agatcctctc ggcgattgcg gccacggtga aaaagaggc gattatcgcc | 360 |
| accaataccct catcgctgtc attgaataag ctggcggcag gcgtcgaaaa taacgcccgt | 420 |
| tttatcggcc tgcacttctt caatccggcc ccgctgatga aactgatcga aattattccg | 480 |
| tcttacttta ccagccgggc caccagcctg cgttgccagc agttggtgac ggtgataggc | 540 |
| aaacagtttg tggtctgcaa agccacgccg ggctttatcg tcaaccggat ggcgcgacct | 600 |
| ttttatctgg aagggtttcg gctgttggaa gagaacgtgg cgctggcgcc gcagatcgac | 660 |
| cgcgcactca aggccggtgg ccacttccgc atgggacctt tagagctgac cgattttatc | 720 |
| ggccaggata ttaactatca ggtcagcagc cagatttggc aggacatgca gtacgacccc | 780 |
| cgctataccc ccggtcattt gcaacgttcg ctggtggatg ccgggctgct ggggaagaaa | 840 |
| aacggccgat cctttttttac cccctcttcc gccacaccca gctccgccga cgcaggcagc | 900 |
| ggcacgccga cctcactgaa ttttttatggt gaacatcccc tgttcgacct gttgcaacag | 960 |
| cgcgctttgg cgctctggcc aaggttgcag attaatcgcc aatcggaaca gccaacgctg | 1020 |
| ggccgcttta tccgggtgaa tgacgcaatg gccatcaaaa ttaccgatgg ccgcaccgcc | 1080 |
| aatctgctgg ctgaattgac cgaactcgat accttcgtga tcgacgccgc gctcaactac | 1140 |
| gccgataccg cctatctggc ggctgcccac agccaggatg ccagcacggc caataaagcg | 1200 |
| ctgtttctga cgctgctgca aacgttgatc ccacaggtgg agtttattaa agactccccg | 1260 |
| ggcctgattg tcgcccgcgt cctgagcagc ctgatcaatg agtcggtgat tatggtggag | 1320 |
| agcggggttt gcagccgggc ggacatcgat atcgccgcgg tggccggcgt taactatgcc | 1380 |
| gatggcatct ttagctggct ggcgcagctt gggcaaaaaa acgtgaagtc gacgctggac | 1440 |
| aatatggctc aactgctgca ttccgcccgc tattacccgc attactcttt gctcaatacc | 1500 |
| ccccggccag agctggccgt cgcgccctaa | 1530 |

<210> SEQ ID NO 69
<211> LENGTH: 1530
<212> TYPE: DNA
<213> ORGANISM: Serratia sp. C-1

<400> SEQUENCE: 69

```
atggcagaga ataattcggc aatccgttca gccgccgtta ttggtgcggg gaccatgggc    60
agaggcatcg cctacctcct ggcactgaac ggcatacgaa ccgtacttta taatcgcaat   120
ggtaataatc tcaatcaggc ccgtgactat attgtcagcg acctggacag aaaaatagat   180
aacggaaaaa taaccctgca gaaaaaaggc cagatattag ccaatattat tttctcggcc   240
gtctttgacg ccataaccga cagcgatctg gtgattgaaa ccattgcgga agatgagcaa   300
accaagcatg aaatcctggc agccattgcg ctacggtaa aaccggaggc gatcattgcg    360
accaataccl cctcgttgtc gctgaacaaa ctggcagcag gggtggaaaa caacccgcgc   420
tttatcggcc tgcattttt caatccggcg ccgctgatga agttgatcga aatcattccc    480
tcttatttta cctcccacgc caccagccta cgctgccaga agttggtaat agcattgggt   540
aaacagtttg tggtctgcaa agccacgccg ggctttattg ttaatcgcat ggcgcggcct   600
ttctatctgg aagggttccg gctgctggag gaaaacgtgg cgctggcgcc acagatcgac   660
cgcgccctca aggccggcgg gcattttcgc atgggccctt tagaactgac ggatttatc    720
ggtcaggata tcaactacca ggtcagcaag cagatttggc aggatatgca gttcgaccct   780
cgctatacccc ctggtcattt gcaacgctcg ctggtggatg ccgggctgct ggggaggaaa   840
aacgggcgct cttttttgc ttcccaaccg gcgacgccgc ccacccccgac acagagagc    900
gacacgccaa cgtcactgca tttttatggg gagcatgctt tattcgatca tctgcaacag   960
cgtgctctgg ccgcctggcc tgcgctgcgc gttcagcggt tgccggaacg gcctgaactg  1020
gggcgattta tcctggtgaa taacgcgctg gcgatcaaaa tcaccgatgg cagaacggca  1080
aacctgctcg ccggcttaac cgctctcgac accttcgtga ttgacgctgc gctgaattac  1140
gccgacaccg cctatctggt ggcagcccac aatcaacatg ccacagagac gaataaagcg  1200
ctgtttctga cgctgctgca aaccgtcatc gctcaggtgg agtttattaa agattcccct  1260
gccctgatcg ttgcccgcgt actgagcagc ctgatcaatg aatcggtgat catggtggag  1320
agcggcgttt gcagccgggc agatatcgat atcgccgccg tggccggcgt gaactatgcc  1380
gacggcattt ttgcctggtt ggcgcagctc gggcagaaaa acgtgaaatc gacgctggat  1440
aacatggcgc aactgctgca ctccgcgcgc tattacccgc attactcttt gctgaacgcg  1500
gcccggcctg agctggccgt agcgccctaa                                   1530
```

<210> SEQ ID NO 70
<211> LENGTH: 509
<212> TYPE: PRT
<213> ORGANISM: Serratia marcescens 532

<400> SEQUENCE: 70

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Gly Ala Val Leu Ala Asn Leu Met Phe Thr Ser
65                  70                  75                  80

Val Phe Glu Ala Ile Thr Asp Ser Glu Leu Val Ile Glu Thr Ile Ala
```

```
            85                  90                  95
Glu Gln Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
            130                 135                 140

His Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
            165                 170                 175

Ala Ala Leu Gly Lys His Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Ala Gln Ile Asp Arg Ala Leu Lys
            210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Thr Ala Pro Pro Val Thr Ala Ala Ser Asn Ala Asp Val Glu
            290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
            325                 330                 335

Leu Pro Gly Leu Gly Ser Ala Val Gln Ile Asn Asp Ala Phe Thr Val
            340                 345                 350

Ser Ile Thr Asp Gly Arg Thr Ala Ser Gln Leu Ala Glu Gln Thr Ala
            355                 360                 365

Ala Asp Ala Phe Val Val Asp Val Ala Leu Asn Tyr Ala Asp Thr Thr
            370                 375                 380

Tyr Leu Ala Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Gly Gly Ile Phe
            450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
            500                 505
```

<210> SEQ ID NO 71
<211> LENGTH: 509
<212> TYPE: PRT
<213> ORGANISM: Serratia marcescens 2880STDY5683033

<400> SEQUENCE: 71

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala His Asp Leu Asn Lys Lys Val Glu Gln Gly Lys Ile
    50                  55                  60

Ala Leu Gln Asp Lys Gly Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys His Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Ala Gln Ile Asp Arg Ala Leu Lys
    210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Thr
        275                 280                 285

Glu Glu Thr Ala Pro Pro Val Thr Ala Ala Ser Asn Ala Asp Val Glu
    290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ser Ala Val Gln Ile Asn Asp Ala Phe Thr Val
            340                 345                 350

Ser Ile Thr Asp Gly Arg Thr Ala Ser Gln Leu Ala Glu Gln Thr Ala
        355                 360                 365

Ala Asp Ala Phe Val Val Asp Val Ala Leu Asn Tyr Ala Asp Thr Thr
```

370                 375                 380
    Tyr Leu Ala Ala Ala His Ser Arg His Ala Ser Ala Ala Asn Lys Ala
    385                 390                 395                 400

Leu Phe Leu Arg Leu Leu His Thr Ala Ile Pro Gln Val Glu Phe Ile
                    405                 410                 415

Lys Asp Ser Pro Ala Leu Ile Val Ala Arg Val Leu Ser Ser Leu Ile
                    420                 425                 430

Asn Glu Ser Val Ile Met Val Glu Ser Gly Val Cys Ser Arg Glu Asp
                    435                 440                 445

Ile Asp Val Ala Ala Val Ala Gly Val Asn Tyr Ala Gly Gly Ile Phe
                    450                 455                 460

Asp Trp Leu Gly Lys Leu Gly Glu Lys Asn Val Arg Thr Thr Leu Ser
    465                 470                 475                 480

Asn Leu Ala Gln Leu Leu His Ala Ala Arg Tyr Ala Pro His Tyr Thr
                    485                 490                 495

Leu Leu His Ala Ala Gln Pro Ala Leu Thr Thr Thr Pro
                    500                 505

<210> SEQ ID NO 72
<211> LENGTH: 509
<212> TYPE: PRT
<213> ORGANISM: Serratia marcescens WW4

<400> SEQUENCE: 72

Met Ala Glu Ser Asn Ala Ala Ile Gln Ser Ala Ala Ile Ile Gly Ala
    1               5                   10                  15

Gly Thr Met Gly Arg Gly Ile Ala Tyr Leu Phe Ala Gln Lys Gly Ile
                    20                  25                  30

Pro Thr Met Leu Tyr Asn Arg Asn Gly Asn Thr Leu Asn Gln Ala Arg
                    35                  40                  45

Glu Tyr Ile Ala Gln Asp Leu Asn Lys Lys Val Glu Gln Gly Lys Ile
    50                  55                  60

Ala Leu Gln Asp Lys Asp Ala Val Leu Ala Asn Leu Met Phe Thr Ser
    65                  70                  75                  80

Val Phe Glu Ala Ile Ala Asp Ser Glu Leu Val Ile Glu Thr Ile Ala
                    85                  90                  95

Glu Gln Glu Gln Thr Lys Leu Glu Val Leu Ala Ala Ile Ala Ala Val
                    100                 105                 110

Val Lys Pro Asp Thr Leu Ile Ala Thr Asn Thr Ser Ser Leu Ser Leu
                    115                 120                 125

Asn Lys Leu Ala Thr Ala Val Thr His Ser Glu Arg Phe Ile Gly Leu
                    130                 135                 140

His Phe Phe Asn Pro Ala Pro Leu Met Lys Leu Ile Glu Ile Ile Pro
    145                 150                 155                 160

Ala Tyr Phe Thr Ala His Ala Thr Thr Glu Arg Cys Arg Gln Leu Val
                    165                 170                 175

Ala Ala Leu Gly Lys Arg Asp Val Val Cys Gln Ala Thr Pro Gly Phe
                    180                 185                 190

Ile Val Asn Arg Met Ala Arg Pro Tyr Tyr Leu Glu Gly Phe Arg Leu
                    195                 200                 205

Leu Glu Glu His Val Ala Arg Ala Gln Ile Asp Arg Ala Leu Lys
                    210                 215                 220

Ala Gly Gly Arg Phe Arg Met Gly Pro Leu Glu Leu Thr Asp Phe Ile
    225                 230                 235                 240

```
Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Pro Val Thr Ala Ala Asn Asn Ala Asp Val Glu
    290                 295                 300

Thr Leu Arg Val Tyr Gly Glu His Pro Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Gln Ile Asn Asp Ala Phe Thr Val
            340                 345                 350

Ser Ile Thr Asp Gly Arg Thr Ala Ser Gln Leu Ala Glu Gln Thr Ala
        355                 360                 365

Ala Asp Ala Phe Val Ile Asp Val Ala Leu Asn Tyr Ala Asp Thr Thr
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Gly Gly Ile Phe
    450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 73
<211> LENGTH: 509
<212> TYPE: PRT
<213> ORGANISM: Serratia marcescens K27

<400> SEQUENCE: 73

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Pro Thr Met Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Asp Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
            100                 105                 110
```

Val Lys Pro Asp Thr Leu Ile Ala Thr Asn Thr Ser Ser Leu Ser Leu
115                 120                 125

Asn Lys Leu Ala Thr Ala Val Thr His Ser Glu Arg Phe Ile Gly Leu
130                 135                 140

His Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
                180                 185                 190

Ile Val Asn Arg Met Ala Arg Pro Tyr Tyr Leu Glu Gly Phe Arg Leu
                195                 200                 205

Leu Glu Glu His Val Ala Arg Ser Ala Gln Ile Asp Arg Ala Leu Lys
210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ala Ala
                275                 280                 285

Glu Glu Thr Ala Pro Pro Val Thr Ala Ala Asn Asn Ala Asp Val Glu
                290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Gln Ile Asn Asp Ala Phe Thr Val
                340                 345                 350

Ser Ile Thr Asp Gly Arg Thr Ala Ser Gln Leu Ala Glu Gln Thr Ala
                355                 360                 365

Ala Asp Ala Phe Val Val Asp Val Ala Leu Asn Tyr Ala Asp Thr Thr
                370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
                435                 440                 445

Ile Asp Val Ala Ala Val Ala Gly Val Asn Tyr Ala Gly Gly Ile Phe
450                 455                 460

Asp Trp Leu Gly Lys Leu Gly Glu Arg Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Pro
                500                 505

<210> SEQ ID NO 74
<211> LENGTH: 509

-continued

```
<212> TYPE: PRT
<213> ORGANISM: Serratia marcescens 280

<400> SEQUENCE: 74
```

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Pro Thr Met Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Asp Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Ala Gln Ile Asp Arg Ala Leu Lys
210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Pro Val Thr Ala Ala Asn Asn Ala Asp Val Glu
    290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Gln Ile Asn Asp Ala Phe Thr Val
            340                 345                 350

Ser Ile Thr Asp Gly Arg Thr Ala Ser Gln Leu Ala Glu Gln Thr Ala
        355                 360                 365

Ala Asp Ala Phe Val Val Asp Val Ala Leu Asn Tyr Ala Asp Thr Thr
    370                 375                 380

Tyr Leu Val Ala Ala His Ser Arg His Ala Ser Ala Ala Asn Lys Ala
385                 390                 395                 400

-continued

```
Leu Phe Leu Leu Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Gly Gly Ile Phe
    450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505
```

<210> SEQ ID NO 75
<211> LENGTH: 509
<212> TYPE: PRT
<213> ORGANISM: Serratia marcescens 19F

<400> SEQUENCE: 75

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Pro Thr Met Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Asp Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
            100                 105                 110

Val Lys His Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Ala Gln Ile Asp Arg Ala Leu Lys
    210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
```

```
                    260                 265                 270
Asp Ala Gly Leu Leu Gly Lys Lys Asn Gly Arg Ser Tyr Phe Ala Ala
                275                 280                 285
Glu Glu Thr Ala Pro Pro Val Thr Ala Asn Asn Ala Asp Val Glu
            290                 295                 300
Thr Leu Arg Val Tyr Gly Glu His Pro Phe Thr Leu Leu Gln Gln
305                 310                 315                 320
Arg Ala Ala Leu Gln Trp Pro Gln Leu Arg Val Glu Gln Arg Pro Ala
                325                 330                 335
Leu Pro Gly Leu Gly Ala Ala Val Gln Ile Asn Asp Ala Phe Thr Val
                340                 345                 350
Ser Ile Thr Asp Gly Arg Thr Ala Ser Gln Leu Ala Glu Gln Thr Ala
                355                 360                 365
Ala Asp Ala Phe Val Val Asp Val Ala Leu Asn Tyr Ala Asp Thr Thr
                370                 375                 380
Tyr Leu Val Ala Ala His Ser Arg His Ala Ser Ala Ala Asn Lys Ala
385                 390                 395                 400
Leu Phe Leu Arg Leu Leu His Thr Ala Ile Pro Gln Val Glu Phe Ile
                405                 410                 415
Lys Asp Ser Pro Ala Leu Ile Val Ala Arg Val Leu Ser Ser Leu Ile
                420                 425                 430
Asn Glu Ser Val Ile Met Val Glu Ser Gly Val Cys Ser Arg Glu Asp
                435                 440                 445
Ile Asp Val Ala Ala Val Ala Gly Val Asn Tyr Ala Gly Gly Ile Phe
                450                 455                 460
Asp Trp Leu Gly Lys Leu Gly Glu Lys Asn Val Arg Thr Thr Leu Ser
465                 470                 475                 480
Asn Leu Ala Gln Leu Leu His Ala Ala Arg Tyr Ala Pro His Tyr Thr
                485                 490                 495
Leu Leu His Ala Ala Gln Pro Ala Leu Thr Thr Thr Pro
                500                 505

<210> SEQ ID NO 76
<211> LENGTH: 509
<212> TYPE: PRT
<213> ORGANISM: Serratia marcescens 1185

<400> SEQUENCE: 76

Met Ala Glu Ser Asn Ala Ala Ile Gln Ser Ala Ala Ile Ile Gly Ala
1               5                   10                  15
Gly Thr Met Gly Arg Gly Ile Ala Tyr Leu Phe Ala Gln Lys Gly Ile
                20                  25                  30
Pro Thr Met Leu Tyr Asn Arg Asn Gly Asn Thr Leu Asn Gln Ala Arg
            35                  40                  45
Glu Tyr Ile Ala Gln Asp Leu Asn Lys Lys Val Glu Gln Gly Lys Ile
        50                  55                  60
Ala Leu Arg Asp Lys Asp Ala Val Leu Ala Asn Leu Met Phe Thr Ser
65                  70                  75                  80
Val Phe Glu Ala Ile Ala Asp Ser Glu Leu Val Ile Glu Thr Ile Ala
                85                  90                  95
Glu Gln Glu Gln Thr Lys Leu Glu Val Leu Ala Ile Ala Ala Val
            100                 105                 110
Val Lys Pro Asp Thr Leu Ile Ala Thr Asn Thr Ser Ser Leu Ser Leu
            115                 120                 125
```

```
Asn Lys Leu Ala Thr Ala Val Thr His Ser Glu Arg Phe Ile Gly Leu
    130                 135                 140

His Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys His Asp Val Val Cys Gln Ala Thr Pro Gly Phe
                180                 185                 190

Ile Val Asn Arg Met Ala Arg Pro Tyr Tyr Leu Glu Gly Phe Arg Leu
                195                 200                 205

Leu Glu Glu His Val Ala Arg Ala Gln Ile Asp Arg Ala Leu Lys
210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ala Ala
                275                 280                 285

Glu Glu Thr Ala Pro Pro Val Thr Ala Ala Asn Asn Ala Asp Val Glu
                290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Gln Ile Asn Asp Ala Phe Thr Val
                340                 345                 350

Ser Ile Thr Asp Gly Arg Thr Ala Ser Gln Leu Ala Glu Gln Thr Ala
                355                 360                 365

Ala Asp Ala Phe Val Val Asp Leu Ala Leu Asn Tyr Ala Asp Thr Thr
                370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
                435                 440                 445

Ile Asp Val Ala Ala Val Ala Gly Val Asn Tyr Ala Gly Gly Ile Phe
450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Ser Ala Leu Thr Thr Thr Pro
                500                 505
```

<210> SEQ ID NO 77
<211> LENGTH: 509
<212> TYPE: PRT
<213> ORGANISM: Serratia marcescens S2I7

<400> SEQUENCE: 77

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Pro Thr Met Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
            50                  55                  60

Ala Leu Gln Asp Lys Asp Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
                100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
130                 135                 140

His Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Ala Gln Ile Asp Arg Ala Leu Lys
            210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Thr Ala Pro Pro Val Thr Ala Ala Asn Asn Ala Asp Val Glu
            290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Cys Val Glu Gln Arg Pro Ala
                325                 330                 335

Leu Pro Gly Leu Gly Ala Ala Val Gln Ile Asn Asp Ala Phe Thr Val
            340                 345                 350

Ser Ile Thr Asp Gly Arg Thr Ala Ser Gln Leu Ala Glu Gln Thr Ala
            355                 360                 365

Ala Asp Ala Phe Val Val Asp Val Ala Leu Asn Tyr Ala Asp Thr Thr
            370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415
```

```
Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Gly Gly Ile Phe
450                 455                 460

Asp Trp Leu Gly Lys Leu Gly Glu Arg Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
            500                 505

<210> SEQ ID NO 78
<211> LENGTH: 509
<212> TYPE: PRT
<213> ORGANISM: Serratia marcescens KHCo-24B

<400> SEQUENCE: 78

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Pro Thr Met Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Arg Asp Lys Asp Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Ala Gln Ile Asp Arg Ala Leu Lys
    210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285
```

Glu Glu Thr Ala Pro Pro Val Thr Ala Ala Asn Asn Ala Asp Val Glu
                290                 295                 300

Thr Leu Arg Val Tyr Gly Glu His Pro Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Gln Ile Asn Asp Ala Phe Thr Val
                340                 345                 350

Ser Ile Thr Asp Gly Arg Thr Ala Ser Gln Leu Ala Glu Gln Ala Ala
                355                 360                 365

Ala Asp Ala Phe Val Val Asp Leu Ala Leu Asn Tyr Ala Asp Thr Thr
                370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
                435                 440                 445

Ile Asp Val Ala Ala Val Ala Gly Val Asn Tyr Ala Gly Gly Ile Phe
                450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505

<210> SEQ ID NO 79
<211> LENGTH: 509
<212> TYPE: PRT
<213> ORGANISM: Serratia marcescens Z6

<400> SEQUENCE: 79

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Pro Thr Met Leu Tyr Asn Arg Asn Gly Asn Thr Leu Asn Gln Ala Arg
                35                  40                  45

Glu Tyr Ile Ala Gln Asp Leu Asn Lys Lys Val Glu Gln Gly Lys Ile
        50                  55                  60

Ala Leu Gln Asp Lys Asp Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
                100                 105                 110

Val Lys Pro Asp Thr Leu Ile Ala Thr Asn Thr Ser Ser Leu Ser Leu
                115                 120                 125

Asn Lys Leu Ala Thr Ala Val Thr His Arg Glu Arg Phe Ile Gly Leu
                130                 135                 140

His Phe Phe Asn Pro Ala Pro Leu Met Lys Leu Ile Glu Ile Ile Pro

```
                145                 150                 155                 160
Ala Tyr Phe Thr Ala His Ala Thr Thr Glu Arg Cys Arg Gln Leu Val
                    165                 170                 175

Ala Ala Leu Gly Lys Arg Asp Val Val Cys Gln Ala Thr Pro Gly Phe
                180                 185                 190

Ile Val Asn Arg Met Ala Arg Pro Tyr Tyr Leu Glu Gly Phe Arg Leu
                195                 200                 205

Leu Glu Glu His Val Ala Arg Ala Ala Gln Ile Asp Arg Ala Leu Lys
            210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                    245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ala Ala
                275                 280                 285

Glu Glu Thr Ala Pro Pro Val Thr Ala Ala Asn Asn Ala Asp Val Glu
            290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Cys Val Glu Gln Arg Pro Ala
                    325                 330                 335

Leu Pro Gly Leu Gly Ala Ala Val Gln Ile Asn Asp Ala Phe Thr Val
                340                 345                 350

Ser Ile Thr Asp Gly Arg Thr Ala Ser Gln Leu Ala Glu Gln Thr Ala
                355                 360                 365

Ala Asp Ala Phe Val Ile Asp Val Ala Leu Asn Tyr Ala Asp Thr Thr
            370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                    405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
                435                 440                 445

Ile Asp Val Ala Ala Val Ala Gly Val Asn Tyr Ala Gly Gly Ile Phe
            450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                    485                 490                 495

Leu Leu His Ala Ala Gln Pro Ala Leu Thr Thr Thr Pro
                500                 505

<210> SEQ ID NO 80
<211> LENGTH: 509
<212> TYPE: PRT
<213> ORGANISM: Serratia marcescens 546

<400> SEQUENCE: 80

Met Ala Glu Ser Asn Ala Ala Ile Gln Ser Ala Ile Ile Gly Ala
1               5                   10                  15
```

```
Gly Thr Met Gly Arg Gly Ile Ala Tyr Leu Phe Ala Gln Lys Gly Ile
         20                  25                  30

Pro Thr Met Leu Tyr Asn Arg Asn Gly Asn Thr Leu Asn Gln Ala Arg
         35                  40                  45

Glu Tyr Ile Ala Gln Asp Leu Asn Lys Lys Val Glu Gln Gly Lys Ile
 50                      55                  60

Ala Leu Arg Asp Lys Asp Ala Val Leu Ala Asn Leu Met Phe Thr Ser
 65                  70                  75                  80

Val Phe Glu Ala Ile Ala Asp Ser Glu Leu Val Ile Glu Thr Ile Ala
                     85                  90                  95

Glu Gln Glu Gln Thr Lys Leu Glu Val Leu Ala Ala Ile Ala Ala Val
                100                 105                 110

Val Lys Pro Asp Thr Leu Ile Ala Thr Asn Thr Ser Ser Leu Ser Leu
        115                 120                 125

Asn Lys Leu Ser Thr Ala Val Thr His Asn Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                    165                 170                 175

Ala Ala Leu Gly Lys Arg Asp Val Val Cys Gln Ala Thr Pro Gly Phe
                    180                 185                 190

Ile Val Asn Arg Met Ala Arg Pro Tyr Tyr Leu Glu Gly Phe Arg Leu
                195                 200                 205

Leu Glu Glu His Val Ala Arg Ala Ala Gln Ile Asp Arg Ala Leu Lys
210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                    245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ala Ala
            275                 280                 285

Glu Glu Thr Ala Pro Pro Val Thr Ala Ala Asn Asn Ala Asp Val Glu
290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Arg Ile Asn Asp Ala Phe Thr Val
                340                 345                 350

Ser Ile Thr Asp Gly Arg Thr Ala Ser Gln Leu Ala Glu Gln Thr Ala
        355                 360                 365

Ala Asp Ala Phe Val Val Asp Val Ala Leu Asn Tyr Ala Asp Thr Thr
        370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
```

```
            435                 440                 445
Ile Asp Val Ala Val Ala Gly Val Asn Tyr Ala Gly Gly Ile Phe
450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 81
<211> LENGTH: 509
<212> TYPE: PRT
<213> ORGANISM: Serratia nematodiphila MB307

<400> SEQUENCE: 81

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Pro Thr Met Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
50                  55                  60

Ala Leu Arg Asp Lys Asp Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Ala Gln Ile Asp Arg Ala Leu Lys
    210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Gln Val Thr Ala Ala Asn Ala Asp Val Glu
    290                 295                 300
```

```
Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Gln Ile Asn Asp Ala Phe Thr Val
            340                 345                 350

Ser Ile Thr Asp Gly Arg Thr Ala Ser Gln Leu Ala Glu Gln Thr Ala
        355                 360                 365

Ala Asp Ala Phe Val Val Asp Leu Ala Leu Asn Tyr Ala Asp Thr Thr
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Gly Gly Ile Phe
    450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 82
<211> LENGTH: 509
<212> TYPE: PRT
<213> ORGANISM: Serratia marcescens VGH107

<400> SEQUENCE: 82

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Pro Thr Met Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
        50                  55                  60

Ala Leu Gln Asp Lys Asp Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ile Ala Ala Val
            100                 105                 110

Val Lys His Asp Thr Leu Ile Ala Thr Asn Thr Ser Ser Leu Ser Leu
    115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175
```

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Ala Gln Ile Asp Arg Ala Leu Lys
            210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Thr Ala Pro Pro Val Thr Ala Ala Asn Asn Ala Asp Val Glu
            290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ala Ala Val Gln Ile Asn Asp Ala Phe Thr Val
            340                 345                 350

Ser Ile Thr Asp Gly Arg Thr Ala Ser Gln Leu Ala Glu Gln Thr Ala
            355                 360                 365

Ala Asp Ala Phe Val Val Asp Val Ala Leu Asn Tyr Ala Asp Thr Thr
            370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Gly Gly Ile Phe
            450                 455                 460

Asp Trp Leu Gly Lys Leu Gly Glu Lys Asn Val Arg Thr Met Leu Ser
465                 470                 475                 480

Asn Leu Ala Gln Leu Leu His Ala Ala Arg Tyr Ala Pro His Tyr Asn
                485                 490                 495

Leu Leu His Ala Ala Gln Pro Ala Leu Thr Thr Thr Pro
            500                 505

<210> SEQ ID NO 83
<211> LENGTH: 509
<212> TYPE: PRT
<213> ORGANISM: Serratia marcescens MCB

<400> SEQUENCE: 83

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg

```
                35                  40                  45
Glu Tyr Ile Ala Gln Asp Leu Asn Lys Lys Val Glu Gln Gly Lys Ile
 50                  55                  60

Ala Leu Gln Asp Lys Ser Ser Val Leu Ala Asn Leu Val Phe Ser Thr
 65                  70                  75                  80

Ala Leu Glu Ala Ile Ala Asp Ser Glu Leu Val Ile Glu Thr Ile Ala
                 85                  90                  95

Glu His Glu Gln Thr Lys Leu Glu Val Leu Ala Ile Ala Ala Val
                100                 105                 110

Val Lys Pro Asp Thr Leu Ile Ala Thr Asn Thr Ser Ser Leu Ser Leu
                115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
                180                 185                 190

Ile Val Asn Arg Met Ala Arg Pro Tyr Tyr Leu Glu Gly Phe Arg Leu
                195                 200                 205

Leu Glu Glu His Val Ala Arg Ala Pro Gln Ile Asp Arg Ala Leu Lys
210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Thr Ala
                275                 280                 285

Glu Glu Thr Ala Pro Pro Val Thr Ala Ala Ile Gly Ala Asp Val Glu
290                 295                 300

Thr Leu Arg Ile Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Val Gly Pro Ala Val Gln Ile Asn Asp Ala Phe Thr Val
                340                 345                 350

Ser Ile Thr Asp Gly Arg Thr Ala Ser Gln Leu Ala Glu Gln Thr Thr
                355                 360                 365

Ala Asp Ala Phe Val Val Asp Ile Ala Leu Asn Tyr Ala Asp Thr Ala
370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
                435                 440                 445

Ile Asp Val Ala Ala Val Ala Gly Val Asn Tyr Ala Gly Gly Ile Phe
450                 455                 460
```

Asp Trp Leu Ser Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 84
<211> LENGTH: 509
<212> TYPE: PRT
<213> ORGANISM: Serratia marcescens AH0650

<400> SEQUENCE: 84

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
50                  55                  60

Ala Leu Gln Asp Lys Ser Ser Val Leu Ala Asn Leu Val Phe Ser Thr
65                  70                  75                  80

Ala Leu Glu Ala Ile Ala Asp Ser Glu Leu Val Ile Glu Thr Ile Ala
                85                  90                  95

Glu His Glu Gln Thr Lys Leu Glu Val Leu Ala Ile Ala Ala Val
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Thr Ala Pro Pro Val Thr Ala Ala Ile Asp Ala Asp Val Glu
            290                 295                 300

Thr Leu Arg Val Tyr Gly Glu His Pro Phe Phe Thr Leu Leu Gln Gln
305                 310                 315                 320

Arg Ala Ala Arg Gln Trp Pro Gln Leu Arg Val Glu Gln Arg Pro Ala

```
                    325                 330                 335
Leu Pro Ser Leu Gly Pro Ala Val Gln Ile Asn Asp Ala Phe Thr Val
                340                 345                 350
Ser Ile Thr Asp Gly Arg Thr Ala Ser Gln Leu Ala Glu Gln Thr Thr
                355                 360                 365
Ala Asp Ala Phe Val Val Asp Ile Ala Leu Asn Tyr Ala Asp Thr Ala
            370                 375                 380
Tyr Leu Val Ala Ala His Asn Arg Tyr Ala Ser Ala Ala Asn Lys Ala
385                 390                 395                 400
Leu Phe Leu Arg Leu Leu His Thr Ala Ile Pro Gln Val Glu Phe Ile
                405                 410                 415
Lys Asp Ser Pro Ala Leu Ile Val Ala Arg Val Leu Ser Ser Leu Ile
                420                 425                 430
Asn Glu Ser Val Ile Met Val Glu Ser Gly Val Cys Ser Arg Glu Asp
                435                 440                 445
Ile Asp Val Ala Ala Val Ala Gly Val Asn Tyr Ala Gly Gly Ile Phe
            450                 455                 460
Asp Trp Leu Gly Lys Leu Gly Glu Lys Asn Val Arg Thr Thr Leu Ser
465                 470                 475                 480
Asn Leu Ala Gln Leu Leu His Ala Ala Arg Tyr Ala Pro His Tyr Thr
                485                 490                 495
Leu Leu His Ala Ala Gln Pro Ala Leu Thr Thr Thr Pro
                500                 505

<210> SEQ ID NO 85
<211> LENGTH: 509
<212> TYPE: PRT
<213> ORGANISM: Serratia marcescens UMH12

<400> SEQUENCE: 85

Met Ala Glu Ser Asn Ala Glu Ile Gln Ser Ala Ala Ile Ile Gly Ala
1               5                   10                  15
Gly Thr Met Gly Arg Gly Ile Ala Tyr Leu Phe Ala Gln Lys Gly Ile
                20                  25                  30
Arg Thr Val Leu Tyr Asn Arg Asn Gly Asn Thr Leu Asn Gln Ala Arg
            35                  40                  45
Glu Tyr Ile Ala Gln Asp Leu Asn Lys Lys Val Glu Gln Gly Lys Ile
    50                  55                  60
Ala Leu Gln Asp Lys Ser Ser Val Leu Ala Asn Leu Val Phe Ser Thr
65                  70                  75                  80
Ala Leu Glu Ala Ile Ala Asp Ser Glu Leu Val Ile Glu Thr Ile Ala
                85                  90                  95
Glu His Glu Gln Thr Lys Leu Glu Val Leu Ala Ala Ile Ala Ala Val
                100                 105                 110
Val Lys Pro Asp Thr Leu Ile Ala Thr Asn Thr Ser Ser Leu Ser Leu
            115                 120                 125
Asn Lys Leu Ala Thr Ala Val Thr His Ser Glu Arg Phe Ile Gly Leu
    130                 135                 140
His Phe Phe Asn Pro Ala Pro Leu Met Lys Leu Ile Glu Ile Ile Pro
145                 150                 155                 160
Ala Tyr Phe Thr Ala His Ala Thr Thr Glu Arg Cys Arg Gln Leu Val
                165                 170                 175
Ala Ala Leu Gly Lys Arg Asp Val Val Cys Gln Ala Thr Pro Gly Phe
            180                 185                 190
```

```
Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Pro Val Thr Ala Ala Ile Asp Ala Asp Val Glu
    290                 295                 300

Thr Leu Arg Val Tyr Gly Glu His Pro Phe Phe Thr Leu Leu Gln Gln
305                 310                 315                 320

Arg Ala Ala Arg Gln Trp Pro Gln Leu Arg Val Glu Gln Arg Pro Ala
                325                 330                 335

Leu Pro Ser Leu Gly Pro Ala Val Gln Ile Asn Asp Ala Phe Thr Val
            340                 345                 350

Ser Ile Thr Asp Gly Arg Thr Ala Ser Gln Leu Ala Glu Gln Thr Thr
        355                 360                 365

Ala Asp Ala Phe Val Val Asp Ile Ala Leu Asn Tyr Ala Asp Thr Ala
    370                 375                 380

Tyr Leu Val Ala Ala His Asn Arg Tyr Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Gly Gly Ile Phe
    450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 86
<211> LENGTH: 509
<212> TYPE: PRT
<213> ORGANISM: Serratia sp. OMLW3

<400> SEQUENCE: 86

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
        50                  55                  60
```

```
Ala Leu Gln Asp Lys Ser Ser Val Leu Ala Asn Leu Val Phe Ser Thr
 65                  70                  75                  80

Ala Leu Val Ala Ile Ala Asp Ser Glu Leu Val Ile Glu Thr Ile Ala
                 85                  90                  95

Glu His Glu Gln Thr Lys Leu Glu Val Leu Ala Ile Ala Ala Val
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
            130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
            210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Thr Ala Pro Pro Val Thr Ala Ala Ile Asp Ala Asp Val Glu
            290                 295                 300

Thr Leu Arg Val Tyr Gly Glu His Pro Phe Phe Thr Leu Leu Gln Gln
305                 310                 315                 320

Arg Ala Ala Arg Gln Trp Pro Gln Leu Arg Val Glu Gln Arg Pro Ala
                325                 330                 335

Leu Pro Ser Leu Gly Pro Ala Val Gln Ile Asn Asp Ala Phe Thr Val
            340                 345                 350

Ser Ile Thr Asp Gly Arg Thr Ala Ser Gln Leu Ala Glu Gln Thr Thr
            355                 360                 365

Ala Asp Ala Phe Val Val Asp Ile Ala Leu Asn Tyr Ala Asp Thr Ala
            370                 375                 380

Tyr Leu Val Ala Ala His Asn Arg Tyr Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Gly Gly Ile Phe
            450                 455                 460

Asp Trp Leu Gly Lys Leu Gly Glu Lys Asn Val Arg Thr Thr Leu Ser
465                 470                 475                 480
```

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
        500                 505

<210> SEQ ID NO 87
<211> LENGTH: 509
<212> TYPE: PRT
<213> ORGANISM: Serratia marcescens UMH11

<400> SEQUENCE: 87

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Ser Gly Asn Thr Leu Asn Gln Ala Arg
        35                  40                  45

Glu Tyr Ile Ala Gln Asp Leu Asn Lys Lys Val Glu Gln Gly Lys Ile
50                  55                  60

Ala Leu Gln Asp Lys Ser Ser Val Leu Ala Asn Leu Val Phe Ser Thr
65                  70                  75                  80

Ala Leu Val Ala Ile Ala Asp Ser Glu Leu Val Ile Glu Thr Ile Ala
                85                  90                  95

Glu His Glu Gln Thr Lys Leu Glu Val Leu Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
210                 215                 220

Ala Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Pro Val Thr Ala Ala Ile Asp Ala Asp Val Glu
290                 295                 300

Thr Leu Arg Val Tyr Gly Glu His Pro Phe Thr Leu Leu Gln Gln
305                 310                 315                 320

Arg Ala Ala Arg Gln Trp Pro Gln Leu Arg Val Glu Gln Arg Pro Ala
                325                 330                 335

Leu Pro Ser Leu Gly Pro Ala Val Gln Ile Asn Asp Ala Phe Thr Val
            340                 345                 350

-continued

```
Ser Ile Thr Asp Gly Arg Thr Ala Ser Gln Leu Ala Glu Gln Thr Thr
            355                 360                 365

Ala Asp Ala Phe Val Val Asp Ile Ala Leu Asn Tyr Ala Asp Thr Ala
    370                 375                 380

Tyr Leu Val Ala Ala His Asn Arg Tyr Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Gly Gly Ile Phe
        450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505
```

<210> SEQ ID NO 88
<211> LENGTH: 509
<212> TYPE: PRT
<213> ORGANISM: Serratia marcescens UMH1

<400> SEQUENCE: 88

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
    50                  55                  60

Ala Leu Gln Asp Lys Ser Ser Val Leu Ala Asn Leu Val Phe Ser Thr
65                  70                  75                  80

Ala Leu Glu Ala Ile Ala Asp Ser Glu Leu Val Ile Glu Thr Ile Ala
                85                  90                  95

Glu His Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
```

```
            210                 215                 220
Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Pro Val Thr Ala Ala Ile Asp Ala Asp Val Glu
    290                 295                 300

Thr Leu Arg Val Tyr Gly Glu His Pro Phe Phe Thr Leu Leu Gln Gln
305                 310                 315                 320

Gln Ala Ala Arg Gln Trp Pro Gln Leu Arg Val Glu Gln Arg Pro Ala
                325                 330                 335

Leu Pro Ser Leu Gly Pro Ala Val Gln Ile Asn Gly Ala Phe Thr Val
            340                 345                 350

Ser Ile Thr Asp Gly Arg Thr Ala Ser Gln Leu Ala Glu Gln Thr Thr
        355                 360                 365

Ala Asp Ala Phe Val Ile Asp Ile Ala Leu Asn Tyr Ala Asp Thr Ala
    370                 375                 380

Tyr Leu Val Ala Ala His Asn Arg Tyr Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Gly Gly Ile Phe
    450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 89
<211> LENGTH: 509
<212> TYPE: PRT
<213> ORGANISM: Serratia marcescens 2880STDY5683020

<400> SEQUENCE: 89

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
        50                  55                  60

Ala Leu Gln Asp Lys Gly Ala Val Leu Ala Asn Leu Val Phe Thr Ser
65                  70                  75                  80
```

-continued

```
Val Phe Glu Thr Ile Ala Asp Ser Asp Leu Val Ile Glu Thr Ile Ala
                 85                  90                  95
Glu Gln Glu Gln Thr Lys Leu Glu Val Leu Ala Ala Ile Ala Ala Ala
            100                 105                 110
Val Lys Pro Asp Thr Leu Ile Ala Thr Asn Thr Ser Ser Leu Ser Leu
        115                 120                 125
Asn Lys Leu Ala Thr Ala Val Thr His Ser Glu Arg Phe Ile Gly Leu
    130                 135                 140
His Phe Phe Asn Pro Ala Pro Leu Met Lys Leu Ile Glu Ile Ile Pro
145                 150                 155                 160
Ala Tyr Phe Thr Ala Arg Ala Thr Thr Glu Arg Cys Arg Gln Leu Val
                165                 170                 175
Ala Ala Leu Gly Lys Arg Asp Val Val Cys Gln Ala Thr Pro Gly Phe
            180                 185                 190
Ile Val Asn Arg Met Ala Arg Pro Tyr Tyr Leu Glu Gly Phe Arg Leu
        195                 200                 205
Leu Glu Glu His Val Ala Arg Ala Pro Gln Ile Asp Arg Ala Leu Lys
    210                 215                 220
Ala Gly Gly His Phe Arg Met Gly Pro Leu Glu Leu Thr Asp Phe Ile
225                 230                 235                 240
Gly Gln Asp Ile Asn Tyr Gln Val Ser Arg Gln Ile Trp Gln Asp Met
                245                 250                 255
Gln Tyr Asp Pro Arg Tyr Thr Pro Gly His Leu Gln Arg Ser Leu Val
            260                 265                 270
Asp Ala Gly Leu Leu Gly Lys Lys Asn Gly Arg Ser Tyr Phe Ala Ala
        275                 280                 285
Glu Glu Asn Ala Leu Pro Val Thr Ala Ala Thr Asp Ala Asp Val Glu
    290                 295                 300
Thr Leu Arg Val Tyr Gly Glu His Pro Phe Phe Thr Leu Leu Gln Gln
305                 310                 315                 320
Arg Ala Ala Leu Gln Trp Pro Arg Leu Arg Val Glu Gln Arg Pro Ala
                325                 330                 335
Leu Pro Gly Leu Gly Pro Ala Val Gln Ile Asn Glu Ala Phe Thr Val
            340                 345                 350
Ser Val Thr Asp Gly Arg Thr Ala Ser Gln Leu Ala Glu Gln Thr Ala
        355                 360                 365
Ala Asp Ala Phe Val Val Asp Val Ala Leu Asn Tyr Ala Asp Thr Ala
    370                 375                 380
Tyr Leu Val Ala Ala His Asn Arg His Ala Ser Ala Ala Asn Lys Ala
385                 390                 395                 400
Leu Phe Leu Arg Leu Leu His Thr Ala Ile Pro Gln Val Glu Phe Ile
                405                 410                 415
Lys Asp Ser Pro Ala Leu Ile Val Ala Arg Val Leu Ser Ser Leu Ile
            420                 425                 430
Asn Glu Ser Val Ile Met Val Glu Ser Gly Val Cys Ser Arg Glu Asp
        435                 440                 445
Ile Asp Val Ala Ala Val Ala Gly Val Asn Tyr Ala Asp Gly Ile Phe
    450                 455                 460
Gly Trp Leu Asp Ser Leu Gly Glu Lys Asn Val Arg Thr Thr Leu Ser
465                 470                 475                 480
Asn Leu Ala Gln Leu Leu His Ala Ala Arg Tyr Ala Pro His Tyr Thr
                485                 490                 495
Leu Leu His Ala Ala Gln Pro Ala Leu Thr Thr Thr Pro
```

<210> SEQ ID NO 90
<211> LENGTH: 509
<212> TYPE: PRT
<213> ORGANISM: Serratia marcescens 99

<400> SEQUENCE: 90

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Asp Leu Val Ile Glu Thr Ile Ala
            85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
            165                 170                 175

Ala Ala Leu Gly Lys Arg Asp Val Val Cys Gln Ala Thr Pro Gly Phe
        180                 185                 190

Ile Val Asn Arg Met Ala Arg Pro Tyr Tyr Leu Glu Gly Phe Arg Leu
    195                 200                 205

Leu Glu Glu His Val Ala Arg Ala Pro Gln Ile Asp Arg Ala Leu Lys
210                 215                 220

Ala Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
        260                 265                 270

Asp Ala Gly Leu Leu Gly Lys Lys Asn Gly Arg Ser Tyr Phe Ala Ala
    275                 280                 285

Glu Glu Asn Ala Leu Pro Val Thr Ala Ala Ser Asn Ala Asp Val Glu
290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
            325                 330                 335

Leu Pro Gly Leu Gly Pro Ala Val Gln Ile Asn Glu Ala Phe Thr Val
        340                 345                 350

Ser Val Thr Asp Gly Arg Thr Ala Ser Gln Leu Ala Glu Leu Thr Ala
    355                 360                 365

```
Ala Asp Ala Phe Val Val Asp Val Ala Leu Asn Tyr Ala Asp Thr Ala
    370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Val Leu Thr Thr Thr Pro
            500                 505

<210> SEQ ID NO 91
<211> LENGTH: 509
<212> TYPE: PRT
<213> ORGANISM: Serratia marcescens 374

<400> SEQUENCE: 91

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Ser Ser Val Leu Ala Asn Leu Val Phe Ser Thr
65                  70                  75                  80

Ala Leu Val Ala Ile Ala Asp Ser Glu Leu Val Ile Glu Thr Ile Ala
                85                  90                  95

Glu His Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240
```

```
Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Pro Val Thr Ala Ala Ile Asp Ala Asp Val Glu
    290                 295                 300

Thr Leu Arg Val Tyr Gly Glu His Pro Phe Phe Thr Leu Leu Gln Gln
305                 310                 315                 320

Gln Ala Ala Arg Gln Trp Pro Gln Leu Arg Val Glu Gln Arg Pro Ala
                325                 330                 335

Leu Pro Ser Leu Gly Pro Ala Val Gln Ile Asn Gly Ala Phe Thr Val
            340                 345                 350

Ser Ile Thr Asp Gly Arg Thr Ala Ser Gln Leu Ala Glu Gln Thr Thr
        355                 360                 365

Ala Asp Ala Phe Val Ile Asp Ile Ala Leu Asn Tyr Ala Asp Thr Ala
    370                 375                 380

Tyr Leu Val Ala Ala His Asn Arg Tyr Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Gly Gly Ile Phe
    450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 92
<211> LENGTH: 509
<212> TYPE: PRT
<213> ORGANISM: Serratia marcescens 2880STDY5683036

<400> SEQUENCE: 92

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Asp Leu Val Ile Glu Thr Ile Ala
                85                  90                  95

Glu Gln Glu Gln Thr Lys Leu Glu Val Leu Ala Ala Ile Ala Ala Ala
```

```
            100                 105                 110
Val Lys Pro Asp Thr Leu Leu Ala Thr Asn Thr Ser Ser Leu Ser Leu
            115                 120                 125

Asn Lys Leu Ala Thr Ala Val Thr His Ser Glu Arg Phe Ile Gly Leu
            130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
            165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
            210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Asn Ala Leu Pro Val Thr Ala Ala Ser Asn Ala Asp Val Glu
            290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
            325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
            355                 360                 365

Ala Asp Ala Phe Val Val Asp Val Ala Leu Asn Tyr Ala Asp Thr Ala
            370                 375                 380

Tyr Leu Val Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
            450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Val Leu Thr Thr Thr Pro
            500                 505

<210> SEQ ID NO 93
```

<211> LENGTH: 509
<212> TYPE: PRT
<213> ORGANISM: Serratia marcescens 2880STDY5683034

<400> SEQUENCE: 93

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Asn Ala Leu Pro Val Thr Ala Ala Thr Asp Ala Asp Val Glu
    290                 295                 300

Thr Leu Arg Ile Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
        355                 360                 365

Ala Asp Ala Phe Val Val Asp Val Ala Leu Asn Tyr Ala Asp Thr Ala
    370                 375                 380

Tyr Leu Val Ala Ala His Asn Arg His Ala Ser Ala Ala Asn Lys Ala
```

```
                385                 390                 395                 400
Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
                435                 440                 445

Ile Asp Val Ala Ala Val Ala Gly Val Asn Tyr Ala Asp Gly Ile Phe
                450                 455                 460

Gly Trp Leu Asp Asn Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505

<210> SEQ ID NO 94
<211> LENGTH: 509
<212> TYPE: PRT
<213> ORGANISM: Serratia marcescens 2880STDY5682892

<400> SEQUENCE: 94

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
        50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Asp Leu Val Ile Glu Thr Ile Ala
                85                  90                  95

Glu Gln Glu Gln Thr Lys Leu Glu Val Leu Ala Ala Ile Ala Ala Ala
                100                 105                 110

Val Lys Pro Asp Thr Leu Ile Ala Thr Asn Thr Ser Ser Leu Ser Leu
                115                 120                 125

Asn Lys Leu Ala Thr Ala Val Thr His Ser Glu Arg Phe Ile Gly Leu
            130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
                165                 170                 175

Ala Ala Leu Gly Lys Arg Asp Val Val Cys Gln Ala Thr Pro Gly Phe
                180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
        210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255
```

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ala Ala
            275                 280                 285

Glu Glu Asn Ala Leu Pro Val Thr Ala Ala Thr Asp Ala Asp Val Glu
        290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
        355                 360                 365

Ala Asp Ala Phe Val Val Asp Val Ala Leu Asn Tyr Ala Asp Thr Ala
    370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
    450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 95
<211> LENGTH: 509
<212> TYPE: PRT
<213> ORGANISM: Serratia marcescens SM39

<400> SEQUENCE: 95

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Val Gln Asp Leu Asn Lys Lys Val Glu Gln Gly Lys Ile
        50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
            165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Asn Ala Leu Pro Val Thr Ala Ala Thr Asp Ala Asp Val Glu
290                 295                 300

Thr Leu Arg Ile Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
            355                 360                 365

Ala Asp Ala Phe Val Val Asp Val Ala Leu Asn Tyr Ala Asp Thr Ala
370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
450                 455                 460

Gly Trp Leu Asp Asn Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 96
<211> LENGTH: 509
<212> TYPE: PRT
<213> ORGANISM: Serratia marcescens 189

<400> SEQUENCE: 96

```
Met Ala Glu Ser Asn Ala Ala Ile Gln Ser Ala Ala Ile Ile Gly Ala
1               5                   10                  15
Gly Thr Met Gly Arg Gly Ile Ala Tyr Leu Phe Ala Gln Lys Gly Ile
            20                  25                  30
Arg Thr Val Leu Tyr Asn Arg Gly Asn Thr Leu Asn Gln Ala Arg
                35                  40                  45
Glu Tyr Ile Ala Gln Asp Leu Asn Lys Lys Val Glu Gln Gly Lys Ile
    50                  55                  60
Ala Leu Gln Asp Lys Gly Ala Val Leu Ala Asn Leu Val Phe Thr Ser
65                  70                  75                  80
Val Phe Glu Thr Ile Ala Asp Ser Asp Leu Val Ile Glu Thr Ile Ala
                85                  90                  95
Glu Gln Glu Gln Thr Lys Leu Glu Val Leu Ala Ala Ile Ala Ala Ala
                100                 105                 110
Val Lys Pro Asp Thr Leu Ile Ala Thr Asn Thr Ser Ser Leu Ser Leu
                115                 120                 125
Asn Lys Leu Ala Thr Ala Val Thr His Ser Glu Arg Phe Ile Gly Leu
    130                 135                 140
His Phe Phe Asn Pro Ala Pro Leu Met Lys Leu Ile Glu Ile Ile Pro
145                 150                 155                 160
Ala Tyr Phe Thr Ala Arg Ala Thr Thr Glu Arg Cys Arg Gln Leu Val
                165                 170                 175
Ala Ala Leu Gly Lys Arg Asp Val Val Cys Gln Ala Thr Pro Gly Phe
                180                 185                 190
Ile Val Asn Arg Met Ala Arg Pro Tyr Tyr Leu Glu Gly Phe Arg Leu
                195                 200                 205
Leu Glu Glu His Val Ala Arg Ala Pro Gln Ile Asp Arg Ala Leu Lys
    210                 215                 220
Ala Gly His Phe Arg Met Gly Pro Leu Glu Leu Thr Asp Phe Ile
225                 230                 235                 240
Gly Gln Asp Ile Asn Tyr Gln Val Ser Arg Gln Ile Trp Gln Asp Met
                245                 250                 255
Gln Tyr Asp Pro Arg Tyr Thr Pro Gly His Leu Gln Arg Ser Leu Val
                260                 265                 270
Asp Ala Gly Leu Leu Gly Lys Lys Asn Gly Arg Ser Tyr Phe Ala Ala
                275                 280                 285
Glu Glu Asn Ala Leu Pro Val Thr Ala Ala Thr Asp Ala Asp Val Glu
    290                 295                 300
Thr Leu Arg Ile Tyr Gly Glu His Pro Phe Phe Thr Leu Leu Gln Gln
305                 310                 315                 320
Arg Ala Ala Leu Gln Trp Pro Arg Leu Arg Val Glu Gln Arg Pro Ala
                325                 330                 335
Leu Pro Gly Leu Gly Pro Ala Val Gln Ile Asn Glu Ala Phe Thr Val
                340                 345                 350
Ser Val Thr Asp Gly Arg Thr Ala Ser Gln Leu Ala Glu Leu Thr Ala
                355                 360                 365
Ala Asp Ala Phe Val Val Asp Val Ala Leu Asn Tyr Ala Asp Thr Ala
    370                 375                 380
Tyr Leu Val Ala Ala His Asn Arg His Ala Ser Ala Ala Asn Lys Ala
385                 390                 395                 400
Leu Phe Leu Arg Leu Leu His Thr Ala Ile Pro Gln Val Glu Phe Ile
                405                 410                 415
```

-continued

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Val Ala Gly Val Asn Tyr Ala Asp Gly Ile Phe
450                 455                 460

Gly Trp Leu Asp Asn Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
            500                 505

<210> SEQ ID NO 97
<211> LENGTH: 509
<212> TYPE: PRT
<213> ORGANISM: Serratia marcescens SMB2099

<400> SEQUENCE: 97

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Asp Leu Val Ile Glu Thr Ile Ala
            85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
            165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
            210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala

```
                275                 280                 285
Glu Glu Asn Ala Leu Pro Val Thr Ala Ala Thr Asp Ala Asp Val Glu
290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
                340                 345                 350

Ser Val Thr Asp Gly Arg Thr Ala Ser Gln Leu Ala Glu Leu Thr Ala
            355                 360                 365

Ala Asp Ala Phe Val Val Asp Val Ala Leu Asn Tyr Ala Asp Thr Ala
370                 375                 380

Tyr Leu Val Ala Ala His Asn Arg His Ala Ser Glu Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 98
<211> LENGTH: 509
<212> TYPE: PRT
<213> ORGANISM: Serratia marcescens 2880STDY5682862

<400> SEQUENCE: 98

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Val Gln Asp Leu Asn Lys Lys Val Glu Gln Gly Lys Ile
        50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Ala
                100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140
```

-continued

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
            165                 170                 175

Ala Ala Leu Gly Lys Arg Asp Val Val Cys Gln Ala Thr Pro Gly Phe
        180                 185                 190

Ile Val Asn Arg Met Ala Arg Pro Tyr Tyr Leu Glu Gly Phe Arg Leu
    195                 200                 205

Leu Glu Glu His Val Ala Arg Ala Pro Gln Ile Asp Arg Ala Leu Lys
210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
        260                 265                 270

Asp Ala Gly Leu Leu Gly Lys Lys Asn Gly Arg Ser Tyr Phe Ala Ala
    275                 280                 285

Glu Glu Asn Ala Leu Pro Val Thr Ala Ala Thr Asp Ala Asp Val Glu
290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
            325                 330                 335

Leu Pro Gly Leu Gly Pro Ala Val Gln Ile Asn Glu Ala Phe Thr Val
        340                 345                 350

Ser Val Thr Asp Gly Arg Thr Ala Ser Gln Leu Ala Glu Leu Thr Ala
    355                 360                 365

Ala Asp Ala Phe Val Val Asp Val Leu Asn Tyr Ala Asp Thr Ala
370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
        420                 425                 430

Asn Glu Ser Val Ile Met Val Glu Ser Gly Val Cys Ser Arg Glu Asp
    435                 440                 445

Ile Asp Val Ala Ala Val Ala Gly Val Asn Tyr Ala Asp Gly Ile Phe
450                 455                 460

Gly Trp Leu Asp Ser Leu Gly Glu Lys Asn Val Arg Thr Thr Leu Ser
465                 470                 475                 480

Asn Met Ala Gln Leu Leu His Ala Ala Arg Tyr Ala Pro His Tyr Thr
            485                 490                 495

Leu Leu His Ala Ala Gln Pro Ala Leu Met Thr Thr Pro
        500                 505

<210> SEQ ID NO 99
<211> LENGTH: 509
<212> TYPE: PRT
<213> ORGANISM: Serratia marcescens SE4145

<400> SEQUENCE: 99

Met Ala Glu Ser Asn Ala Glu Ile Gln Ser Ala Ala Ile Ile Gly Ala
1               5                   10                  15

```
Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
            35                  40                  45

Glu Tyr Ile Val Gln Asp Leu Asn Lys Val Glu Gln Gly Lys Ile
50                      55                  60

Ala Leu Gln Asp Lys Gly Ala Val Leu Ala Asn Leu Val Phe Thr Ser
65                      70                  75                  80

Val Phe Glu Thr Ile Ala Asp Ser Glu Leu Val Ile Glu Thr Ile Ala
            85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
130                     135                 140

His Phe Phe Asn Pro Ala Pro Leu Met Lys Leu Ile Glu Ile Ile Pro
145                     150                 155                 160

Ala Tyr Phe Thr Ala Arg Ala Thr Thr Glu Arg Cys Arg Gln Leu Val
            165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
            210                 215                 220

Ala Gly Gly His Phe Arg Met Gly Pro Leu Glu Leu Thr Asp Phe Ile
225                     230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Asn Ala Leu Pro Val Thr Ala Ala Thr Asp Ala Asp Val Glu
            290                 295                 300

Thr Leu Arg Ile Tyr Gly Glu His Pro Phe Phe Thr Leu Leu Gln Gln
305                     310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
            355                 360                 365

Ala Asp Ala Phe Val Val Asp Val Ala Leu Asn Tyr Ala Asp Thr Ala
            370                 375                 380

Tyr Leu Val Ala Ala His Asn Arg His Ala Ser Ala Ala Asn Lys Ala
385                     390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430
```

-continued

```
Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
        450                 455                 460

Gly Trp Leu Asp Asn Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505
```

<210> SEQ ID NO 100
<211> LENGTH: 509
<212> TYPE: PRT
<213> ORGANISM: Serratia marcescens 2880STDY5682876

<400> SEQUENCE: 100

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Gly Lys Gly Ala Val Leu Ala Asn Leu Val Phe Thr Ser
65                  70                  75                  80

Val Phe Glu Thr Ile Ala Asp Ser Asp Leu Val Ile Glu Thr Ile Ala
                85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Asn Ala Leu Pro Val Thr Ala Ala Thr Asp Ala Asp Val Glu
    290                 295                 300
```

```
Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
        355                 360                 365

Ala Asp Ala Phe Val Val Asp Val Ala Leu Asn Tyr Ala Asp Thr Ala
370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 101
<211> LENGTH: 509
<212> TYPE: PRT
<213> ORGANISM: Serratia marcescens 709

<400> SEQUENCE: 101

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
        50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Asp Leu Val Ile Glu Thr Ile Ala
                85                  90                  95

Glu Gln Glu Gln Thr Lys Leu Glu Val Leu Ala Ala Ile Ala Ala Ala
                100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
```

```
                165                 170                 175
Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
            210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ala Ala
                275                 280                 285

Glu Glu Asn Ala Leu Pro Val Thr Ala Ala Thr Asp Ala Asp Val Glu
                290                 295                 300

Thr Leu Arg Val Tyr Asp Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
                340                 345                 350

Ser Val Thr Asp Gly Arg Thr Ala Ser Gln Leu Ala Glu Leu Thr Ala
                355                 360                 365

Ala Asp Ala Phe Val Val Asp Val Ala Leu Asn Tyr Ala Asp Thr Ala
                370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
                435                 440                 445

Ile Asp Val Ala Ala Val Ala Gly Val Asn Tyr Ala Asp Gly Ile Phe
                450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505

<210> SEQ ID NO 102
<211> LENGTH: 509
<212> TYPE: PRT
<213> ORGANISM: Serratia marcescens MGH136

<400> SEQUENCE: 102

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30
```

```
Arg Thr Val Leu Tyr Asn Arg Asn Gly Asn Thr Leu Asn Gln Ala Arg
         35                  40                  45

Glu Tyr Ile Ala Gln Asp Leu Asn Lys Lys Val Glu Gln Asp Lys Ile
 50                  55                  60

Ala Leu Gln Asp Lys Gly Ala Val Leu Ala Asn Leu Val Phe Thr Ser
 65                  70                  75                  80

Val Phe Glu Thr Ile Ala Asp Ser Asp Leu Val Ile Glu Thr Ile Ala
                 85                  90                  95

Glu Gln Glu Gln Thr Lys Leu Glu Val Leu Ala Ala Ile Ala Ala Ala
                100                 105                 110

Val Lys Pro Asp Thr Leu Ile Ala Thr Asn Thr Ser Ser Leu Ser Leu
                115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala Arg Val Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
        210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ala Ala
            275                 280                 285

Glu Glu Asn Ala Leu Pro Val Thr Ala Ala Thr Asp Ala Asp Val Glu
        290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
        355                 360                 365

Ala Asp Ala Phe Val Val Asp Val Ala Leu Asn Tyr Ala Asp Thr Ala
    370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
```

```
                  450                 455                 460
Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505

<210> SEQ ID NO 103
<211> LENGTH: 509
<212> TYPE: PRT
<213> ORGANISM: Serratia marcescens 2880STDY5682884

<400> SEQUENCE: 103

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Ala
                100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
        210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Asn Ala Leu Pro Val Thr Ala Ala Thr Asp Ala Asp Val Glu
290                 295                 300

Thr Leu Arg Ile Tyr Gly Glu His Pro Phe Phe Thr Leu Leu Gln Gln
305                 310                 315                 320
```

```
Arg Ala Thr Leu Gln Trp Pro Arg Leu Arg Val Glu Gln Arg Pro Ala
            325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Met Ala
            355                 360                 365

Ala Asp Ala Phe Val Val Asp Val Ala Leu Asn Tyr Ala Asp Thr Ala
370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
            450                 455                 460

Gly Trp Leu Asp Ser Leu Gly Glu Lys Asn Val Arg Met Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Pro
            500                 505

<210> SEQ ID NO 104
<211> LENGTH: 509
<212> TYPE: PRT
<213> ORGANISM: Serratia marcescens D-3

<400> SEQUENCE: 104

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
            35                  40                  45

Glu Tyr Ile Ala Gln Asp Leu Asn Lys Lys Val Glu Gln Gly Lys Ile
        50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Asp Leu Val Ile Glu Thr Ile Ala
            85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
            165                 170                 175

Ala Ala Leu Gly Lys Arg Asp Val Val Cys Gln Ala Thr Pro Gly Phe
            180                 185                 190
```

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
        210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
            275                 280                 285

Glu Glu Asn Ala Leu Pro Val Thr Ala Ala Ile Asp Ala Asp Val Glu
            290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
            325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
            355                 360                 365

Ala Asp Ala Phe Val Val Asp Val Ala Leu Asn Tyr Ala Asp Thr Ala
            370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
            450                 455                 460

Gly Leu Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
            500                 505

<210> SEQ ID NO 105
<211> LENGTH: 509
<212> TYPE: PRT
<213> ORGANISM: Serratia marcescens 2880STDY5682957

<400> SEQUENCE: 105

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Glu Leu Asp Leu Asn Lys Lys Val Glu Gln Gly Lys Ile

```
                50                  55                  60
Ala Leu Gln Asp Lys Gly Ala Val Leu Ala Asn Leu Val Phe Thr Ser
 65                  70                  75                  80

Ala Phe Glu Thr Ile Ala Asp Ser Glu Leu Val Ile Glu Thr Ile Ala
                     85                  90                  95

Glu Gln Glu Gln Thr Lys Leu Glu Val Leu Ala Ala Ile Ala Ala Ala
                100                 105                 110

Val Lys Pro Asp Thr Leu Ile Ala Thr Asn Thr Ser Ser Leu Ser Leu
                115                 120                 125

Asn Lys Leu Ala Thr Ala Val Thr His Ser Glu Arg Phe Ile Gly Leu
                130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Glu Arg Cys Arg Gln Leu Val
                165                 170                 175

Ala Ala Leu Gly Lys Arg Asp Val Val Cys Gln Ala Thr Pro Gly Phe
                180                 185                 190

Ile Val Asn Arg Met Ala Arg Pro Tyr Tyr Leu Glu Gly Phe Arg Leu
                195                 200                 205

Leu Glu Glu His Val Ala Arg Ala Pro Gln Ile Asp Arg Ala Leu Lys
                210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ala Ala
                275                 280                 285

Glu Glu Asn Ala Leu Pro Val Thr Ala Ala Thr Asp Ala Asp Val Glu
                290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
                340                 345                 350

Ser Val Thr Asp Gly Arg Thr Ala Ser Gln Leu Ala Glu Leu Thr Ala
                355                 360                 365

Ala Asp Ala Phe Val Val Asp Val Ala Leu Asn Tyr Ala Asp Thr Ala
                370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
                435                 440                 445

Ile Asp Val Ala Ala Val Ala Gly Val Asn Tyr Ala Asp Gly Ile Phe
                450                 455                 460

Gly Trp Leu Asp Ser Leu Gly Glu Lys Asn Val Arg Thr Thr Leu Ser
465                 470                 475                 480
```

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
            500                 505

<210> SEQ ID NO 106
<211> LENGTH: 509
<212> TYPE: PRT
<213> ORGANISM: Serratia marcescens YDC563

<400> SEQUENCE: 106

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Glu Leu Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Ala Phe Glu Thr Ile Ala Asp Ser Glu Leu Val Ile Glu Thr Ile Ala
            85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
            165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Asn Ala Leu Pro Val Thr Ala Ala Thr Asp Ala Asp Val Glu
    290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
            325                 330                 335

Leu Pro Gly Leu Gly Pro Ala Val Gln Ile Asn Glu Ala Phe Thr Val

```
              340                 345                 350
Ser Val Thr Asp Gly Arg Thr Ala Ser Gln Leu Ala Glu Gln Thr Ala
            355                 360                 365

Ala Asp Ala Phe Val Val Asp Val Ala Leu Asn Tyr Ala Asp Thr Ala
370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
    450                 455                 460

Gly Trp Leu Asp Ser Leu Gly Glu Lys Asn Val Arg Thr Thr Leu Ser
465                 470                 475                 480

Asn Met Ala Gln Leu Leu His Ala Ala Arg Tyr Ala Pro His Tyr Thr
                485                 490                 495

Leu Leu His Ala Ala Gln Pro Ala Leu Met Thr Thr Pro
            500                 505

<210> SEQ ID NO 107
<211> LENGTH: 509
<212> TYPE: PRT
<213> ORGANISM: Serratia marcescens 2880STDY5683035

<400> SEQUENCE: 107

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Asp Leu Val Ile Glu Thr Ile Ala
                85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205
```

Leu Glu Glu His Val Ala Arg Ala Pro Gln Ile Asp Arg Ala Leu Lys
210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
        260                 265                 270

Asp Ala Gly Leu Leu Gly Lys Lys Asn Gly Arg Ser Tyr Phe Ala Ala
    275                 280                 285

Glu Glu Asn Ala Leu Pro Val Thr Ala Ala Ile Asp Ala Asp Val Glu
290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Gln Arg Pro Ala
            325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
            355                 360                 365

Ala Asp Val Phe Val Val Asp Val Ala Leu Asn Tyr Ala Asp Thr Ala
370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
    450                 455                 460

Gly Leu Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Pro
            500                 505

<210> SEQ ID NO 108
<211> LENGTH: 509
<212> TYPE: PRT
<213> ORGANISM: Serratia marcescens 2880STDY5682930

<400> SEQUENCE: 108

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

```
Val Phe Glu Thr Ile Ala Asp Ser Asp Leu Val Ile Glu Thr Ile Ala
                85                  90                  95

Glu Gln Glu Gln Thr Lys Leu Glu Val Leu Ala Ile Ala Ala Ala
           100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Asn Ala Leu Pro Val Thr Ala Ala Thr Asp Ala Asp Val Glu
    290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Ile Asn Glu Ala Phe Thr Val
            340                 345                 350

Ser Val Thr Asp Gly Arg Thr Ala Ser Gln Leu Ala Glu Leu Thr Ala
        355                 360                 365

Ala Asp Ala Phe Val Val Asp Val Ala Leu Asn Tyr Ala Asp Thr Ala
    370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asn Val Ala Ala Val Ala Gly Val Asn Tyr Ala Asp Gly Ile Phe
    450                 455                 460

Gly Leu Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495
```

Leu Leu His Ala Ala Gln Pro Val Leu Thr Thr Thr Pro
            500                 505

<210> SEQ ID NO 109
<211> LENGTH: 509
<212> TYPE: PRT
<213> ORGANISM: Serratia marcescens 790

<400> SEQUENCE: 109

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
50                  55                  60

Ala Leu Arg Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Arg Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Asn Ala Leu Pro Val Thr Ala Ala Thr Asp Ala Asp Val Glu
290                 295                 300

Thr Leu Arg Val Tyr Gly Glu His Pro Phe Phe Thr Leu Leu Gln Gln
305                 310                 315                 320

Arg Ala Ala Leu Gln Trp Pro Arg Leu Arg Val Glu Gln Arg Pro Ala
                325                 330                 335

Leu Pro Gly Leu Gly Pro Ala Val Gln Thr Asn Glu Ala Phe Thr Val
            340                 345                 350

Ser Val Thr Asp Gly Arg Thr Ala Asn Gln Leu Ala Glu Leu Thr Ala
        355                 360                 365

-continued

```
Ala Asp Ala Phe Val Asp Val Ala Leu Asn Tyr Ala Asp Thr Ala
    370                 375                 380

Tyr Leu Val Ala Ala His Asn Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
    450                 455                 460

Gly Trp Leu Asp Ser Leu Gly Glu Lys Asn Val Arg Thr Thr Leu Ser
465                 470                 475                 480

Asn Met Ala Gln Leu Leu His Ala Ala Arg Tyr Ala Pro His Tyr Thr
            485                 490                 495

Leu Leu His Ala Ala Gln Pro Ala Leu Met Thr Thr Pro
            500                 505

<210> SEQ ID NO 110
<211> LENGTH: 509
<212> TYPE: PRT
<213> ORGANISM: Serratia marcescens UMH5

<400> SEQUENCE: 110

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Ser Gln Ala Arg
        35                  40                  45

Asp Tyr Ile Glu Leu Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Thr Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Cys Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
```

```
            225                 230                 235                 240
        Gly Gln Asp Ile Asn Tyr Gln Val Ser Arg Gln Ile Trp Gln Asp Met
                        245                 250                 255

Gln Tyr Asp Ala Arg Tyr Thr Pro Gly His Leu Gln Arg Ser Leu Val
                    260                 265                 270

Asp Ala Gly Leu Leu Gly Lys Lys Asn Gly Arg Ser Tyr Phe Ala Val
                    275                 280                 285

Glu Glu Asn Ala Pro Pro Val Met Ala Ala Thr Asp Ala Asp Ile Glu
                    290                 295                 300

Thr Leu His Val Tyr Gly Glu His Pro Phe Phe Thr Leu Leu Gln Gln
        305                 310                 315                 320

Arg Ala Ala Leu Gln Trp Pro Arg Leu Arg Val Glu Gln Arg Gln Ala
                        325                 330                 335

Leu Pro Gly Leu Gly Pro Ala Val Arg Ile Asn Asp Ala Phe Thr Ile
                    340                 345                 350

Ser Ile Thr Asp Gly Arg Thr Ala Asn Gln Leu Ala Glu Gln Thr Ala
                    355                 360                 365

Ala Asp Ala Phe Val Val Asp Val Ala Leu Asn Tyr Ala Asp Thr Ala
        370                 375                 380

Tyr Leu Val Ala Ala His Ser Arg His Ala Ser Gly Ala Asn Lys Ala
        385                 390                 395                 400

Leu Phe Leu Arg Leu Leu His Thr Ala Ile Pro Gln Val Glu Phe Ile
                        405                 410                 415

Lys Asp Ser Pro Ala Leu Ile Val Ala Arg Val Leu Ser Ser Leu Ile
                    420                 425                 430

Asn Glu Ser Val Ile Met Val Glu Ser Gly Val Cys Ser Arg Glu Asp
                    435                 440                 445

Ile Asp Val Ala Ala Val Ala Gly Val Asn Tyr Ala Asp Gly Ile Phe
        450                 455                 460

Gly Trp Leu Asp Ser Leu Gly Glu Lys Asn Val Arg Thr Thr Leu Ser
        465                 470                 475                 480

Asn Leu Ala Gln Leu Leu His Ala Ala Arg Tyr Ala Pro His Tyr Thr
                        485                 490                 495

Leu Leu His Ala Ala Gln Pro Ala Leu Thr Thr Pro
                    500                 505

<210> SEQ ID NO 111
<211> LENGTH: 509
<212> TYPE: PRT
<213> ORGANISM: Serratia marcescens 2880STDY5682988

<400> SEQUENCE: 111

Met Ala Glu Ser Asn Ala Ala Ile Gln Ser Ala Ala Ile Ile Gly Ala
        1               5                   10                  15

Gly Thr Met Gly Arg Gly Ile Ala Tyr Leu Phe Ala Gln Lys Gly Ile
                    20                  25                  30

Arg Thr Val Leu Tyr Asn Arg Asn Gly Asn Thr Leu Ser Gln Ala Arg
                        35                  40                  45

Asp Tyr Ile Glu Leu Asp Leu Asn Lys Lys Val Glu Gln Gly Lys Ile
                    50                  55                  60

Ala Leu Gln Asp Lys Gly Ala Val Leu Ala Asn Leu Val Phe Thr Ser
        65                  70                  75                  80

Val Phe Glu Thr Ile Ala Asp Ser Glu Leu Val Ile Glu Thr Ile Ala
                        85                  90                  95
```

-continued

```
Glu Gln Glu Gln Thr Lys Leu Glu Val Leu Ala Thr Ile Ala Ala
            100                 105                 110
Val Lys Pro Asp Thr Leu Ile Ala Thr Asn Thr Ser Ser Leu Ser Leu
        115                 120                 125
Asn Lys Leu Ala Thr Ala Val Thr His Ser Glu Arg Phe Ile Gly Leu
    130                 135                 140
His Phe Phe Asn Pro Ala Pro Leu Met Lys Leu Ile Glu Ile Ile Pro
145                 150                 155                 160
Ala Tyr Cys Thr Ala His Ala Thr Thr Glu Arg Cys Arg Gln Leu Val
                165                 170                 175
Ala Ala Leu Gly Lys Arg Asp Val Val Cys Gln Ala Thr Pro Gly Phe
            180                 185                 190
Ile Val Asn Arg Met Ala Arg Pro Tyr Tyr Leu Glu Gly Phe Arg Leu
        195                 200                 205
Leu Glu Glu His Val Ala Arg Ala Pro Gln Ile Asp Arg Ala Leu Lys
    210                 215                 220
Ala Gly Gly His Phe Arg Met Gly Pro Leu Glu Leu Thr Asp Phe Ile
225                 230                 235                 240
Gly Gln Asp Ile Asn Tyr Gln Val Ser Arg Gln Ile Trp Gln Asp Met
                245                 250                 255
Gln Tyr Asp Ala Arg Tyr Thr Pro Gly His Leu Gln Arg Ser Leu Val
            260                 265                 270
Asp Ala Gly Leu Leu Gly Lys Lys Asn Gly Arg Ser Tyr Phe Ala Val
        275                 280                 285
Glu Glu Asn Ala Pro Pro Val Met Ala Ala Thr Asp Ala Asp Ile Glu
    290                 295                 300
Thr Leu His Val Tyr Gly Glu His Pro Phe Phe Thr Leu Leu Gln Gln
305                 310                 315                 320
Arg Ala Ala Leu Gln Trp Pro Arg Leu Arg Val Glu Gln Arg Gln Ala
                325                 330                 335
Leu Pro Gly Leu Gly Pro Ala Val Arg Ile Asn Asp Ala Phe Thr Ile
            340                 345                 350
Ser Ile Thr Asp Gly Arg Thr Ala Asn Gln Leu Ala Glu Gln Thr Ala
        355                 360                 365
Thr Asp Ala Phe Val Val Asp Val Ala Leu Asn Tyr Ala Asp Thr Ala
    370                 375                 380
Tyr Leu Val Ala Ala His Ser Arg His Ala Ser Gly Ala Asn Lys Ala
385                 390                 395                 400
Leu Phe Leu Arg Leu Leu His Thr Ala Ile Pro Gln Val Glu Phe Ile
                405                 410                 415
Lys Asp Ser Pro Ala Leu Ile Val Ala Arg Val Leu Ser Ser Leu Ile
            420                 425                 430
Asn Glu Ser Val Ile Met Val Glu Ser Gly Val Cys Ser Arg Glu Asp
        435                 440                 445
Ile Asp Val Ala Ala Val Ala Gly Val Asn Tyr Ala Asp Gly Ile Phe
    450                 455                 460
Gly Trp Leu Asp Ser Leu Gly Glu Lys Asn Val Arg Thr Thr Leu Ser
465                 470                 475                 480
Asn Leu Ala Gln Leu Leu His Ala Ala Arg Tyr Ala Pro His Tyr Thr
                485                 490                 495
Leu Leu His Ala Ala Gln Pro Ala Leu Thr Thr Thr Pro
            500                 505
```

<210> SEQ ID NO 112
<211> LENGTH: 509
<212> TYPE: PRT
<213> ORGANISM: Serratia marcescens 945154301

<400> SEQUENCE: 112

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Asp Tyr Ile Glu Leu Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Ala Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Asn Ala Pro Pro Val Met Ala Ala Thr Asp Ala Asp Ile Glu
    290                 295                 300

Thr Leu His Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Pro Ala Val Arg Ile Asn Asp Ala Phe Ser Val
            340                 345                 350

Ser Ile Thr Asp Gly Arg Thr Ala Asn Gln Leu Ala Glu Gln Thr Ala
        355                 360                 365

Ala Asp Ala Phe Val Val Asp Val Ala Leu Asn Tyr Ala Asp Thr Ala
    370                 375                 380
```

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
    450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505

<210> SEQ ID NO 113
<211> LENGTH: 509
<212> TYPE: PRT
<213> ORGANISM: Serratia marcescens at10508

<400> SEQUENCE: 113

Met Ala Glu Ser Asn Ala Ala Ile Gln Ser Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Asp Tyr Ile Glu Leu Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ile Ala Ala Ala
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Pro
145                 150                 155                 160

Ala Tyr Phe Thr Ala His Ala Thr Thr Glu Arg Cys Arg Gln Leu Val
                165                 170                 175

Thr Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Ala Arg Tyr Thr Pro Gly His Leu Gln Arg Ser Leu Val
                260             265                 270

Asp Ala Gly Leu Leu Gly Lys Lys Asn Gly Arg Ser Tyr Phe Ala Val
            275                 280                 285

Glu Glu Asn Ala Pro Pro Val Met Ala Ala Thr Asp Ala Asp Ile Glu
290                 295                 300

Thr Leu His Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Pro Ala Val Arg Ile Asn Asp Ala Phe Thr Val
            340                 345                 350

Ser Ile Thr Asp Gly Arg Thr Ala Asn Gln Leu Ala Glu Gln Thr Ala
        355                 360                 365

Ala Asp Ala Phe Val Val Asp Val Ala Leu Asn Tyr Ala Asp Thr Ala
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
    450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Pro
            500                 505

<210> SEQ ID NO 114
<211> LENGTH: 509
<212> TYPE: PRT
<213> ORGANISM: Serratia marcescens ML2637

<400> SEQUENCE: 114

Met Ala Glu Ser Asn Ala Ala Ile Gln Ser Ala Ile Ile Gly Ala
1               5                   10                  15

Gly Thr Met Gly Arg Gly Ile Ala Tyr Leu Phe Ala Gln Lys Gly Ile
                20                  25                  30

Arg Thr Val Leu Tyr Asn Arg Asn Gly Asn Thr Leu Asn Gln Ala Arg
            35                  40                  45

Asp Tyr Ile Glu Leu Asp Leu Asn Lys Lys Val Glu Gln Gly Lys Ile
        50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu

```
            115                 120                 125
Asn Lys Leu Ala Thr Ala Val Thr His Ser Glu Arg Phe Ile Gly Leu
            130                 135                 140
His Phe Phe Asn Pro Ala Pro Leu Met Lys Leu Ile Glu Ile Ile Pro
145                 150                 155                 160
Ala Tyr Phe Thr Ala His Ala Thr Thr Glu Arg Cys Arg Gln Leu Val
                165                 170                 175
Thr Ala Leu Gly Lys Arg Asp Val Val Cys Gln Ala Thr Pro Gly Phe
            180                 185                 190
Ile Val Asn Arg Met Ala Arg Pro Tyr Tyr Leu Glu Gly Phe Arg Leu
            195                 200                 205
Leu Glu Glu His Val Ala Arg Ala Pro Gln Ile Asp Arg Ala Leu Lys
            210                 215                 220
Ala Gly Gly His Phe Arg Met Gly Pro Leu Glu Leu Thr Asp Phe Ile
225                 230                 235                 240
Gly Gln Asp Ile Asn Tyr Gln Val Ser Arg Gln Ile Trp Gln Asp Met
                245                 250                 255
Gln Tyr Asp Ala Arg Tyr Thr Pro Gly His Leu Gln Arg Ser Leu Val
            260                 265                 270
Asp Ala Gly Leu Leu Gly Lys Lys Asn Gly Arg Ser Tyr Phe Ala Val
            275                 280                 285
Glu Glu Asn Ala Pro Pro Val Met Ala Ala Thr Asp Ala Asp Ile Glu
            290                 295                 300
Thr Leu His Val Tyr Gly Glu His Pro Phe Phe Thr Leu Leu Gln Gln
305                 310                 315                 320
Arg Ala Ala Leu Gln Trp Pro Gln Leu Arg Val Glu Gln Arg Pro Ala
                325                 330                 335
Leu Pro Gly Leu Gly Pro Ala Val Arg Ile Asn Asp Ala Phe Thr Val
            340                 345                 350
Ser Ile Thr Asp Gly Arg Thr Ala Asn Gln Leu Ala Glu Gln Thr Ala
            355                 360                 365
Ala Asp Ala Phe Val Val Asp Val Ala Leu Asn Tyr Ala Asp Thr Ala
            370                 375                 380
Tyr Leu Val Ala Ala His Ser Arg His Ala Ser Ala Ala Asn Lys Ala
385                 390                 395                 400
Leu Phe Leu Arg Leu Leu His Thr Ala Ile Pro Gln Val Glu Phe Ile
                405                 410                 415
Lys Asp Ser Pro Ala Leu Ile Val Ala Arg Val Leu Ser Ser Leu Ile
            420                 425                 430
Asn Glu Ser Val Ile Met Val Glu Ser Gly Val Cys Ser Arg Glu Asp
            435                 440                 445
Ile Asp Val Ala Ala Val Ala Gly Val Asn Tyr Ala Asp Gly Ile Phe
            450                 455                 460
Gly Trp Leu Asp Ser Leu Gly Glu Lys Asn Val Arg Thr Thr Leu Ser
465                 470                 475                 480
Asn Leu Ala Gln Leu Leu His Ala Ala Arg Tyr Ala Pro His Tyr Thr
                485                 490                 495
Leu Leu His Ala Val Gln Pro Ala Leu Thr Thr Thr Pro
            500                 505

<210> SEQ ID NO 115
<211> LENGTH: 509
<212> TYPE: PRT
<213> ORGANISM: Serratia marcescens SM1978
```

<400> SEQUENCE: 115

Met Ala Glu Ser Asn Ala Ala Ile Gln Ser Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Asp Tyr Ile Glu Leu Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Thr Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Ala Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Asn Ala Pro Pro Val Met Ala Ser Thr Asp Ala Asp Ile Glu
    290                 295                 300

Thr Leu His Val Tyr Gly Glu His Pro Phe Phe Thr Leu Leu Gln Gln
305                 310                 315                 320

Arg Ala Ala Leu Gln Trp Pro Gln Leu Arg Val Gln Arg Pro Ala
                325                 330                 335

Leu Pro Gly Leu Gly Pro Ala Val Arg Ile Asn Asp Ala Phe Ser Val
            340                 345                 350

Ser Ile Thr Asp Gly Arg Thr Ala Asn Gln Leu Ala Glu Gln Thr Thr
        355                 360                 365

Ala Asp Ala Phe Val Val Asp Val Ala Leu Asn Tyr Ala Asp Thr Ala
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile

```
                    405                 410                 415
Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
    450                 455                 460

Gly Trp Leu Asp Ser Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
            500                 505

<210> SEQ ID NO 116
<211> LENGTH: 509
<212> TYPE: PRT
<213> ORGANISM: Serratia marcescens PWN146

<400> SEQUENCE: 116

Met Ala Glu Ser Asn Ala Ala Ile Gln Ser Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Asp Tyr Ile Glu Leu Asp Leu Asn Lys Lys Val Glu Gln Gly Lys Ile
    50                  55                  60

Ala Leu Gln Asp Lys Gly Ala Val Leu Ala Asn Leu Val Phe Thr Ser
65                  70                  75                  80

Val Phe Glu Thr Ile Ala Asp Ser Gly Leu Val Ile Glu Thr Ile Ala
                85                  90                  95

Glu Gln Glu Gln Thr Lys Leu Glu Val Leu Ala Thr Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys Arg Asp Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Ala Arg Tyr Thr Pro Gly His Leu Gln Arg Ser Leu Val
            260                 265                 270
```

Asp Ala Gly Leu Leu Gly Lys Lys Asn Gly Arg Ser Tyr Phe Ala Val
            275                 280                 285

Glu Glu Asn Ala Pro Pro Val Met Ala Ala Thr Asp Ala Asp Ile Glu
290                 295                 300

Thr Leu His Val Cys Gly Glu His Pro Phe Phe Thr Leu Leu Gln Gln
305                 310                 315                 320

Arg Ala Ala Leu Gln Trp Pro Arg Leu Arg Val Gln Arg Pro Ala
            325                 330                 335

Leu Pro Gly Leu Gly Pro Ala Val Trp Ile Asn Asp Ala Phe Thr Val
            340                 345                 350

Ser Ile Thr Asp Gly Arg Thr Ala Asn Gln Leu Ala Glu Gln Thr Ala
            355                 360                 365

Ala Asp Ala Phe Val Val Asp Val Ala Leu Asn Tyr Ala Asp Thr Ala
370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
450                 455                 460

Gly Trp Leu Asp Ser Leu Gly Glu Lys Asn Val Arg Ala Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Pro
            500                 505

<210> SEQ ID NO 117
<211> LENGTH: 509
<212> TYPE: PRT
<213> ORGANISM: Serratia marcescens H1q

<400> SEQUENCE: 117

Met Ala Glu Arg Asn Ala Ala Ile Gln Ser Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Ile Gln Ala Arg
            35                  40                  45

Glu Tyr Ile Val Gln Asp Leu Asp Lys Lys Val Glu Gln Gly Arg Leu
50                  55                  60

Ala Pro Gln Asp Lys Asp Ala Val Leu Ala Asn Leu Gln Phe Ser Ser
65                  70                  75                  80

Val Phe Glu Ala Ile Val Asp Ser Asp Leu Val Leu Glu Thr Ile Ala
            85                  90                  95

Glu Gln Glu Gln Ala Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
            130                 135                 140

His Phe Phe Asn Pro Ala Pro Leu Met Lys Leu Ile Glu Ile Ile Pro
145                 150                 155                 160

Ala Tyr Phe Thr Ala Gln Ala Thr Thr Glu Thr Cys Arg Gln Leu Val
            165                 170                 175

Ala Ala Leu Gly Lys Arg Asp Val Val Cys Gln Ala Thr Pro Gly Phe
        180                 185                 190

Ile Val Asn Arg Met Ala Arg Pro Tyr Tyr Leu Glu Gly Phe Arg Leu
    195                 200                 205

Leu Glu Glu His Val Ala Arg Ala Pro Gln Ile Asp Arg Ala Leu Lys
210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
        275                 280                 285

Glu Glu Thr Ala Pro Pro Val Glu Ala Ala Val Glu Ala Asp Val Glu
    290                 295                 300

Thr Leu Arg Ile Tyr Gly Glu His Pro Leu Phe Thr Leu Leu Gln Gln
305                 310                 315                 320

Arg Ala Ala Leu Gln Trp Pro Gln Leu Arg Val Glu Gln Arg Pro Ala
            325                 330                 335

Leu Ser Gly Leu Gly Ala Ala Ile Gln Val Asn Asp Ala Phe Thr Val
            340                 345                 350

Ser Ile Thr Asp Gly Arg Thr Ala Asn Gln Leu Ala Glu Gln Thr Ala
        355                 360                 365

Ala Asp Ala Phe Val Val Asp Val Ala Leu Asn Tyr Ala Asp Thr Ala
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Leu Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
    450                 455                 460

Gly Trp Leu Thr Arg Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Pro
            500                 505

<210> SEQ ID NO 118
<211> LENGTH: 509
<212> TYPE: PRT
<213> ORGANISM: Serratia marcescens UMH6

<400> SEQUENCE: 118

Met Ala Glu Ser Asn Ala Ala Ile Gln Ser Ala Ala Ile Ile Gly Ala

-continued

```
1               5                   10                  15
Gly Thr Met Gly Arg Gly Ile Ala Tyr Leu Phe Ala Gln Lys Ser Ile
                20                  25                  30
Arg Thr Val Leu Tyr Asn Arg Asn Gly Asn Thr Leu Asn Gln Ala Arg
                35                  40                  45
Asp Ala Ile Val Gln Asp Leu Asn Lys Lys Val Glu Gln Gly Lys Leu
            50                  55                  60
Ala Leu Gln Asp Lys Asp Ala Val Leu Ala Asn Leu Thr Phe Ser Ala
65                  70                  75                  80
Glu Phe Gly Ala Ile Ala Asp Ser Asp Leu Val Ile Glu Thr Ile Ala
                85                  90                  95
Glu His Glu Gln Ala Lys Leu Glu Val Leu Ala Ala Ile Ala Ala Thr
                100                 105                 110
Val Lys Pro Asp Thr Leu Ile Ala Thr Asn Thr Ser Ser Leu Ser Leu
            115                 120                 125
Asn Lys Leu Ala Thr Ala Val Thr His Ser Glu Arg Phe Ile Gly Leu
130                 135                 140
His Phe Phe Asn Pro Ala Pro Leu Met Lys Leu Ile Glu Ile Ile Pro
145                 150                 155                 160
Ala Tyr Phe Thr Ala Gln Val Thr Thr Glu Arg Cys Arg Gln Leu Val
                165                 170                 175
Ala Ala Leu Gly Lys Arg Asp Val Val Cys Gln Ala Thr Pro Gly Phe
                180                 185                 190
Ile Val Asn Arg Met Ala Arg Pro Tyr Tyr Leu Glu Gly Phe Arg Leu
            195                 200                 205
Leu Glu Glu His Val Ala Arg Ala Pro Gln Ile Asp Arg Ala Leu Lys
    210                 215                 220
Ala Gly Gly His Phe Arg Met Gly Pro Leu Glu Leu Thr Asp Phe Ile
225                 230                 235                 240
Gly Gln Asp Ile Asn Tyr Gln Val Ser Arg Gln Ile Trp Gln Asp Met
                245                 250                 255
Gln Tyr Asp Pro Arg Tyr Thr Pro Gly His Leu Gln Arg Ser Leu Val
                260                 265                 270
Asp Ala Gly Leu Leu Gly Lys Lys Asn Gly Arg Ser Tyr Phe Ser Ala
            275                 280                 285
Glu Glu Ser Pro Pro Leu Ala Ala Ala Val Asp Ala Glu Val Glu
    290                 295                 300
Thr Leu Arg Ile Tyr Gly Glu His Pro Leu Phe Thr Leu Leu Gln Gln
305                 310                 315                 320
Arg Ala Ala Leu Gln Trp Pro Arg Leu Arg Val Glu Gln Arg Pro Thr
                325                 330                 335
Leu Pro Gly Leu Gly Ala Ala Ile Gln Val Asn Asp Ala Phe Thr Val
            340                 345                 350
Ser Val Thr Asp Gly Arg Thr Ala Asn Gln Leu Ala Glu Gln Thr Ala
            355                 360                 365
Ala Asp Ala Phe Val Val Asp Val Ala Leu Asn Tyr Gly Asp Thr Ala
        370                 375                 380
Tyr Leu Val Ala Ala His Ser Arg His Ala Ser Ala Ala Asn Lys Ala
385                 390                 395                 400
Leu Phe Leu Arg Leu Leu His Thr Ala Ile Pro Gln Val Glu Phe Ile
                405                 410                 415
Lys Asp Ser Pro Ala Leu Ile Val Ala Arg Val Leu Ser Ser Leu Ile
            420                 425                 430
```

```
Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
            450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
            500                 505

<210> SEQ ID NO 119
<211> LENGTH: 509
<212> TYPE: PRT
<213> ORGANISM: Serratia nematodiphila WCU338

<400> SEQUENCE: 119

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Ser Ile
            20                  25                  30

Arg Thr Val Leu Tyr Asn Arg Asn Gly Asn Thr Leu Asn Gln Ala Arg
        35                  40                  45

Asp Ala Ile Val Gln Asp Leu Asn Lys Lys Val Glu Gln Gly Lys Leu
    50                  55                  60

Ala Leu Gln Asp Lys Asp Ala Val Leu Ala Asn Leu Thr Phe Ser Ala
65                  70                  75                  80

Glu Phe Gly Ala Ile Ala Asp Ser Asp Leu Val Ile Glu Thr Ile Ala
                85                  90                  95

Glu His Glu Gln Ala Lys Leu Glu Val Leu Ala Ala Ile Ala Ala Thr
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala Gln Ile Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
        275                 280                 285

Glu Glu Ser Pro Pro Pro Leu Ala Ala Ala Val Asp Ala Glu Val Glu
```

```
            290                 295                 300
Thr Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
        355                 360                 365

Ala Asp Ala Phe Val Val Asp Val Ala Leu Asn Tyr Gly Asp Thr Ala
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Val Ala Gly Val Asn Tyr Ala Asp Gly Ile Phe
    450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Pro
            500                 505

<210> SEQ ID NO 120
<211> LENGTH: 509
<212> TYPE: PRT
<213> ORGANISM: Serratia sp. OLEL1

<400> SEQUENCE: 120

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
                20                  25                  30

Arg Thr Val Leu Tyr Asn Arg Asn Gly Asn Thr Leu Asn Gln Ala Arg
            35                  40                  45

Asp Ala Ile Val Gln Asp Leu Asn Lys Lys Val Glu Gln Gly Lys Leu
        50                  55                  60

Ala Leu Gln Asp Lys Asp Ala Val Leu Ala Asn Leu Thr Phe Ser Ala
65                  70                  75                  80

Glu Phe Gly Ala Ile Ala Asp Ser Asp Leu Val Ile Glu Thr Ile Ala
                85                  90                  95

Glu His Glu Gln Ala Lys Leu Glu Val Leu Ala Ala Ile Ala Ala Thr
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
                145                 150                 155                 160
```

```
Ala Tyr Phe Thr Ala Gln Val Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
        275                 280                 285

Glu Glu Ser Pro Pro Leu Ala Ala Val Asp Ala Glu Val Glu
    290                 295                 300

Thr Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
        355                 360                 365

Ala Asp Ala Phe Val Val Asp Val Ala Leu Asn Tyr Gly Asp Thr Ala
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
    450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 121
<211> LENGTH: 509
<212> TYPE: PRT
<213> ORGANISM: Serratia marcescens 7209

<400> SEQUENCE: 121

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Ser Ile
            20                  25                  30
```

-continued

```
Arg Thr Val Leu Tyr Asn Arg Asn Gly Asn Thr Leu Asn Gln Ala Arg
             35                  40                  45

Asp Ala Ile Val Gln Asp Leu Asn Lys Lys Val Glu Gln Gly Lys Leu
 50                  55                  60

Ala Leu Gln Asp Lys Asp Ala Val Leu Ala Asn Leu Thr Phe Ser Ala
 65                  70                  75                  80

Glu Phe Gly Val Ile Ala Asp Ser Asp Leu Val Ile Glu Thr Ile Ala
                 85                  90                  95

Glu His Glu Gln Ala Lys Leu Glu Val Leu Ala Ala Ile Ala Ala Thr
                100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
        275                 280                 285

Glu Glu Ser Pro Pro Leu Ala Ala Ala Val Asp Ala Glu Val Glu
    290                 295                 300

Thr Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
        355                 360                 365

Ala Asp Ala Phe Val Val Asp Val Ala Leu Asn Tyr Gly Asp Thr Ala
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445
```

```
Ile Asp Val Ala Ala Val Ala Gly Val Asn Tyr Ala Asp Gly Ile Phe
    450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 122
<211> LENGTH: 509
<212> TYPE: PRT
<213> ORGANISM: Serratia marcescens sicaria (Ss1)

<400> SEQUENCE: 122

Met Ala Glu Ser Asn Ala Ala Ile Gln Ser

Arg Ala Ala Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
                340                 345                 350

Ser Val Thr Asp Gly Arg Thr Ala Asn Gln Leu Ala Glu Gln Thr Ala
            355                 360                 365

Ala Asp Ala Phe Val Val Asp Val Ala Leu Asn Tyr Gly Asp Thr Ala
        370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
        450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
                500                 505

<210> SEQ ID NO 123
<211> LENGTH: 509
<212> TYPE: PRT
<213> ORGANISM: Serratia sp. OLFL2

<400> SEQUENCE: 123

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
                20                  25                  30

Arg Thr Val Leu Tyr Asn Arg Asn Gly Asn Thr Leu Asn Gln Ala Arg
            35                  40                  45

Asp Ala Ile Val Gln Asp Leu Asn Lys Lys Val Glu Gln Gly Lys Leu
        50                  55                  60

Ala Leu Gln Asp Lys Asp Ala Val Leu Ala Asn Leu Thr Phe Ser Ala
65                  70                  75                  80

Glu Phe Gly Ala Ile Ala Asp Ser Asp Leu Val Ile Glu Thr Ile Ala
                85                  90                  95

Glu His Glu Gln Ala Lys Leu Asp Val Leu Ala Ala Ile Ala Ala Thr
                100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
                165                 170                 175

Ala Ala Leu Gly Lys Arg Asp Val Val Cys Gln Ala Thr Pro Gly Phe

```
                    180                 185                 190
        Ile Val Asn Arg Met Ala Arg Pro Tyr Tyr Leu Glu Gly Phe Arg Leu
                    195                 200                 205
        Leu Glu Glu His Val Ala Arg Ala Pro Gln Ile Asp Arg Ala Leu Lys
                    210                 215                 220
        Ala Gly Gly His Phe Arg Met Gly Pro Leu Glu Leu Thr Asp Phe Ile
        225                 230                 235                 240
        Gly Gln Asp Ile Asn Tyr Gln Val Ser Arg Gln Ile Trp Gln Asp Met
                            245                 250                 255
        Gln Tyr Asp Pro Arg Tyr Thr Pro Gly His Leu Gln Arg Ser Leu Val
                    260                 265                 270
        Asp Ala Gly Leu Leu Gly Lys Lys Asn Gly Arg Ser Tyr Phe Ser Ala
                    275                 280                 285
        Glu Glu Ser Pro Pro Leu Ala Ala Val Asp Ala Glu Val Glu
                    290                 295                 300
        Thr Leu Arg Ile Tyr Gly Glu His Pro Leu Phe Thr Leu Leu Gln Gln
        305                 310                 315                 320
        Arg Ala Ala Leu Gln Trp Pro Arg Leu Arg Val Glu Gln Arg Pro Thr
                    325                 330                 335
        Leu Pro Gly Leu Gly Ala Ala Ile Gln Val Asn Asp Ala Phe Thr Val
                    340                 345                 350
        Ser Val Thr Asp Gly Arg Thr Ala Asn Gln Leu Ala Glu Gln Thr Ala
                    355                 360                 365
        Ala Asp Ala Phe Val Val Asp Val Ala Leu Asn Tyr Gly Asp Thr Ala
                    370                 375                 380
        Tyr Leu Val Ala Ala His Ser Arg His Ala Ser Ala Ala Asn Lys Ala
        385                 390                 395                 400
        Leu Phe Leu Arg Leu Leu His Thr Ala Ile Pro Gln Val Glu Phe Ile
                    405                 410                 415
        Lys Asp Ser Pro Ala Leu Ile Val Ala Arg Val Leu Ser Ser Leu Ile
                    420                 425                 430
        Asn Glu Ser Val Ile Met Val Glu Ser Gly Val Cys Ser Arg Glu Asp
                    435                 440                 445
        Ile Asp Val Ala Ala Val Ala Gly Val Asn Tyr Ala Asp Gly Ile Phe
                    450                 455                 460
        Gly Trp Leu Thr Arg Leu Gly Glu Glu Asn Val Arg Thr Thr Leu Ser
        465                 470                 475                 480
        Asn Leu Ala Gln Leu Leu His Ala Ala Arg Tyr Ala Pro His Tyr Thr
                    485                 490                 495
        Leu Leu His Ala Ala Gln Pro Ala Leu Thr Thr Pro
                    500                 505

<210> SEQ ID NO 124
<211> LENGTH: 509
<212> TYPE: PRT
<213> ORGANISM: Serratia marcescens BIDMC 81

<400> SEQUENCE: 124

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
            20                  25                  30

Arg Thr Val Leu Tyr Asn Arg Asn Gly Asn Thr Leu Asn Gln Ala Arg
        35                  40                  45
```

```
Asp Ala Ile Val Gln Asp Leu Asn Lys Lys Val Glu Gln Gly Lys Leu
    50                  55                  60

Ala Leu Gln Asp Lys Asp Ala Val Leu Ala Asn Leu Thr Phe Ser Ala
65                  70                  75                  80

Glu Phe Gly Ala Ile Ala Asp Ser Asp Leu Val Ile Glu Thr Ile Ala
                85                  90                  95

Glu His Glu Gln Ala Lys Leu Glu Val Leu Ala Ala Ile Ala Ala Thr
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
            275                 280                 285

Glu Glu Ser Pro Pro Leu Ala Ala Val Asp Ala Glu Val Glu
            290                 295                 300

Thr Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu Gln Arg Pro Thr
                325                 330                 335

Leu Pro Asp Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
            355                 360                 365

Ala Asp Ala Phe Val Val Asp Val Ala Leu Asn Tyr Gly Asp Thr Ala
370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
450                 455                 460

Gly Trp Leu Thr Arg Leu Gly Glu Glu Asn Val Arg Thr Thr Leu Ser
```

Asn Leu Ala Gln Leu Leu His Ala Ala Arg Tyr Ala Pro His Tyr Thr
465                 470                 475                 480

Leu Leu His Ala Ala Gln Pro Ala Leu Thr Thr Thr Pro
            485                 490                 495

<210> SEQ ID NO 125
<211> LENGTH: 509
<212> TYPE: PRT
<213> ORGANISM: Serratia marcescens BIDMC 50

<400> SEQUENCE: 125

Met Ala Glu Ser Asn Ala Ala Ile Gln Ser Ala Ile Ile Gly Ala
1               5                   10                  15

Gly Thr Met Gly Arg Gly Ile Ala Tyr Leu Phe Ala Gln Lys Ser Ile
                20                  25                  30

Arg Thr Val Leu Tyr Asn Arg Asn Gly Asn Thr Leu Asn Gln Ala Arg
                35                  40                  45

Asp Ala Ile Val Gln Asp Leu Asn Lys Lys Val Glu Gln Gly Lys Leu
        50                  55                  60

Ala Leu Gln Asp Lys Asp Val Val Leu Ala Asn Leu Thr Phe Ser Ala
65                  70                  75                  80

Glu Phe Gly Ala Ile Ala Asp Ser Asp Leu Val Ile Glu Thr Ile Ala
                    85                  90                  95

Glu His Glu Gln Ala Lys Leu Glu Val Leu Ala Ala Ile Ala Ala Thr
                100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
                    165                 170                 175

Ala Ala Leu Gly Lys Arg Asp Val Val Cys Gln Ala Thr Pro Gly Phe
                180                 185                 190

Ile Val Asn Arg Met Ala Arg Pro Tyr Tyr Leu Glu Gly Phe Arg Leu
            195                 200                 205

Leu Glu Glu His Val Arg Ala Pro Gln Ile Asp Arg Ala Leu Lys
        210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                    245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ser Ala
            275                 280                 285

Glu Glu Ser Pro Pro Leu Ala Ala Ala Val Asp Ala Glu Val Glu
        290                 295                 300

Thr Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu Gln Arg Pro Thr
                    325                 330                 335

```
Leu Pro Asp Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
            355                 360                 365

Ala Asp Ala Phe Val Val Asp Val Ala Leu Asn Tyr Gly Asp Thr Ala
        370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
        450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 126
<211> LENGTH: 509
<212> TYPE: PRT
<213> ORGANISM: Serratia marcescens UMH7

<400> SEQUENCE: 126

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
            20                  25                  30

Arg Thr Val Leu Tyr Asn Arg Asn Gly Asn Thr Leu Asn Gln Ala Arg
        35                  40                  45

Asp Ala Ile Val Gln Asp Leu Asn Lys Lys Val Glu Gln Gly Lys Leu
    50                  55                  60

Ala Leu Gln Asp Lys Asp Thr Val Leu Ala Asn Leu Thr Phe Ser Ala
65                  70                  75                  80

Glu Phe Gly Ala Ile Ala Asp Ser Asp Leu Val Ile Glu Thr Ile Ala
                85                  90                  95

Glu His Glu Gln Ala Lys Leu Glu Val Leu Ala Ala Ile Ala Ala Thr
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205
```

```
Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
                260                 265                 270

Asp Ala Gly Leu Leu Gly Lys Lys Asn Gly Arg Ser Tyr Phe Ser Ala
            275                 280                 285

Glu Glu Ser Pro Pro Leu Ala Ala Val Asp Ala Glu Val Glu
        290                 295                 300

Thr Leu Arg Ile Tyr Gly Glu His Pro Leu Phe Thr Leu Leu Gln Gln
305                 310                 315                 320

Arg Ala Thr Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
                340                 345                 350

Ser Val Thr Asp Gly Arg Thr Ala Asn Gln Leu Ala Glu Gln Thr Ala
            355                 360                 365

Ala Asp Ala Phe Val Val Asp Val Ala Leu Asn Tyr Gly Asp Thr Ala
        370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
        450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505

<210> SEQ ID NO 127
<211> LENGTH: 509
<212> TYPE: PRT
<213> ORGANISM: Serratia marcescens RSC-14

<400> SEQUENCE: 127

Met Ala Glu Ser Asn Ala Ala Ile Gln Ser Ala Ile Ile Gly Ala
1               5                   10                  15

Gly Thr Met Gly Arg Gly Ile Ala Tyr Leu Leu Ala Gln Lys Ser Ile
                20                  25                  30

Arg Thr Val Leu Tyr Asn Arg Asn Gly Asn Thr Leu Asn Gln Ala Arg
            35                  40                  45

Asp Ala Ile Val Gln Asp Leu Asn Lys Lys Val Glu Gln Gly Lys Leu
        50                  55                  60

Ala Leu Gln Asp Lys Asp Ala Val Leu Ala Asn Leu Thr Phe Ser Thr
```

```
                65                  70                  75                  80
Glu Phe Gly Ala Ile Ala Asp Ser Asp Leu Val Ile Glu Thr Ile Ala
                    85                  90                  95
Glu His Glu Gln Ala Lys Leu Glu Val Leu Ala Ile Ala Ala Thr
                100                 105                 110
Val Lys Pro Asp Arg Leu Ile Ala Thr Asn Thr Ser Ser Leu Ser Leu
                115                 120                 125
Asn Lys Leu Ala Thr Ala Val Thr His Ser Glu Arg Phe Ile Gly Leu
130                 135                 140
His Phe Phe Asn Pro Ala Pro Leu Met Lys Leu Ile Glu Ile Ile Pro
145                 150                 155                 160
Ala Tyr Phe Thr Ala Gln Val Thr Thr Glu Arg Cys Arg Gln Leu Val
                165                 170                 175
Ala Ala Leu Gly Lys Arg Asp Val Val Cys Gln Ala Thr Pro Gly Phe
                180                 185                 190
Ile Val Asn Arg Met Ala Arg Pro Tyr Tyr Leu Glu Gly Phe Arg Leu
                195                 200                 205
Leu Glu Glu His Val Ala Arg Ala Pro Gln Ile Asp Arg Ala Leu Lys
        210                 215                 220
Ala Gly Gly His Phe Arg Met Gly Pro Leu Glu Leu Thr Asp Phe Ile
225                 230                 235                 240
Gly Gln Asp Ile Asn Tyr Gln Val Ser Arg Gln Ile Trp Gln Asp Met
                245                 250                 255
Gln Tyr Asp Pro Arg Tyr Thr Pro Gly His Leu Gln Arg Ser Leu Val
                260                 265                 270
Asp Ala Gly Leu Leu Gly Lys Lys Asn Gly Arg Ser Tyr Phe Ser Ala
        275                 280                 285
Glu Glu Ser Pro Pro Leu Ala Ala Val Asp Ala Glu Val Glu
        290                 295                 300
Thr Leu Arg Ile Tyr Gly Glu His Pro Leu Phe Thr Leu Leu Gln Gln
305                 310                 315                 320
Arg Ala Ala Leu Gln Trp Pro Arg Leu Arg Val Glu Gln Pro Thr
                325                 330                 335
Leu Pro Gly Leu Gly Ala Ala Ile Gln Val Asn Asp Ala Phe Thr Val
                340                 345                 350
Ser Val Thr Asp Gly Arg Thr Ala Asn Gln Leu Ala Glu Gln Thr Ala
                355                 360                 365
Ala Asp Ala Phe Val Val Asp Val Ala Leu Asn Tyr Gly Asp Thr Ala
                370                 375                 380
Tyr Leu Val Ala Ala His Ser Arg His Ala Ser Ala Ala Asn Lys Ala
385                 390                 395                 400
Leu Phe Leu Arg Leu Leu His Thr Ala Ile Pro Gln Val Glu Phe Ile
                405                 410                 415
Lys Asp Ser Pro Ala Leu Ile Val Ala Arg Val Leu Ser Ser Leu Ile
                420                 425                 430
Asn Glu Ser Val Ile Met Val Glu Ser Gly Val Cys Ser Arg Glu Asp
                435                 440                 445
Ile Asp Val Ala Ala Val Ala Gly Val Asn Tyr Ala Asp Gly Ile Phe
        450                 455                 460
Gly Trp Leu Thr Arg Leu Gly Glu Glu Asn Val Arg Thr Thr Leu Ser
465                 470                 475                 480
Asn Leu Ala Gln Leu Leu His Ala Ala Arg Tyr Ala Pro His Tyr Thr
                485                 490                 495
```

```
Leu Leu His Ala Ala Gln Pro Ala Leu Thr Thr Thr Pro
            500                 505
```

<210> SEQ ID NO 128
<211> LENGTH: 509
<212> TYPE: PRT
<213> ORGANISM: Serratia marcescens SM03

<400> SEQUENCE: 128

```
Met Ala Glu Arg Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Ile Gln Ala Arg
        35                  40                  45

Glu Tyr Ile Val Gln Asp Leu Asp Lys Lys Val Glu Gln Gly Arg Leu
    50                  55                  60

Ala Pro Gln Asp Lys Asp Ala Val Leu Ala Asn Leu Gln Phe Ser Ser
65                  70                  75                  80

Val Phe Glu Ala Ile Val Asp Ser Asp Leu Val Leu Glu Thr Ile Ala
                85                  90                  95

Glu Gln Glu Gln Ala Lys Leu Glu Val Leu Ala Ala Ile Ala Ala Ala
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Gln Ala Thr Thr Glu Thr Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
        275                 280                 285

Glu Glu Thr Ala Pro Pro Val Glu Ala Ala Glu Ala Asp Val Glu
    290                 295                 300

Thr Leu Arg Ile Tyr Gly Glu His Pro Leu Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Ser Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
```

```
                355                 360                 365
Ala Asp Ala Phe Val Val Asp Val Ala Leu Asn Tyr Ala Asp Thr Ala
            370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Leu Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
            450                 455                 460

Gly Trp Leu Thr Arg Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
            500                 505

<210> SEQ ID NO 129
<211> LENGTH: 509
<212> TYPE: PRT
<213> ORGANISM: Serratia marcescens 90-166

<400> SEQUENCE: 129

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Ile Gln Ala Arg
            35                  40                  45

Glu Tyr Ile Val Gln Asp Leu Asp Lys Lys Ile Glu Gln Gly Arg Val
        50                  55                  60

Ala Pro Gln Asp Lys Asp Ala Val Leu Ala Asn Leu Thr Phe Ser Ala
65                  70                  75                  80

Glu Phe Gly Ala Ile Val Asp Ser Asp Leu Val Ile Glu Thr Ile Ala
            85                  90                  95

Glu His Glu Gln Ala Lys Leu Glu Val Leu Ala Ala Ile Ala Ala Thr
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
        130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
            165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
        210                 215                 220
```

```
Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
        260                 265                 270

Asp Ala Gly Leu Leu Gly Lys Lys Asn Gly Arg Ser Tyr Phe Ser Ala
    275                 280                 285

Glu Glu Ser Pro Pro Leu Ala Ala Val Asp Ala Glu Ile Glu
    290                 295                 300

Thr Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu His Arg Pro Thr
                325                 330                 335

Leu Pro Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
        355                 360                 365

Ala Asp Ala Phe Val Val Asp Val Ala Leu Asn Tyr Gly Asp Thr Ala
    370                 375                 380

Tyr Leu Ala Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
        450                 455                 460

Val Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Ser Thr Pro
            500                 505

<210> SEQ ID NO 130
<211> LENGTH: 509
<212> TYPE: PRT
<213> ORGANISM: Serratia marcescens UMH2

<400> SEQUENCE: 130

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
                20                  25                  30

Arg Thr Val Leu Tyr Asn Arg Asn Gly Asn Thr Leu Asn Gln Ala Arg
            35                  40                  45

Asp Ala Ile Val Gln Asp Leu Asn Lys Lys Val Glu Gln Gly Lys Leu
        50                  55                  60

Ala Leu Gln Asp Lys Asp Ala Val Leu Ala Asn Leu Thr Phe Ser Thr
65                  70                  75                  80

Glu Phe Gly Ala Ile Ala Asp Ser Asp Leu Val Ile Glu Thr Ile Ala
                85                  90                  95
```

-continued

Glu His Glu Gln Ala Lys Leu Glu Val Leu Ala Ala Ile Ala Ala Thr
            100                 105                 110

Val Lys Pro Asp Thr Leu Ile Ala Thr Asn Thr Ser Ser Leu Ser Leu
            115                 120                 125

Asn Lys Leu Ala Thr Ala Val Thr His Ser Glu Arg Phe Ile Gly Leu
130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
            165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
            195                 200                 205

Leu Glu Glu His Val Ala Arg Ala Pro Gln Ile Asp Arg Ala Leu Lys
            210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
            245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ser Ala
            275                 280                 285

Glu Glu Ser Pro Pro Leu Ala Ala Val Asp Ala Glu Val Glu
            290                 295                 300

Ala Leu Arg Ile Tyr Gly Glu His Pro Leu Phe Thr Leu Leu Gln Gln
305                 310                 315                 320

Arg Ala Ala Leu Gln Trp Pro Arg Leu Arg Val Glu Gln Arg Pro Thr
            325                 330                 335

Leu Pro Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
            355                 360                 365

Ala Asp Ala Phe Val Val Asp Val Ala Leu Asn Tyr Gly Asp Thr Ala
            370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
            405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
            435                 440                 445

Ile Asp Val Ala Ala Val Ala Gly Val Asn Tyr Ala Asp Gly Ile Phe
            450                 455                 460

Gly Trp Leu Thr His Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
            485                 490                 495

Leu Leu His Ala Ala Gln Pro Ala Leu Thr Thr Thr Pro
            500                 505

<210> SEQ ID NO 131
<211> LENGTH: 509
<212> TYPE: PRT
<213> ORGANISM: Serratia plymuthica AS9

<400> SEQUENCE: 131

```
Met Ala Glu Asn Asn Ser Ala Ile Arg Ser Ala Ala Val Ile Gly Ala
1               5                   10                  15

Gly Thr Met Gly Arg Gly Ile Ala Tyr Leu Leu Ala Leu Asn Gly Ile
            20                  25                  30

Arg Thr Val Leu Tyr Asn Arg Asn Gly Asn Asn Leu Asn Gln Ala Arg
        35                  40                  45

Asp Tyr Ile Val Ser Asp Leu Asp Arg Lys Met Asp Asn Gly Lys Ile
    50                  55                  60

Thr Leu Gln Lys Lys Gly Gln Ile Leu Ala Asn Ile Ile Phe Ser Ala
65                  70                  75                  80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ala Ile Ala Ala Thr
            100                 105                 110

Val Lys Pro Glu Ala Ile Ile Ala Thr Asn Thr Ser Ser Leu Ser Leu
        115                 120                 125

Asn Lys Leu Ala Ala Gly Val Glu Asn Asn Pro Arg Phe Ile Gly Leu
    130                 135                 140

His Phe Phe Asn Pro Ala Pro Leu Met Lys Leu Ile Glu Ile Ile Pro
145                 150                 155                 160

Ser Tyr Phe Thr Ser His Thr Thr Ser Leu Arg Cys Gln Gln Leu Val
                165                 170                 175

Ile Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Gln Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
                245                 250                 255

Gln Phe Asp Ser Arg Tyr Thr Pro Gly His Leu Gln Arg Ser Leu Val
            260                 265                 270

Asp Ala Gly Leu Leu Gly Arg Lys Asn Gly Arg Ser Phe Phe Ala Ser
        275                 280                 285

Leu Pro Ala Thr Pro Pro Thr Pro Ala Thr Glu Ser Asp Thr Pro Thr
    290                 295                 300

Ser Leu His Phe Tyr Gly Glu His Ala Leu Phe Asp His Leu Gln Gln
305                 310                 315                 320

Arg Ala Leu Ala Thr Trp Pro Ala Leu Arg Val Gln Arg Leu Pro Glu
                325                 330                 335

Arg Pro Glu Leu Gly Arg Leu Ile Leu Val Asn Asn Thr Leu Ala Ile
            340                 345                 350

Lys Ile Thr Asp Gly Arg Thr Ala Asn Leu Leu Ala Gly Leu Thr Ala
        355                 360                 365

Leu Asp Thr Phe Val Ile Asp Ala Ala Leu Asn Tyr Ala Asp Thr Ala
    370                 375                 380
```

```
Tyr Leu Val Ala Ala His Asn Gln His Ala Thr Glu Ala Asn Lys Ala
385                 390                 395                 400

Leu Phe Leu Ser Leu Leu Gln Thr Val Ile Ala Gln Val Glu Phe Ile
            405                 410                 415

Lys Asp Ser Pro Ala Leu Ile Val Ala Arg Val Leu Ser Ser Leu Ile
        420                 425                 430

Asn Glu Ser Val Ile Met Val Glu Ser Gly Val Cys Ser Arg Ala Asp
    435                 440                 445

Ile Asp Ile Ala Ala Val Ala Gly Val Asn Tyr Ala Asp Gly Ile Phe
450                 455                 460

Ala Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Ala Ala Arg Pro Glu Leu Ala Val Ala Pro
            500                 505
```

<210> SEQ ID NO 132
<211> LENGTH: 509
<212> TYPE: PRT
<213> ORGANISM: Serratia plymuthica tumat 205

<400> SEQUENCE: 132

```
Met Ala Glu Asn Asn Ser Ala Ile Arg Ser Ala Ala Val Ile Gly Ala
1               5                   10                  15

Gly Thr Met Gly Arg Gly Ile Ala Tyr Leu Leu Ala Leu Asn Gly Ile
            20                  25                  30

Arg Thr Val Leu Tyr Asn Arg Asn Gly Asn Asn Leu Asn Gln Ala Arg
        35                  40                  45

Asp Tyr Ile Val Ser Asp Leu Asp Arg Lys Ile Asp Asn Gly Lys Ile
    50                  55                  60

Thr Leu Gln Lys Lys Gly Gln Ile Leu Ala Asn Ile Ile Phe Ser Ala
65                  70                  75                  80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ile Ala Ala Thr
            100                 105                 110

Val Lys Pro Glu Ala Ile Ile Ala Thr Asn Thr Ser Ser Leu Ser Leu
        115                 120                 125

Asn Lys Leu Ala Ala Gly Val Glu Asn Asn Pro Arg Phe Ile Gly Leu
    130                 135                 140

His Phe Phe Asn Pro Ala Pro Leu Met Lys Leu Ile Glu Ile Ile Pro
145                 150                 155                 160

Ser Tyr Phe Thr Ser His Ala Thr Ser Leu Arg Cys Gln Gln Leu Val
                165                 170                 175

Ile Ala Leu Gly Lys Gln Phe Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
```

245                 250                 255

Gln Phe Asp Pro Arg Tyr Thr Pro Gly His Leu Gln Arg Ser Leu Val
                260                 265                 270

Asp Ala Gly Leu Leu Gly Arg Lys Asn Gly Arg Ser Phe Phe Ala Ser
            275                 280                 285

Gln Pro Val Thr Pro Thr Pro Thr Thr Glu Ser Asp Thr Pro Thr
290                 295                 300

Ser Leu His Phe Tyr Gly Glu His Ala Leu Phe Asp His Leu Gln Gln
305                 310                 315                 320

Arg Ala Leu Ala Thr Trp Pro Ala Leu Arg Val Gln Arg Leu Pro Glu
                325                 330                 335

Arg Pro Glu Leu Gly Arg Phe Ile Leu Val Asn Asn Ala Met Ala Ile
                340                 345                 350

Lys Ile Thr Asp Gly Arg Thr Ala Asn Leu Leu Ala Gly Leu Thr Ala
                355                 360                 365

Leu Asp Thr Phe Val Ile Asp Ala Ala Leu Asn Tyr Ala Asp Thr Ala
                370                 375                 380

Tyr Leu Val Ala Ala His Asn Gln His Ala Thr Glu Thr Asn Lys Ala
385                 390                 395                 400

Leu Phe Leu Thr Leu Leu Gln Thr Val Ile Ala Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Ala Asp
                435                 440                 445

Ile Asp Ile Ala Ala Val Ala Gly Val Asn Tyr Ala Asp Gly Ile Phe
            450                 455                 460

Ala Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Ala Ala Arg Pro Glu Leu Ala Val Ala Pro
            500                 505

<210> SEQ ID NO 133
<211> LENGTH: 509
<212> TYPE: PRT
<213> ORGANISM: Serratia plymuthica A30

<400> SEQUENCE: 133

Met Ala Glu Asn Asn Ser Ala Ile Arg Ser Ala Ala Val Ile Gly Ala
1               5                   10                  15

Gly Thr Met Gly Arg Gly Ile Ala Tyr Leu Leu Ala Leu Asn Gly Ile
                20                  25                  30

Arg Thr Val Leu Tyr Asn Arg Asn Gly Asn Asn Leu Asn Gln Ala Arg
            35                  40                  45

Asp Tyr Ile Val Ser Asp Leu Asp Arg Lys Ile Asp Asn Gly Lys Ile
        50                  55                  60

Thr Leu Gln Lys Lys Gly Gln Ile Leu Ala Asn Ile Phe Ser Ala
65                  70                  75              80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ala Ile Ala Ala Thr
            100                 105                 110

Val Lys Pro Glu Ala Ile Ile Ala Thr Asn Thr Ser Ser Leu Ser Leu
115                 120                 125

Asn Lys Leu Ala Ala Gly Val Glu Asn Asn Pro Arg Phe Ile Gly Leu
130                 135                 140

His Phe Phe Asn Pro Ala Pro Leu Met Lys Leu Ile Glu Ile Ile Pro
145                 150                 155                 160

Ser Tyr Phe Thr Ser His Ala Thr Ser Leu Arg Cys Gln Lys Leu Val
                165                 170                 175

Ile Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
                245                 250                 255

Gln Phe Asp Pro Arg Tyr Thr Pro Gly His Leu Gln Arg Ser Leu Val
            260                 265                 270

Asp Ala Gly Leu Leu Gly Arg Lys Asn Gly Arg Ser Phe Phe Ala Ser
        275                 280                 285

Gln Pro Ala Thr Pro Pro Asn Pro Thr Thr Glu Gly Asp Thr Pro Thr
    290                 295                 300

Ser Leu His Phe Tyr Gly Glu His Ala Leu Phe Asp His Leu Gln Gln
305                 310                 315                 320

Arg Ala Leu Ala Thr Trp Pro Ala Leu Arg Val Gln Arg Leu Pro Glu
                325                 330                 335

Arg Pro Glu Leu Gly Arg Phe Ile Leu Met Asn Asn Arg Leu Ala Ile
            340                 345                 350

Lys Ile Thr Asp Gly Arg Thr Ala Asn Leu Leu Ala Gly Leu Thr Ala
        355                 360                 365

Leu Asp Thr Phe Val Ile Asp Ala Ala Leu Asn Tyr Ala Asp Thr Ala
    370                 375                 380

Tyr Leu Val Ala Ala His Asn Gln His Ala Thr Glu Thr Asn Lys Ala
385                 390                 395                 400

Leu Phe Leu Thr Leu Leu Gln Thr Leu Ile Ala Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Ala Asp
        435                 440                 445

Ile Asp Ile Ala Ala Val Ala Gly Val Asn Tyr Ala Asp Gly Ile Phe
    450                 455                 460

Ala Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Ala Ala Arg Pro Glu Leu Ala Val Ala Pro
            500                 505

<210> SEQ ID NO 134
<211> LENGTH: 509
<212> TYPE: PRT

-continued

<213> ORGANISM: Serratia plymuthica 4Rx13

<400> SEQUENCE: 134

| | | | | | | | | | | | | | | | |
|---|---|---|---|---|---|---|---|---|---|---|---|---|---|---|---|

Met Ala Glu Asn Asn Ser Ala Ile Arg Ser Ala Ala Val Ile Gly Ala
1               5                   10                  15

Gly Thr Met Gly Arg Gly Ile Ala Tyr Leu Leu Ala Leu Asn Gly Ile
            20                  25                  30

Arg Thr Val Leu Tyr Asn Arg Asn Gly Asn Ser Leu Asn Gln Ala Arg
        35                  40                  45

Asp Tyr Ile Val Ser Asp Leu Asp Arg Lys Ile Asp Asn Gly Lys Ile
    50                  55                  60

Thr Leu Gln Lys Lys Gly Gln Ile Leu Ala Asn Ile Ile Phe Ser Ala
65                  70                  75                  80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ala Ile Ala Ala Thr
            100                 105                 110

Val Lys Pro Glu Ala Ile Ile Ala Thr Asn Thr Ser Ser Leu Ser Leu
        115                 120                 125

Asn Lys Leu Ala Ala Gly Val Glu Asn Asn Pro Arg Phe Ile Gly Leu
130                 135                 140

His Phe Phe Asn Pro Ala Pro Leu Met Lys Leu Ile Glu Ile Ile Pro
145                 150                 155                 160

Ser Tyr Phe Thr Ser His Ala Thr Ser Leu Arg Cys Gln Lys Leu Val
                165                 170                 175

Ile Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
                245                 250                 255

Gln Phe Asp Pro Arg Tyr Thr Pro Gly His Leu Gln Arg Ser Leu Val
            260                 265                 270

Asp Ala Gly Leu Leu Gly Arg Lys Asn Gly Arg Ser Phe Phe Ala Ser
        275                 280                 285

Gln Pro Ala Thr Pro Pro Thr Pro Thr Thr Glu Ser Asp Thr Pro Thr
    290                 295                 300

Ser Leu His Phe Tyr Gly Glu His Ala Leu Phe Asp His Leu Gln Gln
305                 310                 315                 320

Arg Ala Leu Ala Thr Trp Pro Ala Leu Ser Val Gln Arg Leu Pro Glu
                325                 330                 335

Arg Pro Glu Leu Gly Arg Phe Ile Leu Val Asn Asn Ala Leu Ala Ile
            340                 345                 350

Lys Ile Thr Asp Gly Arg Thr Ala Asn Leu Leu Ala Gly Leu Thr Ala
        355                 360                 365

Leu Asp Thr Phe Val Ile Asp Ala Ala Leu Asn Tyr Ala Asp Thr Ala
    370                 375                 380

Tyr Leu Val Ala Ala His Asn Gln His Ala Thr Glu Thr Asn Lys Ala
385                 390                 395                 400

```
Leu Phe Leu Thr Leu Leu Gln Thr Val Ile Ala Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Ala Asp
            435                 440                 445

Ile Asp Ile Ala Ala Val Ala Gly Val Asn Tyr Ala Asp Gly Ile Phe
        450                 455                 460

Ala Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Ala Ala Arg Pro Glu Leu Ala Val Ala Pro
            500                 505

<210> SEQ ID NO 135
<211> LENGTH: 509
<212> TYPE: PRT
<213> ORGANISM: Serratia plymuthica V4

<400> SEQUENCE: 135

Met Ala Glu Asn Asn Ser Ala Ile Arg Ser Ala Ala Val Ile Gly Ala
1               5                   10                  15

Gly Thr Met Gly Arg Gly Ile Ala Tyr Leu Leu Ala Leu Asn Gly Ile
                20                  25                  30

Arg Thr Val Leu Tyr Asn Arg Asn Gly Asn Asn Leu Asn Gln Ala Arg
            35                  40                  45

Asp Tyr Ile Val Ser Asp Leu Asp Arg Lys Ile Asp Asn Gly Lys Ile
        50                  55                  60

Thr Leu Gln Lys Lys Gly Gln Ile Leu Ala Asn Ile Ile Phe Ser Ala
65                  70                  75                  80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ala Ile Ala Ala Thr
            100                 105                 110

Val Lys Pro Glu Ala Ile Ile Ala Thr Asn Thr Ser Ser Leu Ser Leu
        115                 120                 125

Asn Lys Leu Ala Ala Gly Val Glu Asn Asn Pro Arg Phe Ile Gly Leu
    130                 135                 140

His Phe Phe Asn Pro Ala Pro Leu Met Lys Leu Ile Glu Ile Ile Pro
145                 150                 155                 160

Ser Tyr Phe Thr Ser His Ala Thr Ser Leu Arg Cys Gln Lys Leu Val
                165                 170                 175

Ile Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
                245                 250                 255

Gln Phe Asp Pro Arg Tyr Thr Pro Gly His Leu Gln Arg Ser Leu Val
            260                 265                 270
```

-continued

```
Asp Ala Gly Leu Leu Gly Arg Lys Asn Gly Arg Ser Phe Phe Ala Ser
            275                 280                 285

Gln Pro Ala Thr Pro Thr Pro Thr Thr Glu Ser Asp Thr Pro Thr
290                 295                 300

Ser Leu His Phe Tyr Gly Glu His Ala Leu Phe Asp His Leu Gln Gln
305                 310                 315                 320

Arg Ala Leu Ala Thr Trp Pro Ala Leu Arg Val Gln Arg Leu Pro Glu
                325                 330                 335

Arg Pro Glu Leu Gly Arg Phe Ile Leu Val Asn Asn Arg Leu Ala Ile
                340                 345                 350

Lys Ile Thr Asp Gly Arg Thr Ala Asn Leu Leu Ala Gly Leu Thr Ala
            355                 360                 365

Leu Asp Thr Phe Val Ile Asp Ala Ala Leu Asn Tyr Ala Asp Thr Ala
370                 375                 380

Tyr Leu Val Ala Ala His Asn Gln His Ala Thr Glu Thr Asn Lys Ala
385                 390                 395                 400

Leu Phe Leu Thr Leu Leu Gln Thr Val Ile Ala Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Ala Asp
            435                 440                 445

Ile Asp Ile Ala Ala Val Ala Gly Val Asn Tyr Ala Asp Gly Ile Phe
450                 455                 460

Ala Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Ala Ala Arg Pro Glu Leu Ala Val Ala Pro
            500                 505

<210> SEQ ID NO 136
<211> LENGTH: 509
<212> TYPE: PRT
<213> ORGANISM: Serratia plymuthica 3Rp8

<400> SEQUENCE: 136

Met Ala Glu Asn Asn Ser Ala Ile Arg Ser Ala Ala Val Ile Gly Ala
1               5                   10                  15

Gly Thr Met Gly Arg Gly Ile Ala Tyr Leu Leu Ala Leu Asn Gly Ile
                20                  25                  30

Arg Thr Val Leu Tyr Asn Arg Asn Gly Asn Asn Leu Asn Gln Ala Arg
            35                  40                  45

Asp Tyr Ile Val Ser Asp Leu Asp Arg Lys Ile Asp Asn Gly Lys Ile
50                  55                  60

Thr Leu Gln Lys Lys Gly Gln Ile Leu Ala Asn Ile Ile Phe Ser Ala
65                  70                  75                  80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ala Ile Ala Ala Thr
                100                 105                 110

Val Lys Pro Glu Ala Ile Ile Ala Thr Asn Thr Ser Ser Leu Ser Leu
            115                 120                 125

Asn Lys Leu Ala Ala Gly Val Glu Asn Asn Pro Arg Phe Ile Gly Leu
```

```
            130                 135                 140
His Phe Phe Asn Pro Ala Pro Leu Met Lys Leu Ile Glu Ile Ile Pro
145                 150                 155                 160

Ser Tyr Phe Thr Ser His Ala Thr Ser Leu Arg Cys Gln Lys Leu Val
                165                 170                 175

Ile Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
                245                 250                 255

Gln Phe Asp Pro Arg Tyr Thr Pro Gly His Leu Gln Arg Ser Leu Val
            260                 265                 270

Asp Ala Gly Leu Leu Gly Arg Lys Asn Gly Arg Ser Phe Phe Ala Ser
        275                 280                 285

Gln Pro Ala Thr Pro Pro Thr Pro Thr Thr Glu Ser Asp Thr Pro Thr
    290                 295                 300

Ser Leu His Phe Tyr Gly Glu His Ala Leu Phe Asp His Leu Gln Gln
305                 310                 315                 320

Arg Ala Leu Ala Thr Trp Pro Ala Leu Arg Val Gln Arg Leu Pro Glu
                325                 330                 335

Arg Pro Glu Leu Gly Arg Phe Ile Leu Val Asn Asn Arg Leu Ala Ile
            340                 345                 350

Lys Ile Thr Asp Gly Arg Thr Ala Asn Leu Leu Ala Gly Leu Thr Ala
        355                 360                 365

Leu Asp Thr Phe Val Ile Asp Ala Ala Leu Asn Tyr Ala Asp Thr Ala
    370                 375                 380

Tyr Leu Val Ala Ala His Asn Gln His Ala Thr Glu Thr Asn Lys Ala
385                 390                 395                 400

Leu Phe Leu Thr Leu Leu Gln Thr Leu Ile Ala Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Ala Asp
        435                 440                 445

Ile Asp Ile Ala Ala Val Ala Gly Val Asn Tyr Ala Asp Gly Ile Phe
    450                 455                 460

Ala Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Ala Ala Arg Pro Glu Leu Ala Val Ala Pro
            500                 505
```

<210> SEQ ID NO 137
<211> LENGTH: 509
<212> TYPE: PRT
<213> ORGANISM: Serratia proteamaculans MFPA44A14

<400> SEQUENCE: 137

```
Met Ala Glu Asn Asn Ser Ala Ile His Ser Val Ala Val Ile Gly Ala
1               5                   10                  15
Gly Thr Met Gly Arg Gly Ile Ala Tyr Leu Leu Ala Gln Asn Gly Ile
            20                  25                  30
Arg Thr Leu Leu Tyr Asn Arg Ser Gly Asn Asn Leu Asp Gln Ala Arg
                35                  40                  45
Asp Tyr Ile Ile Arg Asp Leu Asp Lys Lys Ile Asp Asn Gly Lys Ile
50                  55                  60
Ser Pro Gln Lys Lys Gly Glu Val Leu Ala Asn Leu Val Phe Ser Pro
65                  70                  75                  80
Ile Phe Asp Ala Ile Ala Asp Ser Asp Leu Val Ile Glu Thr Ile Ala
                85                  90                  95
Glu His Glu Thr Thr Lys His Glu Ile Leu Ala Ala Ile Ala Ala Thr
                100                 105                 110
Val Lys Gln Glu Ala Ile Ile Ala Thr Asn Thr Ser Ser Leu Ser Leu
                115                 120                 125
Asn Lys Leu Ala Ala Gly Val Glu Asn Asn Ala Arg Phe Ile Gly Leu
    130                 135                 140
His Phe Phe Asn Pro Ala Pro Leu Met Lys Leu Ile Glu Ile Ile Pro
145                 150                 155                 160
Ser Tyr Phe Thr Ser Arg Ala Thr Ser Leu Arg Cys Gln Gln Leu Val
                165                 170                 175
Thr Ala Leu Gly Lys Gln Phe Val Val Cys Lys Ala Thr Pro Gly Phe
                180                 185                 190
Ile Val Asn Arg Met Ala Arg Pro Phe Tyr Leu Glu Gly Phe Arg Leu
                195                 200                 205
Leu Glu Glu Asn Val Ala Leu Ala Pro Gln Ile Asp Arg Ala Leu Lys
    210                 215                 220
Ala Gly Gly His Phe Arg Met Gly Pro Leu Glu Leu Thr Asp Phe Ile
225                 230                 235                 240
Gly Gln Asp Ile Asn Tyr Gln Val Ser Ser Gln Ile Trp Gln Asp Met
                245                 250                 255
Gln Tyr Asp Pro Arg Tyr Thr Pro Gly His Leu Gln Arg Ser Leu Val
                260                 265                 270
Asp Ala Gly Leu Leu Gly Lys Lys Asn Gly Arg Ser Phe Phe Ala Ala
                275                 280                 285
Pro Ser Ala Glu Ser Asn Leu Leu Asp Ala Gly Asn Gly Thr Leu Thr
            290                 295                 300
Ser Leu His Phe Tyr Gly Glu His Thr Leu Phe Asp Leu Leu Gln Gln
305                 310                 315                 320
Arg Ala Leu Ala Thr Trp Pro Thr Leu Gln Ile Ile His Gln Pro Glu
                325                 330                 335
Arg Pro Thr Leu Gly Arg Phe Ile Arg Val Asn Asp Ala Leu Ala Val
                340                 345                 350
Lys Ile Thr Asp Gly Arg Thr Ala Asn Leu Leu Ala Glu Leu Thr Asp
                355                 360                 365
Leu Asp Thr Phe Val Ile Asp Ala Ala Leu Asn Tyr Ser Asp Thr Thr
                370                 375                 380
Tyr Leu Val Ala Ala His Asn Gln Asp Ala Glu Ala Asn Lys Ala
385                 390                 395                 400
Leu Phe Leu Ser Leu Leu Gln Thr Leu Ile Pro Gln Val Glu Phe Ile
                405                 410                 415
Lys Asp Ser Pro Gly Leu Ile Val Ala Arg Val Leu Ser Ser Leu Ile
```

```
                    420                 425                 430
Asn Glu Ser Val Ile Met Val Glu Ser Gly Val Cys Ser Arg Ala Asp
                435                 440                 445

Ile Asp Ile Ala Ala Val Ala Gly Val Asn Tyr Ala Asp Gly Ile Phe
        450                 455                 460

Ala Trp Leu Thr Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Ile Pro Arg Pro Glu Leu Ala Val Ala Pro
                500                 505

<210> SEQ ID NO 138
<211> LENGTH: 509
<212> TYPE: PRT
<213> ORGANISM: Serratia plymuthica A153

<400> SEQUENCE: 138

Met Ala Glu Asn Asn Ser Ala Ile Arg Ser Ala Ala Val Ile Gly Ala
1               5                   10                  15

Gly Thr Met Gly Arg Gly Ile Ala Tyr Leu Leu Ala Leu Asn Gly Ile
            20                  25                  30

Arg Thr Val Leu Tyr Asn Arg Asn Gly Asn Asn Leu Asn Gln Ala Arg
        35                  40                  45

Asp Tyr Ile Val Ser Asp Leu Asp Arg Lys Ile Asp Asn Gly Lys Ile
    50                  55                  60

Thr Leu Gln Lys Lys Gly Gln Ile Leu Ala Asn Ile Ile Phe Ser Asp
65                  70                  75                  80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ala Ile Ala Ala Thr
            100                 105                 110

Val Lys Pro Glu Ala Ile Ile Ala Thr Asn Thr Ser Ser Leu Ser Leu
        115                 120                 125

Asn Lys Leu Ala Ala Gly Val Glu Asn Asn Pro Arg Phe Ile Gly Leu
    130                 135                 140

His Phe Phe Asn Pro Ala Pro Leu Met Lys Leu Ile Glu Ile Ile Pro
145                 150                 155                 160

Ser Tyr Phe Thr Ser Arg Ala Thr Ser Leu Arg Cys Gln Gln Leu Val
                165                 170                 175

Thr Ala Leu Gly Lys Leu Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
                245                 250                 255

Gln Phe Asp Pro Arg Tyr Thr Pro Gly His Leu Gln Arg Ser Leu Val
            260                 265                 270

Asp Ala Gly Leu Leu Gly Arg Lys Asn Gly Arg Ser Phe Phe Ala Ser
        275                 280                 285
```

```
Gln Pro Ala Thr Pro Pro Asn Pro Thr Thr Glu Gly His Thr Pro Thr
    290                 295                 300

Ser Leu Leu Phe Tyr Gly Glu His Ala Leu Phe Asp His Leu Gln Gln
305                 310                 315                 320

Arg Ala Leu Ala Thr Trp Pro Ala Leu Arg Val Gln Arg Leu Pro Glu
                325                 330                 335

Arg Pro Glu Leu Gly Arg Phe Ile Leu Val Asn Asn Arg Leu Ala Ile
                340                 345                 350

Lys Ile Thr Asp Gly Arg Thr Ala Asn Leu Leu Ala Gly Leu Thr Ala
                355                 360                 365

Leu Asp Thr Phe Val Ile Asp Ala Ala Leu Asn Tyr Ala Asp Thr Ala
370                 375                 380

Tyr Leu Val Ala Ala His Asn Gln His Ala Thr Glu Pro Asn Lys Ala
385                 390                 395                 400

Leu Phe Leu Thr Leu Leu Gln Thr Leu Ile Ala Gln Val Glu Phe Ile
                405                 410                 415

Lys Asp Ser Pro Ala Leu Ile Val Ala Arg Val Leu Ser Ser Leu Ile
                420                 425                 430

Asn Glu Ser Val Ile Met Val Glu Ser Gly Val Cys Ser Arg Ala Asp
                435                 440                 445

Ile Asp Ile Ala Ala Val Ala Gly Val Asn Tyr Ala Asp Gly Ile Phe
450                 455                 460

Ala Trp Leu Ala Gln Leu Gly Gln Lys Asn Val Lys Ser Thr Leu Asp
465                 470                 475                 480

Asn Met Ala Gln Leu Leu His Ser Thr Arg Tyr Tyr Pro His Tyr Ser
                485                 490                 495

Leu Leu Asn Ala Ala Arg Pro Glu Leu Ala Val Ala Pro
                500                 505

<210> SEQ ID NO 139
<211> LENGTH: 1530
<212> TYPE: DNA
<213> ORGANISM: Serratia marcescens 532

<400> SEQUENCE: 139
atggcagaaa gtaatgcggc aattcaatcg gctgcgatta tcggcgcggg aacgatgggc      60
agaggcatcg cttatctttt cgcgcaaaaa ggcattcgca cggtgcttta taatcgcaac     120
ggcaatagcc tcaatcaggc tcgcgaatat atcgcgcaag acctgaacaa gaaagtcgaa     180
cagggcaaga tcgcgctgca ggataaaggc gcggtgctgg ccaatctgat gttcacttca     240
gtgtttgagg ccatcaccga cagcgagctg gtgatagaaa ccatcgccga gcaagaacaa     300
accaaacttg aggtgctggc ggccatcgcc gcggtggtca agcccgacac gctgatcgcc     360
accaataccc tcctcactgt cgcttaacaag ctggctactg cggtgacgca cagcgaacgc     420
tttatcggtt tgcatttttt caaccccgcg ccgctgatga agctgattga atcattccg      480
gcctacttta ccgcgcacgc caccaccgaa cgctgccgcc aactggtggc ggcgttgggg     540
aaacacgatg tcgtctgcca ggccacgccg gggttcatcg tcaatcgcat ggcccgcccc     600
tactacctgg aagggttccg tctgttggaa gaacacgtgg cgcgcgcggc gcagatcgac     660
cgcgctctca aggccggcgg cgcttccgc atggggccgc tcgagctgac cgattttatc     720
ggccaagaca tcaactatca ggtcagtcgg caaatctggc aggacatgca atacgacccg     780
cgctataccc ccggtcatct gcagcgttca ctggtcgatg ccggtctgtt ggggaaaaag     840
aacggccgct cctatttgc cgccgaagaa accgccccgc cggtgacggc cgccagcaat     900
```

-continued

```
gcagacgtcg agacgctgcg cgtttacggc gagcacccct ttttttacccct gttacagcag    960 cgagccgcgc ttcagtggcc acagctgcgc gtggaacaac ggccggcatt accggggctg   1020
gggtcggccg tccagatcaa tgacgctttc accgtcagca tcaccgatgg ccgcacggcg   1080
agccaactgg ccgagcagac ggcagcagat gcctttgtgg tcgatgtcgc cctgaactac   1140
gccgacacga cgtatctggc ggcggcgcac agccgccacg cctctgcggc caataaggcg   1200
ctgtttttac gcctgctgca cacggcaatc ccgcaggttg aatttatcaa ggactctccg   1260
gcgcttatcg tcgcccgcgt cctcagcagc ctgatcaatg agtcggtgat catggtggaa   1320
agcggcgtct gcagccggga agacatcgat gtcgccgccg tcgcgggcgt taactacgcc   1380
ggcggcattt tcgactggct cggcaaactg ggggagaaaa acgtcaggac aacactgagc   1440
aatctggctc agctgctgca cgcggcgcgc tatgcgccgc attacaccct tctgcacgcc   1500
gcgcaaccgg cgctgacgac cacgccttaa   1530
```

<210> SEQ ID NO 140
<211> LENGTH: 1530
<212> TYPE: DNA
<213> ORGANISM: Serratia marcescens 2880STDY5683033

<400> SEQUENCE: 140

```
atggcagaaa gtaatgcggc aattcaatcg gctgcgatta tcggcgcggg aacgatgggc     60
agaggcatcg cttatctttt cgcgcaaaaa ggcattcgca cggtgcttta taatcgcaac    120
ggcaataccc tcaatcaggc tcgcgaatat atcgcgcacg acctgaacaa gaaagtcgaa    180
caaggcaaga tcgcgctgca ggataaaggc gcggtgctgg ccaatctaat gttcacttca    240
gtgtttgagg ccatcgccga cagcgagctg gtgatagaaa ccatcgccga gcaagaacaa    300
accaaacttg aggtgctggc ggccatcgcc gcggtggtca agcccgacac gctgatcgcc    360 accaataccct cctcactgtc gcttaacaag ctggctactg cggtgacgca cagcgaacgc    420
tttatcggtt tgcattttt caaccccgcg ccgctgatga agctgattga aatcattccg    480 gcctactttta ccgcgcacgc caccaccgaa cgctgccgcc aactggtagc ggcgttgggg    540
aaacacgatg tcgtctgcca ggccacgccg gggttcatcg tcaatcgcat ggcccgcccc    600
tactacctgg aagggttccg cctgttggaa gaacacgtgg cgcgcgcggc gcagatcgac    660
cgcgccctca aggccggcgg gcgcttccg atggggccgc tcgagctgac cgatttttatc    720 ggccaagaca tcaactatca ggtcagtcgg caaatctggc aggatatgca atacgacccg    780 cgctatacccc ccggtcatct gcagcgttca ctggtcgatg ccggtctgtt ggggaaaaag    840
aacggccgct cctatttttgc caccgaagaa accgccccgc cggtgacggc cgccagcaat    900
gcagacgtcg agacgctgcg cgtttacggc gagcacccct ttttttacccct gttacagcag    960 cgagccgcgc ttcagtggcc acagctgcgc gtggaacaac ggccggcatt accggggctg   1020
gggtcggccg tccagatcaa tgacgctttc accgtcagca tcaccgatgg ccgcacggcg   1080
agccaactgg ccgagcagac ggcagcggat gcctttgtgg tcgatgtcgc cctgaactac   1140
gccgacacga cgtatctggc ggcggcgcac agccgccacg cctctgcggc caataaggcg   1200
ctgtttttac gcctgctgca cacggcaatc ccgcaggttg aatttatcaa ggactctccg   1260
gcgcttatcg tcgcccgcgt cctcagcagc ctgatcaatg agtcggtgat catggtggaa   1320
agcggcgtct gcagccggga agacatcgat gtcgccgccg tcgcgggcgt taactacgcc   1380
ggcggcattt tcgactggct cggcaaactg ggggagaaaa acgtcaggac aacgctgagc   1440
```

```
aatctggctc agctgctgca cgcggcgcgc tatgcgccgc attacaccct tctgcacgcc    1500
gcgcaaccgg cgctgacgac cacgccttaa                                     1530

<210> SEQ ID NO 141
<211> LENGTH: 1530
<212> TYPE: DNA
<213> ORGANISM: Serratia marcescens WW4

<400> SEQUENCE: 141
atggcagaaa gtaatgcggc aattcaatcg gctgcgatta tcggcgcggg aacgatgggc     60
agaggcatcg cttatctttt cgcgcaaaaa ggcattccca cgatgcttta taatcgcaac    120
ggcaataccc tcaatcaagc tcgcgaatat atcgcgcaag acctgaacaa gaaagtcgaa    180
cagggcaaga tcgcgctgca ggataaagac gcggtgctgg ccaatctgat gttcacttcc    240
gtgtttgagg ccatcgccga cagcgagctg gtgatagaaa ccatcgccga gcaagaacaa    300
accaaacttg aggtgctggc ggccatcgcc gcagtggtca agcccgacac gctgatcgcc    360
accaataccc tcctcactgtc gcttaacaag ctggcaactg cggtgacgca cagcgagcgc    420
tttatcggtt tgcatttttt caaccccgcg ccgctgatga agctgattga aatcattccg    480
gcctacttta ccgcacacgc caccacgaaa cgctgccgcc aactggtggc ggcgttgggg    540
aaacgcgatg tcgtctgcca ggccacgccg gggttcatcg tcaatcgcat ggcccgcccc    600
tactacctgg aagggttccg cctgttggaa gaacatgtgg cgcgcgcggc gcagatcgac    660
cgcgccctca aggccggcgg gcgcttccgc atggggccgc tcgagctgac cgattttatc    720
ggccaagaca ttaactatca ggtcagccgg caaatctggc aggacatgca atacgacccg    780
cgctataccc ctggtcatct gcagcgttca ctggtcgatg ccggtctgtt ggggaaaaag    840 aacgccgct cctattttgc cgccgaagaa ccgccccgc cggtgacggc cgccaacaat    900
gcagacgtcg agacgctgcg cgtttacggc gagcatcctt tttttaccct gttgcagcag    960
cgagccgcgc ttcagtggcc acagctgcgc gtggaacaac ggccggcatt ccgggggctg   1020
ggagcggccg tccagatcaa tgacgctttc accgtcagca tcaccgatgg ccgcacggcg   1080
agccaactgg ccgagcagac ggcagcggat gcctttgtga tcgatgtcgc cctgaactac   1140
gccgacacca cgtatctggt ggcggcgcac agccgccacg cttctgcggc caataaggcg   1200
ctgtttttac gcctgctgca cacggcaatc ccgcaggttg aatttatcaa ggactccccg   1260
gcgcttatcg tcgcccgcgt cctcagcagc ctgatcaatg agtcggtgat catggtggaa   1320
agcggcgtct gcagccggga agacatcgat gtcgccgccg tcgcgggcgt taactacgcc   1380
ggcggcattt tcgactggct cggcaaactg ggggagaaaa acgtcaggac gacgctgagc   1440
aatctggcgc agctgctgca cgcggcgcgc tatgcgccgc attacaccct tctgcacgcc   1500
gcgcaaccgg cgctgacgac cacgccttaa                                    1530

<210> SEQ ID NO 142
<211> LENGTH: 1530
<212> TYPE: DNA
<213> ORGANISM: Serratia marcescens K27

<400> SEQUENCE: 142
atggcagaaa gtaatgcggc aattcaatcg gctgcgatta tcggcgcggg aacgatgggc     60
agaggcatcg cttatctttt cgcgcaaaaa ggcattccca cgatgcttta taatcgcaac    120
ggcaataccc tcaatcaagc tcgcgaatat atcgcgcaag acctgaataa gaaagtcgaa    180
cagggcaaga tcgcgctgca ggataaagac gcggtgctgg ccaatctgat gttcacttcc    240
```

| | | |
|---|---|---|
| gtgtttgagg ccatcgccga cagcgagctg gtaatagaaa ccatcgccga gcaagaacaa | 300 |
| accaaacttg aggtgctggc ggccatcgcc gcggtggtca agcccgacac gctgatcgcc | 360 |
| accaatacct cctcactgtc gctcaacaag ctggcaactg cggtgacgca cagcgaacgc | 420 |
| tttatcggtt tacatttttt caaccccgcg ccgctgatga agctgattga aatcattccg | 480 |
| gcctacttta ccgcgcacgc caccacggaa cgctgccgcc aactggtggc ggcgttaggg | 540 |
| aaacgcgatg tcgtctgcca ggccacgccg gggttcatcg tcaatcgcat ggcccgcccc | 600 |
| tactacctgg aagggttccg cctgttggaa gaacatgtgg cgcgctcggc gcagatcgac | 660 |
| cgcgccctca aggccggcgg cgcgcttccg catggggccgc tcgagctgac cgatttatc | 720 |
| ggccaagaca ttaactatca ggtcagccgg caaatctggc aggacatgca atacgacccg | 780 |
| cgctataccc ctggtcatct gcagcgttca ctggtcgatg ccggtctgtt ggggaaaaag | 840 |
| aacggccgct cctatttгc cgccgaagaa accgccccgc cggtgacggc cgccaacaat | 900 |
| gcagacgtcg agacgctgcg cgtttacggc gagcatcctt tttttaccct gttgcagcag | 960 |
| cgagccgcgc ttcagtggcc acagctgcgc gtggaacaac ggccggcatt accggggctg | 1020 |
| ggagcggccg tccagatcaa tgacgctttc accgtcagca tcaccgatgg ccgcacggcg | 1080 |
| agccaactgg ccgagcagac ggcagcggat gcctttgtgg tcgatgtcgc cctgaactac | 1140 |
| gccgacacca cgtatctggt ggcggcgcac agccgccacg cttctgcggc caataaggcg | 1200 |
| ctgtttttac gcctgctgca cacggcaatc ccgcaggttg aatttatcaa ggactctccg | 1260 |
| gcgcttatcg tcgcccgcgt cctcagcagc ctgatcaatg agtcggtgat catggtggaa | 1320 |
| agcggcgtct gcagccggga agacatcgat gtcgccgccg tcgcgggcgt taactacgcc | 1380 |
| ggcggcattt tcgactggct cggcaaactg ggggagagaa acgtcaggac gacgctgagc | 1440 |
| aatctggcgc agctgctgca cgcggcgcgc tatgcgccgc attacaccct tctgcacgcc | 1500 |
| gcgcaaccgg cgctgacgac cacgccttaa | 1530 |

<210> SEQ ID NO 143
<211> LENGTH: 1530
<212> TYPE: DNA
<213> ORGANISM: Serratia marcescens 280

<400> SEQUENCE: 143

| | |
|---|---|
| atggcagaaa gtaatgcggc aattcaatcg gctgcgatta tcggcgcggg aacgatgggc | 60 |
| agaggcatcg cttatctttt cgcgcaaaaa ggcattccca cgatgcttta taatcgcaac | 120 |
| ggcaataccc tcaatcaagc tcgcgaatat atcgcgcaag acctgaataa gaaagtcgaa | 180 |
| cagggcaaga tcgcgctgca ggataaagac gcggtgctgg ccaatctgat gttcacttcc | 240 |
| gtgtttgagg ccatcgccga cagcgagctg gtaatagaaa ccatcgccga gcaagaacaa | 300 |
| accaaacttg aggtgctggc ggccatcgcc gcagtggtca agcccgacac gctgatcgcc | 360 |
| accaatacct cctcactgtc gcttaacaag ctggcaactg cggtaacgca cagcgaacgc | 420 |
| tttatcggtt tgcatttttt caaccccgcg ccgctgatga agctgattga aatcattccg | 480 |
| gcctacttta ccgcgcacgc caccacggaa cgctgccgcc aactggtggc ggcgтттgggg | 540 |
| aaacgcgatg tcgtctgcca ggccacgccg gggttcatcg tcaatcgcat ggcccgcccc | 600 |
| tactacctgg aagggttccg cctgttggaa gaacatgtgg cgcgcgcggc gcagatcgac | 660 |
| cgcgccctca aggctggcgg cgcgcttccg catggggccgc tcgagctgac cgattttatc | 720 |
| ggccaagaca tcaactatca ggtcagccgg caaatctggc aggacatgca atacgacccg | 780 |

```
cgctataccc ctggtcatct gcagcgttca ctggtcgatg ccggtctgtt ggggaaaaag      840
aacggccgct cctatttgc cgccgaagaa accgccccgc cggtgacggc cgccaacaat      900
gcagacgtcg agacgctgcg cgtttacggc gagcacccct tttttaccct gttgcagcag      960
cgagccgcgc ttcagtggcc acagctgcgc gtggaacaac ggccggcatt accggggctg     1020
ggagcggccg tccagatcaa tgacgctttc accgtcagca tcaccgatgg ccgcacggcg     1080
agccaactgg ccgagcagac ggcagcggat gcctttgtgg tcgatgtcgc cctgaactac     1140
gccgacacca cgtatctggt ggcggcgcac agccgccacg cttctgctgc caataaggcg     1200 ctgttttac cctgctgca cacggcaatc ccgcaggttg aatttatcaa ggactccccg      1260
gcgcttatcg tcgcccgcgt cctcagcagc ctgatcaatg agtcggtgat catggtggaa     1320
agcggcgtct gcagccggga agacatcgat gtcgccgccg tcgcgggcgt taactacgcc     1380
ggcggcattt tcgactggct cggcaagctg ggggagaaaa acgtcaggac gacgctgagc     1440
aatctggcgc agctgctgca cgcggcgcgc tatgcgccgc attacaccct tctgcacgcc     1500
gcgcaaccgg cgctgacgac cacgccttaa                                     1530

<210> SEQ ID NO 144
<211> LENGTH: 1530
<212> TYPE: DNA
<213> ORGANISM: Serratia marcescens 19F

<400> SEQUENCE: 144
atggcagaaa gtaatgcggc aattcaatcg gctgcgatta tcggcgcggg aacgatgggc       60
agaggcatcg cttatctttt cgcgcaaaaa ggcattccca cgatgcttta taatcgcaac      120
ggcaataccc tcaatcaagc tcgcgaatat atcgcgcaag acctgaacaa gaaagtcgaa      180
cagggcaaga tcgcgctgca ggataaggac gcggtgctgg ccaatctgat gttcacttcc      240
gtgtttgagg ccatcgccga cagcgagctg gtaatagaaa ccatcgccga gcaagaacaa      300
accaaacttg aggtgctggc ggccatcgcc gcggtggtca agcacgacac gctgatcgcc      360
accaatacct cctcactgtc gcttaacaag ctggcaactg cggtgacgca cagcgaacgc      420
tttatcggtt tgcatttttt caaccccgcg ccgctgatga agctgattga aatcattccg      480
gcctacttta ccgcgcacgc caccacggaa cgctgccgcc aactggtggc ggcgttgggg      540
aaacgcgatg tcgtctgcca ggccacgccg gggttcatcg tcaatcgcat ggcccgcccc      600
tactacctgg aagggttccg cctgttggaa gaacatgtgg cgcgcgcggc gcagatcgac      660
cgcgccctca aggccggcgg gcgcttccgc atggggccgc tcgagctgac cgattttatc      720
ggccaagaca ttaactatca ggtcagccgg caaatctggc aggacatgca atacgacccg      780
cgctataccc ctggtcatct gcagcgttca ctggtcgatg ccggtctgtt ggggaaaaag      840
aacggccgct cctatttgc cgccgaagaa accgccccgc cggtgacggc cgccaacaat      900
gcagacgtcg agacgctgcg cgtttacggc gagcatcctt tttttaccct gttgcagcag      960
cgagccgcgc ttcagtggcc acagctgcgc gtggaacaac ggccggcatt accggggctg     1020
ggagcggccg tccagatcaa tgacgctttc accgtcagca tcaccgatgg ccgcacggcg     1080
agccaactgg ccgagcagac ggcagcggat gcctttgtgg tcgatgtcgc cctgaactac     1140
gccgacacca cgtatctggt ggcggcgcac agccgccacg cttctgcggc caataaggcg     1200 ctgttttac gcctgctgca cacggcaatc ccgcaggttg aatttatcaa ggactccccg      1260
gcgcttatcg tcgcccgcgt cctcagcagc ctgatcaatg agtcggtgat catggtggaa     1320
agcggcgtct gcagccggga agacatcgat gtcgccgccg tcgcgggcgt taactacgcc     1380
```

```
ggcggcattt tcgactggct cggcaaactg ggggagaaaa acgtcaggac gacgctgagc   1440
aatctggcgc agctgctgca cgcggcgcgc tatgcgccgc attacaccct tctgcacgcc   1500
gcgcaaccgg cgctgacgac cacgccttaa                                     1530

<210> SEQ ID NO 145
<211> LENGTH: 1530
<212> TYPE: DNA
<213> ORGANISM: Serratia marcescens 1185

<400> SEQUENCE: 145
atggcagaaa gtaatgcggc aattcaatcg gctgcgatta tcggcgcggg aacgatgggc     60
agaggcatcg cttatctttt cgcgcaaaaa ggcattccca cgatgcttta taatcgcaac    120
ggcaataccc tcaatcaagc tcgcgaatat atcgcgcaag acctgaacaa gaaagtcgaa    180
cagggcaaga tcgcgctgcg ggataaagac gcggtgctgg ccaatctgat gttcacttcc    240
gtgtttgagg ccatcgccga cagcgagctg gtgatagaaa ccatcgccga gcaagaacaa    300
accaaacttg aggtgctggc ggccatcgcc gcggtggtca agcccgacac gctgatcgcc    360
accaatacct cctcactgtc gcttaacaag ctggctactg cggtgacgca cagcgaacgc    420
tttatcggtt tgcatttttt caaccccgcg ccgctgatga agctgattga aatcattccg    480
gcctacttta ccgcgcacgc caccaccgaa cgctgccgcc aactggtggc ggcgttgggg    540
aaacacgatg tcgtctgcca ggccacgccg gggttcatcg tcaatcgcat ggcccgcccc    600
tactacctgg aagggttccg cctgttggaa gaacatgtgg cgcgcgcggc gcagatcgac    660
cgcgccctca aggccggcgg gcgcttccgc atggggccgc tcgagctgac cgattttatc    720
ggccaagaca tcaactatca ggtcagccgg caaatctggc aggacatgca atacgacccg    780
cgctataccc ctggtcatct gcagcgttca ctggtcgatg ccggtctgtt ggggaaaaag    840
aacggccgct cttattttgc cgccgaagaa accgccccgc cggtgacggc cgccaacaat    900
gcagacgtcg agacgctgcg cgtttacggc gagcatcctt ttttaccct gttgcagcag    960 cgagccgcgc ttcagtggcc acagctgcgc gtggaacaac ggccggcatt accggggctg   1020
ggagcggccg tccagatcaa tgacgctttc accgtcagca tcaccgatgg ccgcacggcg   1080
agccaactgg ccgagcagac ggcagcggat gcctttgtgg tcgatctcgc cctgaactac   1140
gccgacacca cgtatctggt ggcggcgcac agccgccacg cttctgcggc caataaggcg   1200
ctgtttttac gcctgctgca cacggcaatc ccgcaggttg aatttatcaa ggactctccg   1260
gcgcttatcg tggcccgcgt cctcagcagc ctgatcaatg agtcggtgat catggtggaa   1320
agcggcgtct gcagccggga agacatcgat gtcgccgccg tcgcgggcgt taactacgcc   1380
ggcggcattt tcgactggct cggcaaactg ggggagaaaa acgtcaggac gacgctgagc   1440
aatctggcgc agctgctgca cgcggcgcgc tatgcgccgc attacaccct tctgcacgcc   1500
gcgcaatcgg cgctgacgac cacgccttaa                                     1530

<210> SEQ ID NO 146
<211> LENGTH: 1530
<212> TYPE: DNA
<213> ORGANISM: Serratia marcescens S2I7

<400> SEQUENCE: 146
atggcagaaa gtaatgcggc aattcaatcg gctgcgatta tcggcgcggg aacgatgggc     60
agaggcatcg cttatctttt cgcgcaaaaa ggcattccca cgatgcttta taatcgcaac    120
```

```
ggcaataccc tcaatcaagc tcgcgaatat atcgcgcaag atctgaataa gaaagtcgaa      180
cagggcaaga tcgcgctgca ggataaggac gcggtgctgg ccaatctgat gttcacttcc      240
gtgtttgagg ccatcgccga cagcgagctg gtgatagaaa ccatcgccga gcaagaacaa      300
accaaacttg aggtgctggc ggccatcgcc gcggtggtca agcccgacac gctgatcgcc      360
accaatacct cctcactgtc gcttaacaag ctggcaactg cggtgacgca cagcgaacgc      420
tttatcggtt tgcatttttt caaccccgcg ccgctgatga agctgattga aatcattccg      480
gcctacttta ccgcgcacgc caccacggaa cgctgccgcc aactggtggc ggcgttgggg      540
aaacgcgatg tcgtctgcca ggccacgccg gggttcatcg tcaatcgcat ggcccgcccc      600
tactacctgg aagggttccg cctgttggaa gaacatgtgg cgcgcgcggc gcagatcgac      660
cgcgccctca aggccggcgg gcgcttccgc atggggccgc tcgagctgac cgattttatc      720
ggccaagaca tcaactatca ggtcagccgg caaatctggc aggacatgca atacgacccg      780
cgctataccc ctggtcatct gcagcgttca ctggtcgatg ccggtctgtt ggggaaaaag      840
aacggccgct cctattttgc cgccgaagaa accgccccgc cggtgacggc cgccaacaat      900
gcagacgtcg agacgctgcg cgtttacggc gagcatcctt tttttaccct gttgcagcag      960
cgagccgcgc ttcagtggcc acagctgtgc gtggaacaac ggccggcatt accggggctg     1020
ggagcggccg tccagatcaa tgacgctttc accgtcagca tcaccgatgg ccgcacggcg     1080
agccaactgg ccgagcagac agcagcggat gcctttgtgg tcgatgtcgc cctgaactac     1140
gccgacacca cgtatctggt ggcagcgcac agccgccacg cttctgcggc caataaggcg     1200
ctgtttttac gcctgctgca cacggcaatc ccgcaggttg aatttatcaa ggactctccg     1260
gcgcttatcg tcgcccgcgt cctcagcagc ctgatcaatg agtcggtgat catggtggaa     1320
agcggcgtct gcagccggga agacatcgat gtcgccgccg tcgcgggcgt taactacgcc     1380
ggcggcattt tcgactggct cggcaaactg ggggagagaa acgtcaggac gacgctgagc     1440
aatctggcgc agctgctgca cgcggcgcgc tatgcgccgc attacaccct tctgcacgcc     1500
gcgcaaccgg cgctgacgac cacgccttaa                                      1530
```

<210> SEQ ID NO 147
<211> LENGTH: 1530
<212> TYPE: DNA
<213> ORGANISM: Serratia marcescens KHCo-24B

<400> SEQUENCE: 147

```
atggcagaaa gtaatgcggc aattcaatcg gctgcgatta tcggcgcggg aacgatgggc       60
agaggcatcg cttatctttt cgcgcaaaaa ggcattccca cgatgcttta taatcgcaac      120
ggcaataccc tcaatcaagc tcgcgaatat atcgcgcaag acctgaataa gaaagtcgaa      180
cagggcaaga tcgcgctgcg ggataaagac gcggtgctgg ccaatctgat gttcacttcc      240
gtgtttgagg ccatcgccga cagcgagctg gtgatagaaa ccatcgccga gcaagaacaa      300
accaaacttg aggtgctggc ggccatcgcc gcagtggtca agcccgacac gctgatcgcc      360
accaatacct cctcactgtc gctcaacaag ctggcaacgg cggtaacgca cagcgaacgc      420
tttatcggtt tgcatttttt caaccccgcg ccgctgatga agctgattga aatcattccg      480
gcctacttta ccgcgcacgc caccacggaa cgctgccgcc aactggtggc ggcgttgggg      540
aaacgcgatg tcgtctgcca ggccacgccg gggttcatcg tcaatcgcat ggcccgcccc      600
tactacctgg aagggttccg cctgttggaa gaacatgtgg cgcgcgcggc gcagatcgac      660
cgcgccctca aggctggcgg gcgcttccgc atggggccgc tcgagctgac cgattttatc      720
```

```
ggccaagaca tcaactatca ggtcagccgg caaatctggc aggacatgca atacgacccg      780
cgctataccc ctggtcatct gcagcgttca ctggtcgatg ccggtctgtt ggggaaaaag      840
aacggccgct cctattttgc cgccgaagaa accgccccgc cggtgacggc cgccaacaat      900
gcagacgtcg agacgctgcg cgtttacggc gagcatcctt tttttacccct gttgcagcag     960 cgagccgcgc ttcagtggcc acagctgcgc gtggaacaac ggccggcatt accggggctg     1020
ggagcggccg tccagatcaa tgacgctttc accgtcagca tcaccgatgg ccgcacggcg     1080
agccaactgg ccgagcaggc ggcagcggat gcctttgtgg tcgatctcgc cctgaactac     1140
gccgacacca cgtatctggt ggcggcgcac agccgccacg cttctgcggc caataaggcg     1200
ctgtttttac gcctgctgca cacggcaatc ccgcaggttg aatttatcaa ggactctccg     1260
gcgcttatcg tcgcccgcgt cctcagcagc ctgatcaatg agtcggtgat catggtggaa     1320
agcggcgtct gcagccggga agacatcgat gtcgccgccg tcgcgggcgt taactacgcc     1380
ggcggcattt tcgactggct cggcaaactg ggggagaaaa acgtcaggac gacgctgagc     1440
aatctggcgc agctgctgca cgcggcgcgc tatgcgccgc attacaccct tctgcacgcc     1500
gcgcaaccgg cgctgacgac cacgcccttaa                                     1530

<210> SEQ ID NO 148
<211> LENGTH: 1530
<212> TYPE: DNA
<213> ORGANISM: Serratia marcescens Z6

<400> SEQUENCE: 148
atggcagaaa gtaatgcggc aattcaatcg gctgcgatta ttggcgcggg aacgatgggc       60
agaggcatcg cttatctttt cgcgcaaaaa ggcattccca cgatgcttta taatcgcaac      120
ggcaatcccc tcaatcaagc tcgcgaatat atcgcgcaag acctgaacaa gaaagtcgaa      180
cagggcaaga tcgcgctgca ggataaagac gcggtgctgg ccaatctgat gttcacttcc      240
gtgtttgagg ccatcgccga cagcgagctg gtgatagaaa ccatcgccga gcaagaacaa      300
accaaacttg aggtgctggc ggccatcgcc gcggtggtca agcccgacac gctgatcgcc      360
accaatacct cctcactgtc gcttaacaag ctggcaactg cggtgacgca cagagagcgc      420
tttatcggtt tgcattttt caaccccgcg ccgctgatga agctgattga aatcattccg       480
gcctacttta ccgcgcacgc caccacgaaa cgctgccgcc aactggtggc ggcgttgggg      540
aaacgcgatg tcgtctgcca ggccacgccg gggttcatcg tcaatcgcat ggcccgcccc      600
tactacctgg aagggttccg cctgttggaa gaacatgtgg cgcgcgcggc gcagatcgac      660
cgcgccctca aggccggcgg gcgcttccgc atggggccgc tcgagctgac cgattttatc      720
ggccaagaca ttaactatca ggtcagccgg caaatctggc aggacatgca atacgacccg      780
cgctataccc ctggtcattt gcagcgttca ctggtcgatg ccggtctgtt ggggaaaaag      840
aacggccgct cctattttgc cgccgaagaa accgccccgc cggtgacggc cgccaacaat      900
gcagacgtcg agacgctgcg cgtttacggc gagcaccctt tttttacccct gttgcagcag    960 cgagccgcgc ttcagtggcc acagctgtgc gtggaacaac ggccggcatt accggggctg     1020
ggagcggccg tccagataaa tgacgctttc accgtcagca tcaccgatgg ccgcacggcg     1080
agccaactgg ccgagcagac ggcagcggat gcctttgtga tcgatgtcgc cctgaactac     1140
gccgacacca cgtatctggt ggcagcgcac agccgccacg cttctgcggc caataaggcg     1200
ctgtttttac gcctgctgca cacggcaatc ccgcaggttg aatttatcaa ggactccccg     1260
```

```
gcgcttatcg tcgcccgcgt cctcagcagc ctgatcaatg agtcggtgat catggtggaa      1320
agcggcgtct gcagccggga agacatcgat gtcgccgccg tcgcgggcgt taactacgcc      1380
ggcggcattt tcgactggct cggcaagctg ggggagaaaa acgtcaggac gacgctgagc      1440
aatctggcgc agctgctgca cgcggcgcgc tatgcgccgc attacaccct cctgcacgcc      1500
gcgcaaccgg cgctgacgac cacgccttaa                                      1530

<210> SEQ ID NO 149
<211> LENGTH: 1530
<212> TYPE: DNA
<213> ORGANISM: Serratia marcescens 546

<400> SEQUENCE: 149
atggcagaaa gtaatgcggc aattcaatcg gctgcgatta tcggcgcggg aacgatgggc       60
agaggcatcg cttatctttt cgcgcaaaaa ggcattccca cgatgcttta taatcgcaac      120
ggcaataccc taaatcaagc tcgcgaatat atcgcgcaag acctgaacaa gaaagtcgaa      180
cagggcaaga tcgcgctgcg ggataaagac gcggtgctgg ccaatctgat gttcacttcc      240
gtgtttgagg ccatcgccga cagcgagctg gtgatagaaa ccatcgccga gcaagaacaa      300
accaaacttg aggtgctggc ggccatcgcc gcagtggtca agcccgacac gctgatcgcc      360
accaataccc tctcactgtc gcttaacaag ctgtcaactg cggtaacgca caacgaacgc      420
tttatcggtt tgcatttttt caaccccgcg ccgctgatga agctgattga atcattccg       480 gcctacttta ccgcgcacgc caccacggaa cgctgccgcc aactggtggc ggcgttgggg      540
aaacgcgatg tcgtctgcca ggccacgccg gggttcatcg tcaatcgcat ggcccgcccc      600
tactacctgg aagggttccg cctgttggaa gaacatgtgg cgcgcgcggc gcagatcgac      660
cgcgccctca aggccggcgg gcgcttccgc atggggccgc tcgagctgac cgattttatc      720
ggccaagaca tcaactatca ggtcagccgg caaatctggc aggacatgca atacgacccg      780
cgctataccc ctggtcatct gcagcgttca ctggtcgatg ccggtctgtt ggggaaaaag      840
aacggccgct cctattttgc cgccgaagaa accgccccgc cggtgacggc cgccaacaat      900
gcagacgtcg agacgctgcg cgtttacggc gagcacccct tttttaccct gttgcagcag      960
cgagccgcgc ttcagtggcc acagctgcgc gtggaacaac ggccggcatt accggggctg     1020
ggagcggccc tccggatcaa tgacgctttc accgtcagca tcaccgatgg ccgcacggcg     1080
agccaactgg ccgagcagac ggcagcggat gcctttgtgg tcgatgtcgc cctgaactac     1140
gccgacacca cgtatctggt ggcggcgcac agccgccacg cttctgcggc caataaggcg     1200
ctgtttttac gcctgctgca cacggcaatc ccgcaggttg aatttatcaa ggactctccg     1260
gcgcttatcg tcgcccgcgt cctcagcagc ctgatcaatg agtcggtgat catggtggaa     1320
agcggcgtct gcagccggga agacatcgat gtcgccgccg tcgcgggcgt taactacgcc     1380
ggcggcattt tcgactggct cggcaaactg ggggagaaaa acgtcaggac gacgctgagc     1440
aatctggcgc agctgctgca cgcggcgcgc tatgcgccgc attacaccct tctgcacgcc     1500
gcgcaaccgg cgctgacgac cacgccttaa                                     1530

<210> SEQ ID NO 150
<211> LENGTH: 1530
<212> TYPE: DNA
<213> ORGANISM: Serratia nematodiphila MB307

<400> SEQUENCE: 150
atggcagaaa gtaatgcggc aattcaatcg gctgcgatta tcggcgcggg aacgatgggc       60
```

```
agaggcatcg cttatctttt cgcgcaaaaa ggcattccca cgatgcttta taatcgcaac      120
ggcaataccc tcaatcaagc tcgcgaatat atcgcgcaag acctgaataa gaaagtcgaa      180
cagggcaaga tcgcgctgcg ggataaagac gcggtgctgg ccaatctgat gttcacttcc      240
gtgtttgagg ccatcgccga cagcgagctg gtgatagaaa ccatcgccga gcaagaacaa      300
accaaacttg aggtgctggc ggccatcgcc gcagtggtca agcccgacac gctgatcgcc      360 accaataccct cctcactgtc gctcaacaag ctggcaacgg cggtaacgca cagcgaacgc      420
tttatcggtt tgcattttttt caaccccgcg ccgctgatga agctgattga aatcattccg      480
gcctacttta ccgcgcacgc caccacgaaa cgctgccgcc aactggtggc ggcgttgggg      540
aaacgcgatg tcgtctgcca ggccacgccg ggtttcatcg tcaatcgcat ggcccgcccc      600
tactacctgg aagggttccg cctgttggaa gaacatgtgg cgcgcgcggc gcagatcgac      660
cgcgccctca aggctggcgg gcgcttccgc atggggccgc tcgagctgac cgattttatc      720
ggccaagaca tcaactatca ggtcagccgg caaatctggc aggacatgca atacgacccg      780 cgctatacccc ctggtcatct gcagcgttca ctggtcgatg ccggtctgtt ggggaaaaag      840
aacggccgct cctattttgc cgccgaagaa accgccccgc aggtgacggc cgccaacaat      900
gcagacgtcg agacgctgcg cgtttacggc gagcatcctt tttttacccct gttgcagcag      960 cgagccgcgc ttcagtggcc acagctgcgc gtggaacaac ggccggcatt accggggctg     1020
ggagcggccg tccagatcaa tgacgctttc accgtcagca tcaccgatgg ccgcacggcg     1080
agccaactgg ccgagcagac ggcagcggat gcctttgtgg tcgatctcgc cctgaactac     1140
gccgacacca cgtatctggt ggcggcgcac agccgccacg cttctgcggc caataaggcg     1200 ctgttttttac gcctgctgca cacggcaatc ccgcaggttg aatttatcaa ggactctccg     1260
gcgcttatcg tcgcccgcgt cctcagcagc ctgatcaatg agtcggtgat catggtggaa     1320
agcggcgtct gcagccggga agacatcgat gtcgccgccg tcgcgggcgt taactacgcc     1380
ggcggcattt tcgactggct cggcaaactg ggggagaaaa acgtcaggac gacgctgagc     1440
aatctggcgc agctgctgca cgcggcgcgc tatgcgccgc attacaccct tctgcacgcc     1500
gcgcaaccgg cgctgacgac cacgccttaa                                     1530

<210> SEQ ID NO 151
<211> LENGTH: 1530
<212> TYPE: DNA
<213> ORGANISM: Serratia marcescens VGH107

<400> SEQUENCE: 151
atggcagaaa gtaatgcggc aattcaatcg gctgcgatta tcggcgcggg aacgatgggc       60
agaggcatcg cttatctttt cgcgcaaaaa ggcattccca cgatgcttta taatcgcaac      120
ggcaataccc tcaatcaagc tcgcgaatat atcgcgcaag acctgaataa gaaagtcgaa      180
cagggcaaga tcgcgctgca ggataaggac gcggtgctgg ccaatctgat gttcacttcc      240
gtgtttgagg ccatcgccga cagcgagctg gtaatagaaa ccatcgccga gcaagaacaa      300
accaaacttg aggtgctggc ggccatcgcc gcggtggtca agcacgacac gctgatcgcc      360 accaataccct cctcactgtc gctcaacaag ctggcaactg cggtgacgca cagcgaacgc      420
tttatcggtt tgcattttttt caaccccgcg ccgctgatga agctgattga aatcattccg      480
gcctacttta ccgcgcacgc caccacgaaa cgctgccgcc aactggtggc ggcgttgggg      540
aaacgcgatg tcgtctgcca ggccacgccg ggtttcatcg tcaatcgcat ggcccgcccc      600
```

```
tactacctgg aagggttccg cctgttggaa gaacatgtgg cgcgcgcggc gcagatcgac    660
cgcgccctca aggccggcgg gcgcttccgc atggggccgc tcgagctgac cgattttatt    720
ggccaagaca ttaactatca ggtcagccgg caaatctggc aggacatgca atacgacccg    780
cgctataccc ctggtcatct gcagcgttca ctggtcgatg ccggtctgtt ggggaaaaag    840
aacggccgct cctatttttgc cgccgaagaa accgccccgc cggtgacggc cgccaacaat    900
gcagacgtcg agacgctgcg cgtttacggc gagcatcctt ttttacccct gttgcagcag    960
cgagccgcgc ttcagtggcc acagctgcgc gtggaacaac ggccggcatt accggggctg   1020
ggagcggccg tccagatcaa tgacgctttc accgtaagca tcaccgatgg ccgcacggcg   1080
agccaactgg ccgagcagac ggcagcggat gcctttgtgg tcgatgtcgc cctgaactac   1140
gccgacacca cgtatctggt ggcggcgcac agccgccacg cttctgcggc caataaggcg   1200
ctgtttttgc gcctgctgca cacggcaatc ccgcaggttg aatttatcaa ggactctccg   1260
gcgcttatcg tcgcccgcgt cctcagcagc ctgatcaatg agtcggtgat catggtggaa   1320
agcggcgtct gcagccggga agacatcgat gtcgccgccg tcgcgggcgt taactacgcc   1380
ggcggcattt tcgactggct cggcaaactg ggggagaaaa acgtcaggac gatgctgagc   1440
aatctggcgc agctgctgca cgcggcgcgc tatgcgccgc attacaacct tctgcacgcc   1500
gcgcaaccgg cgctgacgac cacgccttaa                                    1530

<210> SEQ ID NO 152
<211> LENGTH: 1530
<212> TYPE: DNA
<213> ORGANISM: Serratia marcescens MCB

<400> SEQUENCE: 152
atggcagaaa gtaatgcggc aattcaatcg gctgcgatta tcggcgcggg aacgatgggc     60
agaggcatcg cttatctttt cgcgcaaaag ggcattcgta cggtgcttta taatcgcaac    120
ggcaataccc tcaatcaggc tcgcgaatat atcgcgcaag acctgaacaa gaaagtcgaa    180
cagggcaaga tcgcgctgca ggataaaagc tcagtgctgg ccaatctggt gttctcgacg    240
gcgcttgagg ctatcgccga cagcgagttg gtgatagaaa ccatcgccga gcatgaacaa    300
accaaacttg aggtgttggc ggccatcgcc gcggtggtca agcccgatac gctgatcgcc    360 accaataccct cctcactgtc gcttaacaag ctggcaaccg cggtgacgca cagcgagcgg    420
tttatcggtt tgcactttt caaccctgcg ccgctgatga aactgattga aatcatcccg    480
gcctacttta ccgcacacgc caccacggaa cgttgccgtc aactggtggc cgcgttgggg    540
aaacgcgatg tcgtctgtca ggccacgccg gggtttatcg ttaaccgcat ggcccgcccc    600
tactacctgg aagggttccg cctgttggaa gaacatgtgg cgcgcgcgcc gcagatcgac    660
cgtgccctca aggccggcgg acacttccgc atggggccgc tcgagctgac cgatttcatc    720
ggccaggaca tcaactatca ggtcagtcgg caaatctggc aggacatgca atacgacccg    780
cgctataccc ccggccatct gcagcgttcg ctggtcgatg ccggtctgtt ggggaaaaag    840
aacggccgtt cctatttta cgccgaagaa accgccccgc cggtgacggc tgccatcggt    900
gcagacgtcg agacgctgcg catttacggc gaacatcctt ttttacccct gttgcaacag    960
cgggccgcac ttcagtggcc acagctgcgc gtggaacaac ggccggcctt accaggcgtg   1020 gggcggccg tccagatcaa tgacgcattc accgtcagca tcaccgacgg ccgtacggcg   1080
agccagttag ccgagcagac gacggctgac gcttttgtgg tcgatatcgc cctgaactac   1140
gccgacacgg cgtacctggt tgcggcgcac aatcgccacg cctctgcggc caataaggcg   1200
```

```
ctgtttttac gcctgttgca caccgcaatt ccgcaggttg aatttatcaa agactcccg    1260 gcgctgatcg tcgctcgcgt cctcagcagc ctgatcaatg agtcggtgat catggtggaa    1320
agcggcgttt gcagccggga agacattgat gtcgccgccg tcgcgggcgt taactacgcc    1380
ggcggcattt tcgactggct cagcaagctg ggggagaaaa acgtcaggac gacgctgagc    1440
aatctggcgc agttgctgca cgcggcgcgt tatgcgccgc attacaccct tctgcacgcc    1500
gcgcaaccgg cgctgacgac cacgccttga                                     1530
```

<210> SEQ ID NO 153
<211> LENGTH: 1530
<212> TYPE: DNA
<213> ORGANISM: Serratia marcescens AH0650

<400> SEQUENCE: 153

```
atggcagaaa gtaatgcggc aattcaatcg gctgcgatta tcggcgcggg aacgatgggc      60
agaggcatcg cttatctttt cgcgcaaaaa ggcattcgta cggtgcttta taatcgcaac    120
ggcaataccc tcaatcaggc tcgcgaatat atcgcgcaag acctgaacaa gaaagtcgaa    180
cagggcaaga tcgcgctgca ggataaaagc tcagtgctgg ccaatctggt gttctcgacg    240
gcgcttgagg ctatcgccga cagcgagttg gtgatagaaa ccatcgccga gcatgaacaa    300
accaaacttg aggtgttggc ggccatcgcc gcggtggtca agcccgatac gctgatcgcc    360
accaatacct cctcactgtc gcttaacaag ctggcaaccg cggtgacgca cagcgagcgg    420
tttatcggtt tgcactttt caaccctgcg ccgctgatga aactgattga aatcatcccg    480
gcctacttta ccgcacacgc caccacggaa cgttgccgtc aactggtggc cgcgttgggg    540
aaacgcgatg tcgtctgtca ggccacgccg gggtttatcg ttaaccgcat ggcccgcccc    600
tactacctgg aagggttccg cctgttggaa gaacacgtgg cgcgcgcgcc gcagatcgac    660
cgtgccctca aggccggcgg acacttccgc atggggccgc tcgagctgac cgattttatc    720
ggccaggaca tcaactatca ggtcagccgg caaatctggc aggacatgca atacgacccg    780
cgctataccc ccggccatct gcagcgttcg ctggtcgatg ccggtctgtt ggggaaaaag    840
aacggccgct cctattttgc cgccgaagaa accgccccgc cagtgacggc cgccatcgat    900
gcagacgtcg agacgctgcg cgtttacggc gaacaccctt ttttaccct gttgcaacag    960 cgagccgcac gtcagtggcc acagctgcgc gtggaacaac ggccggcctt accgagcctg   1020
gggccggccg tccagatcaa tgacgcattc accgtcagca tcaccgatgg ccgcacggcg   1080
agccagttag ccgagcagac gacggctgac gcttttgtgg tcgacatcgc cctgaactac   1140
gccgacacgg cgtatctggt tgcggcgcac aatcgctatg cctctgcggc caataaggcg   1200
ctgtttttac gcctgctgca cactgcgatc ccgcaggttg aatttatcaa agactccccg   1260
gcgctgatcg tcgctcgtgt cctcagcagc ctgatcaatg agtcggtgat catggtggaa   1320
agcggcgttt gcagccggga agacattgat gtcgccgccg tcgcgggcgt taactacgcc   1380
ggcggcattt tcgactggct cggcaaactg ggggagaaaa acgtcaggac gacgctgagc   1440
aatctggcgc agctgctgca cgcagcgcgc tatgcgccgc attacaccct tctgcacgcc   1500
gcgcaaccgg cgctgacgac cacgccttga                                    1530
```

<210> SEQ ID NO 154
<211> LENGTH: 1530
<212> TYPE: DNA
<213> ORGANISM: Serratia marcescens UMH12

<400> SEQUENCE: 154

```
atggcagaaa gtaatgcgga aattcaatcg gctgcgatta tcggcgcggg aacgatgggc    60
agaggcatcg cttatctttt cgcgcaaaaa ggcattcgta cggtgcttta taatcgcaac   120
ggcaataccc tcaatcaggc tcgcgaatat atcgcgcaag acctgaacaa gaaagtcgaa   180
cagggcaaga tcgcgctgca ggataaaagc tcagtgctgg ccaatctggt gttctcgacg   240
gcgcttgagg ctatcgccga cagcgagttg gtgatagaaa ccatcgccga gcatgaacaa   300
accaaacttg aggtgttggc ggccatcgcc gcggtggtca agcccgatac gctgatcgcc   360
accaatacct cctcactgtc gcttaacaag ctggcaaccg cggtgacgca cagcgagcgg   420
tttatcggtt tgcactttt caaccctgcg ccgctgatga aactgattga aatcatcccg    480
gcctacttta ccgcacacgc caccacggaa cgttgccgtc aactggtggc cgcgttgggg   540
aaacgcgatg tcgtctgtca ggccacgccg gggtttatcg ttaaccgcat ggcccgcccc   600
tactacctgg aagggttccg cctgttggaa gaacacgtgg cgcgcgcgcc gcagatcgac   660
cgtgccctca aggccggcgg acacttccgc atggggccgc tcgagctgac cgattttatc   720
ggccaggaca tcaactatca ggtcagccgg caaatctggc aggacatgca atacgacccg   780
cgctataccc ccgccatctg cagcgttcg ctggtcgatg ccggtctgtt ggggaaaaag    840
aacggccgct cctattttgc cgccgaagaa accgccccgc cagtgacggc cgccatcgat   900
gcagacgtcg agacgctgcg cgtttacggc gaacacccct ttttaccct gttgcaacag    960
cgagccgcac gtcagtggcc acagctgcgc gtggaacaac ggccggcctt accgagcctg  1020
gggccggccg tccagatcaa tgacgcattc accgtcagca tcaccgatgg ccgcacggcg  1080
agccagttag ccgagcagac gacggctgac gctttttgtgg tcgacatcgc cctgaactac  1140
gccgacacgc gtatctggt tgcggcgcac aatcgctatg cctctgcggc caataaggcg   1200
ctgttttta cgcctgctgca cactgcgatc ccgcaggttg aatttatcaa agactccccg  1260
gcgctgatcg tcgctcgtgt cctcagcagc ctgatcaatg agtcggtgat catggtggaa  1320
agcggcgttt gcagccggga agacattgat gtcgccgccg tcgcgggcgt taactacgcc  1380
ggcggcattt tcgactggct cggcaaactg ggggagaaaa acgtcaggac gacgctgagc  1440
aatctggcgc agctgctgca cgcagcgcgc tatgcgccgc attacaccct tctgcacgcc  1500
gcgcaaccgg cgctgacgac cacgccttga                                   1530
```

<210> SEQ ID NO 155
<211> LENGTH: 1530
<212> TYPE: DNA
<213> ORGANISM: Serratia sp. OMLW3

<400> SEQUENCE: 155

```
atggcagaaa gtaatgcggc aattcaatcg gctgcgatta tcggcgcggg aacgatgggc    60
agaggcatcg cttatctttt cgcgcaaaaa ggcattcgta cggtgcttta taatcgcaac   120
ggcaataccc tcaatcaggc tcgcgaatat atcgcgcaag acctgaacaa gaaagtcgaa   180
cagggcaaga tcgcgctgca ggataaaagc tcagtgctgg ccaatctggt gttctcgacg   240
gcgcttgtgg ctatcgccga cagcgagttg gtgatagaaa ccatcgccga gcatgaacaa   300
accaaacttg aggtgttggc ggccatcgcc gcggtggtca agcccgatac gctgatcgcc   360
accaatacct cctcactgtc gcttaacaag ctggcaaccg cggtgacgca cagcgagcgg   420
tttatcggtt tgcactttt caaccctgcg ccgctgatga aactgattga aatcatcccg    480
gcctacttta ccgcacacgc caccacggaa cgttgccgtc aactggtggc cgcgttgggg   540
```

```
aaacgcgatg tcgtctgtca ggccacgccg gggtttatcg tcaaccgcat ggcccgcccc      600
tactacctgg aagggttccg cctgttggaa gagcacgtgg cgcgcgcgcc gcagatcgac      660
cgtgccctca aggccggcgg acacttccgc atggggccgc tcgagctgac cgattttatc      720
ggccaggaca tcaactatca ggtcagccgg caaatctggc aggacatgca atacgacccg      780
cgctataccc ccggccatct gcagcgttcg ctggtcgatg ccggtctgtt ggggaaaaag      840 aacgccgct cctattttgc cgccgaagaa accgccccgc cagtgacggc cgccatcgat       900
gcagacgtcg agacgctgcg cgtttacggc gaacacccctt tttttaccct gttgcaacag    960
cgagccgcac gtcagtggcc acagctgcgc gtggaacaac ggccggcctt accgagcctg     1020
gggccggccg tccagatcaa tgacgcattc accgtcagca tcaccgatgg ccgcacggcg     1080
agccagttag ccgagcagac gacggctgac gcttttgtgg tcgacatcgc cctgaactac     1140
gccgacacgg cgtatctggt tgcggcgcac aatcgctatg cctctgcggc caataaggcg     1200 ctgttttttac gcctgctgca cactgcgatc ccgcaggttg aatttatcaa agattccccg    1260
gcgctgatcg tcgctcgcgt cctcagcagc ctgatcaatg agtcggtgat catggtggaa     1320
agcggcgtct gcagccggga agacattgat gtcgccgccg tcgcgggcgt taactacgcc     1380
ggcggcattt tcgactggct cggcaaactg ggggagaaaa acgtcaggac gacgctgagc     1440
aatctggcgc agctgctgca cgcagcgcgc tatgcgccgc attacaccct tctgcacgcc     1500
gcgcaaccgg cgctgacgac cacgccttga                                      1530
```

<210> SEQ ID NO 156
<211> LENGTH: 1530
<212> TYPE: DNA
<213> ORGANISM: Serratia marcescens UMH11

<400> SEQUENCE: 156

```
atggcagaaa gtaatgcggc aattcaatcg gctgcgatta tcggcgcggg aacgatgggc       60
agaggcatcg cttatctttt cgcgcaaaaa ggcattcgta cggtgcttta taatcgcagc      120
ggcaataccc tcaatcaggc tcgcgaatat atcgcgcaag acctgaacaa gaaagtcgaa      180
cagggcaaga tcgcgctgca ggataaaagc tcagtgctgg ccaatctggt gttctcgacg     240
gcgcttgtgg ctatcgccga cagcgagttg gtgatagaaa ccatcgccga gcatgaacaa      300
accaaacttg aggtgttggc ggccatcgcc gcggtggtca agcccgatac gctgatcgcc      360 accaataccct cctcactgtc gcttaacaag ctggcaaccg cggtgacgca cagcgagcgg     420
tttatcggtt tgcactttt caaccctgcg ccgctgatga aactgattga aatcatcccg      480
gcctacttta ccgcacacgc caccacggaa cgttgccgtc aactggtggc cgcgttgggg     540
aaacgcgatg tcgtctgtca ggccacgccg gggtttatcg tcaaccgcat ggcccgcccc      600
tactacctgg aagggttccg cctgttggaa gagcacgtgg cgcgcgcgcc gcagatcgac      660
cgtgccctca aggccggcgg acacttccgc atggggccgc tcgagctgac cgattttatc      720
ggccaggaca tcaactatca ggtcagccgg caaatctggc aggacatgca atacgacccg      780
cgctataccc ccggccatct gcagcgttcg ctggtcgatg ccggtctgtt ggggaaaaag      840 aacgccgct cctattttgc cgccgaagaa accgccccgc cagtgacggc cgccatcgat       900
gcagacgtcg agacgctgcg cgtttacggc gaacacccctt tttttaccct gttgcaacag    960
cgagccgcac gtcagtggcc acagctgcgc gtggaacaac ggccggcctt accgagcctg     1020
gggccggccg tccagatcaa tgacgcattc accgtcagca tcaccgatgg ccgcacggcg     1080
```

| | | | |
|---|---|---|---|
| agccagttag | ccgagcagac | gacggctgac | gcttttgtgg tcgacatcgc cctgaactac 1140 |
| gccgacacgg | cgtatctggt | tgcggcgcac | aatcgctatg cctctgcggc caataaggcg 1200 |
| ctgttttta c | gcctgctgca | cactgcgatc | ccgcaggttg aatttatcaa agattccccg 1260 |
| gcgctgatcg | tcgctcgcgt | cctcagcagc | ctgatcaatg agtcggtgat catggtggaa 1320 |
| agcggcgtct | gcagccggga | agacattgat | gtcgccgccg tcgcgggcgt taactacgcc 1380 |
| ggcggcattt | tcgactggct | cggcaaactg | ggggagaaaa acgtcaggac gacgctgagc 1440 |
| aatctggcgc | aactgctgca | cgcagcgcgc | tatgcgccgc attacaccct tctgcacgcc 1500 |
| gcgcaaccgg | cgctgacgac | cacgccttga | 1530 |

<210> SEQ ID NO 157
<211> LENGTH: 1530
<212> TYPE: DNA
<213> ORGANISM: Serratia marcescens UMH1

<400> SEQUENCE: 157

| | | | |
|---|---|---|---|
| atggcagaaa | gtaatgcggc | aattcaatcg | gctgcgatta tcggcgcggg aacgatgggc 60 |
| agaggtatcg | cttatctttt | cgcgcaaaaa | ggcattcgta cggtgcttta taatcgcaac 120 |
| ggcaatacccc | tcaatcaggc | tcgcgaatat | atcgcgcaag acctgaacaa gaaagtcgaa 180 |
| cagggcaaga | tcgcgctgca | ggataaaaagc | tcagtgctgg ccaatctggt gttctcgacg 240 |
| gcgcttgagg | ctatcgccga | cagcgagttg | gtgatagaaa ccatcgctga gcatgaacaa 300 |
| accaaacttg | aggtgttggc | ggccatcgcc | gcggtggtca agcccgatac gctgatcgcc 360 |
| accataccct | cctcactgtc | gcttaacaag | ctggcaaccg cggtgacgca cagcgagcgg 420 |
| tttatcggtt | tgcacttttt | caaccctgcg | ccgctgatga aactgattga atcatcccg 480 |
| gcctacttta | ccgcacatgc | caccacgaa | cgttgccgtc aactggtggc cgcgttgggg 540 |
| aaacgcgatg | tcgtctgcca | ggccacgccg | gggtttatcg ttaaccgcat ggcccgcccc 600 |
| tactacctgg | aagggttccg | cctgttggaa | gaacacgtgg cgcgcgcgcc gcagatcgac 660 |
| cgtgccctca | aggccggcgg | acacttccgc | atggggccgc tcgagctgac cgattttatc 720 |
| ggccaggaca | tcaactatca | ggtcagccgg | caaatctggc aggacatgca atacgacccg 780 |
| cgctataccc | ccggccatct | gcagcgttcg | ctggtcgatg ccggtctgtt ggggaaaaag 840 |
| aacgccgct | cctattttgc | cgccgaagaa | accgccccgc cagtgacggc cgccatcgat 900 |
| gcagacgtcg | agacgctgcg | cgtttacggc | gaacacccctt ttttaccct gttgcaacag 960 |
| caagccgcac | gtcagtggcc | acagctgcgc | gtggaacaac ggccggcctt accgagcctg 1020 |
| gggccggccg | tccagatcaa | tggcgcattc | accgtcagca tcaccgatgg ccgcacggcg 1080 |
| agccagttag | ccgagcagac | gacggctgac | gcttttgtga tcgacatcgc cctgaactac 1140 |
| gccgacacgg | cgtatctggt | tgcggcgcac | aatcgctatg cctctgcggc caataaggcg 1200 |
| ctgtttttac | gcctgctgca | cactgcgatc | ccgcaggttg aatttatcaa agactccccg 1260 |
| gcgctgatcg | tcgctcgtgt | cctcagcagc | ctgatcaatg agtcggtgat catggtggaa 1320 |
| agcggcgttt | gcagccggga | agacattgat | gtcgccgccg tcgcgggcgt taactacgcc 1380 |
| ggcggcattt | tcgactggct | cggcaaactg | ggggagaaaa acgtcaggac gacgctgagc 1440 |
| aatctggcgc | agctgctgca | cgcagcgcgc | tatgcgccgc attacaccct tctgcacgcc 1500 |
| gcgcaaccgg | cgctgacgac | cacgccttga | 1530 |

<210> SEQ ID NO 158
<211> LENGTH: 1530

```
<212> TYPE: DNA
<213> ORGANISM: Serratia marcescens 2880STDY5683020

<400> SEQUENCE: 158
atggcagaaa gtaatgcggc aattcaatcg gctgcgatta tcggcgcggg aacgatgggc    60
agaggcatcg cttatctttt cgcgcaaaaa ggcattcgca cggtgcttta taatcgcaac   120
ggcaataccc tcaatcaggc tcgcgaatat atcgcgcaag acctgaacaa gaaagtcgaa   180
cagggcaaga tcgcgctgca ggataaaggc gcagtgctgg ccaatctggt gttcacctcg   240
gtgtttgaga ctatcgccga cagcgatctg gtgatagaaa ccatcgccga gcaagagcaa   300
accaaacttg aggtgctggc ggccatcgcc gcggcggtca agcccgacac gctgatcgcc   360
accaataccc tcctcactgt cgcttaacaag ctggcaaccg cggtgacgca cagcgagcgg   420
tttatcggtt tgcacttttt caatcccgcg ccgctgatga aactgattga aatcatcccg   480
gcctacttta ccgcacgcgc caccaccgaa cgttgccgtc agctggtagc cgcgttgggg   540
aaacgcgatg tcgtctgcca ggccacgccg gggtttatcg tcaaccgcat ggcccgcccc   600
tactacctgg aagggttccg cctgttggaa gaacacgtgg cgcgcgcgcc gcagatcgac   660
cgcgccctca aggccggcgg gcactttcgc atggggccgc tcgagctgac cgattttatc   720
ggccaggaca tcaactatca ggtcagccgg caaatctggc aggacatgca atacgatccg   780
cgctataccc ccggccatct gcagcgttcg ctggtcgatg ccggtctgtt ggggaaaaag   840
aacggccgct cctatttgc cgccgaagaa aacgccttac cggtaacggc cgccaccgat   900
gcagacgtcg agacgctgcg cgtttacggc gaacacccct ttttttaccct gttgcaacag   960 cgggccgcgc ttcagtggcc acggctgcgc gtggagcaac ggccggcctt accgggcctg  1020
gggccggccg tccagatcaa tgaggctttc accgtcagcg tcaccgatgg ccgcacggcg  1080
agccagttgg cggagcagac ggcggcggat gcctttgtgg tcgatgtcgc cctgaattac  1140
gccgacacgg cgtatctggt ggcagcgcac aaccgccacg cctctgcggc caataaggcg  1200
ctgtttttac gcctgctgca cacggcaatc ccgcaggttg aatttatcaa ggactccccg  1260
gcgctgatcg tcgcccgcgt cctcagcagc ctgatcaacg agtcggtgat catggtggaa  1320
agcggcgtct gcagccggga agacatcgat gtcgccgccg tcgccggcgt taactacgcc  1380
gacggcattt tcggctggct cgatagcctg ggggagaaaa acgtcaggac gacgctgagc  1440
aacctggcgc agctgctgca cgcggcacgc tatgcgccgc attacaccct tctgcacgcc  1500
gcgcaaccgg cgctgacgac cacgccttaa                                   1530

<210> SEQ ID NO 159
<211> LENGTH: 1530
<212> TYPE: DNA
<213> ORGANISM: Serratia marcescens 99

<400> SEQUENCE: 159
atggcagaaa gtaatgcggc aattcaatcg gctgcgatta tcggtgcggg aacgatgggc    60
agaggcatcg cttatctttt cgcgcaaaaa ggcattcgca cggtgcttta taatcgcaac   120
ggcaataccc tcaatcaggc tcgcgaatat atcgcgcaag acctgaacaa gaaagtcgaa   180
cagggcaaga tcgcgctgca ggataaaggc gcagtgctgg ccaatctggt gttcacctcg   240
gtgtttgaga ctatcgccga cagcgatctg gtgatagaaa ccatcgccga gcaagagcaa   300
accaaacttg aggtgctggc ggccatcgcc gcggcggtca agcccgacac gctgatcgcc   360
accaataccc tcctcactgt cgcttaacaag ctggcaaccg cggtgacgca cagcgagcgg   420
```

| | | |
|---|---|---|
| tttatcggtt tgcactttt caatcccgcg ccgctgatga aactgattga aatcatcccg | 480 | |
| gcctacttta ccgcacgcgc caccaccgaa cgttgccgtc agctggtggc cgcgttgggg | 540 | |
| aaacgcgatg tcgtctgcca ggccacgccg gggtttatcg tcaaccgcat ggcccgcccc | 600 | |
| tactacctgg aagggttccg cctgttggaa gaacacgtgg cgcgcgcgcc gcagatcgac | 660 | |
| cgcgccctca aggccggcgg gcactttcgc atggggccgc tcgagctgac cgattttatc | 720 | |
| ggccaggaca tcaactatca ggtcagccgg caaatctggc aggacatgca atacgatccg | 780 | |
| cgctataccc ccggccatct gcagcgttcg ctggtcgatg ccggtctgtt ggggaaaaag | 840 | |
| aacggccgct cctattttgc cgccgaagaa aacgccttac cggtaacggc cgcctccaat | 900 | |
| gcagacgtcg agacgctgcg cgtttacggc gaacacccct tttttaccct gttgcaacag | 960 | |
| cgggccgcgc ttcagtggcc acggctgcgc gtggagcaac ggccggcctt accgggtctg | 1020 | |
| gggccggccg tccagatcaa tgaggctttc accgtcagcg tcaccgatgg ccgcacggcg | 1080 | |
| agccaattgg cggagctgac ggcggcggat gcctttgtgg tcgatgtcgc cctgaactac | 1140 | |
| gccgacacgg cgtatctggt ggcagcgcac aaccgccacg cctctgcggc caataaggcg | 1200 | |
| ctgttttta c gcctgctgca cacggcaatc ccgcaggttg aatttatcaa ggactccccg | 1260 | |
| gcgctgatcg tcgcccgcgt cctcagcagc ctgatcaacg agtcggtgat catggtggaa | 1320 | |
| agcggcgtct gcagccggga agacatcgat gtcgccgccg tcgccggcgt taactacgcc | 1380 | |
| gacggcattt tcggctggct cgatagcctg ggggagaaaa acgtcaggac gacgctgagc | 1440 | |
| aacctggcgc agctgctgca cgcggcacgc tatgcgccgc attacacccct tctacacgcc | 1500 | |
| gcgcaaccgg tgctgacgac cacgccttaa | 1530 | |

<210> SEQ ID NO 160
<211> LENGTH: 1530
<212> TYPE: DNA
<213> ORGANISM: Serratia marcescens 374

<400> SEQUENCE: 160

| | | |
|---|---|---|
| atggcagaaa gtaatgcggc aattcaatcg gctgcgatta tcggcgcggg aacgatgggc | 60 | |
| agaggcatcg cttatctttt cgcgcaaaag ggcattcgta cggtgcttta taatcgcaac | 120 | |
| ggcaatacccc tcaatcaggc tcgcgaatat atcgcgcaag acctgaacaa gaaagtcgaa | 180 | |
| cagggcaaga tcgcgctgca ggataaaagc tcagtgctgg ccaatctggt gttctcgacg | 240 | |
| gcgcttgtgg ctatcgccga cagcgagttg gtgatagaaa ccatcgccga gcatgaacaa | 300 | |
| accaaacttg aggtgttggc ggccatcgcc gcggtggtca agcccgatac gctgatcgcc | 360 | |
| accaatacct cctcactgtc gcttaacaag ctggcaaccg cggtgacgca cagcgagcgg | 420 | |
| tttatcggtt tgcactttt caaccctgcg ccgctgatga aactgattga aatcatcccg | 480 | |
| gcctacttta ccgcacacgc caccacggaa cgttgccgtc aactggtggc cgcgttgggg | 540 | |
| aaacgcgatg tcgtctgtca ggccacgccg gggtttatcg tcaaccgcat ggcccgcccc | 600 | |
| tactacctgg aagggttccg cctgttggaa gagcacgtgg cgcgcgcgcc gcagatcgac | 660 | |
| cgtgccctca aggccggcgg acacttccgc atggggccgc tcgagctgac cgattttatc | 720 | |
| ggccaggaca tcaactatca ggtcagccgg caaatctggc aggacatgca atacgacccg | 780 | |
| cgctataccc ccggccatct gcagcgttcg ctggtcgatg ccggtctgtt ggggaaaaag | 840 | |
| aacggccgct cctattttgc cgccgaagaa accgccccgc cagtgacggc cgccatcgat | 900 | |
| gcagacgtcg agacgctgcg cgtttacggc gaacacccct tttttaccct gttgcaacag | 960 | |
| caagccgcac gtcagtggcc acagctgcgc gtggaacaac ggccggcctt accgagcctg | 1020 | |

```
gggccggccg tccagatcaa tggcgcattc accgtcagca tcaccgatgg ccgcacggcg    1080
agccagttag ccgagcagac gacggctgac gcttttgtga tcgacatcgc cctgaactac    1140
gccgacacgg cgtatctggt tgcggcgcac aatcgctatg cctctgcggc caataaggcg    1200 ctgttttac gcctactgca cactgcgatc ccgcaggttg aatttatcaa agactccccg     1260
gcgctgatcg tcgctcgtgt cctcagcagc ctgatcaatg agtcggtgat catggtggaa    1320
agcggcgttt gcagccggga agacattgat gtcgccgccg tcgcgggcgt taactacgcc    1380
ggcggcattt tcgactggct cggcaaactg ggggagaaaa acgtcaggac gacgctgagc    1440
aatctggcgc agctgctgca cgcagcgcgc tatgcgccgc attacaccct tctgcacgcc    1500
gcgcaaccgg cgctgacgac cacgccttga                                     1530

<210> SEQ ID NO 161
<211> LENGTH: 1530
<212> TYPE: DNA
<213> ORGANISM: Serratia marcescens 2880STDY5683036

<400> SEQUENCE: 161
atggcagaaa gtaatgcggc aattcaatcg gctgcgatta tcggtgcggg aacgatgggc      60
agaggcatcg cttatctttt cgcgcaaaaa ggcattcgca cggtgcttta taatcgcaac     120
ggcaataccc tcaatcaggc tcgcgaatat atcgcgcaag acctgaacaa gaaagtcgaa     180
cagggcaaga tcgcgctgca ggataaaggc gcagtgctgg ccaatctggt gttcacctcg     240
gtgtttgaga ctatcgccga cagcgatctg gtgatagaaa ccatcgccga gcaagagcaa     300
accaaacttg aggtgctggc ggccatcgcc gcggcggtca agcccgacac gctgctcgcc     360
accaataccc tcctcactgt cgcttaacaag ctggcaaccg cggtgacgca cagcgagcgg    420
tttatcggtt tgcactttt caatcccgcg ccgctgatga aactgattga aatcatcccg      480
gcctacttta ccgcacgcgc caccaccgaa cgttgccgtc agctggtggc cgcgttgggg    540
aaacgcgatg tcgtctgcca ggccacgccg gggtttatcg tcaaccgcat ggcccgcccc    600
tactacctgg aagggttccg cctgttggaa gaacacgtgg cgcgcgcgcc gcagatcgac    660
cgcgccctca aggccggcgg gcactttcgc atggggccgc tcgagctgac cgattttatc     720
ggccaggaca tcaactatca ggtcagccgg caaatctggc aggacatgca atacgatccg     780
cgctataccc ccgccatct gcagcgttcg ctggtcgatg ccggtctgtt ggggaaaaag      840
aacggccgct cctatttgc cgccgaagaa aacgccttac cggtaacggc cgcctccaat     900
gcagacgtcg agacgctgcg cgtttacggc gaacacccct tttttaccct gttgcaacag    960
cgggccgcgc ttcagtggcc acggctgcgc gtggagcaac ggccggcctt accgggtctg   1020
gggccggccg tccagatcaa tgaggctttc accgtcagcg tcaccgatgg ccgcacggcg   1080
agccaattgg cggagctgac ggcggcggat gcctttgtgg tcgatgtcgc cctgaactac   1140
gccgacacgg cgtatctggt ggcagcgcac aaccgccacg cctctgcggc caataaggcg   1200 ctgttttac gcctgctgca cacggcaatc ccgcaggttg aatttatcaa ggactccccg    1260
gcgctgatcg tcgcccgcgt cctcagcagc ctgatcaacg agtcggtgat catggtggaa   1320
agcggcgtct gcagccggga agacatcgat gtcgccgccg tcgccggcgt taactacgcc   1380
gacggcattt tcggctggct cgatagcctg ggggagaaaa acgtcaggac gacgctgagc   1440
aacctggcgc agctgctgca cgcggcacgc tatgcgccgc attacaccct tctacacgcc   1500
gcgcaaccgg tgctgacgac cacgccttaa                                    1530
```

<210> SEQ ID NO 162
<211> LENGTH: 1530
<212> TYPE: DNA
<213> ORGANISM: Serratia marcescens 2880STDY5683034

<400> SEQUENCE: 162

```
atggcagaaa gtaatgcggc aattcaatcg gctgcgatta tcggcgcggg aacgatgggc      60
agaggcatcg cttatctttt cgcgcaaaaa ggcattcgca cggtgcttta taatcgcaac     120
ggcaataccc tcaatcaggc tcgcgaatat atcgcgcaag acctgaacaa gaaagtcgaa     180
cagggcaaga tcgcgctgca ggataaaggc gcagtgctgg ccaatctggt gttcacctcg     240
gtgtttgaga ctatcgccga cagcgagctg gtgatagaaa ccatcgccga gcaagagcaa     300
accaaacttg aggtgctggc ggccatcgcc gcggcggtca agcccgacac gctgatcgcc     360
accaatacct cctcactgtc gcttaacaag ctggcaaccg cggtgacgca cagcgagcgg     420
tttatcggtt tgcactttt caatcccgcg ccgctgatga aactgattga atcatcccg      480
gcctacttta ccgcacgcgc caccaccgaa cgctgccgtc agttggtggc cgcgttgggg     540
aaacgcgatg tcgtctgcca ggccacgccg ggtttatcg tcaaccgcat ggcccgcccc     600
tactacctgg aagggttccg cctgttggaa gaacacgtgg cgcgcgcgcc gcagatcgac     660
cgcgccctca aggccggcgg gcactttcgc atggggccgc tcgagctgac cgattttatc     720
ggccaggaca tcaactatca ggtcagccgg caaatctggc aggacatgca atacgatccg     780
cgctatcccc ccggccatct gcagcgttcg ctggtcgatg ccggtctgtt ggggaaaaag     840
aacgccgct cctattttgc cgccgaagaa aacgccttac cggtaacggc cgccaccgat     900
gcagacgtcg agacgctgcg catttacggc gaacaccctt tttttaccct gttgcaacag     960
cgggccgcgc ttcagtggcc acggctgcgc gtggagcaac ggccggcctt accgggcctg    1020
gggccggccg tccagatcaa tgaggctttc accgtcagcg tcaccgatgg ccgcacggcg    1080
agccagttgg cggagctgac ggcggcggat gcctttgtgg tcgatgtcgc cctgaactac    1140
gccgacacgg cgtatctggt ggcagcgcac aaccgccacg cctctgcggc caataaggcg    1200
ctgttttttac gcctgctgca cacggcaatc ccgcaggttg aatttatcaa ggactccccg    1260
gcgctgatcg tcgcccgcgt cctcagcagc ctgatcaacg agtcggtgat catggtggaa    1320
agcggcgtct gcagccggga agacatcgat gtcgccgccg tcgccggcgt taactacgcc    1380
gacggcattt tcggctggct cgataacctg ggggagaaaa acgtcaggac gacgctgagc    1440
aacctggcgc agctgctgca cgcggcacgc tatgcgccgc attacaccct tctacacgcc    1500
gcgcaaccgg cgctgacgac cacgccttaa                                     1530
```

<210> SEQ ID NO 163
<211> LENGTH: 1530
<212> TYPE: DNA
<213> ORGANISM: Serratia marcescens 2880STDY5682892

<400> SEQUENCE: 163

```
atggcagaaa gtaatgcggc aattcaatcg gctgcgatta tcggtgcggg aacgatgggc      60
agaggcatcg cttatctttt cgcgcaaaaa ggcattcgca cggtgcttta taatcgcaac     120
ggcaataccc tcaatcaggc tcgcgaatat atcgcgcaag acctgaacaa gaaagtcgaa     180
cagggcaaga tcgcgctgca ggataaaggc gcagtgctgg ccaatctggt gttcacctcg     240
gtgtttgaga ctatcgccga cagcgatctg gtgatagaaa ccatcgccga gcaagagcaa     300
accaaacttg aggtgctggc ggccatcgcc gcggcggtca agcccgacac gctgatcgcc     360
```

```
accaataccct cctcactgtc gcttaacaag ctggcaaccg cggtgacgca cagcgagcgg    420
tttatcggtt tgcactttttt caatcccgcg ccgctgatga aactgattga aatcatcccg    480
gcctacttta ccgcacgcgc caccaccgaa cgttgccgtc agctggtagc cgcgttgggg    540
aaacgcgatg tcgtctgcca ggccacgccg gggtttatcg tcaaccgcat ggcccgcccc    600
tactacctgg aagggttccg cctgttggaa gaacacgtgg cgcgcgcgcc gcagatcgac    660
cgcgccctca aggccggcgg gcactttcgc atggggccgc tcgagctgac cgattttatc    720
ggccaggaca tcaactatca ggtcagccgg caaatctggc aggacatgca atacgatccg    780
cgctataccc ccgccatctg cagcgttcg ctggtcgatg ccggtctgtt ggggaaaaag    840
aacggccgct cctatttgc cgccgaagaa aacgccttac cggtaacggc cgccaccgat    900
gcagacgtcg agacgctgcg cgtttacggc gaacacccctt ttttttacccct gttgcaacag    960 cgggccgcgc ttcagtggcc acggctgcgc gtggagcaac ggccggcctt accgggcctg   1020 gggccggcc tccagatcaa tgaggctttc accgtcagcg tcaccgatgg ccgcacggcg   1080
agccagttgg cggagctgac ggcggcggat gcctttgtgg tcgatgtcgc cctgaactac   1140
gccgacacgg cgtatctggt ggcagcgcac aaccgccacg cctctgcggc caataaggcg   1200 ctgttttttac gcctgctgca cacggcaatc ccgcaggttg aatttatcaa ggactccccg   1260
gcgctgatcg tcgcccgcgt cctcagcagc ctgatcaacg agtcggtgat catggtggaa   1320
agcggcgtct gcagccggga agacatcgat gtcgccgccg tcgccggcgt taactacgcc   1380
gacggcattt tcggctggct cgatagcctg ggggagaaaa acgtcaggac gacgctgagc   1440
aacctggcgc agctgctgca cgcggcacgc tatgcgccgc attacaccct tctgcacgcc   1500
gcgcaaccgg cgctgacgac cacgccttaa                                    1530

<210> SEQ ID NO 164
<211> LENGTH: 1530
<212> TYPE: DNA
<213> ORGANISM: Serratia marcescens SM39

<400> SEQUENCE: 164
atggcagaaa gtaatgcggc aattcaatcg gctgcgatta tcggcgcggg aacgatgggc     60
agaggcatcg cttatctttt cgcgcaaaaa ggcattcgca cggtgcttta taatcgcaac    120
ggcaataccc tcaatcaggc tcgcgaatat atcgtgcaag acctgaacaa gaaagtcgaa    180
cagggcaaga tcgcgctgca ggataaaggc gcagtgctgg ccaatctggt gttcacctcg    240
gtgtttgaga ctatcgccga cagcgagctg gtgatagaaa ccatcgccga gcaagagcaa    300
accaaacttg aggtgctggc ggccatcgcc gcggcggtca gcccgacac gctgatcgcc    360 accaataccct cctcactgtc gcttaacaag ctggcaaccg cggtgacgca cagcgagcgg    420
tttatcggtt tgcactttttt caatcccgcg ccgctgatga aactgattga aatcatcccg    480
gcctacttta ccgcacgcgc caccaccgaa cgttgccgtc agctggtggc cgcgttgggg    540
aaacgcgatg tcgtctgcca ggccacgccg gggtttatcg tcaaccgcat ggcccgcccc    600
tactacctgg aagggttccg cctgttggaa gaacacgtgg cgcgcgcgcc gcagatcgac    660
cgcgccctca aggccggcgg gcactttcgc atggggccgc tcgagctgac cgattttatc    720
ggccaggaca tcaactatca ggtcagccgg caaatctggc aggacatgca atacgatccg    780
cgctataccc ccgccatctg cagcgttcg ctggtcgatg ccggtctgtt ggggaaaaag    840
aacggccgct cctatttgc cgccgaagaa aacgccttac cggtaacggc cgccaccgat    900
```

```
gcagacgtcg agacgctgcg catttacggc gaacacccett tttttaccct gttgcaacag    960
cgggccgcgc ttcagtggcc acggctgcgc gtggagcaac ggccggcctt accgggcctg   1020
gggccggccg tccagatcaa tgaggctttc accgtcagcg tcaccgatgg ccgcacggcg   1080
agccagttgg cggagctgac ggcggcggat gcctttgtgg tcgatgtcgc cctgaactac   1140
gccgacacgg cgtatctggt ggcagcgcac aaccgccacg cctctgcggc caataaggcg   1200
ctgttttttac gcctgctgca cacggcaatc ccgcaggttg aatttatcaa ggactccccg   1260
gcgctgatcg tcgcccgcgt cctcagcagc ctgatcaacg agtcggtgat catggtggaa   1320
agcggcgtct gcagccggga agacatcgat gtcgccgccg tcgccggcgt taactacgcc   1380
gacggcattt tcggctggct cgataacctg ggggagaaaa acgtcaggac gacgctgagc   1440
aacctggcgc agctgctgca cgcggcacgc tatgcgccgc attacaccct tctacacgcc   1500
gcgcaaccgg cgctgacgac cacgccttaa                                    1530

<210> SEQ ID NO 165
<211> LENGTH: 1530
<212> TYPE: DNA
<213> ORGANISM: Serratia marcescens 189

<400> SEQUENCE: 165
atggcagaaa gtaatgcggc aattcaatcg gctgcgatta tcggcgcggg aacgatgggc    60
agaggcatcg cttatctttt cgcgcaaaaa ggcattcgca cggtgcttta taatcgcaac   120
ggcaataccc tcaatcaggc tcgcgaatat atcgcgcaag acctgaacaa gaaagtcgaa   180
cagggcaaga tcgcgctgca ggataaaggc gcagtgctgg ccaatctggt gttcacctcg   240
gtgtttgaga ctatcgccga cagcgatctg gtgatagaaa ccatcgccga gcaagagcaa   300
accaaacttg aggtgctggc ggccatcgcc gcggcggtca agcccgacac gctgatcgcc   360
accaatacct cctcactgtc gcttaacaag ctggcaaccg cggtgacgca cagcgagcgg   420
tttatcggtt tgcactttt caatcccgcg ccgctgatga aactgattga aatcatcccg   480
gcctacttta ccgcacgcgc caccaccgaa cgttgccgtc agctggtagc cgcgttgggg   540
aaacgcgatg tcgtctgcca ggccacgccg gggtttatcg tcaaccgcat ggcccgcccc   600
tactacctgg aagggttccg cctgttggaa gaacacgtgg cgcgcgcgcc gcagatcgac   660
cgcgccctca aggccggcgg gcactttcgc atggggccgc tcgagctgac cgatttatc   720
ggccaggaca tcaactatca ggtcagccgg caaatctggc aggacatgca atacgatccg   780
cgctataccc ccggccatct gcagcgttcg ctggtcgatg ccggtctgtt ggggaaaaag   840
aacggccgct cctatttgc cgccgaagaa aacgccttac cggtaacggc cgccaccgat   900
gcagacgtcg agacgctgcg catttacggc gaacacccett tttttaccct gttgcaacag   960
cgggccgcgc ttcagtggcc acggctgcgc gtggagcaac ggccggcctt accgggcctg   1020
gggccggccg tccagatcaa tgaggctttc accgtcagcg tcaccgatgg ccgcacggcg   1080
agccagttgg cggagctgac ggcggcggat gcctttgtgg tcgatgtcgc cctgaactac   1140
gccgacacgg cgtatctggt ggcagcgcac aaccgccacg cctctgcggc caataaggcg   1200
ctgttttttac gcctgctgca cacggcaatc ccgcaggttg aatttatcaa ggactccccg   1260
gcgctgatcg tcgcccgcgt cctcagcagc ctgatcaacg agtcggtgat catggtggaa   1320
agcggcgtct gcagccggga agacatcgat gtcgccgccg tcgccggcgt taactacgcc   1380
gacggcattt tcggctggct cgataacctg ggggagaaaa acgtcaggac gacgctgagc   1440
aacctggcgc agctgctgca cgcggcacgc tatgcgccgc attacaccct tctacacgcc   1500
```

```
gcgcaaccgg cgctgacgac cacgccttaa                               1530
```

<210> SEQ ID NO 166
<211> LENGTH: 1530
<212> TYPE: DNA
<213> ORGANISM: Serratia marcescens SMB2099

<400> SEQUENCE: 166

```
atggcagaaa gtaatgcggc aattcaatcg gctgcgatta tcggcgcggg aacgatgggc     60
agaggcatcg cttatctttt cgcgcaaaaa ggcattcgca cggtgcttta taatcgcaac    120
ggcaataccc tcaatcaggc tcgcgaatat atcgcgcaag acctgaacaa gaaagtcgaa    180
cagggcaaga tcgcgctgca ggataaaggc gcagtgctgg ccaatctggt gttcacctcg    240
gtgtttgaga ctatcgccga cagcgatctg gtgatagaaa ccatcgccga gcaagagcaa    300
accaaacttg aggtgctggc ggccatcgcc gcggcggtca gcccgacac gctgatcgcc     360
accaatacct cctcactgtc gcttaacaag ctggcaaccg cggtgacgca cagcgagcgg    420
tttatcggtt tgcactttt caatcccgcg ccgctgatga aactgattga atcatcccg      480
gcctacttta ccgcacgcgc caccaccgaa cgttgccgtc agctggtggc cgcgttgggg    540
aaacgcgatg tcgtctgcca ggccacgccg gggtttatcg tcaaccgcat ggcccgcccc    600
tactacctgg aagggttccg cctgttggaa gaacacgtgg cgcgcgcgcc gcagatcgac    660
cgcgccctca aggccggcgg gcactttcgc atggggccgc tcgagctgac cgattttatc    720
ggccaggaca tcaactatca ggtcagccgg caaatctggc aggacatgca atacgatccg    780
cgctatatccc ccggccatct gcagcgttcg ctggtcgatg ccggtctgtt ggggaaaaag    840
aacggccgct cctatttgc cgccgaagaa aacgccttac cggtaacggc cgccaccgat     900
gcagacgtcg agacgctgcg cgtttacggc gaacacccctt ttttacccct gttgcaacag   960
cgggccgcgc ttcagtggcc acggctgcgc gtggagcaac ggccggcctt accgggcctg   1020
gggccggccg tccagatcaa tgaggctttc accgtcagcg tcaccgatgg ccgcacggcg   1080
agccagttgg cggagctgac ggcggcggat gccttttgtgg tcgatgtcgc cctgaactac   1140
gccgacacgg cgtatctggt ggcagcgcac aaccgccacg cctctgaggc caataaggcg   1200
ctgttttttac gcctgctgca cacggcaatc ccgcaggttg aatttatcaa ggactccccg   1260
gcgctgatcg tcgcccgcgt cctcagcagc ctgatcaacg agtcggtgat catggtggaa   1320
agcggcgtct gcagccggga agacatcgat gtcgccgccg tcgccggcgt taactacgcc   1380
gacggcattt tcggctggct cgatagcctg ggggagaaaa acgtcaggac gacgctgagc   1440
aacctggcgc agctgctgca cgcggcacgc tatgcgccgc attacacccct tctacacgcc   1500
gcgcaaccgg cgctgacgac cacgccttaa                                    1530
```

<210> SEQ ID NO 167
<211> LENGTH: 1530
<212> TYPE: DNA
<213> ORGANISM: Serratia marcescens 2880STDY5682862

<400> SEQUENCE: 167

```
atggcagaaa gtaatgcggc aattcaatcg gctgcgatta tcggcgcggg aacgatgggc     60
agaggcatcg cttatctttt cgcgcaaaaa ggcattcgca cggtgcttta taatcgcaac    120
ggcaataccc tcaatcaggc tcgcgaatat atcgtgcaag acctgaacaa gaaagtcgaa    180
cagggcaaga tcgcgctgca ggataaaggc gcagtgctgg ccaatctggt gttcacctcg    240
```

```
gtgtttgaga ccattgccga cagcgagctg gtgatagaaa ccatcgccga gcaagagcaa      300
accaaacttg aggtgctggc ggccatcgcc gcggcggtca agcccgacac gctgatcgcc      360
accaatacct cctcactgtc gcttaacaag ctggcaaccg cggtgacgca cagcgagcgg      420
tttatcggtt tgcactttt caatcccgcg ccgctgatga aactgattga aatcatcccg       480
gcctacttta ccgcacgcgc caccaccgaa cgttgccgtc agctggtagc cgcgttgggg      540
aaacgcgatg tcgtctgcca ggccacgccg gggtttatcg tcaaccgcat ggcccgcccc      600
tactacctgg aagggttccg cctgttggaa gaacacgtgg cgcgcgcgcc gcagatcgac      660
cgcgccctca aggccggcgg gcactttcgc atggggccgc tcgagctgac cgattttatc      720
ggccaggaca tcaactatca ggtcagccgg caaatctggc aggacatgca atacgatccg      780
cgctataccc ccggccatct gcagcgttcg ctggtcgatg ccggtctgtt ggggaaaaag      840
aacggccgct cctattttgc cgccgaagaa acgccttac cggtaacggc cgccaccgat       900
gcagacgtcg agacgctgcg cgtttacggc gaacacccttt ttttaccct gttgcaacag      960
cgggccgcgc ttcagtggcc acggctgcgc gtggagcaac ggccggcctt accgggcctg     1020
gggccggccg tccagatcaa tgaggctttc accgtcagcg tcaccgatgg ccgcacggcg     1080
agccagttgg cggagctgac ggcggcggat gcctttgtgg tcgatgtcgc cctgaactac     1140
gccgacacgg cgtatctggt ggcagcgcac aaccgccacg cctctgcggc caataaggcg     1200
ctgttttttac gcctgctgca cacggcaatc ccgcaggttg aatttatcaa ggactccccg    1260
gcgctgatcg tcgcccgcgt cctcagcagc ctgatcaacg agtcggtgat catggtggaa     1320
agcggcgtct gcagccggga agacatcgat gtcgccgccg tcgctggcgt taactacgcc     1380
gacggcattt tcggctggct cgatagcctg ggggagaaaa acgtcaggac gacgctgagc     1440
aacatggcgc agctgctgca cgcggcacgc tatgcgccgc attacacccct tctgcacgcc    1500
gcgcaaccgg cgctgatgac cacgccttaa                                      1530
```

<210> SEQ ID NO 168
<211> LENGTH: 1530
<212> TYPE: DNA
<213> ORGANISM: Serratia marcescens SE4145

<400> SEQUENCE: 168

```
atggcagaaa gtaatgcgga aattcaatcg gctgcgatta tcggcgcggg aacgatgggc       60
agaggcatcg cttatctttt cgcgcaaaaa ggcattcgca cggtgcttta taatcgcaac      120
ggcaataccc tcaatcaggc tcgcgaatat atcgtgcaag acctgaacaa gaaagtcgaa      180
cagggcaaga tcgcgctgca ggataaaggc gcagtgctgg ccaatctggt gttcacctcg      240
gtgtttgaga ctatcgccga cagcgagctg gtgatagaaa ccatcgccga gcaagagcaa      300
accaaacttg aggtgctggc ggccatcgcc gcggcggtca agcccgacac gctgatcgcc      360
accaatacct cctcactgtc gcttaacaag ctggcaaccg cggtgacgca cagcgagcgg      420
tttatcggtt tgcactttt caatcccgcg ccgctgatga aactgattga aatcatcccg       480
gcctacttta ccgcacgcgc caccaccgaa cgttgccgtc agctggtagc cgcgttgggg      540
aaacgcgatg tcgtctgcca ggccacgccg gggtttatcg tcaaccgcat ggcccgcccc      600
tactacctgg aagggttccg cctgttggaa gaacacgtgg cgcgcgcgcc gcagatcgac      660
cgcgccctca aggccggcgg gcactttcgc atggggccgc tcgagctgac cgattttatc      720
ggccaggaca tcaactatca ggtcagccgg caaatctggc aggacatgca atacgatccg      780
cgctataccc ccggccatct gcagcgttcg ctggtcgatg ccggtctgtt ggggaaaaag      840
```

```
aacggccgct cctatttgc cgccgaagaa acgccttac cggtaacggc cgccaccgat      900
gcagacgtcg agacgctgcg catttacggc gaacacccctt tttttacccct gttgcaacag   960 cgggccgcgc ttcagtggcc acggctgcgc gtggagcaac ggccggcctt accgggcctg   1020
gggccggccg tccagatcaa tgaggctttc accgtcagcg tcaccgatgg ccgcacggcg   1080
agccagttgg cggagctgac ggcggcggat gcctttgtgg tcgatgtcgc cctgaactac   1140
gccgacacgg cgtatctggt ggcagcgcac aaccgccacg cctctgcggc caataaggcg   1200
ctgtttttac gcctgctgca cacggcaatc ccgcaggttg aatttatcaa ggactccccg   1260
gcgctgatcg tcgcccgcgt cctcagcagc ctgatcaacg agtcggtgat catggtggaa   1320
agcggcgtct gcagccggga agacatcgat gtcgccgccg tcgccggcgt taactacgcc   1380
gacggcattt tcggctggct cgataacctg ggggagaaaa acgtcaggac gacgctgagc   1440
aacctggcgc agctgctgca cgcggcacgc tatgcgccgc attacaccct tctacacgcc   1500
gcgcaaccgg cgctgacgac cacgccttaa                                    1530

<210> SEQ ID NO 169
<211> LENGTH: 1530
<212> TYPE: DNA
<213> ORGANISM: Serratia marcescens 2880STDY5682876

<400> SEQUENCE: 169
atggcagaaa gtaatgcggc aattcaatcg gctgcgatta tcggtgcggg aacgatgggc    60
agaggcatcg cttatctttt cgcgcaaaaa ggcattcgca cggtgcttta taatcgcaac   120 ggcaatacccc tcaatcaggc tcgcgaatat atcgcgcaag acctgaacaa gaaagtcgaa   180
cagggcaaga tcgcgctgca gggtaaaggc gcagtgctgg ccaatctggt gttcaccctcg   240 gtgtttgaga ctatcgccga cagcgatctg gtgatagaaa ccatcgccga gcaagagcaa   300
accaaacttg aggtgctggc ggccatcgcc gcggcggtca agcccgacac gctgatcgcc   360 accaataccct cctcactgtc gcttaacaag ctggcaaccg cggtgacgca cagcgagcgg   420
tttatcggtt tgcactttt caatcccgcg ccgctgatga aactgattga aatcatcccg   480
gcctacttta ccgcacgcgc caccaccgaa cgttgccgtc agctggtagc cgcgttgggg   540
aaacgcgatg tcgtctgcca ggccacgccg gggtttatcg tcaaccgcat ggcccgcccc   600
tactacctgg aagggttccg cctgttggaa gaacacgtgg cgcgcgcgcc gcagatcgac   660 cgcgcccctca aggccggcgg gcactttcgc atggggccgc tcgagctgac cgattttatc   720
ggccaggaca tcaactatca ggtcagccgg caaatctggc aggacatgca atacgatccg   780
cgctataccc ccggccatct gcagcgttcg ctggtcgatg ccggtctgtt ggggaaaaag   840
aacggccgct cctatttgc cgccgaagaa acgccttac cggtaacggc cgccaccgat      900
gcagacgtcg agacgctgcg cgtttacggc gaacacccctt tttttacccct gttgcaacag   960 cgggccgcgc ttcagtggcc acggctgcgc gtggagcaac ggccggcctt accgggcctg   1020
gggccggccg tccagatcaa tgaggctttc accgtcagcg tcaccgatgg ccgcacggcg   1080
agccagttgg cggagctgac ggcggcggat gcctttgtgg tcgatgtcgc cctgaactac   1140
gccgacacgg cgtatctggt ggcagcgcac aaccgccacg cctctgcggc caataaggcg   1200
ctgtttttac gcctgctgca cacggcaatc ccgcaggttg aatttatcaa ggactccccg   1260
gcgctgatcg tcgcccgcgt cctcagcagc ctgatcaacg agtcggtgat catggtggaa   1320
agcggcgtct gcagccggga agacatcgat gtcgccgccg tcgccggcgt taactacgcc   1380
```

```
gacggcattt tcggctggct cgatagcctg ggggagaaaa acgtcaggac gacgctgagc      1440
aacctggcgc agctgctgca cgcggcacgc tatgcgccgc attacaccct tctgcacgcc      1500
gcgcaaccgg cgctgacgac cacgccttaa                                      1530

<210> SEQ ID NO 170
<211> LENGTH: 1530
<212> TYPE: DNA
<213> ORGANISM: Serratia marcescens 709

<400> SEQUENCE: 170
atggcagaaa gtaatgcggc aattcaatcg gctgcgatta tcggcgcggg aacgatgggc       60
agaggcatcg cttatctttt cgcgcaaaaa ggcattcgca cggtgcttta taatcgcaac      120
ggcaataccc tcaatcaggc tcgcgaatat atcgcgcaag acctgaacaa gaaagtcgaa      180
cagggcaaga tcgcgctgca ggataaaggc gcagtgctgg ccaatctggt gttcacctcg      240
gtgtttgaga ctatcgccga cagcgatctg gtgatagaaa ccatcgccga gcaagagcaa      300
accaaacttg aggtgctggc ggccatcgcc gcggcggtca agcccgacac gctgatcgcc      360 accaataccct cctcactgtc gcttaacaag ctggcaaccg cggtgacgca cagcgagcgg      420
tttatcggtt tgcactttt caatcccgcg ccgctgatga aactgattga aatcatcccg       480
gcctacttta ccgcacgcgc caccaccgaa cgttgccgtc agctggtagc cgcgttgggg      540
aaacgcgatg tcgtctgcca ggccacgccg gggtttatcg tcaaccgcat ggcccgcccc      600
tactacctgg aagggttccg cctgttggaa gaacacgtgg cgcgcgcgcc gcagatcgac      660
cgcgccctca aggccggcgg gcactttcgc atggggccgc tcgagctgac cgattttatc      720
ggccaggaca tcaactatca ggtcagtcgg caaatctggc aggacatgca atacgatccg      780
cgctataccc ccgccatctt gcagcgttcg ctggtcgatg ccggtctgtt ggggaaaaag      840
aacggccgct cctatttgc cgccgaagaa aacgccttac cggtaacggc cgccaccgat      900
gcagacgtcg agacgctgcg cgtttacgac gaacacccctt tttttaccct gttgcaacag      960
cgggccgcgc ttcagtggcc acggctgcgc gtggagcaac ggccggcctt accgggcctg     1020
gggccggccc tccagatcaa tgaggctttc accgtcagcg tcaccgatgg ccgcacggcg     1080
agccagttgg cggagctgac ggcggcggat gcctttgtgg tcgatgtcgc cctgaactac     1140
gccgacacgg cgtatctggt ggcagcgcac aaccgccacg cctctgcggc caataaggcg     1200 ctgttttac gcctgctgca cacggcaatc ccgcaggttg aatttatcaa ggactccccg      1260
gcgctgatcg tcgcccgcgt cctcagcagc ctgatcaacg agtcggtgat catggtggaa     1320
agcggcgtct gcagccggga agacatcgat gtcgccgccg tcgccggcgt taactacgcc     1380
gacggcattt tcggctggct cgatagcctg ggggagaaaa acgtcaggac gacgctgagc     1440
aacctggcgc agctgctgca cgcggcacgc tatgcgccgc attacaccct tctgcacgcc     1500
gcgcaaccgg cgctgacgac cacgccttaa                                     1530

<210> SEQ ID NO 171
<211> LENGTH: 1530
<212> TYPE: DNA
<213> ORGANISM: Serratia marcescens MGH136

<400> SEQUENCE: 171
atggcagaaa gtaatgcggc aattcaatcg gctgcgatta tcggcgcggg aacgatgggc       60
agaggcatcg cttatctttt cgcgcaaaaa ggcattcgca cggtgcttta taatcgcaac      120
ggcaataccc tcaatcaggc tcgcgaatat atcgcgcaag acctgaacaa gaaagtcgaa      180
```

```
caggacaaga tcgcgctgca ggataaaggc gcagtgctgg ccaatctggt gttcacctcg    240
gtgtttgaga ctatcgccga cagcgatctg gtgatagaaa ccatcgccga gcaagagcaa    300
accaaacttg aggtgctggc ggccatcgcc gcggcggtta agcccgacac gctgatcgcc    360
accaatacct cctcactgtc gcttaacaag ctggcaaccg cggtgacgca cagcgagcgg    420
tttatcggtt tgcacttttt caatcccgcg ccgctgatga aactgattga aatcatcccg    480
gcctacttta ccgcacgcgt caccaccgaa cgttgccgtc agctggtggc cgcgttgggg    540
aaacgcgatg tcgtctgcca ggccacgccg gggtttatcg tcaaccgcat ggcccgcccc    600
tactacctgg aagggttccg tctgttagaa gaacacgtgg cgcgcgcgcc gcagatcgac    660
cgcgccctca aggccggcgg gcactttcgc atggggccgc tcgagctgac cgattttatc    720
ggccaggaca tcaactatca ggtcagccgg caaatctggc aggacatgca atacgatccg    780
cgctataccc ccggccatct gcagcgttcg ctggtcgatg ccggtctgtt ggggaaaaag    840 aacgccgct cctattttgc cgccgaagaa aacgccttac cggtaacggc cgccaccgat    900
gcagacgtcg agacgctgcg cgtttacggc gaacaccctt tttttaccct gttgcaacag    960
cgggccgcgc tt cagtggcc acggctgcgc gtggagcaac ggccggcctt accgggcctg   1020
gggccggccg tccagatcaa tgaggctttc accgtcagcg tcaccgatgg ccgcacggcg   1080
agccagttgg cggagctgac ggcggcggat gcctttgtgg tcgatgtcgc cctgaactac   1140
gccgacacgg cgtatctggt ggcagcgcac aaccgccacg cctctgcggc caataaggcg   1200
ctgtttttac gcctgctgca cacggcaatc ccgcaggttg aatttatcaa ggactccccg   1260
gcgctgatcg tcgcccgcgt cctcagcagc ctgatcaacg agtcggtgat catggtggaa   1320
agcggcgtct gcagccggga agacatcgat gtcgccgctg tcgccggcgt taactacgcc   1380
gacggcattt tcggctggct cgatagcctg ggggagaaaa acgtcagaac gacgctgagc   1440
aacctggcgc agctgctgca cgcggcacgc tatgcgccgc attacaccct tctgcacgcc   1500
gcgcaaccgg cgctgacgac cacgccttaa                                    1530

<210> SEQ ID NO 172
<211> LENGTH: 1530
<212> TYPE: DNA
<213> ORGANISM: Serratia marcescens 2880STDY5682884

<400> SEQUENCE: 172
atggcagaaa gtaatgcggc aattcaatcg gctgcgatta tcggcgcggg aacgatgggc     60
agaggcatcg cttatctttt cgcgcaaaaa ggcattcgca cggtgcttta taatcgcaac    120 ggcaatacccc tcaatcaggc tcgcgaatat atcgcgcaag acctgaacaa gaaagtcgaa    180
cagggcaaga tcgcgctgca ggataaaggc gcagtgctgg ccaatctggt gttcacctcg    240
gtgtttgaga ctatcgccga cagcgagctg gtgatagaaa ccatcgccga gcaagagcaa    300
accaaacttg aggtgctggc ggccatcgcc gcggcggtca agcccgacac gctgatcgcc    360
accaatacct cctcactgtc gcttaacaag ctggcaaccg cggtgacgca cagcgagcgg    420

tttatcggtt tgcacttttt caatcccgcg ccgctgatga aactgattga aatcatcccg    480
gcctacttta ccgcacgcgc caccaccgaa cgctgccgtc agttggtggc cgcgttgggg    540
aaacgcgatg tcgtctgcca ggccacgccg gggtttatcg tcaaccgcat ggcccgcccc    600
tactacctgg aagggttccg cctgttggaa gaacacgtgg cgcgcgcgcc gcagatcgac    660
cgcgccctca aggccggcgg gcactttcgc atggggccgc tcgagctgac cgattttatc    720
```

```
ggccaggaca tcaactatca ggtcagccgg caaatctggc aggacatgca atacgatccg      780
cgctataccc ccggccatct gcagcgttcg ctggtcgatg ccggtctgtt ggggaaaaag      840
aacggccgct cctatttttgc cgccgaagaa aacgccttac cggtaacggc cgccaccgat     900
gcagacgtcg agacgctgcg catttacggc gaacacccctt tttttacccct gttgcaacag   960 cgggccacgc ttcagtggcc acggctgcgc gtggagcaac ggccggcctt accgggcctg     1020
gggccggccg tccagatcaa tgaggctttc accgtcagcg tcaccgatgg ccgcacggcg     1080
agccagttgg cggagctgat ggcggcggat gcctttgtgg tcgatgtcgc cctgaactac     1140
gccgacacgg cgtatctggt ggcagcgcac aaccgccacg cctctgcggc caataaggcg     1200 ctgttttttac gcctgctgca cacggcaatc ccgcaggttg aatttatcaa ggactccccg    1260
gcgctgatcg tcgcccgcgt cctcagcagc ctgatcaacg agtcggtgat catggtggaa    1320
agcggcgtct gcagtcggga agacatcgat gtcgccgccg tcgccggcgt taactacgcc    1380
gacggcattt tcggctggct cgatagcctg ggggagaaaa acgtcaggat gacgctgagc    1440
aacctggcgc agctgctgca cgcggcacgc tatgcgccgc attacaccct tctacacgcc     1500
gcgcaaccgg cgctgacgac cacgccttaa                                     1530

<210> SEQ ID NO 173
<211> LENGTH: 1530
<212> TYPE: DNA
<213> ORGANISM: Serratia marcescens D-3

<400> SEQUENCE: 173
atggcagaaa gtaatgcggc aattcaatcg gctgcgatta tcggcgcggg aacgatgggc       60
agaggcatcg cttatctttt cgcgcaaaaa ggcattcgca cggtgcttta taatcgcaac      120
ggcaataccc tcaatcaggc tcgcgaatat atcgcgcaag acctgaacaa gaaagtcgaa      180
cagggcaaga tcgcgctgca ggataaaggc gcagtgctgg ccaatctggt gttcacctcg      240
gtgtttgaga ctatcgccga cagcgatctg gtgatagaaa ccatcgccga gcaagagcaa      300
accaaacttg aggtgctggc ggccatcgcc gcggcggtca agcccgacac gctgatcgcc      360 accaataccct cctcactgtc gcttaacaag ctggcaaccg cggtgacgca cagcgagcgg      420
tttatcggtt tgcactttttt caatcccgcg ccgctgatga aactgattga aatcatcccg     480
gcctacttta ccgcacgcgc caccaccgaa cgttgccgtc agctggtggc cgcgttgggg     540
aaacgcgatg tcgtctgcca ggccacgccg gggtttatcg tcaaccgcat ggcccgcccc     600
tactacctgg aagggttccg cctgttggaa gaacacgtgg cgcgcgcgcc gcagatcgac    660
cgcgccctca aggccggcgg gcactttcgc atggggccgc tcgagctgac cgatttttatc   720 ggccaggaca tcaactatca ggtcagccgg caaatctggc aggacatgca atacgatccg     780
cgctataccc ccggccatct gcagcgttcg ctggtcgatg ccggtctgtt ggggaaaaag    840
aacggccgct cctatttttgc cgccgaagaa aacgccttac cggtaacggc cgccatcgat    900
gcagacgtcg agacgctgcg cgtttacggc gaacacccctt tttttacccct gttgcaacag  960 cgggccgcgc ttcagtggcc acggctgcgc gtggagcaac ggccggcctt accgggcctg   1020
gggccggccg tccagatcaa tgaggctttc accgtcagcg tcaccgatgg ccgcacggcg   1080
agccagttgg cggagctgac ggcggcggat gcctttgtgg tcgatgtcgc cctgaactac   1140
gccgacacgg cgtatctggt ggcagcgcac aaccgccacg cctctgcggc caataaggcg   1200 ctgttttttac gcctgctgca cacggcaatc ccgcaggttg aatttatcaa ggactccccg  1260
gcgctgatcg tcgcccgcgt cctcagcagc ctgatcaacg agtcggtgat catggtggaa  1320
```

```
agcggcgtct gcagccggga agacatcgat gtcgccgccg tcgccggcgt taactacgcc    1380
gacggcattt tcggcttgct cgatagcctg ggggagaaaa acgtcaggac gacgctgagc    1440
aacctggcgc agctgctgca cgcggcacgc tatgcgccgc attacaccct tctacacgcc    1500
gcgcaaccgg cgctgacgac cacgccttaa                                    1530
```

<210> SEQ ID NO 174
<211> LENGTH: 1530
<212> TYPE: DNA
<213> ORGANISM: Serratia marcescens 2880STDY5682957

<400> SEQUENCE: 174

```
atggcagaaa gtaatgcggc aattcaatcg gctgcgatta tcggcgcggg aacgatgggc    60
agaggcatcg cttatctttt cgcacaaaaa ggcattcgca cggtgcttta taatcgcaac    120
ggcaataccc tcaatcaggc tcgcgaatat atcgagctag acctgaacaa gaaagtcgaa    180
cagggcaaga tcgcgctgca ggataaaggc gcggtgctgg ccaatctggt gttcacctcg    240
gcgtttgaga ccattgccga cagcgagctg gtgatagaaa ccatcgccga gcaagagcaa    300
accaaacttg aggtgctggc ggccatcgcc gcggcggtca agcccgacac gctgatcgcc    360
accaatacct cctcactgtc gcttaacaag ctggcaaccg cggtgacgca cagcgagcgg    420
tttatcggtt tgcactttt caatcccgcg ccgctgatga aactgattga atcatcccg    480 gcctacttta ccgcacgcgc caccaccgaa cgttgccgtc agctggtagc cgcgttgggg    540
aaacgcgatg tcgtctgcca ggccacgccg gggtttatcg tcaaccgcat ggcccgcccc    600
tactacctgg aagggttccg cctgttggaa gaacacgtgg cgcgcgcgcc gcagatcgac    660
cgcgccctca aggccggcgg gcactttcgc atggggccgc tcgagctgac cgattttatc    720
ggccaggaca tcaactatca ggtcagccgg caaatctggc aggacatgca atacgatccg    780
cgctataccc ccggccatct gcagcgttcg ctggtcgatg ccggtctgtt ggggaaaaag    840
aacggccgct cctattttgc cgccgaagaa acgccttac cggtaacggc cgccaccgat    900
gcagacgtcg agacgctgcg cgtttacggc gaacacccct tttttaccct gttgcaacag    960
cgggccgcgc ttcagtggcc acggctgcgc gtggagcaac ggccgccctt accgggcctg    1020
gggccggccg tccagatcaa tgaggctttc accgtcagcg tcaccgatgg ccgcacggcg    1080
agccagttgg cggagctgac ggcggcggat gcctttgtgg tcgatgtcgc cctgaactac    1140
gccgacacgg cgtatctggt ggcagcgcac aaccgccacg cctctgcggc aataaggcg    1200 ctgttttac gcctgctgca cacggcaatc ccgcaggttg aatttatcaa ggactccccg    1260
gcgctgatcg tcgcccgcgt cctcagcagc ctgatcaacg agtcggtgat catggtggaa    1320
agcggcgtct gcagccggga agacatcgat gtcgccgccg tcgccggcgt taactacgcc    1380
gacggtattt tcggctggct cgatagcctg ggggagaaaa acgtcaggac gacgctgagc    1440
aacctggcgc agctgctgca cgcggcacgc tatgcgccgc attacaccct tctacacgcc    1500
gcgcaaccgg cgctgacgac cacgccttaa                                    1530
```

<210> SEQ ID NO 175
<211> LENGTH: 1530
<212> TYPE: DNA
<213> ORGANISM: Serratia marcescens YDC563

<400> SEQUENCE: 175

```
atggcagaaa gtaatgcagc aattcagtcg gctgcgatta tcggcgcggg aacgatgggc    60
```

| | |
|---|---|
| agaggcatcg cttatctttt cgcacaaaaa ggcattcgca cggtgcttta taatcgcaac | 120 |
| ggcaataccc tcaatcaggc tcgcgaatat atcgagctag acctgaacaa gaaagtcgaa | 180 |
| cagggcaaga tcgcgctgca ggataaaggc gcggtgctgg ccaatctggt gttcacctcg | 240 |
| gcgtttgaga ccattgccga cagcgagctg gtgatagaaa ccatcgccga gcaagagcaa | 300 |
| accaaacttg aggtgctggc ggccatcgcc gcggcggtca agcccgacac gctgatcgcc | 360 |
| accaatacct cctcactgtc gcttaacaag ctggcaaccg cggtgacgca cagcgagcgg | 420 |
| tttatcggtt tgcacttttt caatcccgcg ccgctgatga aactgattga aatcatcccg | 480 |
| gcctacttta ccgcacgcgc caccaccgaa cgttgccgtc agctggtagc gcgcgttgggg | 540 |
| aaacgcgatg tcgtctgcca ggccacgccg gggtttatcg tcaaccgcat ggcccgcccc | 600 |
| tactacctgg aagggttccg cctgttggaa gaacacgtgg cgcgcgcgcc gcagatcgac | 660 |
| cgcgccctca aggccggcgg gcactttcgc atggggccgc tcgagctgac cgattttatc | 720 |
| ggccaggaca tcaactatca ggtcagccgg caaatctggc aggacatgca atacgatccg | 780 |
| cgctataccc ccggccatct gcagcgttcg ctggtcgatg ccggtctgtt ggggaaaaag | 840 |
| aacggccgct cctattttgc cgccgaagaa aacgccttac cggtaacggc cgccaccgat | 900 |
| gcagacgtcg agacgctgcg cgtttacggc gaacaccctt tttttaccct gttgcaacag | 960 |
| cgggccgcgc ttcagtggcc acggctgcgc gtggagcaac ggccggcctt accgggcctg | 1020 |
| gggccggccg tccagatcaa tgaggctttc accgtcagcg tcaccgatgg ccgcacggcg | 1080 |
| agccagttgg cggagcagac ggcggcggat gcctttgtgg tcgatgtcgc cctgaattac | 1140 |
| gccgacacgc cgtatctggt ggcagcgcac aaccgccacg cctctgcggc caataaggcg | 1200 |
| ctgtttttac gcctgctgca cacggcaatc ccgcaggttg aatttatcaa ggactccccg | 1260 |
| gcgctgatcg tcgcccgcgt cctcagcagc ctgatcaacg agtcggtgat catggtggaa | 1320 |
| agcggcgtct gcagccggga agacatcgat gtcgccgccg tcgctggcgt taactacgcc | 1380 |
| gacggcattt tcggctggct cgatagcctg ggggagaaaa acgtcaggac gacgctgagc | 1440 |
| aacatggcgc agctgctgca cgcggcacgc tatgcgccgc attacaccct tctgcacgcc | 1500 |
| gcgcaaccgg cgctgatgac cacgccttaa | 1530 |

<210> SEQ ID NO 176
<211> LENGTH: 1530
<212> TYPE: DNA
<213> ORGANISM: Serratia marcescens 2880STDY5683035

<400> SEQUENCE: 176

| | |
|---|---|
| atggcagaaa gtaatgcggc aattcaatcg gctgcgatta tcggcgcggg aacgatgggc | 60 |
| agaggcatcg cttatctttt cgcgcaaaaa ggcattcgca cggtgcttta taatcgcaac | 120 |
| ggcaataccc tcaatcaggc tcgcgaatat atcgcgcaag acctgaacaa gaaagtcgaa | 180 |
| cagggcaaga tcgcgctgca ggataaaggc gcagtgctgg ccaatctggt gttcacctcg | 240 |
| gtgtttgaga ctatcgccga cagcgatctg gtgatagaaa ccatcgccga gcaagagcaa | 300 |
| accaaacttg aggtgctggc ggccatcgcc gcggcggtca agcccgacac gctgatcgcc | 360 |
| accaatacct cctcactgtc gcttaacaag ctggcaaccg cggtgacgca cagcgagcgg | 420 |
| tttatcggtt tgcacttttt caatcccgcg ccgctgatga aactgattga aatcatcccg | 480 |
| gcctacttta ccgcacgcgc caccaccgaa cgttgccgtc agctggtggc gcgcgttgggg | 540 |
| aaacgcgatg tcgtctgcca ggccacgccg gggtttatcg tcaaccgcat ggcccgcccc | 600 |
| tactacctgg aagggttccg cctgttggaa gaacacgtgg cgcgcgcgcc gcagatcgac | 660 |

```
cgcgccctca aggccggcgg gcactttcgc atggggccgc tcgagctgac cgattttatc      720
ggccaggaca tcaactatca ggtcagccgg caaatctggc aggacatgca atacgatccg      780
cgctataccc ccggccatct gcagcgttcg ctggtcgatg ccggtctgtt ggggaaaaag      840
aacggccgct cctattttgc cgccgaagaa aacgccttac cggtaacggc cgccatcgat      900
gcagacgtcg agacgctgcg cgtttacggc gaacacccct ttttaccct gttgcaacag       960 cgggccgcgc ttcagtggcc acggctgcgc gtggagcaac ggccggcctt accgggcctg     1020
gggccggccg tccagatcaa tgaggctttc accgtcagcg tcaccgatgg ccgcacggcg     1080
agccagttgg cggagctgac ggcggcggat gtctttgtgg tcgatgtcgc cctgaactac     1140
gccgacacgg cgtatctggt ggcagcgcac aaccgccacg cctctgcggc caataaggcg     1200 ctgttttttac gcctgctgca cacggcaatc ccgcaggttg aatttatcaa ggactccccg    1260
gcgctgatcg tcgcccgcgt cctcagcagc ctgatcaacg agtcggtgat catggtggaa     1320
agcggcgtct gcagccggga agacatcgat gtcgccgccg tcgccggcgt taactacgcc     1380
gacggcattt tcggcttgct cgatagcctg ggggagaaaa acgtcaggac gacgctgagc     1440
aacctggcgc agctgctgca cgcggcacgc tatgcgccgc attacaccct tctacacgcc     1500
gcgcaaccgg cgctgacgac cacgccttaa                                     1530

<210> SEQ ID NO 177
<211> LENGTH: 1530
<212> TYPE: DNA
<213> ORGANISM: Serratia marcescens 2880STDY5682930

<400> SEQUENCE: 177
atggcagaaa gtaatgcggc aattcaatcg gctgcgatta tcggcgcggg aacgatgggc       60
agaggcatcg cttatctttt cgcgcaaaaa ggcattcgca cggtgcttta taatcgcaac      120
ggcaataccc tcaatcaggc tcgcgaatat atcgcgcaag acctgaacaa gaaagtcgaa      180
cagggcaaga tcgcgctgca ggataaaggc gcagtgctgg ccaatctggt gttcacctcg      240
gtgtttgaga ctatcgccga cagcgatctg gtgatagaaa ccatcgccga gcaagagcaa      300
accaaacttg aggtgctggc ggccatcgcc gcggcggtca gcccgacac gctgatcgcc       360 accaatacat cctcactgtc gcttaacaag ctggcaaccg cggtgacgca cagcgagcgg      420
tttatcggtt tgcactttt caatcccgcg ccgctgatga aactgattga aatcatcccg       480 gcctactta ccgcacgcgc caccaccgaa cgttgccgtc agctggtggc cgcgttgggg        540
aaacgcgatg tcgtctgcca ggccacgccg gggtttatcg tcaaccgcat ggcccgcccc      600
tactacctgg aagggttccg cctgttggaa gaacacgtgg cgcgcgcgcc gcagatcgac      660
cgcgccctca aggccggcgg gcactttcgc atggggccgc tcgagctgac cgattttatc      720
ggccaggaca tcaactatca ggtcagccgg caaatctggc aggacatgca atacgatccg      780
cgctataccc ccggccatct gcagcgttcg ctggtcgatg ccggtctgtt ggggaaaaag      840
aacggccgct cctattttgc cgccgaagaa aacgccttac cggtaacggc cgccaccgat      900
gcagacgtcg agacgctgcg cgtttacggc gaacacccct ttttaccct gttgcaacag       960 cgggccgcgc ttcagtggcc acggctgcgc gtggagcaac ggccggcctt accgggcctg     1020
gggccggccg tccagatcaa tgaggctttc accgtcagcg tcaccgatgg ccgcacggcg     1080
agccagttgg cggagctgac ggcggcggat gcctttgtgg tcgatgtcgc cctgaactac     1140
gccgacacgg cgtatctggt ggcagcgcac aaccgccacg cctctgcggc caataaggcg     1200
```

```
ctgttttac gcctgctgca cacggcaatc ccgcaggttg aatttatcaa ggactccccg    1260
gcgctgatcg tcgcccgcgt cctcagcagc ctgatcaacg agtcggtgat catggtggaa    1320
agcggcgtct gcagccggga agacatcaat gtcgccgccg tcgccggcgt taactacgcc    1380
gacggcattt tcggcttgct cgatagcctg ggggagaaaa acgtcaggac gacgctgagc    1440
aacctggcgc agctgctgca cgcggcacgc tatgcgccgc attacaccct tctacacgcc    1500
gcgcaaccgg tgctgacgac cacgccttaa                                     1530
```

<210> SEQ ID NO 178
<211> LENGTH: 1530
<212> TYPE: DNA
<213> ORGANISM: Serratia marcescens 790

<400> SEQUENCE: 178

```
atggcagaaa gtaatgcggc aattcaatcg gctgcgatta tcggcgcggg aacgatgggc      60
agaggcatcg cttatctttt cgcgcaaaaa ggcattcgca cggtgcttta taatcgcaac     120
ggcaataccc tcaatcaggc tcgcgaatat atcgcgcaag acctgaacaa gaaagtcgaa     180
cagggcaaga tcgcgctgcg ggataaaggt gcagtgctag ccaatctggt gttcacctcg     240
gtgtttgaga ctatcgccga cagcgagctg gtgatagaaa ccatcgccga gcaagagcaa     300
accaaacttg aggtgctggc ggccatcgcc gcggcggtca gcccgacac gctgatcgcc     360 accaatacct cctcactgtc gcttaacaag ctggcaaccg cggtgacgca cagcgagcgg     420
tttatcggtt tgcacttttt caatcccgcg ccgctgatga aactgattga aatcatcccg     480
gcctacttta ccgcacgcgc caccaccgaa cgttgccgtc agctggtagc gcgcgttggg     540
aaacgcgatg tcgtctgcca ggccacgccg gggtttatcg tcaaccgcat ggcccgcccc     600
tactacctgg aagggttccg cctgttggaa gaacacgtgg cgcgcgcgcc gcagatcgac     660
cgcgccctca aggccggcgg gcactttcgc atggggccgc tcgagctgac cgattttatc     720
ggccaggaca tcaactatca ggtcagccgg caaatctggc aggacatgca atacgatccg     780
cgctataccc ccggccatct gcagcgttcg ctggtcgatg ccggtctgtt ggggaaaaag     840
aacggccgct cctattttgc cgccgaagaa acgcccttac cggtaacggc cgccaccgat     900
gcagacgtcg agacgctgcg cgtttacggc gaacacccct tttttaccct gttgcaacag     960
cggggccgcg ttcagtggcc acggctgcgc gtggagcaac ggccggcctt accgggcctg    1020
gggccggccg tccagaccaa tgaggctttc accgtcagcg tcaccgatgg ccgcacggcg    1080
aaccagttgg cggagctgac ggcggcggat gcctttgtgg tcgatgtcgc cctgaactac    1140
gccgacacgg cgtatctggt ggcagcgcac aaccgccacg cctctgcggc caataaggcg    1200
ctgtttttac gcctgctgca cacggcaatc ccgcaggttg aatttatcaa ggactccccg    1260
gcgctgatcg tcgcccgcgt cctcagcagc ctgatcaacg agtcggtgat catggtggaa    1320
agcggcgtct gcagccggga agacatcgat gtcgccgccg tcgctggcgt taactacgcc    1380
gacggcattt tcggctggct cgatagcctg ggggagaaaa acgtcaggac gacgctgagc    1440
aacatggcgc agctgctgca cgcggcacgc tatgcgccgc attacaccct tctgcacgcc    1500
gcgcaaccgg cgctgatgac cacgccttaa                                     1530
```

<210> SEQ ID NO 179
<211> LENGTH: 1530
<212> TYPE: DNA
<213> ORGANISM: Serratia marcescens UMH5

<400> SEQUENCE: 179

```
atggcagaaa gtaatgcggc aattcagtcg gctgcgatta tcggcgcggg aacgatgggc    60
agaggcatcg cttatctttt cgcgcaaaaa ggcattcgca cggtgcttta taatcgcaac   120
ggcaataccc tcagtcaggc tcgcgactat atcgagctag acctgaacaa gaaagtcgaa   180
cagggcaaga tcgcgctgca ggataaaggc gcggtgttgg ccaatctggt gttcacctcg   240
gtatttgaga ccattgccga cagcgagctg gtgatagaaa ccatcgccga gcaagagcaa   300
accaaacttg aggtgctggc gaccatcgcc gctgcagtca agcccgacac gctgatcgcc   360
accaatacct cctcactgtc gctaaataag ctggcaaccg cggtgacgca cagcgagcgg   420
tttatcggtt tgcacttttt caaccccgcg ccgctgatga aactgattga aatcatcccg   480
gcctactgta ccgcacacgc caccacggag cgttgccgcc agctggtggc cgcgttgggg   540
aaacgtgacg tcgtctgcca ggccacgccg gggtttatcg tcaaccgcat ggcccgcccc   600
tactacctgg aagggttccg cctattggaa gaacacgtgg cgcgcgcgcc gcagatcgac   660
cgtgccctca aggccggtgg gcactttcgt atggggccac tcgaactgac cgattttatc   720
ggccaggaca tcaactatca ggtcagtcgg caaatctggc aggacatgca atacgacgcg   780
cgctataccc ccgccacct gcagcgttcg ctggtcgatg ccggtctatt gggaaaaaag   840
aacggccgct cctattttgc cgtcgaagaa aacgccccgc cggtgatggc cgccaccgat   900
gcagacattg agacgctgca cgtttacggc gaacaccctt tttttaccct gttacaacag   960
cgggccgcgc tcagtggcc acggctgcgc gtggaacaac ggcaggcatt accgggcctg  1020
gggccggccg tccggatcaa tgacgctttc accatcagca tcaccgatgg ccgcacggca  1080
aaccagctgg ccgagcagac ggcggcggat gcctttgtgg tcgatgttgc cctgaattac  1140
gccgacacgg cgtatctggt ggcagcgcac agccgccacg cctctgggc caataaagcg  1200
ctgttcttac gcctgctgca cacggcaatc ccgcaggttg aatttatcaa ggattccccg  1260
gccttgatcg tcgcccgcgt cctcagcagc ctaatcaacg agtcggtgat catggtggaa  1320
agcggcgtct gcagccggga agacatcgat gtcgccgccg tcgccggcgt taactacgcc  1380
gacggcattt tcggctggct cgataгcctg ggggagaaaa acgtcaggac gacgctgagc  1440
aacctggcgc agttgctgca cgcggcgcgc tatgcgccgc attacaccct tctgcacgcc  1500
gcgcaaccgg cgctgacgac cacgccttaa                                   1530
```

<210> SEQ ID NO 180
<211> LENGTH: 1530
<212> TYPE: DNA
<213> ORGANISM: Serratia marcescens 2880STDY5682988

<400> SEQUENCE: 180

```
atggcagaaa gtaatgcggc aattcagtcg gctgcgatta tcggcgcggg aacgatgggc    60
agaggcatcg cttatctttt cgcgcaaaaa ggcattcgca cggtgcttta taatcgcaac   120
ggcaataccc tcagtcaggc tcgcgactat atcgagctag acctgaacaa gaaagtcgaa   180
cagggcaaga tcgcgctgca ggataaaggc gcggtgttgg ccaatctggt gttcacctcg   240
gtatttgaga ccattgccga cagcgagctg gtgatagaaa ccatcgccga gcaagagcaa   300
accaaacttg aggtgctggc gaccatcgcc gctgcagtca agcccgacac gctgatcgcc   360
accaatacct cctcactgtc gctaaataag ctggcaaccg cggtgacgca cagcgagcgg   420
tttatcggtt tgcacttttt caaccccgcg ccgctgatga aactgattga aatcatcccg   480
gcctactgta ccgcacacgc caccacggag cgttgccgcc agctggtggc cgcgttgggg   540
```

```
aaacgtgacg tcgtctgcca ggccacgccg gggtttatcg tcaaccgcat ggcccgcccc      600
tactacctgg aagggttccg cctattggaa gaacacgtgg cgcgcgcgcc gcagatcgac      660
cgtgccctca aggccggtgg gcactttcgt atggggccac tcgaactgac cgattttatc      720
ggccaggaca tcaactatca ggtcagtcgg caaatctggc aggacatgca atacgacgcg      780
cgctataccc ccggccacct gcagcgttcg ctggtcgatg ccggtctatt gggaaaaaag      840
aacggccgct cctatttgc cgtcgaagaa aacccccgc cggtgatggc cgccaccgat       900
gcagacattg agacgctgca cgtttacggc gaacacccct tttttacccct gttacaacag      960 cggggccgcg ttcagtggcc acggctgcgc gtggaacaac ggcaggcatt accgggcctg     1020
gggccggccg tccggatcaa tgacgctttc accatcagca tcaccgatgg ccgcacggca     1080
aaccagctgg ccgagcagac ggcgacggat gcctttgtgg tcgatgttgc cctgaattac     1140
gccgacacgg cgtatctggt ggcagcgcac agccgccacg cctctggggc caataaagcg     1200
ctgttcttac gcctgctgca cacggcaatc ccgcaggttg aatttatcaa ggattccccg     1260
gccttgatcg tcgcccgcgt cctcagcagc ctaatcaacg agtcggtgat catggtggaa     1320
agcggcgtct gcagccggga agacatcgat gtcgccgccg tcgccggcgt taactacgcc     1380
gacggcattt tcggctggct cgatagcctg ggggagaaaa acgtcaggac gacgctgagc     1440
aacctggcgc agttgctgca cgcggcgcgc tatgcgccgc attacaccct tctgcacgcc     1500
gcgcaaccgg cgctgacgac cacgccttaa                                      1530

<210> SEQ ID NO 181
<211> LENGTH: 1530
<212> TYPE: DNA
<213> ORGANISM: Serratia marcescens 945154301

<400> SEQUENCE: 181
atggcagaaa gtaatgcggc aattcagtcg gctgcgatta tcggcgcggg aacgatgggc       60
agaggcatcg cttatctttt cgcgcaaaaa ggcattcgca cggtgcttta taatcgcaac      120
ggcaataccc tcaatcaggc tcgcgactat atcgagctag acctgaacaa gaaagtcgaa      180
cagggcaaga tcgcgctgca ggataaaggc gcggtgttgg ccaatctggt gttcacctcg      240
gtatttgaga ccattgccga cagcgagctg gtgatagaaa ccatcgccga gcaagagcaa      300
accaaacttg aggtgctggc ggccatagcc gcggcagtca agcccgacac gctgatcgcc      360
accaatacct cctcactgtc gctgaataag ctggcaaccg cggtgacgca cagcgagcgg      420
tttatcggtt tgcactttt taacccccgcg ccgctgatga aactgattga aatcatcccg      480
gcctacttta ccgcacacgc caccacggag cgttgccgtc aactggtggc cgcgttgggg      540
aaacgcgatg ttgtctgcca ggccacgccg gggtttatcg tcaaccgcat ggcccgcccc      600
tactacctgg aagggttccg cctattggaa gaacacgtgg cgcgcgcgcc gcagatcgac      660
cgtgccctca aggctggcgg gcactttcgt atggggccgc tcgagctgac cgattttatc      720
ggccaggaca tcaactatca ggtcagtcgg caaatctggc aggacatgca atacgacgcg      780
cgctataccc ccggccacct gcagcgttcg ctggtcgatg ccggtctatt gggaaaaaag      840
aacggccgct cctatttgc cgccgaagaa aacccccgc cggtgatggc cgccaccgat       900
gcagacattg agacgctgca cgtttacggc gaacacccct tttttacccct gttacaacaa      960 cgtgccgcgc ttcagtggcc acagctgcgc gtggaacaac ggccggcatt accgggcctg     1020
gggccggccg tccggatcaa tgacgctttc agcgtcagca tcaccgatgg ccgcacggca     1080
aaccagctgg ccgagcagac ggcggcggat gcctttgtgg tcgatgtcgc cctgaattac     1140
```

```
gccgacacgg cgtatctggt ggcagcgcac agccgccatg cctctgcagc caataaagcg    1200
ctgttcttac gcctgctgca cacggcaatc ccgcaggttg aatttatcaa ggattccccg    1260
gcgctgatcg tcgcccgcgt cctcagcagc ctaatcaacg agtcggtgat catggtggaa    1320
agcggcgtct gcagccggga agacatcgat gtcgccgccg tcgccggcgt taactacgcc    1380
gacggcattt tcggctggct agatagcctg ggggagaaaa acgtcaggac gacgctgagc    1440
aacctggcgc agctgctgca cgcagcacgc tatgcgccgc attacaccct tctgcacgcc    1500
gcgcaaccgg cgctgacgac cacgccttaa                                    1530
```

<210> SEQ ID NO 182  
<211> LENGTH: 1530  
<212> TYPE: DNA  
<213> ORGANISM: Serratia marcescens at10508

<400> SEQUENCE: 182

```
atggcagaaa gtaatgcggc aattcagtcg gctgcgatta tcggcgcggg aacgatgggc     60
agaggcatcg cttatctttt cgcgcaaaaa ggcattcgca cggtgcttta taatcgcaac    120
ggcaataccc tcaatcaggc tcgcgactat atcgagctag acctgaacaa gaaagtcgaa    180
cagggcaaga tcgcgctgca ggataaaggc gcggtgttgg ccaatctggt gttcacctcg    240
gtatttgaga ccattgccga cagcgagctg gtgatagaaa ccatcgccga gcaagagcaa    300
accaaacttg aggtgctggc ggccatcgcc gcggcagtca gcccgacac gctgatcgcc    360 accataccct cctcactgtc gctgaataag ctggcaaccg cggtgacgca cagcgagcgg    420
tttatcggtt tgcactttt taaccccgcg ccgctgatga aactgattga aatcatcccg    480 gcctactta ccgcacacgc caccacgag cgttgccgtc aactggtgac cgcgttgggg    540
aaacgcgatg ttgtctgcca ggccacgccg gggtttatcg tcaaccgcat ggcccgcccc    600
tactacctgg aagggttccg cctattggaa gaacacgtgg cgcgcgcgcc gcagatcgac    660
cgtgccctca aggccggcgg gcactttcgt atggggccgc tcgagctgac cgatttttatc    720 ggccaggaca tcaactatca ggtcagtcgg caaatctggc aggacatgca atacgacgcg    780
cgctataccc ccggccacct gcagcgttcg ctggtcgatg ccggtctatt gggaaaaaag    840
aacggccgct cctatttgc cgtcgaagaa aacgccccgc cggtgatggc cgccaccgat    900
gcagacattg agacgctgca cgtttacggc gaacacccctt ttttaccct gttacaacaa    960 cgtgccgcgc ttcagtggcc acagctgcgc gtggaacaac ggccggcatt accgggcctg   1020
gggccggccg tccggatcaa tgacgctttc accgtcagca tcaccgatgg ccgcacggca   1080
aaccagctgg ccgagcagac ggcggcggat gcctttgtgg tcgatgtcgc cctgaattac   1140
gccgacacgg cgtatctggt ggcagcgcac agccgccatg cctctgcagc caataaagcg   1200
ctgttcttac gcctgctgca cacggcaatc ccgcaggttg aatttatcaa ggattccccg   1260
gcgctgatcg tcgcccgcgt cctcagcagc ctaatcaacg agtcggtgat catggtggaa   1320
agcggcgtct gcagccggga agacatcgat gtcgccgccg tcgccggcgt taactacgcc   1380
gacggcattt tcggctggct agatagcctg ggggagaaaa acgtcaggac gacgctgagc   1440
aacctggcgc agctgctgca cgcagcacgc tatgcgccgc attacaccct tctgcacgcc   1500
gcgcaaccgg cgctgacgac cacgccttaa                                   1530
```

<210> SEQ ID NO 183  
<211> LENGTH: 1530  
<212> TYPE: DNA

<213> ORGANISM: Serratia marcescens ML2637

<400> SEQUENCE: 183

| | | | | | |
|---|---|---|---|---|---|
| atggcagaaa | gtaatgcggc | aattcagtcg | gctgcgatta | tcggcgcggg | aacgatgggc | 60 |
| agaggcatcg | cttatctttt | cgcgcaaaaa | ggcattcgca | cggtgcttta | taatcgcaac | 120 |
| ggcaataccc | tcaatcaggc | tcgcgactat | atcgagctag | acctgaacaa | gaaagtcgaa | 180 |
| cagggcaaga | tcgcgctgca | ggataaaggc | gcggtgttgg | ccaatctggt | gttcacctcg | 240 |
| gtatttgaga | ccattgccga | cagcgagctg | gtgatagaaa | ccatcgccga | gcaagagcaa | 300 |
| accaaacttg | aggtgctggc | ggccatcgcc | gcggcagtca | agcccgacac | gctgatcgcc | 360 |
| accaatacct | cctcactgtc | gctgaataag | ctggcaaccg | cggtgacgca | cagcgagcgg | 420 |
| tttatcggtt | tgcacttttt | taaccccgcg | ccgctgatga | aactgattga | aatcatcccg | 480 |
| gcctacttta | ccgcacacgc | caccacggag | cgttgccgtc | aactggtgac | cgcgttgggg | 540 |
| aaacgcgatg | ttgtctgcca | ggccacgccg | gggtttatcg | tcaaccgcat | ggcccgcccc | 600 |
| tactacctgg | aagggttccg | cctattggaa | gaacacgtgg | cgcgcgcgcc | gcagatcgac | 660 |
| cgtgccctca | aggccggcgg | gcactttcgt | atggggccgc | tcgagctgac | cgattttatc | 720 |
| ggccaggaca | tcaactatca | ggtcagtcgg | caaatctggc | aggacatgca | atacgacgcg | 780 |
| cgctataccc | ccggccacct | acagcgttcg | ctggtcgatg | ccggtctatt | gggaaaaaag | 840 |
| aacgccgct | cctattttgc | cgtcgaagaa | acgcccccgc | cggtgatggc | cgccaccgat | 900 |
| gcagacattg | agacgctgca | cgtttacggc | gaacaccctt | tttttaccct | gttacaacaa | 960 |
| cgtgccgcgc | ttcagtggcc | acagctgcgc | gtggaacaac | ggccggcatt | accgggcctg | 1020 |
| gggccggccg | tccggatcaa | tgacgctttc | accgtcagca | tcaccgatgg | ccgcacggca | 1080 |
| aaccagctgg | ccgagcagac | ggcggcggat | gcctttgtgg | tcgatgtcgc | cctgaattac | 1140 |
| gccgacacgg | cgtatctggt | ggcagcgcac | agccgccacg | cctctgcagc | caataaagcg | 1200 |
| ctgttcttac | gcctgctgca | cacggcaatc | ccgcaggttg | aatttatcaa | ggattccccg | 1260 |
| gcgctgatcg | tcgcccgcgt | cctcagcagc | ctaatcaacg | agtcggtgat | catggtggaa | 1320 |
| agcggcgtct | gcagccggga | agacatcgat | gtcgccgccg | tcgccggcgt | taactacgcc | 1380 |
| gacggcattt | tcggctggct | agatagcctg | ggggagaaaa | acgtcaggac | gacgctgagc | 1440 |
| aacctggcgc | agctgctgca | cgcagcacgc | tatgcgccgc | attacaccct | tctgcacgcc | 1500 |
| gtgcaaccgg | cgctgacgac | cacgccttaa | | | | 1530 |

<210> SEQ ID NO 184
<211> LENGTH: 1530
<212> TYPE: DNA
<213> ORGANISM: Serratia marcescens SM1978

<400> SEQUENCE: 184

| | | | | | |
|---|---|---|---|---|---|
| atggcagaaa | gtaatgcggc | aattcagtcg | gctgcgatta | tcggcgcggg | aacgatgggc | 60 |
| agaggcatcg | cttatctttt | cgcgcaaaaa | ggcattcgca | cggtgcttta | taatcgcaac | 120 |
| ggcaataccc | tcaatcaggc | tcgcgactat | atcgagctag | acctgaacaa | gaaagtcgaa | 180 |
| cagggcaaga | tcgcgctgca | ggataaaggc | gcggtgttgg | ccaatctggt | gttcacctcg | 240 |
| gtatttgaga | ccattgccga | cagcgagctg | gtgatagaaa | ccatcgccga | gcaagagcaa | 300 |
| accaaacttg | aggtgctggc | ggccatagcc | gcggcagtca | agcccgacac | gctgatcgcc | 360 |
| accaatacct | cctcactgtc | gctgaataag | ctggcaaccg | cggtgacgca | cagcgagcgg | 420 |
| tttatcggtt | tgcacttttt | taaccccgcg | ccgctgatga | aactgattga | aatcatcccg | 480 |

| | |
|---|---|
| gcctacttta ccgcacacgc caccacggag cgttgccgtc aactggtgac cgcgttgggg | 540 |
| aaacgcgatg ttgtctgcca ggccacgccg gggtttatcg tcaaccgcat ggcccgcccc | 600 |
| tactacctgg aagggttccg cctattggaa gaacacgtgg cgcgcgcgcc gcagatcgac | 660 |
| cgtgccctca aggccggcgg gcactttcgt atggggccgc tcgagctgac cgattttatc | 720 |
| ggccaggaca tcaactatca ggtcagtcgg caaatctggc aggacatgca atacgacgcg | 780 |
| cgctataccc ccgccacct gcagcgttcg ctggtcgatg ccggtctatt gggaaaaaag | 840 |
| aacggccgct cctatttgc cgccgaagaa aacgccccgc cggtgatggc ctccaccgat | 900 |
| gcagacattg agacgctgca cgtttacggc gaacacccctt tttttacccct gttacaacaa | 960 |
| cgtgccgcgc ttcagtggcc acagctgcgc gtggaacaac ggccggcatt accgggcctg | 1020 |
| gggccggccg tccggatcaa tgacgctttc agcgtcagca tcaccgatgg ccgcacggca | 1080 |
| aaccagctgg ccgagcagac gacggcggat gcctttgtgg tcgatgtcgc cctgaattac | 1140 |
| gccgacacgg cgtatctggt ggcagcgcac agccgccacg cctctgcagc caataaagcg | 1200 |
| ctgttcttac gcctgctgca cacggcaatc ccgcaggttg aatttatcaa ggattccccg | 1260 |
| gcgctgatcg tcgcccgcgt cctcagcagc ctaatcaacg agtcggtgat catggtggaa | 1320 |
| agcggcgtct gcagccggga agacatcgat gtcgccgccg tcgccggcgt taactacgcc | 1380 |
| gacggcattt tcggctggct agatagcctg ggggagaaaa acgtcaggac gacgctgagc | 1440 |
| aacctggcgc agctgctgca cgcagcacgc tatgcgccgc attacaccct tctgcacgcc | 1500 |
| gcgcaaccgg cgctgacgac cacgcccttaa | 1530 |

<210> SEQ ID NO 185
<211> LENGTH: 1530
<212> TYPE: DNA
<213> ORGANISM: Serratia marcescens PWN146

<400> SEQUENCE: 185

| | |
|---|---|
| atggcagaaa gtaatgcggc aattcagtcg gctgcgatta tcggcgcggg aacgatgggc | 60 |
| agaggcatcg cttatctttt cgcgcaaaaa ggcattcgca cggtgcttta taatcgcaac | 120 |
| ggcaatacccc tcaatcaggc tcgcgactat atcgagctag acctgaacaa gaaagtcgaa | 180 |
| cagggcaaga tcgcgctaca ggataaaggc gcggtgttgg ccaatctggt gttcacctcg | 240 |
| gtatttgaga ccattgccga cagcgagctg gtgatagaaa ccatcgccga gcaagagcaa | 300 |
| accaaacttg aggtgctggc gaccatcgcc gcggcagtca agcccgacac gctgatcgcc | 360 |
| accaatacct cctcactgtc gctaaataag ctggcaaccg cggtgacgca cagcgagcgg | 420 |
| tttatcggtt tgcacttttt taaccccgcg ccgctgatga aactgattga aatcatcccg | 480 |
| gcctacttta ccgcacacgc caccacggag cgttgccgtc aactggtggc cgcgttggga | 540 |
| aaacgcgacg ttgtctgcca ggccacgccg gggtttatcg tcaaccgcat ggcccgcccc | 600 |
| tactacctgg aagggttccg cctattggaa gaacacgtgg cgcgcgcgcc gcagatcgac | 660 |
| cgtgccctca aggccggcgg gcactttcgt atggggccgc tcgaactgac cgattttatc | 720 |
| ggccaggaca tcaactatca ggtcagccgg caaatctggc aggacatgca atacgacgcg | 780 |
| cgctataccc ccgccacct gcagcgttcg ctggtcgatg ccggtctatt gggaaaaaag | 840 |
| aacggccgct cctatttgc cgtcgaagaa aacgccccgc cggtgatggc cgccaccgat | 900 |
| gcagacattg agacgctgca cgtctgcggc gaacacccctt tttttactct gttgcaacag | 960 |
| cgagccgcac ttcagtggcc acggctgcgc gtggaacaac ggccggcctt gccgggcctg | 1020 |

-continued

```
gggcccgccg tctggatcaa tgacgctttc accgtcagca tcaccgatgg ccgcacggca    1080
aaccagctgg ccgagcagac ggcggcggat gcctttgtgg tcgatgtcgc cctgaattac    1140
gccgacacgg cgtatctggt ggcagcacac agccgccacg cctctgcggc caataaagcg    1200
ctgttcttac gcctgctgca caccgcaatc ccgcaggttg aatttatcaa ggattccccg    1260
gcgctgatcg tcgctcgcgt cctcagcagc ctgatcaatg agtcggtgat catggtggaa    1320
agcggcgtct gcagccggga agacatcgat gtcgccgccg tcgccggcgt taactacgcc    1380
gacggcattt tcggctggct cgatagcctg ggggagaaaa acgtcagggc gacgctgagc    1440
aacttggcgc agctgctgca cgcggcgcgc tatgcgccgc attacaccct tctgcacgcc    1500
gcgcaaccgg cgctgacgac cacgccttaa                                    1530
```

<210> SEQ ID NO 186
<211> LENGTH: 1530
<212> TYPE: DNA
<213> ORGANISM: Serratia marcescens H1q

<400> SEQUENCE: 186

```
atggcagaac gtaatgcggc aattcaatcg gctgcgatta tcggcgcggg aacgatgggc     60
agaggcatcg cttatctttt cgcgcaaaaa ggcattcgta cggtgcttta taatcgcaac    120
ggcaataccc tcattcaggc tcgtgaatat atcgtgcaag acctggacaa aaaggtcgaa    180
cagggcaggc tcgcgccgca ggataaagac gcggtgctgg ccaatctgca gttctcatcg    240
gtgtttgaag ctatcgtcga cagcgatttg gtgctcgaaa ctatcgccga gcaagagcaa    300
gccaaactcg aggtgctggc cgccatcgct gcggcggtca aacccgacac gctgatcgcc    360
accaatacgt cctcattgtc gctcaataag ctggcaacgg cggtgaccca cagcgaacgc    420
tttatcggtt tgcactttt caaccccgca ccgctaatga agctgattga aatcattccg    480
gcctacttta ccgcccaagc caccactgaa acttgccgcc aactggtggc ggcattgggg    540
aaacgcgatg tcgtctgcca ggctacgccg gggttcatcg tcaaccgtat ggcccgcccc    600
tactacctgg aaggctttcg cctgttggaa gagcacgtgg cgcgcgcgcc gcagatcgac    660
cgcgccctca aggccggcgg acactttcgc atggggccgc tcgagctgac cgattttatc    720
ggccaggaca tcaactatca ggtcagccgg caaatttggc aggacatgca gtacgacccg    780
cgctataccc ccggccatct gcagcgttcg ctggtcgatg ccgggctgct ggggaaaaag    840
aacggtcgct cctattttc cgccgaagaa accgccccgc cggttgaggc cgccgtcgag    900
gcggatgtcg agacgctgcg catttacggc gaacacccct tgtttaccct gctgcaacag    960
cgagccgcac tgcaatggcc gcagttgcgc gtggaacagc ggccggcctt gtcgggcctg   1020
ggagcggcca ttcaggtcaa tgacgctttc accgtcagca tcaccgatgg ccgcacggca   1080
aatcagttgg ccgagcagac ggcggcggac gcctttgtgg tcgatgtcgc cctgaactac   1140
gccgacacgg cgtatctggt ggcggcgcac agccgccacg cctctgcggc taataaggcg   1200
ttgtttttgc gcctgctgca caccgcgctt ccgcaggttg aatttatcaa ggactccccg   1260
gcgctgatcg tcgcccgcgt cctcagcagc ctgatcaacg agtcggtgat catggtggaa   1320
agcggcgtct gcagccggga agacatcgat gtcgccgccg tcgccggcgt gaactacgcc   1380
gacggcattt tcggctggct cactcgcctg ggggagaaaa acgtcaggac gacgctgagc   1440
aacctggcgc agctgctgca cgcggccgc tatgcgccgc attacaccct tctgcacgcc   1500
gcccaaccgg cgctgaccac cacgccttaa                                    1530
```

<210> SEQ ID NO 187
<211> LENGTH: 1530
<212> TYPE: DNA
<213> ORGANISM: Serratia marcescens UMH6

<400> SEQUENCE: 187

```
atggcagaaa gtaatgcggc aattcaatcg gctgcgatta tcggcgcggg aacgatgggc      60
agaggcatcg cttatctttt tgcgcaaaaa agcattcgta cggtgcttta taatcgcaac     120
ggcaataccc tcaatcaagc tcgcgacgct atcgtgcaag acctgaacaa aaaggtggaa     180
cagggcaagc tcgcgctgca ggacaaagac gcggtgctgg ctaatctgac gttctccgcg     240
gaatttgggg ccatcgccga cagcgatctg gtgatcgaaa ccatcgcaga gcatgagcaa     300
gccaaactcg aagtgctggc ggccatcgcc gcgacggtca gcccgacac  gctgatcgcc     360
accaataccct cctcactgtc gcttaataag ctggcgacag cggtgacgca cagcgaacgc     420
tttatcggtt tgcactttt  caaccccgcg ccgctgatga agctgattga aatcattccg     480
gcctatttta ccgcacaggt caccaccgaa cgttgccgtc aactggtggc ggcgttgggg     540
aaacgcgatg tcgtctgcca ggccacgccg ggatttatcg tcaaccgtat ggcccgcccc     600
tactatctgg aagggttccg cctgttggaa gaacacgtgg cgcgtgcgcc gcagatcgac     660
cgcgccctca agccggcgg  acactttcgc atggggccgc tcgagctgac cgattttatc     720
ggtcaggaca tcaactatca ggtcagccgg caaatttggc aggacatgca gtacgatccg     780
cgctataccc cgggccatct gcagcgctcg ctggtcgatg ccggtctgtt gggcaaaaag     840
aacggccgct cctatttctc cgccgaagaa tctcccccgc cgcttgcggc cgccgtcgat     900
gcggaggtcg agacgctacg catttacggt gaacatcctc tctttaccct gctacagcag     960
cgggccgccc tgcaatggcc gcggctgcgc gttgaacaac ggccgacatt accgggcctg    1020
ggcgccgcca ttcaggtcaa tgacgctttc accgtcagcg ttaccgatgg ccgcacggca    1080
aaccagcttg ccgaacagac cgcggcggac gcctttgtcg tcgatgttgc cctgaactac    1140
ggcgatacgg cgtacctggt ggcggcacat agccgccacg cctctgcggc caataaggcg    1200
ctgtttttac gcctgctgca caccgcgatc ccgcaggtgg aatttatcaa ggattccccg    1260
gccctgatcg tcgcccgcgt gctcagcagc ctgatcaacg agtcggtgat catggtggaa    1320
agcggcgtct gcagccggga agacattgat gtcgccgccg tcgccggcgt gaactacgcc    1380
gacggtattt tcggctggct cactcgcctc ggggaggaaa atgtcaggac gacgctgagc    1440
aacctggcgc aattgctgca cgcggcgcgc tatgcgccgc attacaccct tctgcacgcc    1500
gcccaaccgg cgctgaccac cacgccttaa                                     1530
```

<210> SEQ ID NO 188
<211> LENGTH: 1530
<212> TYPE: DNA
<213> ORGANISM: Serratia nematodiphila WCU338

<400> SEQUENCE: 188

```
atggcagaaa gtaatgcggc aattcaatcg gctgcgatta tcggcgcggg aacgatgggc      60
agaggcatcg cttatctttt cgcgcaaaaa agcattcgta cggtgcttta taatcgcaac     120
ggcaataccc tcaatcaagc tcgcgacgct atcgtgcaag acctgaacaa aaaggtggaa     180
cagggcaagc tcgcgctgca ggataaagac gcggtgctgg ctaatctgac gttctccgcg     240
gaatttgggg ccatcgccga cagcgatctg gtgatcgaaa ccatcgcaga acatgagcaa     300
gccaaactcg aggtgctggc ggccatcgcc gcgacggtca gcccgacac  gctgatcgcc     360
```

```
accaataccct cctcactgtc gctgaataag ctggcgacgg cggtgacgca cagcgaacgc    420
tttatcggtt tgcactttt  caacccccgcg ccgctgatga agctgattga aatcattccg    480
gcctatttta ccgcacagat caccaccgaa cgttgccgtc aactggtggc ggcattgggg    540
aaacgcgatg tcgtctgtca ggccacgccg gggtttatcg tcaaccgtat ggctcgcccc    600
tactatctgg aaggattccg cctgttggaa gaacacgtgg cgcgtgcgcc gcagatcgac    660
cgcgccctca aagccggcgg acactttcgc atggggccgc tcgagctgac cgattttatc    720
ggtcaggaca tcaactatca ggtcagccgg caaatttggc aggacatgca gtacgatccg    780
cgctataccc cgggccatct gcagcgctcg ctggtcgatg ccggtttgct ggggaaaaag    840
aacggccgct cctatttttc cgccgaagaa tctcccccgc cgcttgcagc cgccgtcgat    900
gcggaggtcg agacgctacg catttacggt gaacatcctc tctttacccct gctacagcag   960 cgggccgccc tgcaatggcc gcggctgcgc gtggaacagc ggccgacatt accaggcctg   1020
ggcgccgcca ttcaggtcaa tgacgctttc accgtcagcg ttaccgatgg ccgcacggca   1080
aaccagcttg ccgaacagac cgcggcggac gcctttgtcg tcgatgtcgc cctgaactac   1140
ggcgatacgg cgtacctggt ggcggcgcat agccgccacg catctgcggc caataaggcg   1200 ctgttttttac gcctgctgca caccgcgatc ccgcaggtgg aatttatcaa ggattccccg   1260
gccttgatcg tcgcccgcgt gctcagcagc ctgatcaacg agtcggtgat catggtggaa   1320
agcggcgtct gcagccggga agacattgat gtcgccgccg tcgccggcgt gaactacgcc   1380 gacggtatt  tcggctggct cactcgcctc ggggaggaaa atgtcaggac gacgctgagc   1440
aacctggcgc aattgctgca cgcggcgcgc tatgcgccgc attacaccct tctgcacgcc   1500
gcccaaccgg cgctgaccac cacgccttaa                                    1530
```

<210> SEQ ID NO 189
<211> LENGTH: 1530
<212> TYPE: DNA
<213> ORGANISM: Serratia sp. OLEL1

<400> SEQUENCE: 189

```
atggcagaaa gtaatgcggc aattcaatcg gctgcgatta tcggcgcggg aacgatgggc     60
agaggcatcg cttatctttt ggcgcaaaaa agcattcgta cggtgcttta taatcgcaac    120
ggcaataccc tcaatcaagc tcgcgacgct atcgtgcaag acctgaacaa aaaggtggaa    180
cagggcaagc tcgcgctgca ggacaaagac gcggtgctgg ctaatctgac gttctccgcg    240
gaatttgggg ccatcgccga cagcgatctg gtgatcgaaa ccatcgcaga gcatgagcaa    300
gccaaactcg aagtgctggc ggccatcgcc gcgacggtca agcccgacac gctgatcgcc    360 accaataccct cctcactgtc gcttaataag ctggcgacgg cggtgacgca cagcgaacgc    420
tttatcggtt tgcactttt  caacccccgcg ccgctgatga agctgattga aatcattccg    480
gcctatttta ccgcacaggt caccaccgaa cgttgccgtc aactggtggc ggcgttgggg    540
aaacgcgatg tcgtctgcca ggccacgccg ggatttatcg tcaaccgtat ggcccgcccc    600
tactatctgg aagggttccg cctgttggaa gaacacgtgg cgcgtgcgcc gcagatcgac    660
cgcgccctca aagccggcgg acactttcgc atggggccgc tcgagctgac cgattttatc    720
ggtcaggaca tcaactatca ggtcagccgg caaatttggc aggacatgca gtacgatccg    780
cgctataccc cgggccatct gcagcgctcg ctggtcgatg ccggtctgtt gggcaaaaag    840
aacggccgct cctatttctc cgccgaagaa tctcccccgc cgcttgcggc cgccgtcgat    900
gcggaggtcg agacgctacg catttacggt gaacatcctc tctttacccct gctacagcag   960
```

```
cgggccgccc tgcaatggcc gcggctgcgc gtggaacaac ggccgacatt accgggcctg   1020
ggcgccgcca ttcaggttaa tgacgctttc accgtcagcg ttaccgatgg ccgcacggca   1080
aaccagcttg ccgaacagac tgcggcggac gcctttgtcg tcgatgtcgc cctgaactac   1140
ggcgatacgg cgtacctggt ggcggcgcat agccgccacg cctctgcggc caataaggcg   1200 ctgttttac gcctgctgca caccgcgatc ccgcaggtgg aatttatcaa ggattccccg   1260
gccttgatcg tcgcccgcgt gctcagcagc ctgatcaacg agtcggtgat catggtggaa   1320
agcggcgtct gcagccggga agacattgat gtcgccgccg tcgccggcgt gaactacgcc   1380
gacggcattt tcggctggct cactcgcctc ggggaggaaa atgtcaggac gacgctgagc   1440
aacctggcgc aattgctgca cgcggcgcgc tatgcgccgc attacaccct tctgcacgcc   1500
gcccaaccgg cgctgaccac cacgccttaa                                   1530

<210> SEQ ID NO 190
<211> LENGTH: 1530
<212> TYPE: DNA
<213> ORGANISM: Serratia marcescens 7209

<400> SEQUENCE: 190
atggcagaaa gtaatgcggc aattcaatcg gctgcgatta tcggcgcggg aacgatgggc    60
agaggcatcg cttatctttt tgcgcaaaaa agcattcgta cggtgcttta taatcgcaac   120
ggcaataccc tcaatcaagc tcgcgacgct atcgtgcaag acctgaacaa aaaggtggaa   180
cagggcaagc tcgcgctgca ggacaaagac gcggtgctgg ctaatctgac gttctccgca   240
gaatttgggg tcatcgccga cagcgatctg gtgatcgaaa ccatcgcaga acatgagcaa   300
gccaaactcg aggtgctggc ggccatcgcc gcgacggtca agcccgacac gctgatcgcc   360
accaatacct cctcactgtc gcttaataag ctggcgacgg cggtgacgca cagcgaacgc   420
tttatcggtt tgcacttttt caaccccgcg ccgctgatga agctgattga aatcattccg   480
gcctatttta ccgcacaggt caccaccgaa cgttgccgtc aactggtggc ggcgttaggg   540
aaacgcgatg tcgtctgtca ggccacgccg ggatttatcg tcaaccgtat ggcccgcccc   600
tactatctgg aagggttccg cctgttggaa gaacacgtgg cgcgtgcgcc gcagatcgac   660
cgcgccctca aagccggcgg acactttcgc atggggccgc tcgagctgac cgattttatc   720
ggtcaggaca tcaactatca ggtcagccgg caaatttggc aggacatgca gtacgatccg   780
cgctataccc cgggccatct gcagcgctcg ctggtcgatg ccggtctgtt gggcaaaaag   840 aacgccgct cctattttc cgccgaagaa tctccccgc cgcttgcggc cgccgtcgat   900
gcggaagtcg agacgctacg catttacggt gaacatcctc tctttaccct gctacagcag   960
cgggccgccc tgcaatggcc gcggctgcgc gtggaacaac ggccgacatt accgggcctg   1020
ggcgccgcca ttcaggtcaa tgacgctttc accgtcagcg ttaccgatgg ccgcacggca   1080
aaccagcttg ccgaacagac cgcggcggac gcctttgtcg tcgatgtcgc cctgaactac   1140
ggcgatacgg cgtacctggt ggcggcacat agccgccatg cctctgcggc caataaggcg   1200 ctgttttac gcctgctgca caccgcgatc ccgcaggtgg aatttatcaa ggattccccg   1260
gccttgatcg tcgcccgcgt gctcagcagc ctgatcaacg agtcggttat catggtggaa   1320
agcggcgtct gcagccggga agacattgat gtcgccgccg tcgccggcgt gaactacgcc   1380
gacggtattt tcggctggct cactcgcctc ggggaggaaa atgtcaggac gacgctgagc   1440
aacctggcgc aattgctgca cgcggcgcgc tatgcgccgc attacaccct tctgcacgcc   1500
```

```
gcccaaccgg cgctgaccac cacgccttaa                                      1530
```

<210> SEQ ID NO 191
<211> LENGTH: 1530
<212> TYPE: DNA
<213> ORGANISM: Serratia marcescens sicaria (Ss1)

<400> SEQUENCE: 191

```
atggcagaaa gtaatgcggc aattcaatcg gctgcgatta tcggcgcggg aacgatgggc      60
agaggcatcg cttatctttt tgcgcaaaaa agcattcgta cggtgcttta taatcgcaac     120
ggcaataccc tcaatcaagc tcgcgacgct atcgtgcaag acctgaacaa aaaggtggaa     180
cagggcaagc tcgcgctgca ggacaaagac gcggtgctgg ctaatctgac gttctccgcg     240
gaatttgggg ccatcgccga cagcgatctg gtgatcgaaa ccatcgcaga gcatgagcaa     300
gccaaactcg aggtgctggc ggccatcgcc gcgacggtca gcccgacac gctgatcgcc      360
accaatacct cctcactgtc gcttaataag ctggcgacgg cggtgacgca cagcgaacgc     420
tttatcggtt tgcacttttt caaccccgcg ccgctgatga gctgattga aatcattccg      480
gcctatttta ccgcacaggt caccaccgaa cgttgccgtc aactggtggc ggcgttgggg     540
aaacgcgatg tcgtctgcca ggccacgccg ggatttatcg tcaaccgtat ggcccgcccc     600
tactatctgg aagggttccg cctgttggaa gaacacgtgg cgcgtgcgcc gcagatcgac     660
cgcgccctca agccggcgg acactttcgc atggggccgc tcgagctgac cgattttatc      720
ggtcaggaca tcaactatca ggtcagccgg caaatttggc aggacatgca gtacgatccg     780
cgctataccc cgggccatct gcagcgctcg ctggtcgatg ccggtctgtt gggcaaaaag     840
aacggccgct cctattttc caccgaagaa tctcccccgc gcttgcggc cgccgtcgat       900
gcggaggtcg agacgctacg catttacggt gaacatcctc tctttaccct gctacagcag     960
cgggccgccc tgcaatggcc gcggctgcgc gtggaacaac ggccgacatt accgggcttg    1020
ggcgccgcca ttcaggtcaa tgacgctttc accgtcagcg ttaccgatgg ccgcacggca    1080
aaccagcttg ccgaacagac cgcggcggac gcctttgtcg tcgatgtcgc cctgaactac    1140
ggcgatacgg cctacctggt ggcggcgcat agccgccacg cctctgcggc caataaggcg    1200
ctgttttttac gcctgctgca caccgcgatc ccgcaggtgg aatttatcaa ggattccccg    1260
gccttgatcg tcgcccgcgt gctcagcagc ctgattaacg agtcggtgat catggtggaa    1320
agcggcgtct gtagccggga agacattgat gtcgccgccg tcgccggcgt gaactacgcc    1380
gacggtattt tcggctggct cactcgcctc ggggaggaaa atgtcaggac gacgctgagc    1440
aacctggcgc aattgctgca gcgggcgcgc tatgcgccgc attacaccct tctgcacgcc    1500
gcccaaccgg cgctgaccac cacgccttaa                                    1530
```

<210> SEQ ID NO 192
<211> LENGTH: 1530
<212> TYPE: DNA
<213> ORGANISM: Serratia sp. OLFL2

<400> SEQUENCE: 192

```
atggcagaaa gtaatgcggc aattcaatcg gctgcgatta tcggcgcggg aacgatgggc      60
agaggcatcg cttatctttt ggcgcaaaaa agcattcgta cggtgcttta taatcgcaac     120
ggcaataccc tcaatcaagc tcgcgacgct atcgtgcaag acctgaacaa aaaggtggaa     180
cagggcaagc tcgcgctgca ggacaaagac gcggtgctgg ctaatctgac gttctccgcg     240
gaatttgggg ccatcgccga cagcgatctg gtgatcgaaa ccatcgcaga gcatgagcaa     300
```

```
gccaaactcg acgtgctggc ggccatcgcc gcgacggtca agcccgacac gctgatcgcc    360
accaatacct cctcactgtc gcttaataag ctggcgacgg cggtgacgca cagcgaacgc    420
tttatcggtt tgcactttt caaccccgcg ccgctgatga agctgattga aatcattccg     480
gcctatttta ccgcacaggt caccaccgaa cgttgccgtc aactggtggc ggcgttgggg    540
aaacgcgatg tcgtctgcca ggccacgccg ggatttatcg tcaaccgtat ggcccgcccc   600
tactatctgg aagggttccg cctgttggaa gaacacgtgg cgcgtgcgcc gcagatcgac    660
cgcgccctca agccggcgg acactttcgc atggggccgc tcgagctgac cgattttatc    720
ggtcaggaca tcaactatca ggtcagccgg caaatttggc aggacatgca gtacgatccg    780
cgctataccc cgggccatct gcagcgctcg ctggtcgatg ccggtctgtt gggcaaaaag    840 aacgccgct cctatttctc cgccgaagaa tctcccccgc cgcttgcggc cgccgtcgat    900
gcggaggtcg agacgctacg catttacggt gaacatcctc tctttaccct gctacagcag   960
cgggccgccc tgcaatggcc gcggctgcgc gtggaacaac ggccgacatt accgggcctg   1020
ggcgccgcca ttcaggttaa tgacgctttc accgtcagcg ttaccgatgg ccgcacggca   1080
aaccagcttg ccgaacagac tgcggcggac gcctttgtcg tcgatgtcgc cctgaactac   1140
ggcgatacgg cgtacctggt ggcggcgcat agccgccacg cctctgcggc caataaggcg   1200 ctgttttac gcctgctgca caccgcgatc ccgcaggtgg aatttatcaa ggattccccg     1260
gccttgatcg tcgcccgcgt gctcagcagc ctgatcaacg agtcggtgat catggtggaa   1320
agcggcgtct gcagccggga agacattgat gtcgccgccg tcgccggcgt gaactacgcc   1380
gacggcattt tcggctggct cactcgcctc ggggaggaaa atgtcaggac gacgctgagc   1440
aacctggcgc aattgctgca cgcggcgcgc tatgcgccgc attacaccct tctgcacgcc   1500
gcccaaccgg cgctgaccac cacgccttaa                                     1530

<210> SEQ ID NO 193
<211> LENGTH: 1530
<212> TYPE: DNA
<213> ORGANISM: Serratia marcescens BIDMC 81

<400> SEQUENCE: 193
atggcagaaa gtaatgcggc aattcaatcg gctgcgatta tcggcgcggg aacgatgggc    60
agaggcatcg cttatctttt ggcgcaaaaa agcattcgta cggtgcttta taatcgcaac   120
ggcaataccc tcaatcaagc tcgcgacgct atcgtgcaag acctgaacaa aaaggtggaa   180
cagggcaagc tcgcgctgca ggacaaagac gcggtgctgg ctaatctgac gttctccgcg   240
gaatttggag ccatcgccga cagcgatctg gtgatcgaaa ccatcgcaga gcatgagcaa   300
gccaaactcg aggtgctggc ggccatcgcc gcgacggtca agcccgacac gctgatcgcc   360
accaatacct cctcactgtc gcttaataag ctggcgacgg cggtaacgca cagcgaacgc   420
tttatcggtt tgcactttt caaccccgcg ccgctgatga agctgattga aatcattccg    480
gcctatttta ccgcacaggt caccaccgaa cgttgccgtc aactggtggc ggcgttgggg    540
aaacgcgatg tcgtctgcca ggccacgccg ggatttatcg tcaaccgtat ggcccgcccc    600
tactatctgg aagggttccg cctgttggaa gaacacgtgg cgcgtgcgcc gcagatcgac    660
cgagccctca agccggcgg acactttcgc atggggccgc tcgagctgac cgattttatc     720
ggtcaggaca tcaactatca ggtcagccgg caaatttggc aggacatgca gtacgatccg    780
cgctataccc cgggccatct gcagcgctcg ctggtcgatg ccggtctgtt gggcaaaaag    840
```

```
aacggccgct cctattttc cgccgaagaa tctccccgc cgcttgcggc cgccgtcgat      900
gcggaggtcg agacgctacg catttacggt gaacatcctc tctttaccct gctacagcag     960
cgggccgccc tgcaatggcc gcggctgcgc gtggaacaac ggccgacatt accggacctg    1020
ggcgccgcca ttcaggtcaa tgacgctttc accgtcagcg ttaccgatgg ccgcacggca    1080
aaccagcttg ccgaacagac cgcggcggac gcctttgtcg tcgatgtcgc cctgaactac    1140
ggcgatacgg cgtacctggt ggcggcgcat agccgccacg cctctgcggc caataaggcg    1200
ctgtttttac gcctgctgca caccgcgatc ccgcaggtgg aatttatcaa ggattccccg    1260
gccttgatcg tcgcccgcgt gctcagcagc ctgatcaacg agtcggtgat catggtggaa    1320
agcggcgtct gcagccggga agacattgat gtcgccgccg tcgccggcgt gaactacgcc    1380
gacggtattt tcggctggct cactcgcctc ggggaggaaa atgtcaggac gacgctgagc    1440
aacctggcgc aattgctgca cgcggcgcgc tatgcgccgc attacaccct tctgcacgcc    1500
gcccaaccgg cgctgaccac cacgcccttaa                                    1530

<210> SEQ ID NO 194
<211> LENGTH: 1530
<212> TYPE: DNA
<213> ORGANISM: Serratia marcescens BIDMC 50

<400> SEQUENCE: 194
atggcagaaa gtaatgcggc aattcaatcg gctgcgatta tcggcgcggg aacgatgggc      60
agaggcatcg cttatctttt tgcgcaaaaa agcattcgta cggtgcttta taatcgcaac     120
ggcaataccc tcaatcaagc tcgcgacgct atcgtgcaag acctgaacaa aaaggtggaa     180
cagggcaagc tcgcgctgca ggacaaagac gtggtgctgg ctaatctgac gttctccgcg     240
gaatttgggg ccatcgccga cagcgatctg gtgatcgaaa ccatcgcaga gcatgagcaa     300
gccaaactcg aggtgctggc ggccatcgcc gcgacggtca agcccgacac gctgatcgcc     360 accaataccct cctcactgtc gcttaataag ctggcgacgg cggtgacgca cagcgaacgc     420
tttatcggtt tgcacttttt caaccccgcg ccgctgatga agctgattga aatcattccg     480
gcctatttta ccgcacaggt caccaccgaa cgttgccgtc aactggtggc ggcgttaggg     540
aaacgcgatg tcgtctgtca ggccacgccg ggatttatcg tcaaccgtat ggcccgcccc     600
tactatctgg aagggttccg cctgttggaa gaacacgtgg cgcgtgcgcc gcagatcgac     660
cgcgccctca aagccggcgg acactttcgc atggggccgc tcgagctgac cgatttatc    720 ggtcaggaca tcaactatca ggtcagccgg caaatttggc aggacatgca gtacgatccg    780
cgctataccc cgggccatct gcagcgctcg ctggtcgatg ccggtctgtt gggcaaaaag    840
aacggccgct cctattttc cgccgaagaa tctccccgc cgcttgcggc cgccgtcgat      900
gcggaggtcg agacgctacg catttacggt gaacatcctc tctttaccct gctacagcag     960
cgggccgccc tgcaatggcc gcggctgcgc gtggaacaac ggccgacatt accggacctg    1020
ggcgccgcca ttcaggtcaa tgacgctttc accgtcagcg ttaccgatgg ccgcacggca    1080
aaccagcttg ccgaacagac cgcggcggac gcctttgtcg tcgatgtcgc cctgaactac    1140
ggcgatacgg cgtacctggt ggcggcacat agccgccatg cctctgcggc caataaggcg    1200
ctgtttttac gcctgctgca caccgcgatc ccgcaggtgg aatttatcaa ggattccccg    1260
gccttgatcg tcgcccgcgt gctcagcagc ctgatcaacg agtcggtgat catggtggaa    1320
agcggcgtct gcagccggga agacattgat gtcgccgccg tcgccggcgt gaactacgcc    1380
gacggtattt tcggctggct cactcgcctc ggggaggaaa atgtcaggac gacgctgagc    1440
```

| | | |
|---|---|---|
| aacctggcgc aattgctgca cgcggcgcgc tatgcgccgc attacaccct tctgcacgcc | | 1500 |
| gcccaaccgg cgctgaccac cacgccttaa | | 1530 |

<210> SEQ ID NO 195
<211> LENGTH: 1530
<212> TYPE: DNA
<213> ORGANISM: Serratia marcescens UMH7

<400> SEQUENCE: 195

| | | |
|---|---|---|
| atggcagaaa gtaatgcggc aattcaatcg gctgcgatta tcggcgcggg aacgatgggc | | 60 |
| agaggcatcg cttatctttt ggcgcaaaaa agcattcgta cggtgcttta taatcgcaac | | 120 |
| ggcaataccc tcaatcaagc tcgcgacgct atcgtgcaag acctgaacaa aaaggtggaa | | 180 |
| cagggcaagc tcgcgctgca ggacaaagac acggtgctgg ctaatctgac gttctccgcg | | 240 |
| gaatttgggg ccatcgccga cagcgatctg gtgatcgaaa ccatcgcaga gcatgagcaa | | 300 |
| gccaaactcg aggtgctggc ggccatcgcc gcgacggtca gcccgacac gctgatcgcc | | 360 |
| accaatacct cctcactgtc gcttaataag ctggcgacgg cggtgacgca cagcgaacgc | | 420 |
| tttatcggtt tgcactttt caaccccgcg ccgctgatga gctgattga aatcattccg | | 480 |
| gcctatttta ccgcacaggt caccaccgaa cgttgccgtc aactggtggc ggcgttgggg | | 540 |
| aaacgcgatg tcgtctgtca ggccacgccg ggatttatcg tcaaccgtat ggcccgcccc | | 600 |
| tactatctgg aagggttccg cctgttggaa gaacacgtgg cgcgtgcgcc gcagatcgac | | 660 |
| cgcgccctca aagccggcgg acactttcgc atggggccgc tcgaactgac cgattttatc | | 720 |
| ggtcaggaca tcaactatca ggtcagccgg caaatttggc aggacatgca gtacgatccg | | 780 |
| cgctataccc cgggccatct gcagcgctcg ctggtcgatg ccggtctgtt ggcaaaaaag | | 840 |
| aacggccgct cctatttttc cgccgaagaa tctcctccgc cgcttgcggc cgccgtcgat | | 900 |
| gcggaggtcg agacgctacg catttacggt gaacatcctc tctttactct gctacagcag | | 960 |
| cgggccaccc tgcaatggcc gcggctgcgc gtggaacaac ggccgacatt accgggcctg | | 1020 |
| ggcgccgcca ttcaggttaa tgacgctttc accgtcagcg ttaccgatgg ccgcacggca | | 1080 |
| aaccagcttg ccgaacagac cgcggcggac gcctttgtcg tcgatgtcgc cctgaactac | | 1140 |
| ggcgatacgg cgtacctggt ggcggcgcat agccgccacg cctctgcagc caataaggcg | | 1200 |
| ctgttttac gcctgctgca caccgcgatc ccgcaggtgg aatttatcaa ggattccccg | | 1260 |
| gccttgatcg tcgcccgcgt gctcagcagc ctgatcaacg agtcggtgat catggtggaa | | 1320 |
| agcggcgtct gcagccggga agacattgat gtcgccgccg tcgccggcgt gaactacgcc | | 1380 |
| gacggtattt tcggctggct cactcgcctc ggggaggaaa atgtcaggac gacgctgagc | | 1440 |
| aacctggcgc aattgctgca cgcggcgcgc tatgcgccgc attacaccct tctgcacgcc | | 1500 |
| gcccaaccgg cgctgaccac cacgccttaa | | 1530 |

<210> SEQ ID NO 196
<211> LENGTH: 1530
<212> TYPE: DNA
<213> ORGANISM: Serratia marcescens RSC-14

<400> SEQUENCE: 196

| | | |
|---|---|---|
| atggcagaaa gtaatgcggc aattcaatcg gctgcgatta tcggcgcggg aacgatgggc | | 60 |
| agaggcatcg cttatctttt ggcgcaaaaa agcattcgta cggtgcttta taatcgcaac | | 120 |
| ggcaataccc tcaatcaagc tcgcgacgct atcgtgcaag acctgaacaa aaaggtggaa | | 180 |

```
caggcaagc tcgcgctgca ggacaaagac gcggtgctgg ctaatctgac gttctccacg    240
gaatttgggg ccatcgccga cagcgatctg gtgatcgaaa ccatcgcaga gcatgagcaa    300
gccaaactcg aagtgctggc ggccatcgcc gcgacggtca agcccgacag gctgatcgcc    360
accaatacct cctcactgtc gcttaataag ctggcgacgg cggtgacgca cagcgaacgc    420
tttatcggtt tgcactttt caaccccgcg ccgctgatga agctgattga aatcattccg    480
gcctatttta ccgcacaggt caccaccgaa cgttgccgtc aactggtggc ggcgttaggg    540
aaacgcgatg tcgtctgtca ggccacgccg ggatttatcg tcaaccgtat ggcccgcccc    600
tactatctgg aagggttccg cctgttggaa gaacacgtgg cgcgtgcgcc gcagatcgac    660
cgcgccctca agccggcgg acactttcgc atggggccgc tcgagctgac cgattttatc    720
ggtcaggaca tcaactatca ggtcagccgg caaatttggc aggacatgca gtacgatccg    780
cgctataccc cgggccatct gcagcgctcg ctggtcgatg ccggtctgtt gggcaaaaag    840
aacggccgct cctatttttc cgccgaagaa tctccccccgc cgcttgcggc cgccgtcgat    900
gcggaagtcg agacgctacg catttacggt gaacatcctc tctttaccct gctacagcag    960
cgggccgccc tgcaatggcc gcggctgcgc gtggaacaac agccgacatt accgggcctg   1020
ggcgccgcca ttcaggtcaa tgacgctttc accgtcagcg ttaccgatgg ccgcacggca   1080
aaccagcttg ccgaacagac cgcggcggac gcctttgtcg tcgatgtcgc cctgaactac   1140
ggcgatacgg cgtacctggt ggcggcacat agccgccatg cctctgcggc caataaggcg   1200
ctgtttttac gcctgctgca caccgcgatc ccgcaggtgg aatttatcaa ggattccccg   1260
gccttgatcg tcgcccgcgt gctcagcagc ctgatcaacg agtcggtgat catggtggaa   1320
agcggcgtct gcagccggga agacattgat gtcgccgccg tcgccggcgt gaactacgcc   1380
gacggtattt tcggctggct cactcgcctc ggggaggaaa atgtcaggac gacgctgagc   1440
aacctggcgc aattgctgca cgcggcgcgc tatgcgccgc attacaccct tctgcacgcc   1500
gcccaaccgg cgctgaccac cacgccttaa                                    1530
```

<210> SEQ ID NO 197
<211> LENGTH: 1530
<212> TYPE: DNA
<213> ORGANISM: Serratia marcescens SM03

<400> SEQUENCE: 197

```
atggcagaac gtaatgcggc aattcaatcg gctgcgatta tcggcgcggg aacgatgggc     60
agaggcatcg cttatctttt cgcgcaaaaa ggcattcgta cggtgcttta taatcgcaac    120
ggcaatacc tcattcaggc tcgtgaatat atcgtgcaag acctggacaa aaaggtcgaa    180
cagggcaggc tcgcgccgca ggataaagac gcggtgctgg ccaatctgca gttctcatcg    240
gtgtttgaag ctatcgtcga cagcgatttg gtgctcgaaa ctatcgccga gcaagagcaa    300
gccaaactcg aggtgctggc cgccatcgct gcggcggtca acccgacac gctgatcgcc    360
accaatacgt cctcattgtc gctcaataag ctggcaacgg cggtgaccca cagcgaacgc    420
tttatcggtt tgcactttt caaccccgca ccgctaatga agctgattga aatcattccg    480
gcctacttta ccgcccaagc caccactgaa acttgccgcc aactggtggc ggcattgggg    540
aaacgcgatg tcgtctgcca ggctacgccg gggttcatcg tcaaccgtat ggcccgcccc    600
tactacctgg aaggctttcg cctgttggaa gagcacgtgg cgcgcgcgcc gcagatcgac    660
cgcgccctca aggccggcgg acactttcgc atggggccgc tcgagctgac cgattttatc    720
ggccaggaca tcaactatca ggtcagccgg caaatttggc aggacatgca gtacgacccg    780
```

```
cgctataccc ccggccatct gcagcgttcg ctggtcgatg ccgggctgct ggggaaaaag    840
aacggtcgct cctattttc cgccgaagaa accgccccgc cggttgaggc cgccgccgag    900
gcggatgtcg agacgctgcg catttacggc gaacacccctt tgtttaccct gctgcaacag    960
cgagccgcac tgcaatggcc gcagttgcgc gtggaacagc ggccggcctt gtcgggcctg   1020
ggagcggcca ttcaggtcaa tgacgctttc accgtcagcg tcaccgatgg ccgcacggca   1080
aatcagttgg ccgagcagac ggcggcggac gcctttgtgg tcgatgtcgc cctgaactac   1140
gccgacacgg cgtatctggt ggcggcgcac agccgccacg cctctgcggc taataaggcg   1200 ttgttttttgc gcctgctgca caccgcgctt ccgcaggttg aatttatcaa ggactccccg   1260
gcgctgatcg tcgcccgcgt cctcagcagc ctgatcaacg agtcggtgat catggtggaa   1320
agcggcgtct gcagccggga agacatcgat gtcgccgccg tcgccggcgt gaactacgcc   1380
gacggcattt tcggctggct cactcgcctg ggggagaaaa acgtcaggac gacgctgagc   1440
aacctggcgc agctgctgca cgcggcccgc tatgcgccgc attacacccct tctgcacgcc   1500 gcccaaccgg cgctgaccac cacgccttaa                                    1530

<210> SEQ ID NO 198
<211> LENGTH: 1530
<212> TYPE: DNA
<213> ORGANISM: Serratia marcescens 90-166

<400> SEQUENCE: 198
atggcagaaa gtaatgcggc aattcaatcg gctgcaatta tcggcgcggg aacgatgggc     60
agaggcatcg cttatctttt cgcgcaaaaa ggcattcgta cggtgctta taatcgcaac    120 ggcaataccc tcattcaggc tcgtgaatat atcgtgcaag acctggacaa aaagatcgaa    180
cagggcaggg tcgcgccgca ggataaagac gcggtgctgg ctaatctgac gttctccgcg    240
gaatttgggg ccatcgtcga cagcgatctg gtgatcgaaa ccattgcaga gcatgagcaa    300
gccaaactcg aggtgctggc ggccatcgcc gcgacggtca agcccgacac gctgatcgcc    360
accaatacct cctcactgtc gctgaataag ctggcgacgg cggtgacgca cagcgaacgc    420
tttatcggtt tgcactttt caaccccgcg ccgctgatga gctgattga aatcattccg    480 gcctattta ccgcacaggt caccaccgaa cgttgccgtc aactggtggc ggcattgggg    540
aaacgcgatg tcgtctgtca ggccacgccg gggtttatcg tcaaccgtat ggctcgcccc    600
tactatctgg aagggttccg cctgttggaa gaacacgtgg cacgtgcgcc gcagatcgac    660 cgcgcccctca aagccggcgg acactttcgc atggggccgc tcgagctgac cgatttttatc    720 ggtcaggaca tcaactatca ggtcagccgg caaatttggc aggacatgca gtacgatccg    780 cgctatacccc cgggccatct gcagcgctcg ctggtcgatg ccggtctgtt gggcaaaaag    840
aacggccgct cctatttttc cgccgaagaa tctcccccgc cgcttgcagc cgccgtcgat    900
gcggagatcg agacgctgcg catttacggt gaacatcctc tctttacccct gctacagcag    960 cgggccgccc tgcaatggcc gcggctgcgc gtggaacacc ggccgacatt accgggcctg   1020
ggcgccgcca ttcaggtcaa tgatgctttc accgtcagcg ttaccgatgg tcgcacggca   1080
aaccagcttg ccgaacagac cgcggcggac gcctttgtcg tcgatgtcgc cctgaactac   1140
ggcgatacgg cgtacctggc ggcggcgcat agccgccacg cctctgcggc caataaggcg   1200 ctgttttttac gcctgctgca caccgcgatc ccccaggtgg aatttatcaa ggattccccg   1260
gccttgatcg tcgcccgcgt gctcagcagc ctgatcaacg agtcggtgat catggtggaa   1320
```

| | |
|---|---|
| agcggcgtct gcagccggga agacattgat gtcgccgccg tcgccggcgt gaactacgcc | 1380 |
| gacggtattt tcgtctggct cactcgcctc ggggaggaaa atgtcaggac gacgctgagc | 1440 |
| aacctggcgc aattgctgca cgcggcgcgc tatgcaccgc attacaccct tctgcacgcc | 1500 |
| gcccaaccgg cgctgacctc cacgccttaa | 1530 |

<210> SEQ ID NO 199
<211> LENGTH: 1530
<212> TYPE: DNA
<213> ORGANISM: Serratia marcescens UMH2

<400> SEQUENCE: 199

| | |
|---|---|
| atggcagaaa gtaatgcggc aattcaatcg gctgcgatta tcggcgcggg aacgatgggc | 60 |
| agaggcatcg cttatctttt ggcgcaaaaa agcattcgta cggtgcttta taatcgcaac | 120 |
| ggcaataccc tcaatcaagc tcgcgacgct atcgtgcaag atctgaacaa aaaggtggaa | 180 |
| cagggcaagc tcgcgctgca ggacaaagac gcggtgctgg ctaatctgac gttctccacg | 240 |
| gaatttgggg ccatcgccga cagcgatctg gtgatcgaaa ccatcgcaga gcatgagcaa | 300 |
| gccaaactcg aagtgctggc ggccatcgcc gcgacggtca agcccgacac gctgatcgcc | 360 |
| accaatacct cctcactgtc gcttaataag ctggcgacgg cggtgacgca cagcgaacgc | 420 |
| tttatcggtt tgcacttttt caaccccgcg ccgctgatga agctgattga aatcattccg | 480 |
| gcctatttta ccgcacaggt caccaccgaa cgttgccgtc aactggtggc ggcgttgggg | 540 |
| aaacgcgatg tcgtctgtca ggccacgccg ggatttatcg tcaaccgtat ggcccgcccc | 600 |
| tactatctgg aagggttccg cctgttggaa gaacacgtgg cgcgtgcgcc gcagatcgac | 660 |
| cgcgccctca agccggcgg acactttcgc atggggccgc tcgagctgac cgattttatc | 720 |
| ggtcaggaca tcaactatca ggtcagccgg caaatttggc aggacatgca gtacgatccg | 780 |
| cgctatacccc cgggccatct gcagcgctcg ctggtcgatg ccggtctgtt gggcaaaaag | 840 |
| aacgccgct cctattttttc cgccgaagaa tctccccccgc gcttgcggc cgccgtcgat | 900 |
| gcggaggtcg aggcgctacg catttacggt gaacatcctc tctttaccct gctacagcag | 960 |
| cgggccgccc tgcaatggcc gcggctgcgc gtggaacaac ggccgacatt accgggcttg | 1020 |
| ggcgccgcca ttcaggtcaa tgacgctttc accgtcagcg ttaccgatgg ccgcacggca | 1080 |
| aaccagcttg ccgaacagac cgcggcggac gcctttgtcg tcgatgtcgc cctgaactac | 1140 |
| ggcgatacgg cgtacctggt ggcggcgcat agccgccacg cctctgcggc caataaggcg | 1200 |
| ctgttttttac gcctgctgca caccgcgatc ccgcaggtgg aatttatcaa ggattccccg | 1260 |
| gccctgatcg tcgcccgcgt gctcagcagc ctgatcaacg agtcggtgat catggtggaa | 1320 |
| agcggcgtct gcagccggga agacattgat gtcgccgccg tcgccggcgt gaactacgcc | 1380 |
| gacggtattt tcggctggct cactcacctc ggggaggaaa atgtcaggac gacgctgagc | 1440 |
| aacctggcgc aattactcca cgcggcgcgc tatgcgccgc attacaccct tctgcacgcc | 1500 |
| gcccaaccgg cgctgaccac cacgccttaa | 1530 |

<210> SEQ ID NO 200
<211> LENGTH: 1530
<212> TYPE: DNA
<213> ORGANISM: Serratia plymuthica AS9

<400> SEQUENCE: 200

| | |
|---|---|
| atggcagaga ataattcggc aatccgttca gccgccgtta ttggtgcggg aaccatgggc | 60 |
| agaggcatcg cctatctcct ggcgctgaac ggcatacgaa ccgtacttta taatcgcaat | 120 |

```
ggtaataatc tcaatcaggc ccgtgactat attgtcagtg acctggacag aaaaatggat    180
aacggaaaaa taaccctgca gaaaaaaggc cagatattag ccaatattat tttctcggcc    240
gtctttgacg ccataaccga cagcgatctg gtgattgaaa ccattgcgga agatgagcaa    300
accaagcatg aaatcctggc agccattgcg gctacggtaa aaccagaggc gatcattgcg    360
accaataccT cctcgttgtc gctgaacaaa ctggcggcgg gggtggaaaa caatccgcgc    420
tttatcggcc tgcattttt  caatccggcg ccgctgatga agttgatcga aatcattccc    480
tcttatttta cctcccacac caccagccta cgctgccagc agttggtaat agcgttgggt    540
aaacagtttg tggtctgcaa agccacgccg ggctttattg ttaatcgcat ggcgcgacct    600
ttctatctgg aagggttccg gctgctggag gaaaacgtgg cacaggctcc acagatcgac    660
cgcgccctca aggcaggcgg gcattttcgc atggggccct tagaactgac tgatttatt    720 ggccaggata tcaactatca ggtcagcaag cagatttggc aggatatgca gttcgactcc    780
cgctatacCC ccggccattt gcaacgctcg ctggtggatg ccgggctgct ggggaggaag    840
aacgggcgct cttttttgc  ttccctaccg gctacaccgc ccaccccggc cacagagagc    900
gacacaccaa cttcactgca tttttatggt gaacacgctt tattcgatca cctgcaacag    960
cgcgctttgg ccacctggcc tgcgctgcgc gttcagcggt tgccggaacg gccggaactg   1020
gggcgtctta tcctggtgaa taacacgctg gcgatcaaaa tcaccgatgg cagaacggcg   1080
aacctgctcg ccggcttaac cgctctcgac accttcgtga ttgacgctgc gctgaattac   1140
gccgacaccg cctatctggt ggccgcccac aatcagcatg ccacagaggc gaataaagcg   1200
ctgtttctgt cgctgctgca aaccgtcatc gctcaggtag agtttattaa agattcccct   1260
gccctgatcg ttgcccgcgt actgagcagc ctgatcaacg aatcggtgat catggtggag   1320
agcggcgttt gcagccgggc ggatatcgat atcgccgccg tggccggcgt gaactatgcc   1380
gacggcattt ttgcctggct ggcgcagctc gggcagaaaa acgtgaagtc gacgctggat   1440
aacatggcgc aattgctgca ctccgcgcgc tattacccgc attactcatt gctgaacgcg   1500
gcccggcctg agctggctgt agcgccctaa                                    1530
```

<210> SEQ ID NO 201
<211> LENGTH: 1530
<212> TYPE: DNA
<213> ORGANISM: Serratia plymuthica tumat 205

<400> SEQUENCE: 201

```
atggcagaga ataattcggc aatccgttca gccgccgtta ttggtgcggg gactatgggc     60
agaggcatcg cctacctctt ggcactgaac ggcatacgaa ccgtacttta taatcgcaat    120
ggtaataatc tcaatcaggc ccgtgactat attgtcagcg acctggacag aaaaatagat    180
aacggaaaaa taaccctgca gaaaaaaggc cagatattag ccaatattat tttctcggcc    240
gtctttgacg ccataaccga cagcgatctg gtgattgaaa ccattgcgga agatgagcaa    300
accaagcatg aaatcctggc agccattgcg gctacggtaa aaccggaggc gatcattgcg    360
accaataccT cctcgttgtc gctgaacaaa ctggcggcag gggtggaaaa caacccgcgc    420
tttatcggcc tgcattttt  caatccggcg ccgctgatga agttgatcga aatcattccc    480
tcttatttta cctcccacgc caccagccta cgctgccagc agttggtaat agcattgggt    540
aaacagtttg tggtctgcaa agccacaccg ggctttattg ttaatcgcat ggcgcggcct    600
ttctatctgg aagggttccg gctgctggag gaaaacgtgg cgctggcgcc acagatcgac    660
```

```
cgcgccctca aggccggcgg gcattttcgc atggggcctt tagaactgac ggattttatc    720
ggtcaggata tcaactacca ggtcagcaag cagatttggc aggatatgca gttcgaccct    780
cgctataccc ctggtcattt gcaacgctcg ctggtggatg ccgggctgct ggggaggaaa    840
aacgggcgct ctttttttgc ttcccaaccg gtgacgccac ccaccccgac cacagagagc    900
gacacgccaa cttcactgca tttttatggg gagcatgctt tattcgatca tctgcaacag    960
cgtgctctgg ccacctggcc tgcgctgcgc gttcagcggt tgccgaacg gcctgaactg     1020 ggcgattta tcctggtgaa taacgcgatg gcgatcaaaa tcaccgatgg cagaacggca      1080
aacctgctcg ccggcttaac cgctctcgac accttcgtga ttgacgctgc gctgaattac     1140
gccgacaccg cctatctggt ggccgcccac aatcaacatg ccacagagac gaataaagcg     1200
ctgtttctga cgctgctgca aaccgtcatc gctcaggtgg agtttattaa agattcccct     1260
gctctgatcg ttgcccgcgt actgagcagc ctgatcaatg aatcggtgat catggtggag     1320
agcggcgttt gcagcgggc agatatcgat atcgccgccg tggccggcgt gaactatgcc      1380
gacggcattt ttgcctggtt ggcgcagctc ggcagaaaa acgtgaaatc gacgctggat     1440
aacatggcgc aactgctgca ctccgcgcgc tattacccgc attactcatt gctgaacgcg    1500
gcccggcctg agctggccgt agcgccctaa                                     1530
```

<210> SEQ ID NO 202
<211> LENGTH: 1530
<212> TYPE: DNA
<213> ORGANISM: Serratia plymuthica A30

<400> SEQUENCE: 202

```
atggcagaga ataattcggc aatccgttca gccgccgtta ttggtgcggg gaccatgggc     60
agaggcatcg cctacctcct ggcactgaac ggcatacgaa ccgtacttta taatcgcaat    120
ggtaataatc tcaatcaggc ccgtgactat attgtcagcg acctggacag aaaaatagat    180
aacggaaaaa taaccctgca gaaaaaaggc cagatattag ccaatattat tttctcggcc    240
gtctttgacg ccataaccga cagcgatctg gtgattgaaa ccattgcgga agatgagcaa    300
accaagcatg aaatcctggc agccattgcg gctacggtaa aaccggaggc gatcattgcg    360
accaatacct cctcgttgtc gctgaacaaa ctggcggcag gggtggaaaa caacccgcgc    420
tttatcggcc tgcattttt caatccggcg ccactgatga agttgatcga atcattccc     480 tcttatttta cctcccacgc caccagccta cgctgccaga agttggtaat agcattgggt    540
aaacagtttg tggtctgcaa agccacgccg ggctttattg ttaatcgcat ggcgcggcct    600
ttctatctgg aagggttccg gctgctggag agaaacgtgg cgctggcgcc acagatcgac    660
cgcgccctca aggccggcgg gcattttcgc atggggcctt tagaactgac ggattttatc    720
ggccaggata tcaactacca ggtcagcaag cagatttggc aggatatgca gttcgaccct    780
cgctataccc ctggtcattt gcaacgctcg ctggtggatg ccgggctgct ggggaggaaa    840
aacgggcgct ctttttttgc ttcccaaccg gcgacgccgc caacccgac cactgagggc     900 gacacgccaa cttcactgca tttttatggt gaacacgctt tattcgatca cctgcaacag    960
cgcgctttgg ccacctggcc tgcgttgcgc gttcagcggt tgccggaacg gccggaactg    1020
ggcgttttta tcctgatgaa taacaggctg gcgatcaaaa tcactgatgg cagaacggcg    1080
aacctgctcg ccggcttaac cgctctcgac accttcgtga ttgacgccgc gctgaactac    1140
gccgacaccg cctatctggt ggccgcccac aatcaacatg ccacagagac gaataaagcg    1200
ctgtttctga cgctgctgca aaccctcatc gctcaggtgg agtttattaa agattcccct    1260
```

```
gccctgatcg ttgcccgcgt actgagcagc ctgatcaatg aatcggtgat catggtggag    1320
agcggcgttt gcagccgggc agatatcgat atcgccgccg tggccggcgt gaactatgcc    1380
gacggtattt ttgcctggtt ggcgcagctc gggcagaaaa acgtgaaatc gacgctggat    1440
aacatggcgc aactgctgca ctccgcgcgc tattacccgc attactcatt gctgaacgcg    1500
gcccggcctg agctggccgt agcgccctaa                                    1530
```

<210> SEQ ID NO 203
<211> LENGTH: 1530
<212> TYPE: DNA
<213> ORGANISM: Serratia plymuthica 4Rx13

<400> SEQUENCE: 203

```
atggcagaga ataattcggc aatccgttca gccgccgtta ttggtgcggg gaccatgggc      60
agaggcatcg cctacctcct ggcgctgaac ggcatacgaa ccgtacttta taatcgcaat     120
ggtaatagtc tcaatcaggc ccgtgactat attgtcagcg acctggacag aaaaatagat     180
aacggaaaaa taaccctgca gaaaaaggc cagatattag ccaatattat tttctcggcc     240
gtctttgacg ccataaccga cagcgatctg gtgattgaaa ccattgcgga agatgagcaa     300
accaagcatg aaatcctggc agccattgcg gctacggtaa aaccggaggc gatcattgcg     360
accaatacct cctcgttgtc gctgaacaaa ctggcggcag gggtggaaaa caacccgcgc     420
tttatcggcc tgcatttttt caatccggcg ccgctgatga agttgatcga aatcattccc     480
tcttatttta cctcccacgc caccagccta cgctgccaga agttggtaat agcattgggt     540
aaacagtttg tggtctgcaa agccacgccg ggctttattg ttaatcgcat ggcgcggcct     600
ttctatctgg aagggttccg gctgctggag gagaacgtgg cgctggcgcc acagatcgac     660
cgcgccctca aggccggcgg gcattttcgc atggggcctt tagaactgac ggatttatc     720 ggtcaggata tcaactacca ggtcagcaag cagatttggc aggatatgca gttcgaccct     780
cgctataccc ccggccactt gcaacgctcg ctggtggatg ccgggctgct ggggaggaaa     840 acgggcgtt cttttttgc ttcccaaccg gcgacgccac ccaccccgac cacagagagc     900
gacacgccaa cttcactgca ttttatggt gagcacgctt tattcgatca tctgcaacag     960
cgcgctctgg ccacctggcc tgcgctgagc gttcagcggt tgccggaacg gcctgaactg    1020
gggcgattta tcctggtgaa taacgcgctg gcgatcaaaa tcaccgatgg cagaacggca    1080
aacctgctcg ccggcttaac cgctctcgac accttcgtga ttgacgctgc gctgaattac    1140
gccgacaccg cctatctggt ggccgcccac aatcaacatg ccacagagac gaataaagcg    1200
ctgtttctga cgctgctgca aaccgtcatc gctcaggtgg agtttattaa agattcccct    1260
gccctgatcg ttgcccgcgt actgagcagc ctgatcaatg aatcggtgat catggtggag    1320
agcggcgttt gcagccgggc agatatcgat atcgccgccg tggccggcgt gaactatgcc    1380
gacggcattt ttgcctggtt ggcgcagctc gggcagaaaa acgtgaaatc gacgctggat    1440
aacatggcgc aactgctgca ttccgcgcgc tattacccgc attactcatt gctgaacgcg    1500
gcccggcctg agctggccgt agcgccctaa                                    1530
```

<210> SEQ ID NO 204
<211> LENGTH: 1530
<212> TYPE: DNA
<213> ORGANISM: Serratia plymuthica V4

<400> SEQUENCE: 204

| | |
|---|---:|
| atggcagaga ataattcggc aatccgttca gccgccgtta ttggtgcggg gaccatgggc | 60 |
| agaggcatcg cctacctcct ggcactgaac ggcatacgaa ccgtacttta taatcgcaat | 120 |
| ggtaataatc tcaatcaggc ccgtgactat attgtcagcg acctggacag aaaaatagat | 180 |
| aacggaaaaa taaccettca gaaaaaaggc cagatattag ccaatattat tttctcggcc | 240 |
| gtctttgacg ccataaccga cagcgatctg gtgattgaaa ccattgcgga agatgagcaa | 300 |
| accaagcatg aaatcctggc agccattgcg gctacggtaa aaccggaggc gatcattgcg | 360 |
| accaatacct cctcgttgtc gctgaacaaa ctggcggcag gggtggaaaa caacccgcgc | 420 |
| tttatcggcc tgcattttt caatccggcg ccgctgatga agttgatcga aatcattccc | 480 |
| tcttatttta cctcccacgc caccagccta cgctgccaga agttggtaat agcattgggt | 540 |
| aaacagtttg tggtctgcaa agccacgccg ggctttattg ttaatcgcat ggcgcggcct | 600 |
| ttctatctgg aagggttccg gctgctggag gaaaacgtgg cgctggcgcc acagatcgac | 660 |
| cgcgccctca aggccggcgg gcattttcgc atgggcccett tagaactgac ggatttatc | 720 |
| ggccaggata tcaactacca ggtcagcaag cagatttggc aggatatgca gttcgaccct | 780 |
| cgctataccc ctggtcattt gcaacgctcg ctggtggatg ccgggctgct ggggaggaaa | 840 |
| aacgggcgct ctttttttgc ttcccaaccg gcgacgccac ccaccccgac cacagagagc | 900 |
| gacacgccaa cttcactgca tttttatggt gaacacgctt tattcgatca cctgcaacag | 960 |
| cgcgctttgg ccacctggcc tgcgttcgcc gttcagcggt tgccggaacg gccggaactg | 1020 |
| gggcgtttta tcctggtgaa taacaggctg gcgatcaaaa tcaccgatgg cagaacggca | 1080 |
| aacctgctcg ccggcttaac cgctctcgac accttcgtga ttgacgctgc gctgaattac | 1140 |
| gccgacaccg cctatctggt ggccgcccac aatcaacatg ccacagagac gaataaagcg | 1200 |
| ctgtttctga cgctgctgca aaccgtcatc gctcaggtgg agtttattaa agattccect | 1260 |
| gccctgatcg ttgcccgcgt actgagcagc ctgatcaatg aatcggtgat catggtggag | 1320 |
| agcggcgttt gcagccgggc agatatcgat atcgccgccg tggccggcgt gaactatgcc | 1380 |
| gacggtattt ttgcctggtt ggcgcagctc gggcagaaaa acgtgaaatc gacgctggat | 1440 |
| aacatggcgc aactgctgca ctccgcgcgc tattacccgc attactcatt gctgaacgcg | 1500 |
| gcccggcctg agctggccgt agcgccctaa | 1530 |

<210> SEQ ID NO 205
<211> LENGTH: 1530
<212> TYPE: DNA
<213> ORGANISM: Serratia plymuthica 3Rp8

<400> SEQUENCE: 205

| | |
|---|---:|
| atggcagaga ataattcggc aatccgttca gccgccgtta ttggtgcggg gaccatgggc | 60 |
| agaggcatcg cctacctcct ggcactgaac ggcatacgaa ccgtacttta taatcgcaat | 120 |
| ggtaataatc tcaatcaggc ccgtgactat attgtcagcg acctggacag aaaaatagat | 180 |
| aacggaaaaa taaccctgca gaaaaaaggc cagatattag ccaatattat tttctcggcc | 240 |
| gtctttgacg ccataaccga cagcgatctg gtgattgaaa ccattgcgga agatgagcaa | 300 |
| accaagcatg aaatcctggc agccattgcg gctacggtaa aaccggaggc gatcattgcg | 360 |
| accaatacct cctcgttgtc gctgaacaaa ctggcggcag gggtggaaaa caacccgcgc | 420 |
| tttatcggcc tgcattttt caatccggcg ccgctgatga agttgatcga aatcattccc | 480 |
| tcttatttta cctcccacgc caccagccta cgctgccaga agttggtaat agcattgggt | 540 |
| aaacagtttg tggtctgcaa agccacgccg ggctttattg ttaatcgcat ggcgcggcct | 600 |

-continued

```
ttctatctgg aagggttccg gctgctggag gagaacgtgg cgctggcgcc acagatcgac      660
cgcgccctca aggccggcgg gcattttcgc atggggcctt tagaactgac ggattttatc      720
ggccaggata tcaactacca ggtcagcaag cagatttggc aggatatgca gttcgaccct      780 cgctatacccc ctggtcattt gcaacgctcg ctggtggatg ccgggctgct ggggaggaaa     840
aacgggcgct ctttttttgc ttcccaaccg gcgacgccac ccaccccgac cacagagagc     900
gacacgccaa cgtcactgca tttttatggt gaacacgctt tattcgatca cctgcaacag     960
cgcgctttgg ccacctggcc tgcgttgcgc gttcagcggt tgccggaacg gccggaactg    1020
gggcgtttta tcctggtgaa taacaggctg gcgatcaaaa tcaccgatgg cagaacggcg    1080
aacctgctcg ccggcttaac cgctctcgac accttcgtga ttgacgccgc gctgaactac    1140
gccgacaccg cctatctggt ggccgcccac aatcaacatg ccacagagac gaataaagcg    1200
ctgtttctga cgctgctgca aaccctcatc gctcaggtgg agtttattaa agattcccct    1260
gctctgatcg ttgcccgcgt actgagcagc ctgatcaatg aatcggtgat catggtggag    1320
agcggcgttt gcagccgggc agatatcgat atcgccgccg tggccggcgt gaactatgcc    1380
gacggcattt ttgcctggtt ggcgcagctc gggcagaaaa acgtgaaatc gacgctggat    1440
aacatggcgc aactgctgca ctccgcgcgc tattacccgc attactcatt gctgaacgcg    1500
gcccggcctg agctggccgt agcgccctaa                                     1530
```

<210> SEQ ID NO 206
<211> LENGTH: 1530
<212> TYPE: DNA
<213> ORGANISM: Serratia proteamaculans MFPA44A14

<400> SEQUENCE: 206

```
atggcagaga ataattcggc aatccattcg gtcgctgtta ttggtgccgg aaccatgggc      60
agaggtattg cctatcttct ggcgcagaac ggcatacgaa ccctgcttta taatcgtagc     120
ggtaataatc tggatcaggc ccgcgactat attatccgtg acctggataa gaaaatagac     180
aacgggaaaa taagcccaca gaaaaaaggc gaagtattgg ccaacctggt tttctctccc     240
atttccgatg ctatcgccga cagcgacctg gtgattgaaa ccatcgcgga gcatgagacc     300
accaagcatg aaatcctcgc ggcgattgcg ccacggtga acaagaggc cattatcgcc      360 accaacacct catcgctgtc gttgaataag ctggcggcag gcgtcgaaaa caacgcccgt     420
tttatcggcc tgcacttctt caatccggcc ccgctgatga aactgatcga gattattccg     480
tcctatttta ccagccgggc caccagcctg cgctgccagc agttggtgac ggcgctaggc     540
aaacagtttg tggtctgcaa agccacgccg ggttttatcg tcaaccggat ggcacggcct     600 tttatatctgg aaggattccg gctgttggaa gaaaacgtgg cattagcacc gcagatcgac     660
cgcgccctca aggccggtgg ccactttcgc atgggccctt tggagctgac cgactttatc     720
ggccaggata ttaactatca ggtcagcagc cagatttggc aggacatgca atacgaccc      780 cgctatacccc ccggtcattt gcaacgttcg ctggtggatg ccgggttgct ggggaagaaa     840
aacggccgat cctttttttgc tgcccctttct gccgaatcca acctcctcga cgcaggcaac     900
ggtacgctga ctttccctgca tttttatggc gaacataccc tgtttgacct gctgcaacag     960
cgcgccttgg ctacttggcc aacgctgcag attattcacc agccggaacg gccaacgctg    1020
ggacgcttta tccgggtgaa tgacgcattg gccgtcaaaa tcaccgacgg ccgcaccgcc    1080
aatctgctcg ctgaattgac cgatctcgac accttttgtga tcgacgccgc actgaattac    1140
```

```
agcgatacca cctatctggt ggccgcccac aatcaggacg ccgccgaggc caataaagcg    1200
ctgtttctgt cgctgctgca aacgttgatc ccgcaggtgg agtttattaa agactctcca    1260
ggcctgatcg tcgcccgggt tctgagcagt ctgatcaatg agtcggtgat catggtggag    1320
agcggggttt gcagccgggc agatatcgat attgccgccg tggcgggcgt taactatgcc    1380
gatggcatct ttgcctggct gacgcagctc gggcaaaaaa acgtgaaatc aacgctggat    1440
aatatggcgc aactgctgca ttccgccgc tattacccgc attactcatt gctgaatatc    1500
ccccggcccg agctggccgt cgcgccgtaa                                    1530
```

<210> SEQ ID NO 207
<211> LENGTH: 1530
<212> TYPE: DNA
<213> ORGANISM: Serratia plymuthica A153

<400> SEQUENCE: 207

```
atggcagaga ataattcggc aatccgttca gccgccgtta ttggtgcggg gaccatgggc     60
agaggcatcg cctatctcct ggcgctgaac ggcatacgaa ccgtacttta taatcgcaat    120
ggtaataatc tcaatcaggc ccgtgactat attgtcagcg acctggacag aaaaatagat    180
aacggaaaaa taaccctgca gaaaaaaggc cagatattag ccaatattat tttctcggac    240
gtctttgacg ccataaccga cagcgatctg gtgattgaaa ccattgcgga agatgagcaa    300
accaagcatg aaatcctggc agccattgcg gcgacgtaa aaccggaggc gatcattgcg    360
accaatactt cctcgctgtc gctgaacaaa ctggcggcgg gggtggaaaa caacccgcgc    420
tttatcggcc tgcatttttt caatccggcg ccgctgatga agttgatcga attattccc     480 tcttatttca cctctcgcgc caccagtcta cgctgccagc agttggtaac agcgttgggt    540
aaactgtttg tggtctgcaa agccacgccg ggctttattg ttaatcgcat ggcgcggcct    600
ttctatctgg aagggttccg gctgctggag gaaaacgtgg cgctggctcc acagatcgac    660 cgcgcctca aggccggcgg gcattttcgc atggggcctt tagaactgac tgatttatc      720 ggccaggata tcaactatca ggtcagcaaa cagatttggc aggatatgca gttcgatccc    780
cgctataccc ccggccattt gcaacgctcg ctggtggatg ccgggctgct ggggaggaaa    840
aacgggcgct cttttttgc ttcccaacct gctacaccgc caacccgac cactgagggc      900 cacacgccaa cttcactgct tttttatggt gaacacgctt tattcgatca cctgcaacag    960
cgcgctttgg ccacctggcc tgcgctgcgc gttcagcggt tgccggaacg gccggaactg   1020
ggacgtttta tcctggtgaa taacaggctg gcgatcaaaa tcaccgatgg cagaacggcg   1080
aacctgctcg ccggcttaac cgctctcgac accttcgtga ttgacgccgc gctgaactac   1140
gccgacaccg cctatctggt ggccgcccac aatcaacatg ccacagagcc gaataaagcg   1200
ctgtttctga cgctgctgca aaccctcatc gctcaggtgg agtttattaa agattcccct   1260
gccctgatcg ttgcccgcgt actgagcagc ctgatcaatg aatcggtgat catggtggag   1320
agcggcgttt gcagccgggc agatatcgat atcgccgccg tggccggcgt gaactatgcc   1380
gacggcattt ttgcctggtt ggcgcagctc gggcagaaaa acgtgaaatc gacgctggat   1440
aacatggcgc aattgctgca ctccacgcgc tattacccgc attactcatt gctgaacgcg   1500
gcccggcctg agctggctgt agcgccctaa                                   1530
```

<210> SEQ ID NO 208
<211> LENGTH: 505
<212> TYPE: PRT
<213> ORGANISM: Pseudomonas putida KT2440

<400> SEQUENCE: 208

Met Ala Ala Leu Ala Ser Asn Val Gln Val Val Ile Gly Ala Gly
1               5                   10                  15

Ala Met Gly Ala Gly Ile Ala Gln Val Ala Ala Gln Ala Gly His Pro
            20                  25                  30

Val Lys Leu Tyr Asp Asn Arg Pro Gly Ala Ala Gln Ala Val Thr
        35                  40                  45

Gly Ile Asp Arg Gln Leu Ala Arg Leu Val Asp Lys Gly Lys Leu Leu
    50                  55                  60

Ala Ala Glu Arg Glu Thr Ile Asn Ala Arg Leu Cys Pro Val Asp Thr
65                  70                  75                  80

Leu Glu Ala Leu Ala Asp Ala Gly Leu Val Ile Glu Ala Ile Val Glu
                85                  90                  95

Asn Leu Gln Val Lys Gln Ala Leu Phe Ser Gln Leu Glu Thr Leu Cys
                100                 105                 110

Ala Ala Asp Cys Ile Leu Ala Ser Asn Thr Ser Ser Leu Ser Ile Thr
            115                 120                 125

Ser Leu Ala Ala Gly Leu Glu Arg Pro Gln His Val Val Gly Met His
130                 135                 140

Phe Phe Asn Pro Ala Pro Leu Met Ala Leu Val Glu Val Val Ser Gly
145                 150                 155                 160

Leu Ala Thr Asp Pro Ala Val Ala Ala Cys Ile Tyr Ala Thr Ala Gln
                165                 170                 175

Ala Trp Gly Lys Gln Pro Val His Ala Arg Ser Thr Pro Gly Phe Ile
            180                 185                 190

Val Asn Arg Val Ala Arg Pro Phe Tyr Ala Glu Ser Leu Arg Leu Leu
        195                 200                 205

Gln Glu Gly Ala Ala Asp Cys Ala Ser Leu Asp Ala Leu Met Arg Asp
210                 215                 220

Ser Gly Gly Phe Arg Met Gly Ala Phe Glu Leu Thr Asp Leu Ile Gly
225                 230                 235                 240

His Asp Val Asn Tyr Ala Val Thr Cys Ser Val Phe Asp Ala Phe Tyr
                245                 250                 255

Gly Asp Phe Arg Phe Gln Pro Ser Leu Val Gln Lys Glu Leu Val Asp
            260                 265                 270

Ala Gly His Leu Gly Arg Lys Thr Gly Gln Gly Phe Tyr Arg Tyr Ala
        275                 280                 285

Glu Gly Val Glu Arg Pro Gln Pro Ala Glu Leu His Ser Ser Ala Cys
    290                 295                 300

Ala Glu Ala Cys Val Val Glu Gly Asn Leu Gly Val Met Gln Pro Leu
305                 310                 315                 320

Val Glu Arg Leu Arg Gln Ser Gly Ile Ala Val Thr Gln Arg Ala Gly
                325                 330                 335

Ser Gly Leu Ile Gln Val Gly Asp Ala Thr Leu Ala Leu Ser Asp Gly
            340                 345                 350

Arg Leu Ala Ser Gln Arg Ala Arg Glu Asp Gly Leu Arg Asn Leu Val
        355                 360                 365

Leu Leu Asp Leu Ala Leu Asp Tyr Ser Ser Ala Thr Arg Ile Ala Ile
        370                 375                 380

Ser Trp Ser Ala Asp Thr Ser Asp Ser Ala Arg Asp Gln Ala Val Ala
385                 390                 395                 400

Leu Leu Gln Arg Ala Gly Leu Lys Val Thr Gly Val Ala Asp Leu Pro

```
                   405                 410                 415

Gly Leu Val Val Leu Arg Thr Val Ala Met Leu Ala Asn Glu Ala Ala
                420                 425                 430

Asp Ala Val Leu Gln Gly Val Gly Ser Ala Ala Asp Ile Asp Leu Ala
                435                 440                 445

Met Arg Ala Gly Val Asn Tyr Pro Cys Gly Pro Leu Ala Trp Ala Ala
            450                 455                 460

Asn Ile Gly Ile Ala His Thr Leu Arg Val Leu Asp Asn Leu Gln Cys
465                 470                 475                 480

Ser Tyr Gly Glu Ser Arg Tyr Arg Pro Ser Leu Leu Leu Arg Arg Cys
                485                 490                 495

Glu Ala Lys Gly Gly Thr Leu His Asp
            500                 505

<210> SEQ ID NO 209
<211> LENGTH: 475
<212> TYPE: PRT
<213> ORGANISM: Escherichia coli str. K-12 substr. MG1655

<400> SEQUENCE: 209

Met Met Ile Asn Val Gln Thr Val Ala Val Ile Gly Ser Gly Thr Met
1               5                   10                  15

Gly Ala Gly Ile Ala Glu Val Ala Ala Ser His Gly His Gln Val Leu
                20                  25                  30

Leu Tyr Asp Ile Ser Ala Glu Ala Leu Thr Arg Ala Ile Asp Gly Ile
            35                  40                  45

His Ala Arg Leu Asn Ser Arg Val Thr Arg Gly Lys Leu Thr Ala Glu
        50                  55                  60

Thr Cys Glu Arg Thr Leu Lys Arg Leu Ile Pro Val Thr Asp Ile His
65                  70                  75                  80

Ala Leu Ala Ala Ala Asp Leu Val Ile Glu Ala Ala Ser Glu Arg Leu
                85                  90                  95

Glu Val Lys Lys Ala Leu Phe Ala Gln Leu Ala Glu Val Cys Pro Pro
                100                 105                 110

Gln Thr Leu Leu Thr Thr Asn Thr Ser Ser Ile Ser Ile Thr Ala Ile
            115                 120                 125

Ala Ala Glu Ile Lys Asn Pro Glu Arg Val Ala Gly Leu His Phe Phe
130                 135                 140

Asn Pro Ala Pro Val Met Lys Leu Val Glu Val Val Ser Gly Leu Ala
145                 150                 155                 160

Thr Ala Ala Glu Val Val Glu Gln Leu Cys Glu Leu Thr Leu Ser Trp
                165                 170                 175

Gly Lys Gln Pro Val Arg Cys His Ser Thr Pro Gly Phe Ile Val Asn
            180                 185                 190

Arg Val Ala Arg Pro Tyr Tyr Ser Glu Ala Trp Arg Ala Leu Glu Glu
        195                 200                 205

Gln Val Ala Ala Pro Glu Val Ile Asp Ala Ala Leu Arg Asp Gly Ala
    210                 215                 220

Gly Phe Pro Met Gly Pro Leu Glu Leu Thr Asp Leu Ile Gly Gln Asp
225                 230                 235                 240

Val Asn Phe Ala Val Thr Cys Ser Val Phe Asn Ala Phe Trp Gln Glu
                245                 250                 255

Arg Arg Phe Leu Pro Ser Leu Val Gln Gln Glu Leu Val Ile Gly Gly
            260                 265                 270
```

```
Arg Leu Gly Lys Lys Ser Gly Leu Gly Val Tyr Asp Trp Arg Ala Glu
            275                 280                 285

Arg Glu Ala Val Val Gly Leu Glu Ala Val Ser Asp Ser Phe Ser Pro
        290                 295                 300

Met Lys Val Glu Lys Lys Ser Asp Gly Val Thr Glu Ile Asp Asp Val
305                 310                 315                 320

Leu Leu Ile Glu Thr Gln Gly Glu Thr Ala Gln Ala Leu Ala Ile Arg
                325                 330                 335

Leu Ala Arg Pro Val Val Ile Asp Lys Met Ala Gly Lys Val Val
                340                 345                 350

Thr Ile Ala Ala Ala Val Asn Pro Asp Ser Ala Thr Arg Lys Ala
        355                 360                 365

Ile Tyr Tyr Leu Gln Gln Gly Lys Thr Val Leu Gln Ile Ala Asp
370                 375                 380

Tyr Pro Gly Met Leu Ile Trp Arg Thr Val Ala Met Ile Ile Asn Glu
385                 390                 395                 400

Ala Leu Asp Ala Leu Gln Lys Gly Val Ala Ser Glu Gln Asp Ile Asp
                405                 410                 415

Thr Ala Met Arg Leu Gly Val Asn Tyr Pro Tyr Gly Pro Leu Ala Trp
                420                 425                 430

Gly Ala Gln Leu Gly Trp Gln Arg Ile Leu Arg Leu Leu Glu Asn Leu
                435                 440                 445

Gln His His Tyr Gly Glu Glu Arg Tyr Arg Pro Cys Ser Leu Leu Arg
        450                 455                 460

Gln Arg Ala Leu Leu Glu Ser Gly Tyr Glu Ser
465                 470                 475

<210> SEQ ID NO 210
<211> LENGTH: 505
<212> TYPE: PRT
<213> ORGANISM: Acinetobacter baylyi ADP1

<400> SEQUENCE: 210

Met Thr His Pro Ile Lys Lys Ile Ala Ile Gly Val Gly Val Met
1               5                   10                  15

Gly Ser Gly Ile Ala Gln Ile Ala Ala Gln Ser Gly His Ile Thr Tyr
                20                  25                  30

Leu Tyr Asp Ala Lys Ala Gly Ala Ala Gln Ala Lys Gln Gln Leu
            35                  40                  45

Ala Ile Thr Phe Gln Lys Leu Leu Asp Lys Asn Lys Ile Thr Thr Glu
        50                  55                  60

Tyr Ala Asp Ala Ala Asn Ala Asn Leu Leu Ile Ala Asn Glu Leu His
65                  70                  75                  80

Asp Leu Lys Asp Cys Asp Leu Ile Val Glu Ala Ile Val Glu Arg Leu
                85                  90                  95

Asp Ile Lys Gln Ser Leu Met Ser Gln Leu Glu Ala Ile Val Pro Glu
            100                 105                 110

Thr Thr Ile Leu Ala Ser Asn Thr Ser Ser Leu Ser Ile Thr Ala Ile
        115                 120                 125

Ala Ser Asn Cys Lys His Pro Glu Arg Val Ala Gly Tyr His Phe Phe
    130                 135                 140

Asn Pro Val Pro Leu Met Lys Val Val Glu Val Ile Gln Gly Leu Lys
145                 150                 155                 160

Thr Asp Pro Lys His Ile Glu Thr Leu Asn Gln Leu Ser Arg Val Leu
                165                 170                 175
```

Gly His Arg Pro Val Ala Lys Asp Thr Pro Gly Phe Ile Ile Asn
            180                 185                 190

His Ala Gly Arg Ala Tyr Gly Thr Glu Ala Leu Lys Ile Leu Asn Glu
            195                 200                 205

Asn Val Thr Asp Ile Ser Glu Ile Asp Arg Ile Leu Arg Asp Gly Val
        210                 215                 220

Gly Phe Arg Met Gly Pro Phe Glu Leu Met Asp Leu Thr Gly Leu Asp
225                 230                 235                 240

Val Ser His Pro Val Met Glu Ser Ile Tyr His Gln Tyr Tyr Glu Glu
                245                 250                 255

Ala Arg Tyr Arg Pro Asn Ser Leu Thr Lys Gln Met Leu Glu Ala Lys
            260                 265                 270

Gln Leu Gly Arg Lys Val Gly Gln Gly Phe Tyr Asp Tyr Arg Thr Gly
            275                 280                 285

Ser Lys Thr Gly Glu Thr Ser Ala Lys Val Ala Glu Arg Leu Thr Leu
        290                 295                 300

Tyr Pro Lys Val Trp Ile Ala Ala Asp Phe Glu Asp Lys Gln Leu
305                 310                 315                 320

Leu Ile Asn Tyr Leu Thr Thr His Asn Ile Gln Leu Asp Val Gly Ala
                325                 330                 335

Lys Pro Gln Ala Asp Ser Leu Cys Leu Leu Ala Cys Tyr Gly Glu Asp
            340                 345                 350

Thr Thr His Ala Ala Leu Arg Leu Asn Val Asn Pro Ala His Ser Val
        355                 360                 365

Ala Ile Asp Met Leu Tyr Gly Ile Glu Lys His Arg Thr Leu Met Pro
    370                 375                 380

Ser Leu Ile Thr Glu Val Thr Tyr Ser His Ala His Ser Ile Phe
385                 390                 395                 400

Asn Leu Asp Gly Ala Met Val Ser Thr Ile Gly Glu Ser Ile Gly Phe
                405                 410                 415

Val Ala Gln Arg Ile Leu Ala Met Val Ile Asn Leu Gly Cys Asp Ile
            420                 425                 430

Ala Gln Gln Ala Ile Ala Ser Val Asp Asp Ile Asn Ala Ala Val Arg
        435                 440                 445

Leu Gly Leu Gly Tyr Pro Phe Gly Pro Ile Glu Trp Gly Asp Glu Ile
    450                 455                 460

Gly Ser Asn Lys Ile Leu Leu Ile Leu Asn Arg Ile Thr Ala Leu Thr
465                 470                 475                 480

Ser Asp Pro Arg Tyr Arg Pro Ser Pro Trp Leu Gln Arg Arg Val Ala
                485                 490                 495

Leu Asn Leu Pro Leu Thr Phe Thr Thr
            500                 505

<210> SEQ ID NO 211
<211> LENGTH: 506
<212> TYPE: PRT
<213> ORGANISM: Serratia plymuthica NBRC102599

<400> SEQUENCE: 211

Met Ser Leu Pro Asn Phe Asn Gly Thr Val Ala Val Ile Gly Ala Gly
1               5                   10                  15

Thr Met Gly Ile Gly Ile Ala Gln Val Ala Ala His Ala Gly His Gln
            20                  25                  30

Val Lys Leu Phe Asp Ile Ala Ala Thr Ala Ala Gln Asn Ala Leu Gly

```
            35                  40                  45
Ala Leu Ser Leu Arg Leu Arg Gln Arg Val Ala Ala Gly Lys Ala Asp
 50                  55                  60

Ala Asp Ala Thr Glu Ala Leu Leu Ala Arg Ile Gln Pro Val Asp Thr
 65                  70                  75                  80

Leu Glu Gln Leu Ala Asp Ser Thr Leu Ile Ile Glu Ala Val Ala Glu
                     85                  90                  95

Lys Leu Ala Ile Lys Gln Ser Leu Phe Arg Glu Leu Glu Ala Leu Cys
                100                 105                 110

Ser Pro Ala Thr Leu Phe Ala Ser Asn Thr Ser Ser Leu Ser Ile Thr
                115                 120                 125

Ala Ile Gly Gly Ala Leu Gln His Pro Gln Arg Leu Ala Gly Leu His
            130                 135                 140

Phe Phe Asn Pro Ala Pro Leu Met Thr Leu Val Glu Ile Val Ser Gly
145                 150                 155                 160

Leu Asp Thr Gly Ala Asp Thr Val Ala Thr Leu Gln Thr Leu Ala Arg
                    165                 170                 175

Gln Trp Gly Lys Gln Ser Val Leu Cys Arg Ser Thr Pro Gly Phe Ile
                180                 185                 190

Val Asn Arg Val Ala Arg Pro Phe Tyr Ala Glu Thr Leu Arg Ala Leu
            195                 200                 205

Glu Glu Arg Val Ala Asp Val Ala Thr Leu Asp Ala Val Met Arg Asp
210                 215                 220

Ala Gly Cys Phe Ala Met Gly Pro Leu Gln Leu Thr Asp Leu Ile Gly
225                 230                 235                 240

Gln Asp Ile Asn Tyr Ala Val Thr Glu Ser Val Phe Gln Ala Phe Phe
                    245                 250                 255

Gln Asp Pro Arg Phe Thr Pro Ser Leu Val Gln Gln Glu Leu Val Ala
                260                 265                 270

Ala Gly Arg Leu Gly Arg Lys Ser Gly Cys Gly Phe Tyr Arg Tyr Asp
            275                 280                 285

Gly Glu Gln Thr Ser Ser Thr Ala Val Cys Leu Pro Leu Ser Gln Ala
290                 295                 300

Glu Pro Pro Arg Ser Ile Gln Leu His Gly Asp Glu Ala Gly Val Ala
305                 310                 315                 320

Phe Leu Ala Gly Leu Leu Thr Gly Asn Ala Glu Ala Ile Ile Gln Pro
                    325                 330                 335

Gly Gln Thr Ser Ala Phe Ala Arg Ile Asp Glu Val Thr Phe Met Leu
                340                 345                 350

Thr Asn Gly Lys Thr Ala Ser Gln Ile Ala Glu Glu Thr Gly Thr Pro
            355                 360                 365

Val Val Leu Phe Asp Leu Ser Ala Asn Tyr Ser Gln Ala Pro Cys Val
370                 375                 380

Ala Ile Ser Cys Ala Met Gln Asn Asp Ala Arg His Asn Asp Lys Val
385                 390                 395                 400

Val Arg Leu Leu Gln Ser Phe Gly Lys Gln Val Ile Leu Leu Pro Asp
                    405                 410                 415

Tyr Pro Gly Leu Leu Val Met Arg Thr Leu Ala Met Leu Ser Asn Glu
                420                 425                 430

Ala Leu Asp Ala Val Asn Lys Gly Val Ala Ser Ala Glu Asp Ile Asp
            435                 440                 445

Ser Ala Leu Arg Cys Gly Val Asn Tyr Pro Arg Gly Pro Leu Glu Trp
450                 455                 460
```

```
Gly Ala Ala Leu Gly Trp Arg Gln Ile Leu Ala Thr Leu Glu Asn Leu
465                 470                 475                 480

His Arg Tyr Tyr Gly Glu Pro Arg Tyr Arg Pro Met Pro Leu Leu Arg
                485                 490                 495

His Tyr Ala Phe Leu Ser Ser Gly Ala Glu
            500                 505

<210> SEQ ID NO 212
<211> LENGTH: 24
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 212

Gly Ala Gly Thr Met Gly Arg Gly Ile Ala Tyr Leu Xaa Ala Xaa Xaa
1               5                   10                  15

Xaa Ile Xaa Thr Xaa Leu Tyr Asn
            20

<210> SEQ ID NO 213
<211> LENGTH: 509
<212> TYPE: PRT
<213> ORGANISM: Serratia liquefaciens FK01

<400> SEQUENCE: 213

Met Ala Glu Asn Asn Thr Ala Ile Asp Ser Val Ala Val Ile Gly Ala
1               5                   10                  15

Gly Thr Met Gly Arg Gly Ile Ala Tyr Leu Leu Ala Leu Asn Gly Ile
                20                  25                  30

Arg Thr Leu Leu Tyr Asn Arg Asn Gly Asn His Leu Asn Gln Ala Arg
            35                  40                  45

Asp Tyr Ile Val Gly Asp Leu Asp Lys Lys Ile Asp Asn Gly Lys Ile
    50                  55                  60

Ser Gln Gln Lys Lys Gly Glu Val Leu Ala Asn Leu Val Phe Ser Pro
65                  70                  75                  80

Val Phe Asp Ala Ile Ala Asp Ser Asp Leu Val Ile Glu Thr Ile Ala
                85                  90                  95

Glu His Glu Pro Thr Lys His Glu Ile Leu Ala Ala Ile Ala Ala Thr
            100                 105                 110

Val Lys Lys Glu Ala Ile Ile Ala Thr Asn Thr Ser Ser Leu Ser Leu
        115                 120                 125

Asn Lys Leu Ala Ala Gly Ile Glu Asn Asn Ser Arg Phe Ile Gly Leu
    130                 135                 140

His Phe Phe Asn Pro Ala Pro Leu Met Lys Leu Ile Glu Ile Ile Pro
145                 150                 155                 160
```

Ser Tyr Phe Thr Ala Arg Ala Thr Thr Leu Arg Cys Gln Gln Leu Val
                165                 170                 175

Thr Ala Ile Gly Lys Lys Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Ser Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Phe Phe Ser Pro
        275                 280                 285

Ser Ala Asp Ala Ala Asn Pro Pro Ala Thr Gly Gly Thr Leu Ser
    290                 295                 300

Ser Leu His Phe Gly Glu His Pro Leu Phe Asp Leu Leu Gln Gln
305                 310                 315                 320

His Ala Phe Ala Thr Trp Ala Pro Leu Ala Ile Thr Arg Gln Pro Glu
                325                 330                 335

His Pro Val Leu Gly Arg Phe Ile Gln Val Asn Asp Ser Leu Ala Val
            340                 345                 350

Lys Ile Thr Asp Gly Arg Thr Ala Asn Gln Leu Ala Glu Leu Ala Gly
        355                 360                 365

Leu Asp Thr Phe Val Val Asp Val Ala Leu Asn Tyr Ala Asn Thr Ala
    370                 375                 380

Phe Leu Val Ala Ala His Ser Gln Gln Ala Thr Glu Ala Asn Lys Glu
385                 390                 395                 400

Leu Phe Leu Thr Leu Leu Gln Thr Val Ile Pro Gln Val Glu Phe Val
                405                 410                 415

Lys Asp Ser Pro Gly Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Ile Ala Ala Val Ala Gly Val Asn Tyr Ala Asp Gly Ile Phe
    450                 455                 460

Ala Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu His Ala Thr Arg Pro Glu Leu Ala Val Ala Pro
            500                 505

<210> SEQ ID NO 214
<211> LENGTH: 1530
<212> TYPE: DNA
<213> ORGANISM: Serratia liquefaciens FK01

<400> SEQUENCE: 214
atggcagaga ataatacggc aatagattcg gtcgccgtga ttggcgccgg aaccatgggc     60
agaggcattg cctatctttt ggcactgaac ggcatacgaa ccctgcttta taatcgaaac    120

```
ggtaatcatc ttaaccaggc ccgggattat attgtcggcg acctggataa aaaaatcgac    180
aacggaaaaa taagccaaca gaaaagggc gaggtcctgg ccaatctggt tttctcgcca     240
gttttcgacg ccattgccga cagtgacctg gtgattgaaa ccatagcgga acatgaaccc    300
accaagcatg agatcctcgc ggccattgcc gccacggtaa aaaagaggc gattatcgcc     360 accaatacct cttcgctgtc gctgaataaa ctggccgcag ggatagaaaa caactcgcgc    420
tttatcggcc tgcatttctt caacccggca ccgctgatga agctgatcga aattatcccg    480
tcctatttta ccgcccgggc caccaccta cgctgccagc agttggtcac ggcgataggc     540
aaaaaatttg tggtctgcaa agccacgccg ggctttatcg tcaatcgcat ggcgcggcct    600
ttttatctgg aaggttttcg cctgctggag gaaaacgtgg cgctggcacc gcaaatcgac    660
cgcgcgctca aggccggagg ccacttccgc atggggcctt tggaactgac tgatttatt    720 ggtcaggaca ttaattatca ggtcagcagc cagatttggc aggacatgca gtatgacccc    780
cgctataccc ccggccattt gcaacgttcg ctggtggatg ccgggctgtt ggggaagaaa    840
aacgggcgct cttttttttc cccctcggct gacgccgcca accaccggc taccggcggc    900 ggtacgctga gctcgctgca ttttttggc gaacatccgc tgtttgatct gctgcaacag    960
cacgccttcg caacctgggc gcccctggca ataacacgtc agccggaaca cccggttctg   1020
ggccgtttta tccaggtgaa tgacagtctg gcagtcaaaa tcaccgacgg gcgaacggcc   1080
aatcagcttg ccgagctggc gggtctcgat accttcgtgg tcgacgttgc actgaactat   1140
gccaacaccg cttttctggt ggcggcccac agccaacagg ctaccgaggc gaataaagag   1200
ctgttcctca cgctgctgca aacggtgatc ccgcaggtgg agtttgttaa agattccca   1260 ggcctgatcg tcgcccgggt tctgagcagc ctgatcaatg agtcggtgat catggtggag   1320
agcggggttt gtagccgaga agacatcgat atcgccgccg tggccggcgt caactatgcc   1380
gacggcattt ttgcctggct ggcgcagctc gggcagaaaa acgtgaaatc gacgctggat   1440
aatatggcgc aactgctgca ttccgcccgc tattacccgc actactcgtt gctccacgct   1500
accaggcccg agctggccgt cgcgccatga                                     1530

<210> SEQ ID NO 215
<211> LENGTH: 34
<212> TYPE: DNA
<213> ORGANISM: Artificial Sequence
<220> FEATURE:
<223> OTHER INFORMATION: primer

<400> SEQUENCE: 215
accacagcca ggatcctatg gcagaaagta atgc                                34

<210> SEQ ID NO 216
<211> LENGTH: 34
<212> TYPE: DNA
<213> ORGANISM: Artificial Sequence
<220> FEATURE:
<223> OTHER INFORMATION: primer

<400> SEQUENCE: 216
gctcgaattc ggatcttaag gcgtggtggt cagc                                34

<210> SEQ ID NO 217
<211> LENGTH: 34
<212> TYPE: DNA
<213> ORGANISM: Artificial Sequence
<220> FEATURE:
<223> OTHER INFORMATION: primer
```

<400> SEQUENCE: 217
accacagcca ggatcctatg gcagagaata attc            34

<210> SEQ ID NO 218
<211> LENGTH: 34
<212> TYPE: DNA
<213> ORGANISM: Artificial Sequence
<220> FEATURE:
<223> OTHER INFORMATION: primer

<400> SEQUENCE: 218
gctcgaattc ggatcttacg gcgcgacggc cagt            34

<210> SEQ ID NO 219
<211> LENGTH: 34
<212> TYPE: DNA
<213> ORGANISM: Artificial Sequence
<220> FEATURE:
<223> OTHER INFORMATION: primer

<400> SEQUENCE: 219
accacagcca ggatcctatg gcagagaata atac            34

<210> SEQ ID NO 220
<211> LENGTH: 34
<212> TYPE: DNA
<213> ORGANISM: Artificial Sequence
<220> FEATURE:
<223> OTHER INFORMATION: Synthetic

<400> SEQUENCE: 220
gctcgaattc ggatctcatg gcgcgacggc cagc            34

<210> SEQ ID NO 221
<211> LENGTH: 672
<212> TYPE: DNA
<213> ORGANISM: Acinetobacter baylyi
<220> FEATURE:
<221> NAME/KEY: misc_feature
<223> OTHER INFORMATION: Acinetobacter baylyi ADP1 dcaI

<400> SEQUENCE: 221
atgattaata aaatcattaa tgatattgag cccattttaa aatcgattcc agatggttca      60
acgattatga caagtggttt tggtacgaca ggtcaacctg aggcactact tgaagcatta     120
attgatttcg ctccaaaaga gttaactatt atcaataata atgcttcatc tggcccgaat     180
ggtttgactc agcttttcac tgctggattg gtcaaaaagc tcatttgctc gtatccaaaa     240
tcaatcagtt cgactgtttt tccagattta tatcgtgcgg gaaaaattga acttgaactg     300
gttcctcagg gaaatcttgc atgtcgtatt caagcagcag gtgctggtct gggagcggta     360
tttaccccca caggctacgg gaccaaaatt gctgaaggca agaaaacgcg cattattaac     420
ggtaaaaatt atgtacttga atatccactt gaagccgatt atgcattcat ttatgcagat     480
aaggcagatc gctgggggaa tttaacttat cgtaaagccg ccagaaattt tggtccgatt     540
atggccaaag ctgcaaaaac aacaattgct caagtcaatc aaactgttga attgggtgat     600
cttgatcccg aatgcattat tacacccggg atatttgtac agcatgtggt gcgattagga     660
gatataaaat ga                                                         672

<210> SEQ ID NO 222
<211> LENGTH: 675

```
<212> TYPE: DNA
<213> ORGANISM: Acinetobacter baylyi
<220> FEATURE:
<221> NAME/KEY: misc_feature
<223> OTHER INFORMATION: Acinetobacter baylyi ADP1 dcaJ

<400> SEQUENCE: 222
atgacgattc agaaaagaag tcgagaagat atcgcaatca tgatagcaaa ggatattcct      60
gatggttcgt atgtcaatct tggaattgga ttaccaaccc atgtcgcaaa atacttgcca     120
aaagataagg aaattttct gcactcagag aatggtgtac tggcatttgg tccacctcct     180
gctgaaggtg aagaagatca ggacttagtc aatgcaggta agagctggt gactttacta     240
tcaggtggat gttttatgca tcatggagat tcatttgaca ttatgcgtgg tggacatctg     300
gatatttgcg ttattggggc atttcaagtc gcgctcaatg gtgatttggc taactggcat     360
acaggtaaag acgatgatgt gcctgctgtt gggggagcaa tggatttggc ggttggggcc     420
aagcgtattt ttgtgtatat ggaacatacc accaaaaaag gcgaacctaa aattgttaaa     480
catctgactt atccaatcac tggtgagcag tgtgttgatc gtatttatac agatttatgt     540
acgattgagc tgaaagatgg acaggcatat gtgattgaaa tggtcgacgg attagatttt     600
gatactttgc aagccttaac tgaatgccca ttaattgatc actgtactta ttcatcgttg     660
attcagctta gataa                                                      675

<210> SEQ ID NO 223
<211> LENGTH: 55
<212> TYPE: DNA
<213> ORGANISM: Artificial Sequence
<220> FEATURE:
<223> OTHER INFORMATION: primer

<400> SEQUENCE: 223
gagcgggttt gagttcaatt gtagctggtg aatatatga ttaataaaat catta            55

<210> SEQ ID NO 224
<211> LENGTH: 34
<212> TYPE: DNA
<213> ORGANISM: Artificial Sequence
<220> FEATURE:
<223> OTHER INFORMATION: primer

<400> SEQUENCE: 224
gagtcattaa gtgtttatc taagctgaat caac                                   34

<210> SEQ ID NO 225
<211> LENGTH: 40
<212> TYPE: DNA
<213> ORGANISM: Artificial Sequence
<220> FEATURE:
<223> OTHER INFORMATION: Synthetic

<400> SEQUENCE: 225
cggccagtga attcgagctc cgtaattgcc ctttaaaatt                            40

<210> SEQ ID NO 226
<211> LENGTH: 41
<212> TYPE: DNA
<213> ORGANISM: Artificial Sequence
<220> FEATURE:
<223> OTHER INFORMATION: primer

<400> SEQUENCE: 226
gatccccggg taccgcatgc tatattccac cagctatttg t                          41
```

<210> SEQ ID NO 227
<211> LENGTH: 1155
<212> TYPE: DNA
<213> ORGANISM: Acinetobacter baylyi
<220> FEATURE:
<221> NAME/KEY: misc_feature
<223> OTHER INFORMATION: Acinetobacter baylyi ADP1 dcaA

<400> SEQUENCE: 227

| | | | | | |
|---|---|---|---|---|---|
| atgattcgcg | atgaagggat | gttgcaacaa | ttactttcga | caatacgaga | ttttgtaaaa | 60 |
| aatgaattga | ttcctcgaga | gcatgaagtt | gcagaaaagg | attgtattcc | tgaagatatt | 120 |
| attcagcaaa | tgcgagaact | aggcctattt | ggtttaacca | ttcccgaaga | atacggtgga | 180 |
| cttggaatca | caatggaaga | agaggtgaat | gtcgcgtttg | aacttggtca | gacatcccca | 240 |
| gcatttcgtt | cattgattgg | cacaaataat | ggcattggtt | caagtggttt | aatcattgat | 300 |
| ggaactgagg | agcaaaaaca | gaaatatttg | ccacgttatg | ccagtggaga | aattattggt | 360 |
| tcattttgct | taactgaacc | agaagcgggt | tcagatgctg | cctctttaaa | aacgacagcg | 420 |
| gtaaaagatg | gtgatttcta | catattaaat | ggaaccaagc | gttttattac | caatgcaccg | 480 |
| catgcagcaa | catttaccgt | aatggcacgc | accaatccag | caattaaagg | ggcaggtgga | 540 |
| atttctgctt | ttttggtaga | agccaataca | ccaggtatca | cactaggcaa | aatagatcag | 600 |
| aaaatgggac | aaaaaggctc | tcatacctgt | gatgtgattt | ttgaaaattg | tcgagtacct | 660 |
| gcatctgcat | taattggtgg | cgttgaaggc | gttggtttta | aaacagcaat | gaaagtgctg | 720 |
| gataaaggcc | gtctacatat | tggtgcatat | agtgtaggtg | ttgcagagcg | tatgttgaat | 780 |
| gatgcactac | attatgctgt | cgagcgtaag | cagtttggtc | aacccattgc | aaattttcaa | 840 |
| ttgattcaag | ccatgctggc | agactctaaa | gccgaaattt | atgcggctaa | atgtatggtt | 900 |
| ttggatgcag | cacgtcgccg | tgatgaaggc | caaaatatta | gtacagaagc | ctcatgtgcc | 960 |
| aagatgtttg | caacagaaat | gtgtggtcga | gtcgcagatc | gctgtgtgca | aattcatggt | 1020 |
| ggggcaggtt | acatcagtga | atattcgatt | gagcgttttt | atcgtgacgt | gcgtttattc | 1080 |
| cgtctttatg | agggtacgac | ccaagttcag | caaattatta | ttgccaaaaa | tatgattaag | 1140 |
| gaagtgacgt | cctaa | | | | | 1155 |

<210> SEQ ID NO 228
<211> LENGTH: 37
<212> TYPE: DNA
<213> ORGANISM: Artificial Sequence
<220> FEATURE:
<223> OTHER INFORMATION: primer

<400> SEQUENCE: 228
tagctggtgg aatatagatg attcgcgatg aagggat        37

<210> SEQ ID NO 229
<211> LENGTH: 41
<212> TYPE: DNA
<213> ORGANISM: Artificial Sequence
<220> FEATURE:
<223> OTHER INFORMATION: primer

<400> SEQUENCE: 229
attacgccaa gcttgtctag attaggacgt cacttcctta a        41

<210> SEQ ID NO 230
<211> LENGTH: 40

```
<212> TYPE: DNA
<213> ORGANISM: Artificial Sequence
<220> FEATURE:
<223> OTHER INFORMATION: primer

<400> SEQUENCE: 230
accaccatca cgtgggtacc atgatagata aaagtgcagc                            40

<210> SEQ ID NO 231
<211> LENGTH: 34
<212> TYPE: DNA
<213> ORGANISM: Artificial Sequence
<220> FEATURE:
<223> OTHER INFORMATION: primer

<400> SEQUENCE: 231
tcatcattcg aaccgttagc cttgtgtcgc atcg                                  34
```